US011186872B2

(12) United States Patent
Gonsky et al.

(10) Patent No.: US 11,186,872 B2
(45) Date of Patent: Nov. 30, 2021

(54) METHODS OF DIAGNOSING INFLAMMATORY BOWEL DISEASE THROUGH RNASET2

(71) Applicant: CEDARS-SINAI MEDICAL CENTER, Los Angeles, CA (US)

(72) Inventors: Rebecca Gonsky, Los Angeles, CA (US); Stephan R. Targan, Santa Monica, CA (US); Richard L. Deem, Azusa, CA (US); Philip Fleshner, Los Angeles, CA (US); Dermot P. McGovern, Los Angeles, CA (US); Janine Bilsborough, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 186 days.

(21) Appl. No.: 16/084,858

(22) PCT Filed: Mar. 17, 2017

(86) PCT No.: PCT/US2017/023082
§ 371 (c)(1),
(2) Date: Sep. 13, 2018

(87) PCT Pub. No.: WO2017/161342
PCT Pub. Date: Sep. 21, 2017

(65) Prior Publication Data
US 2019/0300957 A1 Oct. 3, 2019

Related U.S. Application Data

(60) Provisional application No. 62/309,817, filed on Mar. 17, 2016, provisional application No. 62/457,048, filed on Feb. 9, 2017.

(51) Int. Cl.
*C12Q 1/6883* (2018.01)
*C12Q 1/6806* (2018.01)
(Continued)

(52) U.S. Cl.
CPC ......... *C12Q 1/6883* (2013.01); *C12Q 1/6806* (2013.01); *C12Q 1/686* (2013.01);
(Continued)

(58) Field of Classification Search
CPC .. C12Q 1/6883; C12Q 1/6806; C12Q 1/6834; C12Q 1/686; C12Q 2600/106;
(Continued)

(56) References Cited

U.S. PATENT DOCUMENTS 3,654,090 A    4/1972  Antonius et al.
3,850,752 A    11/1974 Schuurs et al.
(Continued)

FOREIGN PATENT DOCUMENTS

AU    698604 B2       11/1998
AU    2014317991 A1   3/2016
(Continued)

OTHER PUBLICATIONS

Adler et al. Anti-tumor necrosis factor [alpha] prevents bowel fibrosis assessed by messenger RNA, histology, and magnetization transfer MRI in rats with Crohn's disease. Inflamm Bowel Dis 19(4):683-690 (2013).
(Continued)

*Primary Examiner* — Jehanne S Sitton
*Assistant Examiner* — Daniel W Nielsen
(74) *Attorney, Agent, or Firm* — Wilson Sonsini Goodrich & Rosati

(57) ABSTRACT

Described herein are methods of diagnosing inflammatory bowel disease, including but not limited to Crohn's Disease (CD), Ulcerative Colitis (UC), and/or Medically Refractive
(Continued)

Ulcerative Colitis (MR-UC), using RNA-SET2, TL1A and/or IFN-Y. The methods may comprise treating inflammatory bowel disease by administering a therapeutically effective amount of a therapeutic agent to a subject. Described further herein are processes for patient identification and/or stratification.

18 Claims, 50 Drawing Sheets

Specification includes a Sequence Listing.

(51) Int. Cl.
  *C12Q 1/686* (2018.01)
  *C12Q 1/6834* (2018.01)
(52) U.S. Cl.
  CPC ..... *C12Q 1/6834* (2013.01); *C12Q 2600/106* (2013.01); *C12Q 2600/154* (2013.01); *C12Q 2600/156* (2013.01); *G01N 2800/065* (2013.01)
(58) Field of Classification Search
  CPC ........ C12Q 2600/154; C12Q 2600/156; G01N 2800/065; C12C 1/6883; C12C 1/6806; C12C 1/6834; C12C 1/686; C12C 2600/106; C12C 2600/154; C12C 2600/156; C07K 16/249
  See application file for complete search history.

(56) References Cited

U.S. PATENT DOCUMENTS

| | | |
|---|---|---|
| 4,016,043 A | 4/1977 | Schuurs et al. |
| 4,265,823 A | 5/1981 | Nobile |
| 4,518,584 A | 5/1985 | Mark et al. |
| 4,698,195 A | 10/1987 | Okumura et al. |
| 4,699,880 A | 10/1987 | Goldstein, I |
| 4,704,692 A | 11/1987 | Ladner |
| 4,737,462 A | 4/1988 | Mark et al. |
| 4,800,159 A | 1/1989 | Mullis et al. |
| 4,880,548 A | 11/1989 | Pall et al. |
| 4,925,572 A | 5/1990 | Pall |
| 4,935,234 A | 6/1990 | Todd, III et al. |
| 4,946,778 A | 8/1990 | Ladner et al. |
| 5,002,873 A | 3/1991 | St. John et al. |
| 5,085,318 A | 2/1992 | Leverick |
| 5,091,302 A | 2/1992 | Newman et al. |
| 5,114,842 A | 5/1992 | Plow et al. |
| 5,137,806 A | 8/1992 | Lemaistre et al. |
| 5,147,637 A | 9/1992 | Wright et al. |
| 5,210,015 A | 5/1993 | Gelfand et al. |
| 5,219,997 A | 6/1993 | Schlossman et al. |
| 5,225,539 A | 7/1993 | Winter |
| 5,227,369 A | 7/1993 | Rosen et al. |
| 5,234,810 A | 8/1993 | Kehrli, Jr. et al. |
| 5,235,049 A | 8/1993 | McClelland et al. |
| 5,236,081 A | 8/1993 | Fitzsimmons et al. |
| 5,263,743 A | 11/1993 | Jones |
| 5,264,554 A | 11/1993 | Newman |
| 5,272,263 A | 12/1993 | Hession et al. |
| 5,284,931 A | 2/1994 | Springer et al. |
| 5,411,842 A | 5/1995 | Ridgway et al. |
| 5,491,063 A | 2/1996 | Fisher et al. |
| 5,494,920 A | 2/1996 | Glasebrook et al. |
| 5,518,488 A | 5/1996 | Schluger |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,590,769 A | 1/1997 | Lin |
| 5,607,879 A | 3/1997 | Wuu et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,683,698 A | 11/1997 | Chavali et al. |
| 5,691,151 A | 11/1997 | Braun et al. |
| 5,713,061 A | 1/1998 | Yoshioka |
| 5,750,355 A | 5/1998 | Targan et al. |
| 5,830,675 A | 11/1998 | Targan et al. |
| 5,840,300 A | 11/1998 | Williams et al. |
| 5,861,155 A | 1/1999 | Lin |
| 5,874,233 A | 2/1999 | Targan et al. |
| 5,885,793 A | 3/1999 | Griffiths et al. |
| 5,905,827 A | 5/1999 | Naganuma et al. |
| 5,916,748 A | 6/1999 | Targan et al. |
| 5,937,862 A | 8/1999 | Targan et al. |
| 5,942,390 A | 8/1999 | Cominelli et al. |
| 5,947,281 A | 9/1999 | Kaneff |
| 5,968,741 A | 10/1999 | Plevy et al. |
| 5,969,108 A | 10/1999 | McCafferty et al. |
| 6,034,102 A | 3/2000 | Aiello |
| 6,074,835 A | 6/2000 | Braun et al. |
| 6,114,395 A | 9/2000 | Aiello |
| 6,172,197 B1 | 1/2001 | McCafferty et al. |
| 6,183,951 B1 | 2/2001 | Plevy et al. |
| 6,215,040 B1 | 4/2001 | Lee et al. |
| 6,297,367 B1 | 10/2001 | Tribouley |
| 6,300,064 B1 | 10/2001 | Knappik et al. |
| 6,348,316 B1 | 2/2002 | Taylor et al. |
| 6,376,176 B1 | 4/2002 | Taylor et al. |
| 6,406,701 B1 | 6/2002 | Pulido-Cejudo |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,607,879 B1 | 8/2003 | Cocks et al. |
| 6,632,976 B1 | 10/2003 | Tomizuka et al. |
| 6,653,068 B2 | 11/2003 | Frisch et al. |
| 6,692,916 B2 | 2/2004 | Bevilacqua et al. |
| 6,706,484 B1 | 3/2004 | Knappik et al. |
| 6,713,061 B1 | 3/2004 | Yu et al. |
| 6,762,042 B2 | 7/2004 | Liu et al. |
| 6,812,339 B1 | 11/2004 | Venter et al. |
| 6,824,767 B2 | 11/2004 | Yu et al. |
| 6,824,989 B1 | 11/2004 | Eisinger et al. |
| 6,835,823 B2 | 12/2004 | Le et al. |
| 6,858,391 B2 | 2/2005 | Nunez et al. |
| 6,869,762 B1 | 3/2005 | Daly et al. |
| 6,905,827 B2 | 6/2005 | Wohlgemuth et al. |
| 6,950,827 B2 | 9/2005 | Jung |
| 7,060,869 B2 | 6/2006 | Tsien et al. |
| 7,138,237 B1 | 11/2006 | Targan et al. |
| 7,186,800 B1 | 3/2007 | Gentz et al. |
| 7,252,971 B2 | 8/2007 | Benson et al. |
| 7,264,963 B1 | 9/2007 | Knappik et al. |
| 7,285,267 B2 | 10/2007 | Gentz et al. |
| 7,332,156 B2 | 2/2008 | Bowman et al. |
| 7,332,631 B2 | 2/2008 | Hogarth et al. |
| 7,361,491 B2 | 4/2008 | Liu et al. |
| 7,361,733 B2 | 4/2008 | Hersberg et al. |
| 7,368,527 B2 | 5/2008 | Rosen et al. |
| 7,534,428 B2 | 5/2009 | Gentz et al. |
| 7,597,886 B2 | 10/2009 | Yu et al. |
| 7,612,181 B2 | 11/2009 | Wu et al. |
| 7,708,996 B2 | 5/2010 | Yu et al. |
| 7,709,218 B2 | 5/2010 | Gentz et al. |
| 7,745,391 B2 | 6/2010 | Mintz et al. |
| 7,759,079 B2 | 7/2010 | Oh et al. |
| 7,820,447 B2 | 10/2010 | Morris et al. |
| 7,820,798 B2 | 10/2010 | Yu et al. |
| 7,838,239 B2 | 11/2010 | Mitsuhashi et al. |
| 7,892,730 B2 | 2/2011 | Morris et al. |
| 7,993,833 B2 | 8/2011 | Begovich et al. |
| 8,003,099 B2 | 8/2011 | Auer et al. |
| 8,003,386 B1 | 8/2011 | Gentz et al. |
| 8,017,122 B2 | 9/2011 | Siadak et al. |

(56) References Cited

U.S. PATENT DOCUMENTS

| | | |
|---|---|---|
| 8,039,240 B2 | 10/2011 | Roiz et al. |
| 8,093,363 B2 | 1/2012 | Yu et al. |
| 8,263,743 B2 | 9/2012 | Smith et al. |
| 8,409,577 B2 | 4/2013 | Thompson et al. |
| 8,524,869 B2 | 9/2013 | Smith et al. |
| 8,642,741 B2 | 2/2014 | Classon et al. |
| 8,715,943 B2 | 5/2014 | Princen et al. |
| 8,728,282 B2 | 5/2014 | Niu |
| 8,728,475 B2 | 5/2014 | Burkly et al. |
| 8,728,482 B2 | 5/2014 | Smith et al. |
| 8,766,034 B2 | 7/2014 | Shih et al. |
| 8,781,750 B2 | 7/2014 | Stuart et al. |
| 8,859,739 B2 | 10/2014 | Kontermann et al. |
| 8,883,975 B2 | 11/2014 | Brandt et al. |
| 8,975,022 B2 | 3/2015 | Begovich et al. |
| 9,017,679 B2 | 4/2015 | Podack et al. |
| 9,068,003 B2 | 6/2015 | Siegel et al. |
| 9,102,733 B2 | 8/2015 | Endl et al. |
| 9,290,576 B2 | 3/2016 | Attinger et al. |
| 9,305,137 B1 | 4/2016 | Targan et al. |
| 9,332,741 B2 | 5/2016 | Shih et al. |
| 9,371,565 B2 | 6/2016 | Begovich et al. |
| 9,416,185 B2 | 8/2016 | Smith et al. |
| 9,556,277 B2 | 1/2017 | Classon et al. |
| 9,580,752 B2 | 2/2017 | Rotter et al. |
| 9,683,998 B2 | 6/2017 | Arch et al. |
| 9,834,606 B2 | 12/2017 | Li et al. |
| 9,839,670 B2 | 12/2017 | Podack et al. |
| 9,896,511 B2 | 2/2018 | Siegel et al. |
| 9,902,996 B2 | 2/2018 | Dubinsky et al. |
| 10,316,083 B2 | 6/2019 | Michelsen et al. |
| 10,322,174 B2 | 6/2019 | Bilsborough et al. |
| 10,626,180 B2 | 4/2020 | McGovern et al. |
| 2001/0006789 A1 | 7/2001 | Maino et al. |
| 2002/0006613 A1 | 1/2002 | Shyjan et al. |
| 2002/0019837 A1 | 2/2002 | Balnaves |
| 2002/0048566 A1 | 4/2002 | El-Deiry et al. |
| 2002/0078757 A1 | 6/2002 | Hines et al. |
| 2002/0106684 A1 | 8/2002 | Kopreski |
| 2002/0150939 A1 | 10/2002 | Taylor et al. |
| 2002/0165137 A1 | 11/2002 | Ruben et al. |
| 2002/0198371 A1 | 12/2002 | Wang |
| 2003/0017518 A1 | 1/2003 | Lam et al. |
| 2003/0092019 A1 | 5/2003 | Meyer et al. |
| 2003/0129189 A1 | 7/2003 | Yu et al. |
| 2003/0129215 A1 | 7/2003 | Mollison et al. |
| 2003/0138781 A1 | 7/2003 | Whitehead |
| 2003/0148345 A1 | 8/2003 | Kopreski |
| 2003/0166871 A1 | 9/2003 | Barbas et al. |
| 2003/0176409 A1 | 9/2003 | Offner |
| 2003/0198640 A1 | 10/2003 | Yu et al. |
| 2003/0229455 A1 | 12/2003 | Bevilacqua et al. |
| 2004/0013655 A1 | 1/2004 | Shiozawa et al. |
| 2004/0053262 A1 | 3/2004 | Lu |
| 2004/0072154 A1 | 4/2004 | Morris et al. |
| 2004/0123343 A1 | 6/2004 | La et al. |
| 2004/0142325 A1 | 7/2004 | Mintz et al. |
| 2004/0181048 A1 | 9/2004 | Wang |
| 2004/0203076 A1 | 10/2004 | Targan et al. |
| 2004/0213761 A1 | 10/2004 | Bowman et al. |
| 2004/0219555 A1 | 11/2004 | Van Heel |
| 2004/0265864 A1 | 12/2004 | Mitsuhashi |
| 2005/0054021 A1 | 3/2005 | Targan et al. |
| 2005/0143333 A1 | 6/2005 | Richards et al. |
| 2005/0163764 A1 | 7/2005 | Medzhitov et al. |
| 2005/0182007 A1 | 8/2005 | McSwiggen et al. |
| 2005/0228172 A9 | 10/2005 | Wang |
| 2005/0260204 A1 | 11/2005 | Allan |
| 2005/0261219 A1 | 11/2005 | Richards et al. |
| 2006/0003392 A1 | 1/2006 | Oh et al. |
| 2006/0008819 A1 | 1/2006 | Curtis et al. |
| 2006/0067936 A1 | 3/2006 | Benson et al. |
| 2006/0100132 A1 | 5/2006 | Corneliussen et al. |
| 2006/0134663 A1 | 6/2006 | Harkin et al. |
| 2006/0141478 A1 | 6/2006 | Brant et al. |
| 2006/0154276 A1 | 7/2006 | Lois et al. |
| 2006/0211020 A1 | 9/2006 | Farrer et al. |
| 2006/0234285 A1 | 10/2006 | Gentz et al. |
| 2007/0015271 A1 | 1/2007 | Rosen et al. |
| 2007/0020268 A1 | 1/2007 | Ashkenazi et al. |
| 2007/0020637 A1 | 1/2007 | Isogai et al. |
| 2007/0037165 A1 | 2/2007 | Venter et al. |
| 2007/0054278 A1 | 3/2007 | Cargill |
| 2007/0054282 A1 | 3/2007 | Liew |
| 2007/0059758 A1 | 3/2007 | Levine |
| 2007/0072180 A1 | 3/2007 | Abreu et al. |
| 2007/0083334 A1 | 4/2007 | Mintz et al. |
| 2007/0161031 A1 | 7/2007 | Trinklein et al. |
| 2007/0196835 A1 | 8/2007 | Bankaitis-Davis et al. |
| 2007/0237770 A1 | 10/2007 | Lai et al. |
| 2007/0254850 A1 | 11/2007 | Lieberman et al. |
| 2007/0275424 A1 | 11/2007 | Gewirtz et al. |
| 2008/0003221 A1 | 1/2008 | Podack et al. |
| 2008/0038746 A1 | 2/2008 | Rosenberg et al. |
| 2008/0038831 A1 | 2/2008 | Benson |
| 2008/0081822 A1 | 4/2008 | Berry et al. |
| 2008/0091471 A1 | 4/2008 | Michon et al. |
| 2008/0095775 A1 | 4/2008 | Lewis et al. |
| 2008/0103180 A1 | 5/2008 | Fleming et al. |
| 2008/0108713 A1 | 5/2008 | Begovich et al. |
| 2008/0131887 A1 | 6/2008 | Stephan et al. |
| 2008/0177048 A1 | 7/2008 | Gagnon |
| 2008/0206762 A1 | 8/2008 | Ferrer Abizanda et al. |
| 2008/0261207 A1 | 10/2008 | Mitsuhashi |
| 2008/0274467 A1 | 11/2008 | Morris et al. |
| 2008/0293582 A1 | 11/2008 | Li et al. |
| 2009/0018031 A1 | 1/2009 | Trinklein et al. |
| 2009/0048119 A1 | 2/2009 | Krjutskov et al. |
| 2009/0099789 A1 | 4/2009 | Stephan et al. |
| 2009/0162350 A1 | 6/2009 | Abbas et al. |
| 2009/0180380 A1 | 7/2009 | Prabhakar et al. |
| 2009/0186034 A1 | 7/2009 | Abbas et al. |
| 2009/0187005 A1 | 7/2009 | Gagnon |
| 2009/0220417 A1 | 9/2009 | Siadak et al. |
| 2009/0221437 A1 | 9/2009 | Harkin et al. |
| 2009/0253133 A1 | 10/2009 | Mitsuhashi et al. |
| 2009/0258848 A1 | 10/2009 | Chakravarti et al. |
| 2009/0297563 A1 | 12/2009 | Borglum et al. |
| 2009/0317388 A1 | 12/2009 | Burkly et al. |
| 2010/0015156 A1 | 1/2010 | Dubinsky et al. |
| 2010/0019016 A1 | 1/2010 | Edoga et al. |
| 2010/0021455 A1 | 1/2010 | Targan et al. |
| 2010/0021917 A1 | 1/2010 | Rotter et al. |
| 2010/0041600 A1 | 2/2010 | Russel et al. |
| 2010/0055700 A1 | 3/2010 | Targan et al. |
| 2010/0099092 A1 | 4/2010 | Song et al. |
| 2010/0105044 A1 | 4/2010 | Fleshner et al. |
| 2010/0136543 A1 | 6/2010 | Georges et al. |
| 2010/0144903 A1 | 6/2010 | Taylor et al. |
| 2010/0184050 A1 | 7/2010 | Rotter et al. |
| 2010/0190162 A1 | 7/2010 | Rotter et al. |
| 2010/0240043 A1 | 9/2010 | Rotter et al. |
| 2010/0240077 A1 | 9/2010 | Targan et al. |
| 2010/0254971 A1 | 10/2010 | Dotan et al. |
| 2010/0266594 A1 | 10/2010 | Reed |
| 2010/0284999 A1 | 11/2010 | Taylor et al. |
| 2010/0291551 A1 | 11/2010 | Belouchi |
| 2010/0298232 A1 | 11/2010 | Liu |
| 2011/0003707 A1 | 1/2011 | Goix et al. |
| 2011/0033486 A1 | 2/2011 | Abbas et al. |
| 2011/0045476 A1 | 2/2011 | Barken et al. |
| 2011/0111418 A1 | 5/2011 | Rhodes et al. |
| 2011/0124644 A1 | 5/2011 | Targan et al. |
| 2011/0136113 A1 | 6/2011 | Uga et al. |
| 2011/0159011 A1 | 6/2011 | Carrier et al. |
| 2011/0160085 A1 | 6/2011 | Li et al. |
| 2011/0177502 A1 | 7/2011 | Hakonarson et al. |
| 2011/0177969 A1 | 7/2011 | Rotter et al. |
| 2011/0189685 A1 | 8/2011 | Taylor et al. |
| 2011/0217310 A1 | 9/2011 | Siegel et al. |
| 2011/0229471 A1 | 9/2011 | Rotter et al. |
| 2011/0243951 A1 | 10/2011 | Podack et al. |
| 2012/0014950 A1 | 1/2012 | Migone et al. |
| 2012/0026371 A1 | 2/2012 | Itano et al. |

(56) References Cited

U.S. PATENT DOCUMENTS

| | | |
|---|---|---|
| 2012/0041082 A1 | 2/2012 | Rotter et al. |
| 2012/0053131 A1 | 3/2012 | Rotter et al. |
| 2012/0073585 A1 | 3/2012 | Rotter et al. |
| 2012/0079611 A1 | 3/2012 | Shih et al. |
| 2012/0094934 A1 | 4/2012 | Collard et al. |
| 2012/0114654 A1 | 5/2012 | Classon et al. |
| 2012/0135011 A1 | 5/2012 | Podack et al. |
| 2012/0190698 A1 | 7/2012 | Dubinsky et al. |
| 2012/0208900 A1 | 8/2012 | Dubinsky et al. |
| 2012/0263718 A1 | 10/2012 | Siegel et al. |
| 2012/0315282 A1 | 12/2012 | Bedinger et al. |
| 2012/0328559 A1 | 12/2012 | Podack et al. |
| 2013/0012602 A1 | 1/2013 | Haritunians et al. |
| 2013/0012604 A1 | 1/2013 | Rotter et al. |
| 2013/0123117 A1 | 5/2013 | Xu et al. |
| 2013/0129668 A1 | 5/2013 | Firestein et al. |
| 2013/0136720 A1 | 5/2013 | McGovern et al. |
| 2013/0142809 A1 | 6/2013 | Welcher et al. |
| 2013/0216551 A1 | 8/2013 | Begovich et al. |
| 2013/0225439 A1 | 8/2013 | Princen et al. |
| 2013/0344621 A1 | 12/2013 | Wang et al. |
| 2014/0017711 A1 | 1/2014 | Taylor et al. |
| 2014/0018447 A1 | 1/2014 | McGovern et al. |
| 2014/0018448 A1 | 1/2014 | Gonsky et al. |
| 2014/0037618 A1 | 2/2014 | Pidasheva et al. |
| 2014/0141983 A1 | 5/2014 | Singh et al. |
| 2014/0162894 A1 | 6/2014 | Hatchwell et al. |
| 2014/0255302 A1 | 9/2014 | Poulton et al. |
| 2015/0026831 A1 | 1/2015 | Shih et al. |
| 2015/0031972 A1 | 1/2015 | Freeman et al. |
| 2015/0072879 A1 | 3/2015 | Princen et al. |
| 2015/0086567 A1 | 3/2015 | Gonsky et al. |
| 2015/0132311 A1 | 5/2015 | Arch et al. |
| 2015/0259744 A1 | 9/2015 | Begovich et al. |
| 2015/0313904 A1 | 11/2015 | Kolatch et al. |
| 2015/0337378 A1 | 11/2015 | Targan et al. |
| 2015/0376612 A1 | 12/2015 | Lee et al. |
| 2015/0376707 A1 | 12/2015 | Targan et al. |
| 2016/0053007 A1 | 2/2016 | Siegel et al. |
| 2016/0060330 A1 | 3/2016 | Presta |
| 2016/0060335 A1 | 3/2016 | Shih et al. |
| 2016/0090629 A1 | 3/2016 | McGovern |
| 2016/0096885 A1 | 4/2016 | Shih et al. |
| 2016/0200833 A1 | 7/2016 | Amann et al. |
| 2016/0208329 A1* | 7/2016 | Targan .................. A61P 1/04 |
| 2016/0215046 A1 | 7/2016 | Michelsen et al. |
| 2016/0222450 A1 | 8/2016 | Schrodi et al. |
| 2016/0333104 A1 | 11/2016 | Poulton et al. |
| 2017/0044615 A1 | 2/2017 | Rotter et al. |
| 2017/0081400 A1 | 3/2017 | Poulton et al. |
| 2017/0096491 A1 | 4/2017 | Classon et al. |
| 2017/0166967 A1 | 6/2017 | Rotter et al. |
| 2018/0021696 A1 | 1/2018 | Wang et al. |
| 2018/0051078 A1 | 2/2018 | Targan et al. |
| 2018/0052175 A1 | 2/2018 | Arch et al. |
| 2018/0078611 A1 | 3/2018 | Podack et al. |
| 2018/0086840 A1 | 3/2018 | Attinger et al. |
| 2018/0110855 A1 | 4/2018 | Bilsborough |
| 2018/0142302 A1 | 5/2018 | Dubinsky |
| 2018/0156781 A1 | 6/2018 | Shih |
| 2018/0208988 A1 | 7/2018 | Targan et al. |
| 2018/0230543 A1 | 8/2018 | McGovern |
| 2018/0305689 A1 | 10/2018 | Sætrom et al. |
| 2019/0060449 A1 | 2/2019 | Singh et al. |
| 2019/0194754 A1 | 6/2019 | McGovern et al. |
| 2020/0216526 A1 | 7/2020 | Michelsen et al. |

FOREIGN PATENT DOCUMENTS

| | | |
|---|---|---|
| CA | 2468316 A1 | 6/2003 |
| CA | 2471840 A1 | 7/2003 |
| CA | 2668691 A1 | 6/2008 |
| CA | 2830351 A1 | 10/2012 |
| CA | 2830362 A1 | 10/2012 |
| CA | 2830365 A1 | 10/2012 |
| CA | 2922381 A1 | 3/2015 |
| CL | 2015002866 A1 | 8/2016 |
| CN | 101198624 A | 6/2008 |
| CN | 101903402 A | 12/2010 |
| CN | 202109170 U | 1/2012 |
| CN | 103149371 A | 6/2013 |
| CN | 105246501 A | 1/2016 |
| CN | 105358713 A | 2/2016 |
| CN | 105636648 A | 6/2016 |
| EP | 0760010 B1 | 10/2001 |
| EP | 1285271 B1 | 8/2005 |
| EP | 1716227 A2 | 11/2006 |
| EP | 1243274 B1 | 6/2008 |
| EP | 2005175 A2 | 12/2008 |
| EP | 2034030 A2 | 3/2009 |
| EP | 2064345 A2 | 6/2009 |
| EP | 2097540 A2 | 9/2009 |
| EP | 1819827 B1 | 8/2010 |
| EP | 2270512 A1 | 1/2011 |
| EP | 2565277 A1 | 3/2013 |
| EP | 2689034 A2 | 1/2014 |
| EP | 2689036 A2 | 1/2014 |
| EP | 2689246 A1 | 1/2014 |
| EP | 2978440 A1 | 2/2016 |
| EP | 2996717 A2 | 3/2016 |
| EP | 2997165 A2 | 3/2016 |
| EP | 2462165 B1 | 5/2016 |
| EP | 3022295 A1 | 5/2016 |
| EP | 3041580 A1 | 7/2016 |
| EP | 2638069 B1 | 1/2018 |
| EP | 3270964 A1 | 1/2018 |
| EP | 3294336 A1 | 3/2018 |
| JP | 2005510225 A | 4/2005 |
| JP | 2005514923 A | 5/2005 |
| JP | 2008518610 A | 6/2008 |
| JP | 2009526756 A | 7/2009 |
| JP | 2009195249 A | 9/2009 |
| JP | 2009535016 A | 10/2009 |
| JP | 2010088432 A | 4/2010 |
| JP | 2014515599 A | 7/2014 |
| JP | 2016522164 A | 7/2016 |
| JP | 2016526875 A | 9/2016 |
| JP | 2016536002 A | 11/2016 |
| JP | 2016198116 A | 12/2016 |
| KR | 20150134393 A | 12/2015 |
| KR | 20160009582 A | 1/2016 |
| KR | 20160052585 A | 5/2016 |
| WO | WO-9116928 A1 | 11/1991 |
| WO | WO-9202819 A2 | 2/1992 |
| WO | WO-9222323 A1 | 12/1992 |
| WO | WO-9307485 A1 | 4/1993 |
| WO | WO-9312248 A1 | 6/1993 |
| WO | WO-9404188 A1 | 3/1994 |
| WO | WO-9521941 A1 | 8/1995 |
| WO | WO-9531575 A1 | 11/1995 |
| WO | WO-9614328 A1 | 5/1996 |
| WO | WO-9725445 A1 | 7/1997 |
| WO | WO-9847004 A1 | 10/1998 |
| WO | WO-0066608 A1 | 11/2000 |
| WO | WO-0076492 A1 | 12/2000 |
| WO | WO-0120036 A2 | 3/2001 |
| WO | WO-0142511 A2 | 6/2001 |
| WO | WO-0157182 A2 | 8/2001 |
| WO | WO-0204643 A1 | 1/2002 |
| WO | WO-0157182 A3 | 3/2002 |
| WO | WO-0228999 A2 | 4/2002 |
| WO | WO-03008583 A2 | 1/2003 |
| WO | WO-03025148 A2 | 3/2003 |
| WO | WO-03040404 A1 | 5/2003 |
| WO | WO-03053220 A2 | 7/2003 |
| WO | WO-03057146 A2 | 7/2003 |
| WO | WO-03059333 A2 | 7/2003 |
| WO | WO-03090694 A2 | 11/2003 |
| WO | WO-03099312 A1 | 12/2003 |
| WO | WO-2004020968 A2 | 3/2004 |
| WO | WO-2004031159 A1 | 4/2004 |
| WO | WO-2004035537 A2 | 4/2004 |
| WO | WO-2004048600 A2 | 6/2004 |
| WO | WO-2004050836 A2 | 6/2004 |

(56) References Cited

FOREIGN PATENT DOCUMENTS

| | | |
|---|---|---|
| WO | WO-2005044792 A2 | 5/2005 |
| WO | WO-2005114469 A1 | 12/2005 |
| WO | WO-2005115115 A2 | 12/2005 |
| WO | WO-2005116251 A1 | 12/2005 |
| WO | WO-2006017173 A1 | 2/2006 |
| WO | WO-2006063093 A2 | 6/2006 |
| WO | WO-2006075254 A2 | 7/2006 |
| WO | WO-2006110091 A1 | 10/2006 |
| WO | WO-2006116721 A1 | 11/2006 |
| WO | WO-2006122079 A1 | 11/2006 |
| WO | WO-2007005608 A2 | 1/2007 |
| WO | WO-2007025989 A2 | 3/2007 |
| WO | WO-2007117611 A2 | 10/2007 |
| WO | WO-2007133816 A2 | 11/2007 |
| WO | WO-2007140625 A1 | 12/2007 |
| WO | WO-2008014400 A2 | 1/2008 |
| WO | WO-2008033239 A2 | 3/2008 |
| WO | WO-2008048902 A2 | 4/2008 |
| WO | WO-2008048984 A2 | 4/2008 |
| WO | WO-2008048986 A2 | 4/2008 |
| WO | WO-2008101133 A2 | 8/2008 |
| WO | WO-2008106451 A2 | 9/2008 |
| WO | WO-2008106579 A2 | 9/2008 |
| WO | WO-2008109782 A2 | 9/2008 |
| WO | WO-2008112990 A2 | 9/2008 |
| WO | WO-2008116150 A2 | 9/2008 |
| WO | WO-2008106451 A3 | 11/2008 |
| WO | WO-2008134569 A2 | 11/2008 |
| WO | WO-2008137762 A2 | 11/2008 |
| WO | WO-2008141148 A2 | 11/2008 |
| WO | WO-2009020403 A1 | 2/2009 |
| WO | WO-2009052512 A2 | 4/2009 |
| WO | WO-2009064854 A2 | 5/2009 |
| WO | WO-2009073628 A2 | 6/2009 |
| WO | WO-2009105590 A2 | 8/2009 |
| WO | WO-2009117122 A2 | 9/2009 |
| WO | WO-2009143278 A2 | 11/2009 |
| WO | WO-2009105590 A3 | 1/2010 |
| WO | WO-2010008858 A1 | 1/2010 |
| WO | WO-2010039931 A2 | 4/2010 |
| WO | WO-2010048415 A1 | 4/2010 |
| WO | WO-2010049933 A1 | 5/2010 |
| WO | WO-2010056682 A2 | 5/2010 |
| WO | WO-2010062960 A2 | 6/2010 |
| WO | WO-2010075579 A2 | 7/2010 |
| WO | WO-2010075584 A1 | 7/2010 |
| WO | WO-2010083234 A1 | 7/2010 |
| WO | WO-2010118210 A1 | 10/2010 |
| WO | WO-2010120814 A1 | 10/2010 |
| WO | WO-2011017120 A1 | 2/2011 |
| WO | WO-2011088237 A1 | 7/2011 |
| WO | WO-2011088306 A1 | 7/2011 |
| WO | WO-2011088380 A1 | 7/2011 |
| WO | WO-2011116111 A1 | 9/2011 |
| WO | WO-2012054532 A1 | 4/2012 |
| WO | WO-2012064682 A1 | 5/2012 |
| WO | WO-2012135142 A1 | 10/2012 |
| WO | WO-2012135144 A2 | 10/2012 |
| WO | WO-2012135146 A2 | 10/2012 |
| WO | WO-2012154253 A1 | 11/2012 |
| WO | WO-2012161856 A1 | 11/2012 |
| WO | WO-2012174338 A2 | 12/2012 |
| WO | WO-2013012604 A1 | 1/2013 |
| WO | WO-2013059732 A1 | 4/2013 |
| WO | WO-2014106602 A1 | 7/2014 |
| WO | WO-2014160463 A1 | 10/2014 |
| WO | WO-2014160883 A1 | 10/2014 |
| WO | WO-2014186665 A2 | 11/2014 |
| WO | WO-2014186750 A2 | 11/2014 |
| WO | WO-2015010108 A1 | 1/2015 |
| WO | WO-2015035261 A1 | 3/2015 |
| WO | WO-2015168699 A1 | 11/2015 |
| WO | WO-2016149282 A1 | 9/2016 |
| WO | WO-2016186972 A1 | 11/2016 |
| WO | WO-2017077715 A1 | 5/2017 |
| WO | WO-2017106383 A1 | 6/2017 |
| WO | WO-2017161342 A1 | 9/2017 |
| WO | WO-2017196663 A1 | 11/2017 |
| WO | WO-2018081074 A1 | 5/2018 |
| WO | WO-2020056036 A1 | 3/2020 |
| WO | WO-2020112890 A1 | 6/2020 |
| WO | WO-2020232125 A1 | 11/2020 |

OTHER PUBLICATIONS

Aggarwal et al. The Role of TNF and its Family Members in Inflammation and Cancer: Lessons from Gene Deletion, CLUT. Drug Targets Inflamm. Allergy, 1(4):327-341, 2002.

Ahmad et al., Clinical relevance of advances in genetics and pharmacogenetics of IBD. Gastroenterology, 126:1533-1549, 2004.

Ahn et al., The First Korean Genome Sequence and Analysis: Full Genome Sequencing for a Socio-Ethnic Group, Genome Res., 2009, vol. 19, pp. 1622-1629.

Aiba et al., The role of TL1A and DR3 in autoimmune and inflammatory diseases. Mediators Inflamm. 2013:#258164, 9 pages.

Al-Iazikani et al., Standard conformations for the canonical structures of immunoglobulins. J. Molec. Biol. 273:927-948, 1997.

Alvarez-Lobos et al., Crohn's Disease patients carrying Nod2/CARD15 gene variants have an increased and early need for first surgery due to stricturing disease and higher rate of surgical recurrence. Ann Surg, 242:693-700, 2005.

Andus et al., Measurement of TNFalpha mRNA in lamina propia lymphocytes (LPL) isolated from mucosal biopsies by quantitative polymerase chain reaction (PCR). Cytokines and cytokine receptor in mucosal immunity Abstract# 2742 p. A1409 (1992).

Annese et al., Variants of CARD15 are Associated with an Aggressive Clinical Course of Crohn's Disease—An IG-IBD Study, American Journal of Gastroenterology, 2005, vol. 100, pp. 84-92.

Australia Patent Application No. 13576/1997 Office Action dated Jul. 7, 1999.

Australia Patent Application No. 13576/1997 Office Action dated Jul. 20, 2000.

Australia Patent Application No. 13576/1997 Office Action dated Sep. 7, 2000.

Australia Patent Application No. 2005314089 Office Action dated Jul. 8, 2010.

Australia Patent Application No. 2638495 Office Action dated Sep. 19, 1997.

Australian Patent Application No. 2014241162 Office Action dated Apr. 16, 2018.

Ausubel, F. M et al., Current protocols in Molecular Biology. Wiley Interscience, New York, 1987 1989. Book not included.

Babbage, A., Human DNA Sequence from Clone RP11-428F18 on Chromosome 9, Complete Sequence, GenBank: AL390240, Dec. 13, 2012, pp. 1-31.

Badger et al., Idoxifene, a novel selective estrogen receptor modulator is effective in a rat model of adjuvant-induced arthritis. J Pharmacology and Experimental Therapeutics vol. 291 pp. 1380-1386 1999.

Bamias et al., Proinflammatory Effects of Th2 Cytokines in a Murine Model of Chronic Small Intestinal Inflammation, Gastroenterol, 128:654-666, 2005.

Bamias et al., Role of TL1A and its Receptor DR3 in Two Models of Chronic Murine Ileitis, PNAS, 103(22):8441-8446, 2006.

Barrett et al., Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.

Barrett et al., Genome-wide association defines more than 30 distinct susceptibility loci for Crohn's disease. Nature Genetics, 40:955-962, 2008.

Barrett et al., In Vivo constitutive expression of an IBD associated gene TNFSF15 causes severe inflammation and induces fibrostenotic disease in 2 marine models of chronic colitis. Gastroenterology, 140(5):Supplement 1, S-151, Abstract 925, 2011.

Bauer et al., A genetic enrichment for mutations constructed by oligodeoxynucleotide-directed mutagenesis. Gene, 37:73-81, 1985.

(56) References Cited

OTHER PUBLICATIONS

Bird et al.: Single-chain antigen-binding proteins; Science, 242:423-42, 1988.
Bomprezzi et al., Gene Expression Profile in Multiple Sclerosis Patients and Healthy Controls: Identifying Pathways Relevant to Disease, Human Molecular Genetics, 12(17):2191-2199, 2003.
Bossuyt et al., Serologic markers in inflammatory bowel disease. Clinical Chemistry, 52(2):171-181, 2006.
Braasch et al., Novel Antisense and Peptide Nucleic Acid Strategies for Controlling Gene Expression, Biochemistry, 41(14):4503-4509, 2002.
Brambs et al., Inflammatory Bowel Disease: Radiographical diagnostics, (reprints available at the Department of Radiography, Albert Ludwigs University Hospital, Freiburg, Federal Republic of Germany 3-49 (2009).
Brand, Crohn's Disease: Th1, Th17 or both? The Change of a Paradigm: New Immunological and Genetic Insights implicate Th17 Cells in the Pathogenesis of Crohn's Disease, GUT, 58(8):1152-1167, 2009.
Braun et al., Chapter 13: Multiparameter analysis of immunogenetic mechanisms in clinical diagnosis and management of inflammatory bowel disease. Immune mechanisms in inflammatory bowel disease edited by Richard S. Blumberg and Markus F. Neurath Mar. 10, 2006, Springer first edition: pp. 209-218.
Brennan et al. Preparation of bispecific antibodies by chemical recombination of monoclonal immunoglobulin G$_{1}$ fragments. Science 229:81-83, 1985.
Brinar et al., P217—Genetic Variants in Autophagy Related Genes and Granuloma Formation in Patients with Crohn's Disease, Journal of Crohn's and Colitis, 2009, vol. 3(1), p. S96.
Brummell et al. Probing the combining site of an anti-carbohydrate antibody by saturation-mutagenesis: Role of the heavy-chain CDR3 residues. Biochem. 32: 1180-1187, 1993.
Bull et al., The death receptor 3-TNF-like protein 1A pathway drives adverse bone pathology in inflammatory arthritis. J.Exp. Med., 205(11):2457-2464, 2008.
Burks et al., In vitro scanning saturation mutagenesis of an antibody binding pocket. Proc. Natl. Acad. Sci. USA 94:412-417, 1997.
Burstein et al., Atrial fibrosis: mechanisms and clinical relevance in atrial fibrillation. J. Am. College Cardiol., 51(8), 8 pages, 2008.
Canadian Patent Application No. 2830365 first substantive Examiner's Report dated Feb. 8, 2018.
Canadian Patent Application No. 2,183,147 Office Action dated Apr. 1, 2005.
Canadian Patent Application No. 2,183,147 Office Action dated Mar. 20, 2006.
Canadian Patent Application No. 2,183,147 Office Action dated Jun. 20, 2007.
Canadian Patent Application No. 2,589,746 Office Action dated Aug. 3, 2010.
Canadian Patent Application No. 2,589,746 Office Action dated May 9, 2011.
Cardullo, et al. Detection of nucleic acid hybridization by nonradiative fluorescence resonance energy transfer. Proc Natl Acad Sci USA. Dec. 1988;85(23):8790-4.
CBI SNP ID rs11209063, 2006, retrieved from: http://www.ncbi.nlm.nih.gov/projects/SNP/snp_ref.cgi?rs=11209063 (3 pgs.).
CBI SNP ID rs12495640, 2006, retrieved from: http://www.ncbi.nlm.nih.gov/projects/SNP/snp_ref.cgi?rs=12495640 (3 pgs.).
CBI SNP ID rs1495964, 2006, retrieved from: http://www.ncbi.nlm.nih.gov/projects/SNP/snp_ref.cgi?rs=1495964 (3 pgs.).
CBI SNP ID rs1908632, 2006, retrieved from: http://www.ncbi.nlm.nih.gov/projects/SNP/snp_ref.cgi?rs=1908632 (3 pgs.).
CBI SNP ID rs6788981,2006, retrieved from: http://www.ncbi.nlm.nih.gov/projects/SNP/snp_ref.cgi?rs-6788981 (3 pgs.).
CBI SNP ID rs7374667, 2006, retrieved from: http://www.ncbi.nlm.nih.gov/projects/SNP/snp_ref.cgi?rs=7374667 (4 pgs).
Chen et al., Discordant protein and mRNA expression in lung adenocarcinomas. Mol. Cell. Proteomics, 4:304-313, 2002.
Chen et al. Screening for genes associated with cardiac fibrosis induced by aldosterone. Xi Bao Yu Fen Zi Mian Yi Xue Za Zhi Journal of Cellular and Molecular Immuno 28(4):350-353 (English Abstract).
Chevillard et al. Two new polymorphisms in the human interferon gamma promoter. Eur J Immunogenetics vol. 29 pp. 52-56 2002.
Cippitelli et al. Retinoic acid-induced transcriptional modulation of the human interferon gamma promoter. J Biol Chemistry vol. 271 p. 26783-26793 1996.
Clarke et al. An anti-TL1A antibody for the treatment of asthma and inflammatory bowel disease. MAbs 10(4):664-677 (2018).
Clunie et al., Relevance of Thiopurine Methyltransferase Status in Rheumatology Patients Receiving Azathioprine, Rheumatology, 2004, vol. 41(1), pp. 13-18.
Cooper et al., Systematic Assessment of Copy Number Variant Detection Via Genome-Wide SNP Genotyping, Nature Genetics, 2008, vol. 40, pp. 1199-1203.
Craik, Charles. Use of oligonucleotides for site-specific mutagenesis. BioTechniques 1985 :12-19, 1985.
dbSNP Short Genetic Variations. Reference SNP(refSNP) Cluster Report: rs4855535. Printed Sep. 10, 2013, 5 pages, www.ncbi.nlm.nih.gov.
dbSNP, Short Genetic Variations, Submitted SNP(ss) Details: ss70756257,, Apr. 27, 2007, 1 page. https://www.ncbi.nlm.nih.gov.
De Domenico et al., The Molecular Basis of Ferroportin Linked Hemochromatosis, Proc Natl Acad Sci USA, 2005, vol. 102(25), pp. 8955-8960.
Diaz-Gallo et al. Differential association of two PTPN22 coding variants with Crohn's disease and ulcerative colitis. Inflammatory Bowel Diseases, vol. 17, No. 11, pp. 2287-2294, 2011.
Drach et al., Interphase Fluorescence in Situ Hybridization Identifies Chromosomal Abnormalities in Plasma Cells from Patients with Monoclonal Gammopathy of Undetermined Significance, Blood, 1995, vol. 86, pp. 3915-3921.
Dubinsky et al., Synergism of NOD2 and ASCA (Anti-Saccharomyces Cerevisiae Antibodies) Contributes to Disease Behavior in Pediatric Crohn's Disease (CD) Patients, Gastroenterology, 2003, vol. 124, pages M1556.
Duerr et al., A Genome-wide association study identifies IL23R as an inflammatory bowel disease gene. Science, 314:1461-1463, 2006.
Elgert, K., Immunology: Understanding the immune system. Wiley-Liss: New York, 1996, p. 323.
European Patent Application No. 05853294 12762965.7 Extended European Search Report dated Mar. 24, 2015.
European Patent Application No. 05853294 12764214.8 Extended European Search Report dated Nov. 18, 2014.
European Patent Application No. 12765854 Extended European Search Report dated Mar. 18, 2015.
European Patent Application No. 12765854.0 Partial Supplementary Search Report dated Nov. 24, 2014.
European Patent Application No. 12762965.7 Partial Supplementary Search Report dated Nov. 26, 2014.
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
European Patent Application No. 05853294 Further Examination Report dated Apr. 30, 2009.
European Patent Application No. 95921264.8 Communication dated Feb. 29, 2000.
European Patent Application No. 95921264.8 Communication dated Feb. 24, 1999.
European Patent Application No. 05853294 European Search Report dated Apr. 29, 2008.
European Patent Application No. 05853294 Office Action dated May 15, 2008.
European Patent Application No. 06772657 ESR dated Dec. 2, 2008.
European Patent Application No. 10171757 European Search Report dated Nov. 10, 2010.
European Patent Application No. 14773989 Extended European Search Report dated Dec. 19, 2016, 10 pages.

(56) References Cited

OTHER PUBLICATIONS

European Patent Application No. 14773989.0 Communication dated Nov. 17, 2017.
European Patent Application No. 14773989.0 Office Action dated Aug. 10, 2018.
European Patent Application No. 14797214 Extended European Search Report dated Feb. 3, 2017, 15 pages.
European Patent Application No. 14797214 Partial European Search Report dated Oct. 28, 2016, 9 pages.
European Patent Application No. 14797214.5 Office Action dated Apr. 19, 2018.
European Patent Application No. 14798650 Extended European Search Report dated Oct. 21, 2016, 12 pages.
European Patent Application No. 14798650.9 Communication dated Jan. 10, 2018.
European Patent Application No. 14826746 Extended European Search Report dated Feb. 1, 2017, 12 pages.
European Patent Application No. 14826746.1 Communication dated Dec. 8, 2017.
European Patent Application No. 14826746.1 Examination Report dated Mar. 13, 2019.
European Patent Application No. 14842590 Extended European Search Report dated Apr. 4, 2017, 10 pages.
European Patent Application No. 14842590 Partial European Search Report dated Jan. 18, 2017, 7 pages.
Fang et al., Essential role of TNF receptor superfamily 25 (TNFRS25) in the development of allergic lung inflammation. J.Exp. Med., 205(5):1037-1048, 2008.
Fawcett et al., Molecular cloning of ICAM-3, a third ligand for LFA-1, constitutively expressed on resting leukocytes. Nature 360:481-4. (1992).
Ferguson et al., IL23R and IL12B SNPs and haplotypes strongly associate with Crohn's disease risk in a New Zealand population. Gastroenterology Research and Practice, 2010:12 pages, 2010.
Fessler et al., A genomic and proteomic analysis of activation of the human neutrophil by Lipopolysaccharide and its mediation by p38 mitogen-activated protein kinase. The Journal of Biological Chemistry, 277(35):31291-31302, 2002.
Fitzpatrick, LR, Novel Pharmacological Approaches for Inflammatory Bowel Disease: Targeting Key Intracellular Pathways and the IL-23/IL-17 Axis, International Journal of Inflammation, vol. 2012, pp. 1-8.
Forcione et al., Anti-Saccharomyces cerevisiae antibody (ASCA) positivity is associated with increased risk for early surgery in Crohn's disease. GUT, 53:1117-1122, 2004.
Franke et al., Genome-Wide Meta-Analysis Increases to 71 the Number of Confirmed Crohn's Disease Susceptibility Loci, Nature Genetics, 2010, vol. 42(12), pp. 1118-1125.
Garcia-Bates et al., GeneBank NM_001198.3, *Homo sapiens* PR Domain Containing 1, with ZNF Domain (PRDM1), Transcript Variant 1, mRNA, 2010 retrieved from: http://www.ncbi.nlm.nih.gov/nuccore/172072683? sat=13&satkey=10378402 on Jul. 7, 2011.
GenBank Accession No. AF134726 (72 pgs.) (Mar. 27, 1999).
GenBank Accession No. AC007728 (31 pgs.) (Jun. 1, 2001).
GenBank Accession No. AF129756.1 (70 pgs.) (revised Nov. 12, 1999).
GenBank Accession No. AF385089 (3 pgs.) (Jul. 4, 2001).
GenBank Accession No. AF513860 (12 pgs.) Jul. 9, 2002).
GenBank Accession No. AX259776 (21 pgs.) (Oct. 26, 2001).
GenBank Accession No. NM022162 (5 pgs.) (Sep. 11, 2011).
GenBank Accession No. U89335 (25 pgs.) (Oct. 22, 1999).
GenBank Accession No. U89336 (27 pgs.) (Feb. 14, 1997).
GenBank AF252829.4 (49 pgs.) (Nov. 8, 2002).
Gene Card for 1L12B(p40) (http://www.genecards.org/cgi-bin/carddisp.pl?gene=1L12B&keywords=i112b) accessed May 8, 2017.
Gene Card for IL17RD retrieved from: http://www.genecards.org/cgi-bin/carddisp.pl?gene=1L17RD&dearch=i117rd (Accessed May 2013).
GeneBank Accession No. AF450133 (10 pgs.) (Dec. 27, 2001).
GeneCard NOD2 gene (16 pgs) (Last update Jul. 2, 2009).
Genecards, BRWD1 Gene-GeneCards | BRWD1 Protein | BRWD1 Antibody. Printed Sep. 10, 2013, 11 pages, www.genecards.org.
Gianfrancesco et al., Identification of a Novel Gene and a Common Variant Associated with Uric Acid Nephrolithiasis in a Sardinian Genetic Isolate, Am. J. Hum. Genet., 2003, vol. 72, pp. 1479-1491.
Gonsky et al., Distinct Methylation of IFNG in the Gut, Journal of Interferon and Cytokine Research, 2009, vol. 29(7), pp. 407-414.
Gout et al., Death receptor-3, a new e-selectin counter-receptor that confers migration and survival advantages to colon carcinoma cells by triggering p38 and ERK MAPK activation. Cancer Research, 66(18):9117-9124, 2006.
Haritunians et al., Genetic Predictors of Medically Refractory Ulcerative Colitis, Inflamm Bowel Dis., 2010, vol. 16 ;11), pp. 1830-1840.
Hirano et al., Association Study of 71 European Crohn's Disease Susceptibility Loci in a Japanese Population, Inflammatory Bowel Diseases, 19(3):526-533, 2013.
Hirschhorn et al., A Comprehensive Review of Genetic Association Studies, Genetics In Medicine, 2002, vol. 4(2) pp. 45-61.
Hodgson, John. Making monoclonals in microbes. Bio/Technology 9:421-425, 1991.
Hoh et al., Trimming, Weighting and Grouping SNPs in Human Case-Control Association Studies, Genome Research, 2001, vol. 1, pp. 2115-2119.
Holliger and Hudson. Engineered antibody fragments and the rise of single domains. Nat. Biotechnol. 23(9):1126-36, 2005.
Honkanen et al., Coxsackievirus up-regulates IL-17 immunity in human type 1 diabetes. Diabetologia, 54:Supp. 1, S1, Abstract S421, 2009.
Hornquist et al., G(alpha) 1 2-Deficient Mice with Colitis Exhibit a Local Increase in Memory CD4+ T Cells and Promflammatmy TH1-Type Cytokines, J Immunol, 158:1068-1077, 1997.
Houdebine et al., Production of Pharmaceutical Proteins from Transgenic Animals, J Biotech, 34 (1994): 269-287.
Hsu et al., Attenuation of TH1 Response in Decoy Receptor 3 Transgenic Mice, J. Immunol, 175:5135-5145, 2005.
Hsu et al. The tale of TL1A in inflammation. Mucosal Immunol 4(4):368-370, 2011.
Huse et al. Generation of a large combinatorial library of the immunoglobulin repertoire in phage lambda. Science 246:1275-1281, 1989.
Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.
Ilumina Press Release dated Jan. 12, 2006, retrieved from: http://investor.illumina.com/phoenix.zhtml? =121278<p=irol-newsArticle&ID=8033958thighlight=.
Ioannidis, J., Why Most Published Research Findings are False, PLoS Med, 2005, vol. 2(8):e124, pp. 0696-0701.
Israeli et al., Anti-Saccharomyces Cerevisiaeand Antineutrophil Cytoplasmic Antibodies as Predictors of Inflammatory Bowel Disease, Gut, 2005, vol. 54(9), pp. 1232-1236.
Japanese Patent Application No. 2016-505570 Office Action dated Oct. 24, 2018.
Japanese Patent Application No. 2016-514143 Notice of Allowance dated Jan. 30, 2019.
Japanese Patent Application No. 2016-514143 Office Action dated Oct. 23, 2018.
Jones et al. Replacing the complementarity-determining regions in a human antibody with those from a mouse. Nature 321:522-525, 1986.
Jung et al., Genotype/Phenotype analyses for 53 Crohn's disease associated genetic polymorphisms. PLOS/One, 7(12):e52223, 2012.
Juppner, H. Functional properties of the PTH/PTHrP receptor. Bone, 17(2):39S-42S, 1995.
Kakuta et al., Su1746 Rare Variants of TNFSF15 Are Significantly Associated With Crohn's Disease in Non-Jewish Caucasian Independent of the Known Common Susceptibility SNPs, Gastroenterology, 144(5): S-466, 2013.
Karpuzoglu-Sahin et al., Interferon-gamma levels are upregulated by 17-beta-estradiol and diethylstibestrol. J Reproductive Immunology 52:113-127 (2001).

(56) References Cited

OTHER PUBLICATIONS

Kasperkovitz et al., Activation of the STAT1 Pathway in Rheumatoid Arthritis, Ann Rheum Dis, . 63:233-239, 2004.
Kasvosve et al., Effect of Ferroportin Q248H Polymorphism on Iron Status in African Children, Am J Clin Nutr, 2005, vol. 82(5), pp. 1102-1106.
Kim et al. Effects of IL-9 blockade on chronic airway inflammation of murine asthma models. Allergy: Eur J Allergy Clin Immunol Suppl 96(67):448, Nov. 2012.
Kim et al. Effects of interleukin-9 blockade on chronic airway inflammation in murine asthma models. Allergy Asthma Immunol Res 5(4):197-206, 2013.
Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.
Kobayashi et al. Tryptophan H33 plays an important role in pyrimidine (6-4) pyrimidone photoproduct binding by a high-affinity antibody. Protein Eng. 12(10):879-884, 1999.
Koga et al., Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.
Kohler and Milstein, Derivation of specific antibody-producing tissue culture and tumor lines by cell fusion. Eur. J. Immunol. 6: 511-519, 1976.
Kuntz et al., Inflammatory Bowel Disease: endoscopic diagnostics. (Reprints available at the Department of Gastroenterology and Hepatology "Bergmannshell" Hospital, University of Bochum, Federal Republic of Germany pp. 3-38 (2009).
Lal et al., Antibiotic Therapy for Crohn's Disease: A Review, Canadian Journal of Gastroenterology, 2006, vol. 20(10), pp. 651-655.
Landegren et al. A Ligase-Mediated Gene Detection Technique. Science 241:1077-1080 (1988).
Lawrance et al., Ulcerative Colitis and Crohn's Disease: Distinctive Gene Expression Profiles and Novel Susceptibility Candidate Genes, Human Molecular Genetics, 10(5):pp. 445-456, 2001.
Leppkes et al., RORy-expressing Th17 cells induce murine chronic intestinal inflammation via redundant effects of IL-17A and IL-17F. Gastroenterology, 136:257-267, 2009.
Levy-Coffman, Ellen, A Mosiac of People: The Jewish Story and a Reassessment of the DNA Evidence, Journal of Genetic Genealogy, 1:12-33, 2005.
Li et al. TNFRSF1B Is Associated with ANCA in IBD. Inflammatory Bowel Diseases. 22(6):1346-1352 (2016).
Lipsky, P. Structure, function and regulation of molecules involved in leukocyte adhesion. New York: Springer-Verlag 1993 Book not included.
Lorenz-Meyer. Inflammatory Bowel Disease Laboratory Diagnostics. (Reprints available from the City Hospital, Friedrichshafen, Federal Republic of Germany):3-29 (2008).
Low et al., High-Throughout Genomic Technology in Research and Clinical Management of Breast Cancer, Evolving Landscape of Genetic Epidemiological Studies, Breast Cancer Research, 8(3):209-214, 2006.
Lucentini, J. Gene association studies typically wrong. Scientist, 18(24):20, 2004.
Maggio-Price et al., Helicobacter Infection is Required for Inflammation and Colon Cancer in Smad3-Deficient Mice, Cancer Research, 2006, vol. 66, pp. 828-838.
Maniatis, et al. Molecular Cloning. Cold Spring Harbor Laboratory, 1982.
Marrakchi et al., Interleukin 10 promoter region polymorphisms in inflammatory bowel disease in Tunisian population. Inflamm. Res., 58:155-160, 2009.
Martinez et al., Regulation and Function of Proinflammatory TH17 Cells, Animals of the New York Academy of Sciences, 1143(1):188-211, 2008.
Medrano et al. Role of TNFRSF1B polymorphisms in the response of Crohn's disease patients to infliximab. Human Immunology 75(1):71-75 (2014).
Meylan et al., The TNF-family cytokine TL1A drives IL-13 dependent small intestinal inflammation. Muscosal Immunol., 4(2):172-185, 2011.
Migone et al., TL1A is a TNF-like Ligand for DR3 and TR6/DcR3 and Functions as a T cell Costimulator, Immunity, 16:479-492, 2002.
Morimoto et al. Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24:107-117, 1993.
Morinaga et al., Database Uniprot (online), Mar. 8, 2011, Database Accession No. P02771.
Morinaga et al., Primary structures of human a-fetoprotein and its mRNA. PNAS, 80:4604-4608, 1983.
Mullins et al., Perspective Series: Molecular Medicine in Genetically Engineered Animals, J Clin Invest, 97:1557-1560, 1996.
Mummidi et al., Evolution of human and non-human primate CC chemokine receptor 5 gene and mRNA. Journal of Biological Chemistry, 275(5):18946-18961 (2000).
Mundwiler et al., Inflammatory Bowel Disease Serologies in Ankylosing Spondylitis Patients: A Pilot Study, Arthritis Research and Therapy, 2009, vol. 11(6), pp. 2-8.
Naundorf et at, IL-10 Interferes Directly with TCR-Induced IFN-[gamma] but not IL-17 Production in Memory T cells, European Journal of Immunology, 39(4):1066-1077, 2009.
Franke et al.: Genome-wide meta-analysis increases to 71 the number of confirmed Crohn's disease susceptibility loci; Nature Genetics; vol. 42, No. 12, nine pages (2010).
Funke et al.: Functional characterisation of decoy receptors in Crohn's disease; Gut 58(40): 483-491 (2009).
Goswami et al.: A Brief History of IL-9; The Journal of Immunology; 186; 3283-3288 (2019).
Takedatsu et al.: TL1A (TNFSF15) Regulates the Development of Chronic Colitis By Modulating both T helper (TH) 1 and TH17 Activation; Gastroenterology; HHS Public Access; 135(2): 552-567 (2009).
Tong Ren Tang Health Center Editorial Board: Fruity Health Care Dictionary; 5 pages (Jan. 31, 2013).
NCBI Accession No. NM_001198.3 (5 pgs.) (Mar. 4, 2010).
NCBI Blast sequence search for SEQ ID No. 7; retrieved from: https://blast.ncbi.nlm.nih.gov/Blast.cgi on Sep. 12, 2018 (3 pgs.).
NCBI Gene Database, Gene ID: 133396, IL31RA interleukin 31 receptor A [*Homo sapiens* (human)}, [Retrieved online Aug. 31, 2018] Retrieved from https://www.ncbi.nlnnih.gov/gene/133396#gene-expression., Aug. 5, 2018 (16 pgs).
NCBI Gene Database, Gene ID: 3458, IFNG interferon gamma [*Homo sapiens* (human)}, [Retrieved online Aug. 31, 2018] Retrieved from< url:<a href="https://www.ncbi.nlnnih.gov/gene/3458#gene-expression">> https://www.ncbi.nlnnih.gov/gene/3458#gene-expression., Aug. 25, 2018 (16 pgs).</url:<a>.
NCBI Reference SNP Cluster Report ID rs2241880; Retrieved from: http://www.ncbi.nlm.nih.gov/projects/SNP/snp_ref. . 1gi?rs=2241880 on Sep. 23, 2016; 5 pages.
"NCBI Reference SNP Cluster Report ID rs2836878; Retrieve from: http://www.ncbi.nlm.nih.gov/projects/SNP/snp_ref. . 1gi?rs=2836878 on Sep. 23, 2016; 3 pages.".
NCBI Reference SNP Cluster Report ID rs3764147; Retrieved from: http://www.ncbi.nlm.nih.gov/projects/SNP/snp_ref. . 1gi?rs=3764147 on Sep. 23, 2016; 4 pages.
NCBI Reference SNP Cluster Report ID rs762421; Retrieved from: http://www.ncbi.nlm.nih.gov/projects/SNP/snp_ref. .1gi?rs=762421 on Sep. 23, 2016; 4 pages.
NCBI Reference SNP Cluster Report ID rs9271568; Retrieved from: http://www.ncbi.nlm.nih.gov/projects/SNP/snp_ref. .1gi?rs=9271568 on Sep. 23, 2016; 3 pages.
NCBI SNP 10 rs12638201 (1 pg.) (Jan. 31, 2001).
NCBI SNP 10 rs2066844 (1 pg.) (created May 2, 1997).
NCBI SNP 10 rs2066845 (1 pg.) (created May 2, 1997).
NCBI SNP 10 rs2302600 (1 pg.) (Feb. 15, 1996).

(56) References Cited

OTHER PUBLICATIONS

NCBI SNP 10 rs746503 (1 pg.) (Dec. 7, 2000).
NCBI SNP 10 rs7613548 (1 pg.) (created Apr. 19, 2000).
NCBI SNP ID rs11209063.
NCBI SNP ID rs12495640.
NCBI SNP ID rs2066847 (1 pg.) (created May 2, 1997).
Pallone et al., Genetic and Pathogenetic Insights into Inflammatory Bowel Disease, Current Gastroenterology Reports, 2003, vol. 5, pp. 487-492.
Papadakis et al., IL1A synergizes with IL-12 and IL-18 to enhance IFN-y production in human T cells and NK cells, The Journal of Immunology, 172:7002-7007, 2004.
Parente et al., Bowel Ultrasound in Assessment of Crohn's Disease and Detection of Related Small Bowel Strictures: A Prospective Comparative Study Versus X Ray and Intraoperative Findings, Gut, 50: 490-495, 2002.
PCT/2011/028694 International Preliminary Report on Patentability dated Sep. 18, 2012.
PCT/2011/028694 International Search Report and Written Opinion dated Jul. 27, 2011.
PCT/2012/030614 International Search Report and Written Opinion dated Sep. 28, 2012.
PCT/US2005/018161 International Preliminary Report on Patentability dated Apr. 15, 2009.
PCT/US2006/22427 International Search Report dated Sep. 5, 2006 EP Application 2006772657.
PCT/US2008/055020 International Preliminary Report on Patentability dated Aug. 26, 2009.
PCT/US2008/055020 International Search Report dated Aug. 14, 2008.
PCT/US2008/055020 Written Opinion dated Aug. 14, 2008.
PCT/US2008/055236 International Preliminary Examination Report dated Sep. 1, 2009.
PCT/US2008/055236 International Search Report and Written Opinion dated Nov. 14, 2008.
PCT/US2008/057820 Written Opinion dated Sep. 11, 2008.
PCT/US2008/062531 International Preliminary Report on Patentability dated Nov. 10, 2009.
PCT/US2008/062531 International Search Report and Written Opinion dated Nov. 18, 2008.
PCT/US2008/080526 International Search Report and Written Opinion dated Mar. 25, 2009, 11 pages.
PCT/US2009/044720 International Preliminary Report on Patentability dated Nov. 23, 2010.
PCT/US2009/048319 International Preliminary Report on Patentability dated Jan. 5, 2011.
PCT/US2009/048319 International Search Report and Written Opinion dated Nov. 6, 2009.
PCT/US2009/059190 International Search Report and Written Opinion dated Mar. 16, 2010.
PCT/US2009/061698 Written Opinion dated Mar. 16, 2010.
PCT/US2009/065928 International Preliminary Report on Patentability dated May 31, 2011.
"PCT/US2009/065928 International Search Report dated Aug. 3, 2010".
PCT/US2009/065928 Written Opinion dated Aug. 3, 2010.
PCT/US2009/069531 International Search Report and Written Opinion dated Aug. 4, 2010, 11 pages.
PCT/US2009/069534 International Search Report dated Mar. 4, 2010.
PCT/US2009/069541 International Search Report dated Mar. 4, 2010.
PCT/US2010/020921 International Reporton Patentability dated Jul. 19, 2011.
PCT/US2010/020921 International Search Report and Written Opinion dated May 5, 2010.
PCT/US2010/030359 International Preliminary Report on Patentability dated Oct. 11, 2011.
PCT/US2010/030359 International Search Report dated Aug. 11, 2010.
PCT/US2010/030359 Written Opinion dated Aug. 11, 2010.
PCT/US2011/021180 International Preliminary Report on Patentability dated Jun. 15, 2011.
PCT/US2011/021180 International Search Report and Written Opinion dated Jun. 15, 2011.
PCT/US2011/021382 International Preliminary Report on Patentability dated Jul. 17, 2012.
PCT/US2012/030611 International Preliminary Report on Patentability dated Oct. 1, 2013.
PCT/US2012/030611 International Search Report dated Sep. 7, 2012.
PCT/US2012/030611 Written Opinion dated Sep. 7, 2012.
PCT/US2012/030616 International Preliminary Report on Patentability dated Nov. 19, 2013.
PCT/US2012/030616 International Search Report and Written Opinion dated Sep. 17, 2012.
PCT/US2014/032054 International Preliminary Report on Patentability dated Sep. 29, 2015, 12 pages.
PCT/US2014/032054 International Search Report and Written Opinion dated Aug. 5, 2014, 14 pages.
PCT/US2014/038333 International Preliminary Report on Patentability dated Nov. 17, 2015.
PCT/US2014/038468 International Preliminary Report on Patentability dated Nov. 17, 2015, 7 pages.
PCT/US2014/038468 International Search Report and Written Opinion dated Nov. 18, 2014, 11 pages.
PCT/US2014/047326 International Preliminary Report on Patentability dated Jan. 19, 2016, 7 pages.
PCT/US2014/047326 International Search Report and Written Opinion dated Dec. 22, 2014, 9 pages.
PCT/US2014/054425 International Search Report and Written Opinion dated Dec. 31, 2014, 12 pages.
PCT/US2016/022494 International Search Report and Written Opinion dated Jun. 3, 2016.
PCT/US2016/032180 International Preliminary Report on Patentability dated Nov. 30, 2017.
PCT/US2016/032180 International Search Report and Written Opinion dated Aug. 19, 2016, 8 pages.
PCT/US2017/058019 International Search Report and Written Opinion dated Feb. 15, 2018.
PCT/US2018/028397 International Search Report and Written Opinion dated Jul. 9, 2018.
Peltekova et al., Functional variants of OCTN cation transporter genes are associated with Crohn disease. Nature Genetics, 16(5):471-475, 2004.
Pennisi, E. A Closer look at SNPs suggests difficulties. Science, 281(5384):1787-1789, 1998.
Pericak-Vance et al., Approaches to gene mapping in complex human diseases. Wiley-Liss New York 1998.
Perkin Elmer Catalog 1992, p. 12.
Picornell et al., TNFSF15 is an ethnic specific IBD gene. Inflamm. Bowel Disease, 13(11):1333-1338, 2007.
Pierik et al. Tumour Necrosis Factor—a Receptor 1 and 2 Polymorphisms in Inflammatory Bowel Disease and their Association with Response to Infliximab. Alimentary Pharmacology & Therapeutics 20(3):303-310 (2004).
Pinchuk et al., Human Colonic Myofibroblast Promote Expansion of CD4+ CD25high Foxp3+ Regulatory T Cells, Gastroenterology, 140(7):2019-2030, pp. 1-19, and p. 8, 2011.
Prideaux et al., Inflammatory Bowel Disease in Asia: A Systematic Review, Journal of Gastroenterology and -lepatology, 27(8):1266-1280, 2012.
Queen et al. A humanized antibody that binds to the interleukin 2 receptor. Proc. Natl. Acad Sci USA 86:10029-10032, 1989.
Raychaudhuri et al., Genetic Variants at CD28, PRDM1 and CD2/CD58 are Associated with Rheumatoid Arthritis Risk, Nature Genetics, 2009, vol. 41(12), pp. 1313-1318, and online methods.
R&D datasheet for human/mouse TL1A/TNFSF15 antibody, catalog No. MAB7441; clone #293327 (Feb. 7, 2018).
Reference SNP Cluster report for rs2986754 retrieved from: http://www.ncbi.nlm.nih.gov/projects/SNP/snp_ref.cgi?rs=2986754 on Sep. 13, 2016; 3 pages.

(56) References Cited

OTHER PUBLICATIONS

Reference SNP Cluster report for rs746503 retrieved from: http://www.ncbi.nlm.nih.gov/projects/SNP/snp_ref.cgi?rs+746503 on Sep. 15, 2016; 4 pages.
Reichwald et al. TL1A induces TCR independent IL-6 and TNF-alpha production and growth of PLZF leukocytes. PLOS ONE 9(1):e85793, 2013.
Richard et al. The TNF-family cytokine TL1A: from lymphocyte costimulator to disease coconspirator. J Leukocyte Biol 98:333-345 2015.
Riechmann et al. Reshaping human antibodies for therapy. Nature, 332.6162 (1988): 323-7.
Rieder et al., Intestinal Fibrosis in Inflammatory Bowel Disease-Current Knowledge and Future Perspectives, J.Crohns Colitis, 2:279-290, 2008.
Rioux et al., Genetic variation in the 5q31 cytokine gene cluster confers susceptibility to Crohn disease. Nature Genetics, 29(2):223-228, 2001.
Rothe et al., The human combinatorial antibody library HuCAL GOLD combines diversification of all six CDRs according to the natural immune system with a novel display method for efficient selection of high-affinity antibodies. J. Mol. Bio. 376:1182-1200, 2008.
Roussomoustakaki et al., Genetic markers may predict disease behavior in patients with ulcerative colitis. Gastroenterology, 112:1845-1853, 1997.
Saruta et al., High frequency haplotypes in the X-chromosome locus TLR8 are associated with both CD and UC in females. Inflammatory Bowel Disease. 15(3):321-327 (2009).
Satsangi et al., Contribution of Genes of the Major Histocompatibility Complexto Susceptibility and Disease Phenotype in Inflammatory Bowel Disease, The Lancet, 347:1212-1217, 1996.
Scientists Discover New Gene Associated with Crohn's Disease. BusinessWire https://www.businesswire.com/news/home/20070124005277/en/Scientists-Discover-New-Gene-Crohns-Disease (Jan. 24, 2017).
Seidelin et al., Upregulation of cIAP2 in Regenerating Coloncytes in Ulcerative Colitis, Virchows Arch, 151:1031-1038, 2007.
Shih et al., Inhibition of a novel fibrogenic factor TI 1a reverses established colonic fibrosis. Mucosal Immunol., 7(6):1492-1503, 2014.
Shih et al., Reversal of murine colitis and fibrosis by neutralizing TL1A antibody: potential novel therapy to alter natural history of Crohn's disease. Gastrolenterol. 142(5):S84, Abstract 357, 2012.
Shih et al. Reversal of murine colitis and fibrosis by neutralizing TL1A antibody: potential novel therapy to alter natural history of Crohn's disease. Gastroenterol 142(5):S84, Abstract #357, 2012.
Shih et at, Constitutive TL1A (TNFSF15) Expression on Lymphoid or Myeloid Cells Leads to Mild Intestinal Inflammation and Fibrosis, PLOS One, 6(1), pp. 1-16, 2011.
Shih et at, Microbial Induction of Inflammatory Bowel Disease Associated Gene TL1A (TNFSF15) in Antigen Presenting Cells, Eur. J. Immunol., 39:3239-3250, 2009.
Sobrino et al., SNP's in Forensic Genetics: A Review on SNP Typing Methodologies, Forensic Science International, 154:181-194, 2005.
Abraham et al., Haplotypic polymorph isms of the TNFB gene. Immunogenetics 33:50-53 (1991).
Abreu et al., Mutations in NOD2 are associated with fibrostenosing disease in patients with Crohn's disease. Gastroenterology 123:679-688 (2002).
Adam et al., Immune response in cancer. Pharmacology & Therapeutics 99:113-132 (2003).
Adams et al., 3400 new expressed sequence tags identify diversity of transcripts in the human brain. Nature Genetics 4:256-267 (1993).
Ahmad et al. The molecular classification of the clinical manifestations of Crohn's disease. Gasterenterology 122:854-866 (2002).

Ajioka et al., Haplotype analysis of hemochromatosis: evaluation of linkage-disequilibrium approaches and evolution of disease chromosome. Am J Hum Genet 60:1439-1447 (1997).
Akolkar et al., The IBD1 locus for susceptibility to Crohn's disease has a greater impact on Ashkenazi Jews with early onset diabetes. Am J Gastroentrol 96:1127-1132 (2001).
Ames et al., Are vitamin and mineral deficiencies a major cancer risk? Nature 694-704 (2002).
An et al., A tumor necrosis factor a-inducible promoter variant of interferon-g accelerates C04+ T cell depletion in human immunodeficiency virus-1 infected individuals. J Infectious Diseases 188:228-213 (2003).
Ando et al. Triplet repeat polymorphism within the NOTCH4 gene located near the junction of the HLA class II and class III regions in narcolepsy. Tissue Antigens 50:646-649 (1997).
Andus et al., Measurement of TNFalpha mRNA in a small number of cells by quantitative polymerase chain reaction. (PCR) Regional Immunology 5:11-17 (1993).
Annese et al., Genetic analysis in Italian families with inflammatory bowel disease supports linkage to the IB01 locus—a GSIC study. Eur J Hum Genet 7:567-573 (1999).
Aron et al., Analysis of hsp70 gene polymorphism in allergic asthma Allergy 54:165-170 (1999).
Ballantyne et al., Short communication, assignment of the gene for intercellular adhesion molecule-1 (ICAM-1) to proximal mouse chromosome 9. Genomics 9:547-550 (1991).
Bamias et al. Circulating levels of TNF-like cytokine 1A (TL1A) and its decoy receptor 3 (DcR3) in rheumatoid arthritis. Clin Immunol 129:249-255, 2008.
Bao et al., Molecular mechanism for gender differences in susceptibility to T Cell mediated autoimmune diabetes in nonobese diabetic mice. J of Immunol 168:5269-5379 (2002).
Becker et al., Clustering of non-major histocompatibility complex susceptibility candidate loci in human autoimmune disease. PNAS USA 95:9979-9984 (1998).
Benoit et al., Presence of somatostatin-28-(1-12) in hypothalamus and pancreas. PNAS USA 79:917-921 (1982).
Beutler et al., Control of cachectin (tumor necrosis factor) synthesis: mechanisms of endotoxin resistance. Science 232:977-980 (1986).
Bioque et al., Further evidence for a genetic association of interleukin-1 receptor antagonist and ulcerative colitis in the Northern and Mediterranean population. Gastroenterology 108:a783 (1995) Abstract only.
Boirivant et al., Hypoproliferative human lamina propia T cells retain the capacity to secrete lymphokines when stimulated via CD2/CD28 pathways. Proceedings of the association of American physicians Abstract Only Proc Assoc Am Physicians 108:55-67 (1996).
Bourinbaiar et al., Pregnancy hormones, estrogen and progesteron prevent HIV-1 synthesis in monocytes but not in lymphocytes. FEBS Letters 302:206-208 (1992).
Brabin. Interactions of the female hormonal environment, susceptibility to viral infection and disease progression. A/OS Patient Care and STDs. 16:211-221 (2002).
Braegger et al., Tumor necrosis factor alpha in stool as a marker of intestinal inflammation. The Lancet 339:89-91 (1992).
Brant et al., American families with Crohn's disease have strong evidence for linkage to chromosomes 16 but not chromosome 12. Gastroentrol 115:1056-1061 (1998).
Bream et al., A single nucleotide polymorphism in the proximal IFN-gamma promoter alters control of gene transcription. Genes and Immunity 3:165-169 (2002).
Buning et al., Heterozygosity for IL23R, p.Arg318 Gin confers a protective effect not only against Crohn's disease but also ulcerative colitis. Aliment. Pharmacal Ther. 26:1025-1033 (2007).
Burks et al., GenBank Nucleic Acids Res (Suppl) 29:2065-2069 (1992).
Bush et al., Cancer chemoresistance: the relationship between p53 and multidrug transporters Int. J Cancer 98:323-330 (2002).
Calemine et al., Immunomodulation by diethylstillbestrol is dose and gender related: effects on thymocyte apoptosis and mitogen-induced proliferation. Toxicology 178:101-118 (2002).

(56) References Cited

OTHER PUBLICATIONS

Casini-Raggi et al., Mucosal imbalance of IL-1 and IL-1 receptor antagonist in inflammatory bowel disease. J Immunol 154:2434-2440 (1995).
Cavanaugh et al., Analysis of Australian Crohn's disease pedigrees refines the localization for susceptibility to inflammatory bowel disease on chromosome 16. Ann Hum Genet 62:291-298 (1998).
Cenci et al., Estrogen deficiency induces bone loss by increasing T cell proliferation and lifespan through IFN-gamma induced class II transactivator. PNAS USA 100:10405-10410 (2003).
Chaudhary et al., Prediction of response to infliximab in Crohn's disease. Digestive and Liver Disease 37:559-563 2005.
Chiaretti et al., Gene expression profile of adult T-cell acute lymphocytic leukemia identifies distinct subsets of patients with different responses to therapy and survival. Blood 103:2771-2778 (2004).
Chinese Patent Application No. 201480038133.6 Second Office Action dated Jan. 21, 2019.
Cho et al., Confirmation of a susceptibility locus for Crohn's disease on chromosome 16. Inflamm Bowel Dis. 3:186-190 (1997).
Cho et al., Identification of novel susceptibility loci for inflammatory bowel disease on chromosome 1p, 3q and 4q: evidence for epistasis between 1p and IBD1. PNAS USA 95:7502-7507 (1998).
Cippitelli et al., Vitamin D3: a transcriptional modulator of the interferon-gamma gene. Eur J Immunol Abstract Only 28:3017-3030 (1998).
Costello et al., Dissection of the inflammatory bowel disease transcriptome using genome wide cDNA microarrays. PloS Medicine 2:0771-0787 (2005).
Curran et al., Genetic analysis of inflammatory bowel disease in a large European cohort supports linkage to chromosome 12 and 16. Gastroenterology 115:1066-1071 (1998).
Cushman et al., Effects of estrogen and selective estrogen receptor modulators in hemostasis and inflammation: potential differences among drugs. Annals of New York Academy of Sciences Abstract Only 949:175-180 (2001).
Cushman et al., Tamoxifen and cardiac risk factors in healthy women—suggestion of an anti-inflammatory effect, arteriosclerosis, thrombosis and vascular biology. Arterioscler Thromb Vase Biol 21:251-266 (2001).
Cuzzocreaet al., 17 beta-estradiol anti-inflammatory activity in Carrageenan-induced pleurisy. Endocrinology 141:1455-1463 (2000).
Derrkx et al., Tumor-necrosis-factor antibody treatment in Crohn's disease. The Lancet 342:173-174 (1993).
Desilva et al., Pharmacogenetics of infliximab in Crohn's disease: the 5q31/IBD5 risk haplotype predict response. Gastroenterology 122:Abstract M1423 (2002).
Devlin et al., NOD2 variants and antibody response to microbial antigens in Crohn's disease patients and their unaffected relatives. Gastroenterology 132:576-586 (2007).
Devlin et al., NOD2 variants are significantly associated with sero-reactivity to microbial antigens in Crohn's disease. AGA Institute Digestive Disease Week, Abstract #442 Only (2006).
Devlin et al., The p631 H variant of the TLR2 gene associated with sera-reactivity to microbial antigens in Jewish patients with Crohn's disease. Abstract Only (2007) Journal unknown.
Diamond et al., Binding of the integrin Mac-1 (CD11 b/CD18) to the third immunoglobulin-like domain of ICAM01 (CD54) and its regulation by glycosylation. Cell 65:961-971 (1991).
Diamond et al., ICAM-1 (CD54): A counter receptor for Mac-1 (CD11b/CD18). J Cell Biol.111:3129-3139 (1990).
Dib et al., A comprehensive genetic map of the human based on 5,264 microsatellites. Nature 380:152-154 (1996).
Dubinsky et al., CARD8: A novel association with childhood onset ulcerative colitis (UC). AGA Institute Abstract# T1983 p. A-587 (2006).
Dubinsky et al., Familial expression of serological immune responses in pediatric IBD. J of Pediatric Gastroenterology and Nutrition Abstract #150 41:539 (2005).

Dubinsky et al., IL-23 receptor (IL-23R) gene protects against pediatric Crohn's disease. Inflamm Bowel Disease 13:511-515 (2007).
Dubinsky et al., Increased immune reactivity predicts aggressive complicating Crohn's disease in children. Abstract only (2007) Journal unknown.
Dubinsky et al., Serum immune responses predict rapid disease progression among children with Crohn's disease: immune responses predict disease progression. Am J. Gastroenterology 101:360-367 (2006).
Duerr et al., Association between ulcerative colitis and a polymorphism in intron 2 of the interleukin-2 receptor antagonist gene. Gastroenterology Abstract Only 108:a812 (1995).
Duerr et al., Homozygosity for an HLA class II group haplotype is associated with pANCA positive and familial ulcerative colitis. Abstract only Gastroenterology 108:a812 (1995).
Duerr et al., Linkage and association between inflammatory bowel disease and a locus on chromosome 12. Am J Hum Genet 63:95-100 (1998).
Email from James Jenkins referencing the "Amazon.com" website regarding exact publication date of "Immune Mechanism in Inflammatory Bowel Disease", edited by Richard S. Blumberg and Markus F. Neurath; Springer first edition. Received Dec. 15, 2010, 2 Pages.
Erlandsson et al., Effects of raloxifene, a selective estrogen receptor modulator on thymus T cell reactivity and inflammation in mice. Cellular Immunology 205:103-109 (2000).
Erlich et al., Chapter 32: HLA DNA typing. PCR protocols. Edited by Innis et al. pp. 261-271 (1990).
Ewens et al., The transmission/disequilibrium test: history, subdivision, and admixture. Am J Hum Genetics 57:455-464 (1995).
Feder et al., A novel MHC class 1-like gene is mutated in patients with hereditary heaemochromatosis. Nature Genetics 13:399-408 (1996).
Ferrante et al., Predictors of early response to infliximab in patients with ulcerative colitis. Inflamm Bowel Disease 13:123-128 (2007).
Ferraris et al., Analysis of CARD15 gene variants in Italian pediatric patients with inflammatory bowel disease. J of Pediatrics 147:272-273 (2005).
Fleshner et al., Both preoperative pANCA and CBir1 flagellin expression in ulcerative colitis (UC) patients influence pouchitis development after illegal pouch-anal anastomosis (IPAA). Abstract only (2006) Journal unknown.
Flores et al. In vitro evaluation of the effects of candidate immunosuppressive drugs: flow cytometry and quantitative real-time PCR as two independent and correlated read-outs. Journal of Immunological Methods 289:123-135 (2004).
Fox et al., Estrogen regulates the IFN-gamma promoter. J Immunol 146:4362-4367 (1991).
Fujikado et al., Identification of arthritis related gene clusters by microarray analysis analysis of two independent mouse models for rheumatoid arthritis. Arthritis Research and Therapy 8:1-13 (2006).
Fujino et al., Increased expression of interleukin 17 in inflammatory bowel disease gene. Gut 52:65-70 (2003).
Garcia-Bates et al., Peroxisome proliferator-activated receptor gamma ligands enhance human B cell antibody production and differentiation. J Immunology 183:6903-6912 (2009).
Gasche et al., A simple classification of Crohn's disease: report of the working party for the world congresses of gastroenterology, Vienna. Inflammatory Bowel Disease 6:8-15 (2000).
Gewirtz et al., Dominant-negative TLR5 polymorphism reduces adaptive immune response to flagellin and negatively associates with Crohn's disease. Am J Physiol Gastrointest Liver Physiol. 290:G1157-G1163 (2006).
Ghosh et al., Anti-TNF therapy in Crohn's disease Novartis Foundation Symposium 263:193-218 (2004).
Giacomelli et al., Combination therapy with cyclosporin and methotrexate in patients with early rheumatoid arthritis soon inhibits TNF production without decreasing TNF mRNA level: an in vivo and in vitro study. Clinical and Experimental Rheumatology 20:365-372 (2002).

(56) References Cited

OTHER PUBLICATIONS

Gilmore et al., Effect of estradiol on cytokine secretion by proteolipid protein-specific T cell clones isolated from multiple sclerosis patients and normal control subjects. Journal of Immunology. Abstract only.158:446-451 (1997).
Gonsky et al., CD2 mediates activation of the IFN-gamma intronic STAT binding region in mucosal T cells. Eur J Immunol 33:1152-1162 (2003).
Gonsky et al., Mucosa-specific targets for regulation of IFN-gamma expression: lamia propia cells use different cis-elements than peripheral blood T cells to regulate transactivation of IFN-gamma expression. J Immunol 164:1399-1407 2000.
Greenstein et al., Perforating and non-perforating indications for repeated operation in Crohn's disease: evidence of two clinical forms. Gut 29:588-592 (1988).
Haertel et al., Dose-dependent immunomodulatory effects of acetylsalicylic acid and indomethacin in human whole blood: potential role of cyclooxygenase-2 inhibition. Scandanavian Journal Immunology 60:412-420 (2004).
Hampe et al., A genomewide analysis provides evidence for novel linkage in inflammatory bowel disease in a large European cohort. Am J Hum Genet 64:808-816 (1999).
Hampe et al., A genome-wide association scan of nonsynonymous SNPs identifies a susceptibility variant for Crohn's disease in ATG16L1 Nature Genetics 39:207-211 (2007).
Hampe et al., Association between insertion mutation in NOD2 gene and Crohn's disease in German and British populations. Lancet 357:1925-1928 (2001).
Hampe et al., Association of NOD2 (CARD15) genotype with clinical course of Crohn's disease: a cohort study. Lancet 359:1661-1665 (2002).
Hanifi et al., Genetic structure of IDDM1: two separate regions in the major histocompatibility complex contribute to susceptibility or protection. Diabetes A Journal of the American Diabetes Association 47:1-7 (1999).
Harnish et al. Beneficial effects of estrogen treatment in the HLA-B27 transgenic rat model of inflammatory bowel disease. Am J Physiol Gastrointest Liver Physiology 286:G118-124 (2004).
Hartel et al., Delayed cytokine mRNA expression kinetics after T-lymphocyte costimulation: A quantitative measure of the efficacy of cyclosporin A-based immunosuppression. Clinical Chemistry 48:2225-2231 (2002).
Hazra et al., Common variant of FUT2 are associated with plasma vitamin B12levels. Nature Genetics 40:1160-1162 (2008).
Hegele, A., SNP Judgments and Freedom of Association, Arteriosclerosis, Thrombosis, and Vascular Biology, 2002, vol. 22, pp. 1058-1061.
Herbon et al. High-resolution SNP scan of chromosome 6p21 in pooled samples from patients with complex diseases. Genomics 81:510-518 (2003).
Heresbach et al., NOD2/CARD15 gene polymorphisms in Crohn's disease: a genotype-phenotype analysis. Eur J Gastroenterology and Hepatology 16:55-62 (2004).
Hess et al., The hydroxylamine of sulfamethoxazole synergizes with FK506 and cyclosporin A inhibiting T-cell proliferation. Journal of Pharmacology and Experimental Techniques. 281:540-548 (1996).
Hlavaty et al., Polymorphisms in apoptosis genes predict response to infliximab therapy in luminal and fistulizing Crohn's disease. Aliment Pharmacol Ther 22:613-626 2005.
Hogg et al., Adhesion molecules in cell interactions. Curr Opin Immunol. 5:383-390 (1993).
Hugot et al., Association of Nod2 leucine-rich repeat variants with susceptibility to Crohn's disease. Nature 411:599-603 (2001).
Hugot et al., Linkage analyses of chromosome 6 loci, including HLA, in familial C255 aggregations of Crohn's disease Get Aid. Am J Med Genet 52:207-213 (1994).
Hugot et al., Mapping of a susceptibility locus for Crohn's disease on chromosome 16. Nature 379:821-823 (1996).
Inohara et al., Human NOD1 confers responsiveness to bacterial lipopolysaccharides. J Biol Chem 276:2551-2554 (2001).

Ioannidis et al., Replication validity of genetic association studies Nature Genetics 29:306-309 (2001).
Ippoliti et al., Combination of innate and adaptive immune alterations increased the likelihood of fibrostenosis in Crohn's disease. Inflamm Bowel Disease 16:1279-1285 (2010).
Ippoliti et al., The relationship between abnormal innate and adaptive immune function and fibrostenosis in Crohn's disease patients. Abstract only. (2006) Journal unknown.
IRIS et al., Dense Alu clustering and a potential new member of the NFkB family within a 90 kilo base HLA Class III segment. Nature Genetics 3:137-145 (1993).
Jacob et al., Definition of microsatellite size variants for Tnfa and Hsp70 in autoimmune and nonautoimmune mouse strains. Immunogenetics 36:182-188 (1992).
Jarjour et al., The 8.5 kb Pstl allele of the stress protein gene Hsp70-2: An independent risk factor for systemic lupus erythematosus in African Americans. Hum Immunol 45:59-63 (1996).
Johnston et al. Present status and future prospects for HIV therapies. Science 260:1286-1293 (1993).
Jongeneel et al., Extensive genetic polymorphism in the human tumor necrosis factor region and relation to extended HLA haplotypes. PNAS USA 88:9717-9721 (1991).
Juhasz et al., Quantification of chemotherapeutic target gene mRNA expression in human breast cancer biopsies: comparison of real-time reverse transcription-PeR vs. relative quantification reverse transcription-PeR utilizing DNA sequence analysis of PCR product. Journal of Clinical Laboratory Analysis 17:184-194 (2003).
Karpuzoglu-Sahin et al., Effects of long-term estrogen treatment on IFN-gamma, IL-2 and IL 4 gene expression and protein synthesis in spleen and thymus of normal C57BL/6 mice. Cytokine 14:208-217 (2001).
Kim et al. DQCAR113and DQCAR115 in combination with HLA-DRB1 alleles are significant markers of susceptibility to rheumatoid arthritis in the Korean population. Tissue Antigens 54:552-559 (1999).
Kirchhausen et al., Location of the domains of ICAM-1 by immunolabeling and single-molecule electron microscopy. J. Leukocyte Biology 53:342-346 (1993).
Kita et al., Sequence and expression of rat ICAM-1. Biochim Biophys Acta 1131:108-111 (1992).
Klein et al., Ex-vivo assessment of candidate anti-inflammatory agents in the treatment of Gram-negative sepsis. Immunology and Infectious Disease 4:33-35 (1994).
Koutroubakis et al., Tumor necrosis factor-alpha polymorphism in inflammatory bowel disease. Hellenic J of Gastroenterology 8:132-135 (1995).
Kugathansan et al., L 1007FsinsC variant of CARD15/NOD2 is strongly associated with early onset and fibrostenosing behavior in pediatric Crohn's disease. Gastroenterology 126(4 Supp 2):A68 524.
Kugathansan et al., Loci on 20q13 and 21q22 are associated with pediatric onset inflammatory bowel disease. Nature Genetics 40:1211-1215 (2008).
Kutyavin, et al. 3'-Minor groove binder-DNA probes increase sequence specificity at PCR extension temperatures. Nucleic Acids Research, 28(2):655-661 (2000).
Kutyavin et al., Oligonucleotides with conjugated dihyropyrroloindole tripeptides: base composition and backbone effects on hybridization. Nucleic Acid Res 25:3718-3723 (1997).
Lakatos et al., NOD2/CARD15 mutations and genotype-phenotype correlations in patients with Crohn's disease. Hungarian multicenter study. Orvosi Hetilap 145:1403-1411 (2004).
Lasky. Selectins: interpreters of cell-specific carbohydrate information during inflammation. Science 258:964-969 (1992).
Latham et al., Estradiol treatment redirects the isotype of the autoantibody response and prevents the development of autoimmune arthritis. J of Immunol 171:5820-5827 (2003).
Laurence et al. Effect of tamoxifen on regulation of viral replication and human immunodeficiency virus (HIV) long terminal repeat-directed transcription in cells chronically infected with HIV-1. Blood 75:696-703 (1990).

(56) References Cited

OTHER PUBLICATIONS

Lee et al., Estrogen-mediated protection against HIV Tat protein-induced inflammatory pathways in human vascular endothelial cells. Cardiovascular Research 63:139-148 (2004).
Lemna et al., Mutation analysis for heterozygote detection and the prenatal diagnosis of cystic fibrosis. N. Eng. J. Med. 322:291-296 (1990).
Lesage et al., CARD15/NOD2 mutational analysis and genotype-phenotype correlation in 612 patients with inflammatory bowel disease. Am J of Human Genetics 70:845-857 (2002).
Leung et al. Expression profiling identifies chemokine (C-C Motif) ligand 18 as an independent prognostic indicator of gastric cancer. Gastroenterology 127:457-469 (2004).
Li et al., Cloning, characterization and the complete 56.8-kilobase DNA sequence of the human NOTCH4 gene. Genomics 51:45-58 (1998).
Li et al., New serological biomarkers of inflammatory bowel disease. World J of Gastroenterology14:5115-5124 (2008).
Limbergen et al., IL23R Arg381 Gin is associated with childhood onset inflammatory bowel disease in Scotland. Gut 56:1173-1174 (2007).
Lindner et al. Tamoxifen enhances interferon regulated gene expression in breast cancer cells. Molecular and Cellular Biochemistry 167:169-177 (1997).
Liu et al., Mucosal gene expression profiles following the colonization of immunocompetent defined-flora C3H mice with Helicobacter bilis: a prelude to typhlocolitis. Microbes and Infection 11:374-383 (2009).
Livak. Allelic discrimination using fluorogenic probes and the 5' nuclease assay. Genetic Analysis 14:143-149 (1999).
Lodes et al., Bacterial flagellin is a dominant antigen in Crohn disease. Journal of Clinical Investigation 113:1296-1306 (2004).
Louis et al. Association between polymorphism in IgG Fc receptor lila coding gene and biological response to infliximab in Crohn's disease. Aliment Pharmacol Ther 19:511-519 (2004).
MacDonald et al., Tumor necrosis factor-alpha and interferon-gamma production measured at the single cell level in normal and inflamed human intestine Clin Exp Immunol 81:301-305 (1990).
Mansfield et al., Novel genetic association between ulcerative colitis and the antiinflammatory cytokine interleukin-1 receptor antagonist. Gastroenterology 106:637-642 (1994).
Martin et al., Recombination rates across the HLA complex: use of microsatellites as a rapid screen for recombinant chromosome. Human Molecular Genetics 4:423-428 (1995).
Martins et al., Transcriptional repressor Blimp-1 regulates T cell homeostasis and function. Nature Immunology 7:457-265 (2006).
Mascheretti et al. Pharmacogenetic investigation of the TNF/TNF-receptor system in patients with Chronic active Crohn's disease treated with infliximib. The Pharmacogenomics Journal 2:127-136 (2002).
Matalka. The effect of estradiol but not progesterone on the production of cytokines in stimulated whole blood is concentration-dependent. Neuro Endocrinology Letters. Abstract only. 24:185-191 (2003).
Matejuk et al., 17-beta-estradiol inhibits cytokine, chemokine and chemokine receptor mRNA expression in the central nervous system of female mice with experimental autoimmune encephalomyelitis. J of Neuroscience Research 65:529-542 (2001).
Matsunaga et al., Application of differential display to identify genes for lung cancer detection in peripheral blood. Int J of Cancer 100:592-599 (2002).
McCall et al., Constitutive expression of TNF-a and of an IL-8 gene is associated with genetic susceptibility to chronic granulomatous enterocolitis in inbred rats. AGA Abstracts p. A740 (1993).
MCEver. Leukocyte—endothelial cell interactions. Curr Opin Cell Bioi 4:840-849 (1992).
McGovern et al., Genetic epistasis of IL23/IL 17 pathway genes in Crohn's disease. Inflamm Bowel Dis. 15:883-889 (2009).

Mehmut et al., Fas ligand and TNF-related apoptosis-inducing ligand induction on infiltrating lymphocytes in bladder carcinoma by Bacillus Calmette-Guerin treatment Urologica International 75:80-87 (2005).
Mei. Association between IL 17 A and Il 17RA genes and inflammatory bowel disease (IBD). Abstract only. (2007) Journal unknown.
Mei et al., Familial expression of anti-Escherichia coli outer membrane porin C in relatives of patients with Crohn's disease. Gasteroenterology 130:1078-1085 (2006).
Melmed et al., A prospective analysis of predictive factors for the diagnosis of Crohn's disease after Ileal pouch-anal anastomosis for ulcerative colitis. Abstract only. (2007) Journal Unknown.
Melmed et al., Patients with inflammatory bowel disease are at risk for vaccine-preventable illness. Am J Gasteroenterol 101:1834-1840 (2006).
Mesange et al., Ligands of the antiestrogen-binding site are able to inhibit virion production of human immunodeficiency virus 1-infected lymphocytes. Molecular Pharmacology 50:75-79 (1996) Abstract only.
Messer et al., Polymorphic structure of the tumor necrosis factor (TNF) locus: an NcoI polymorphism in the first intron of TNF-8 gene correlates with a variant in amino acid position 26 and a reduced level ofTNF-8 production. J Exp Med 173:209-219 (1991).
Michelsen et al., IBD-Associated TL 1A Gene (TNFSF15) Haplotypes Determine Increased Expression of TL 1A Protein. PLoS ONE. 4:e4719 (2009).
Milner et al. Polymorphic analysis of the three MHC-linked HSP70 genes. Immunogenetics 36:357-362 (1992).
Mingjia et al., How oestrogen or progesterone might change a woman's susceptibility to HIV 1 infections. The Australian and New Zealand Journal of Obstetrics and Gynecology Abstract only. 42:472-475 (2002).
Misiewicz et al., The estrogen antagonist tamoxifen inhibits carrageenan induced inflammation in Lewin female rats. Life Sciences 58:PL281-286 (1996).
Moghaddam et al., Genetic structure of IDDM1: two separate regions in the major histocompatibility complex contribute to susceptibility or protection. Diabetes 47:263-269 (1998).
Mow et al., Association of antibody responses to microbial antigens and complications of small bowel Crohn's disease. Gastroenterology 126:414-424 (2004).
Murch et al., Location of tumor necrosis factor alpha by immunochemistry in chronic inflammatory bowel disease. Gut 34:1705-1709 (1993).
Murillo et al., CARD15 gene and the classification of Crohn's disease. Immunogenetics 54:59-61 (2002).
Murray et al., GenBank Accession No. G08322 (Feb. 5, 1997).
Nadal et al., Imbalance in the composition of the duodenal microbiata of children with coeliac disease. J Medical Microbiol. 56:1669-1674 (2007).
Nakamura et al., In situ expression of the cell adhesion molecules in Inflammatory Bowel Disease; evidence of immunologic activation of vascular endothelial cells. Lab Investig 69(1):77-85 (1993).
Nakaya et al., Estrogenic compounds suppressed interferon-gamma production in mouse splenocytes through direct cell-cell interaction. In Vitro Cell Dev Biol Anim 39:383-387 (2003).
NCBI SNIP ID rs7374667 (2011).
Nedospasov et al., DNA sequence polymorphism at the human tumor necrosis factor (TNF) locus. Numerous TNF/lymphotoxin alleles tagged by two closely linked microsatellitesin the upstream region of the lymphotoxin (TNF-beta) gene. J. Immunol. 147:1053-1059 (1991).
Nedospasov et al., Genetic polymorphism of the human gene locus containing genes for tumor necrosis factors: ethnic differences in allele frequency distribution. Chemical Abstracts, 120(5):47183y (1994).
Ogura et al., A frameshift mutation in NOD2 associates with susceptibility to Crohn's disease. Nature 411:603-606 (2001).
Ogura et al., NOD2, a Nod1/Apaf-1 family member that is restricted to monocytes and activates NF-kB. J Biol Chem 276:4812-4818 (2001).

(56) References Cited

OTHER PUBLICATIONS

Ohmen et al., Susceptibility locus for inflammatory bowel disease on chromosome 16 has a role in Crohn's disease, but not in ulcerative colitis. Hum Mol Genet 5:1679-1683 (1996).
Okazaki et al., Contributions of the IBD5, IL23R, ATG16L 1, and NOD2 to Crohn's disease risk in a population-based case-controlled study: evidence of gene-gene interaction. Inflamm Bowel Disease 14:1528-1541 (2008).
Orholm et al., Familial occurrence of inflammatory bowel disease. New England Journal of Medicine 324:84-88 (1991).
Over et al., Thromphilia and inflammatory bowel disease: does factor V mutation have a role? European Journal of Gastroenterology and Hepatology 10:827-829 (1998).
Owerbach et al. The HOXD8 locus (2q31) is linked to type I diabetes—interaction with chromosome 6 and 11 disease susceptibility genes. Diabetes 44:132-136 (1995).
Papadakis et al., An interaction between IL-23R and IL-17A and between IL-23R and IL 17RA haplotypes is necessary for susceptibility to Crohn's disease. Abstract only. (2007) Journal unknown.
Papadakis et al., Anti-Flagellin (Cbir1) phenotypic and genetic Crohn's Disease associations, Inflamm Bowel Dis 13(5):524-530 (2007).
Papadakis et al., Phenotypic and functional characterization of CCR9+ T lymphocytes in small intestinal Crohn's disease. Abstract only. (2006). Journal unknown.
Papp et al., Seroreactivity to microbial components in Crohn's disease is associated with Ileal involvement, noninflammatory disease behavior and NOD2/CARD15 genotype but not with risk for surgery in a Hungarian cohort of IBO patients. Inflamm Bowel Disease 13:984-992 (2007).
Parkes et al., Susceptibility loci in inflammatory bowel disease. Lancet 348:1588 (1996).
Parrello et al., Upregulation of the IL-12 receptor beta 2 chain in Crohn's disease. J Immunol 165:7234-7239 (2000).
Partanen et al., Low degree of DNA polymorphism in the HLA-linked lymphotoxin (tumor necrosis factor-B) gene. Scand J. Immunol. 28:313-316 (1988).
Paul. Chapter 19. Fundamental Immunology 4th edition pp. 663-665 (1998).
PCT/US1995/001434 International Preliminary Examination Report dated May 22, 1996.
PCT/US1995/001434 International Search Report dated Jul. 21, 1995.
PCT/US1995/001434 Written Opinion dated Nov. 17, 1995.
PCT/US1995/006107 International Preliminary Examination Report dated Jun. 5, 1996.
PCT/US1995/006107 International Search Report dated Oct. 6, 1995.
PCT/US1995/006107 Written Opinion dated Feb. 12, 1996.
PCT/US1997/000042 International Preliminary Examination Report dated Apr. 1, 1998.
PCT/US1997/000042 International Search Report dated Apr. 21, 1997, dated May 14, 1997.
PCT/US1997/000042 Written Opinion dated Oct. 29, 1997.
PCT/US2000/025112 International Preliminary Examination Report dated Dec. 20, 2001.
PCT/US2000/025112 International Search Report dated Aug. 6, 2001.
PCT/US2003/023926 International Preliminary Examination Report dated Aug. 19, 2004.
PCT/US2003/023926 International Search Report dated Jun. 23, 2004.
PCT/US2005/018161 International Search Report dated Jun. 4, 2008.
PCT/US2005/018161 Written Opinion dated Jun. 4, 2008.
PCT/US2005/044335 International Preliminary Examination Report dated Jun. 13, 2007.
PCT/US2005/044335 International Search Report dated Sep. 22, 2006.
PCT/US2005/044335 Written Opinion dated Sep. 22, 2006; dated Aug. 26, 2006.
PCT/US2007/008597 International Preliminary Examination Report dated Oct. 8, 2008.
PCT/US2007/008597 International Search Report dated Jun. 4, 2008.
PCT/US2007/008597 Written Opinion dated Jun. 4, 2008.
PCT/US2008/054033 International Preliminary Examination Report dated Aug. 19, 2009.
PCT/US2008/054033 International Search Report dated Aug. 21, 2008.
PCT/US2008/054033 Written Opinion dated Aug. 21, 2008.
PCT/US2008/056103 International Preliminary Report on Patentability dated Nov. 24, 2009.
PCT/US2008/056103 International Search Report dated Sep. 3, 2008.
PCT/US2008/056103 Written Opinion dated Sep. 3, 2008.
PCT/US2008/057028 International Preliminary Report on Patentability dated Sep. 15, 2009.
PCT/US2008/057028 International Search Report dated Oct. 10, 2008.
PCT/US2008/057028 Written Opinion dated Oct. 10, 2008.
PCT/US2008/057820 International Search Report dated Sep. 11, 2008.
PCT/US2008/061652 International Preliminary Report on Patentability dated Oct. 27, 2009.
PCT/US2008/061652 International Search Report dated Dec. 1, 2008.
PCT/US2008/061652 Written Opinion dated Dec. 1, 2008.
PCT/US2008/063202 International Preliminary Examination Report dated Nov. 10, 2009.
PCT/US2008/063202 International Search Report dated Nov. 18, 2008.
PCT/US2008/063202 Written Opinion dated Nov. 18, 2008.
PCT/US2008/080526 International Search Report dated Mar. 25, 2009.
PCT/US2008/080526 Written Opinion dated Mar. 25, 2009.
PCT/US2009/044720 International Search Report dated Nov. 5, 2009.
PCT/US2009/044720 Written Opinion dated Nov. 5, 2009.
PCT/US2009/061698 International Search Report dated Mar. 16, 2010.
PCT/US2009/069531 Written Opinion dated Aug. 4, 2010.
PCT/US2009/069541 International Preliminary Report on Patentability dated Jun. 29, 2011.
PCT/US2009/069541 Written Opinion dated Mar. 4, 2010.
PCT/US2010/043427 International Search Report dated Dec. 3, 2010.
PCT/US2011/021382 International Search Report dated Mar. 15, 2011.
PCT/US2011/021382 Written Opinion dated Mar. 15, 2011.
PCT/US2011/028694 International Search Report dated Jul. 27, 2011.
PCT/US2011/028694 Written Opinion dated Jul. 27, 2011.
Plevy et al., A role of TNF-alpha and mucosal T-helper-1 cytokines in the pathogenesis of Crohn's disease. The Journal of Immunology 84:1397-1398 (2004).
Plevy et al., Increased mucosal tnf-alpha mrna levels and numbes of tnf-alpha producing cells are unique to mucosal inflammation in crohn's disease, Faseb Journal, Abstract 5849 8:A1010 (Apr. 1994).
Plevy et al., The tumor necrosis factor (TNF) microsatellite haplotype A2B1C204E1 correlates with increased TNF production in Crohn's disease. Abstract only AASLD at Digestive disease week (1995).
Plevy et al. TNF-alpha MRNA levels differentiated mucosal inflammation in crohn's disease from ulcerative colitis. J. Immunology 150:10a (1993).
Plevy et al., Tumor necrosis factor microsatellites define Crohn's disease—associated haplotype on chromosome 6. Gasteroenterology 110:1053-1060 (1996).
Plevy et al., Tumor necrosis factor (TFN) microsatellite associations with HLA-DR2+ patients define Crohn's disease (cd) and ulcerative colitis (uc)-specific genotypes. Gastroenterology 106:A754 (1994).

(56) References Cited

OTHER PUBLICATIONS

Pociot et al., A tumor necrosis factor beta gene polymorphism in relation to monokine secretion and insulin dependent diabetes mellitus. Scand J. Immunol., 33:37-49 (1991).
Pociot et al., Association of tumor necrosis factor and class II major histocompatibility complex alles with secretion of tnf alfa and tnf beta by human mononuclear cells: a possible link to insulin-dependent diabetes mellitus. Abstract only. Eur. J. Immunology 23:224-231 (1993).
Poicot et al., Polymorphic analysis of the human MHC-linked heat shock protein 70 (HSP70-and HSP70-Hom genes in insulin-dependent diabetes mellitus (IOOM). Scand J Immunol 38:491-495 (1993).
Polanczyk et al., The protective effect of 17beta-estradiol on experimental autoimmune encephalomyelitis is mediated through estrogen receptor-a. American J of Pathology 163:1599-1605 (2003).
Potts et al., Using microbicides to fight the spread of HIV. Science 300:431 (2003).
Radlmayr et al., The c-insertion mutation of the NOD2 gene is associated with fistulizing and fibrostenotic phenotypes in Crohn's diseases. Gasterenterology 122:2091-2095 (2002).
Rector et al., Mannan-binding lectin (MBL) gene polymorphisms in ulcerative colitis and Crohn's disease. Genes and Immunity 2:323-328 (2001).
Redon et al. Global variation in copy number in the human genome. Nature. 444(7118): 444-54 (2006).
Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).
Rioux et al., Genome-wide association study identifies new susceptibility loci for Crohn disease and implicates autophagy in disease pathogenesis. Nature Genetics 39(5):596-604 (2007).
Rodriguez-Caballero et al., A new simple whole blood flow cytometry-based method for simultaneous identification of activated cells and quantitative evaluation of cytokines released during activation Laboratory Investigation 84:1387-1398 (2004).
Roth et al., Familial empiric risk estimates of inflammatory bowel disease in Ashkenazi Jews. Gastroenterology 96:1016-1020 (1989).
Roth et al., Geographic origins of Jewish patients with inflammatory bowel disease. Gastroenterology 97:900-904 (1989).
Rotter et al., TLR5 polymorphisms are associated with OmpC and CBir1 expression and with severity of Crohn's disease in Ashkenazi Jews. Abstract only (2004). Journal unknown.
Rozen et al., Crohn's disease in the Jewish population of Tei-Aviv-Yafo: epidemiologic and clinical aspects. Gastroenterology 76:25-30 (1979).
Salem. Estrogen, a double-edged sword: modulation of TH1- and THw- medicated inflammations by differential regulation of T J1/TH2 cytokine production. Inflammation and Allergy 3:97-104 (2004).
Salem et al., Mediation of the immunomodulatory effect of beta-estradiol on inflammatory response by inhibition of recruitment and activation of inflammatory cells and their gene expression of TNF-alpha and IFN-gamma. Inti Archives of Allergy and Immunology Abstract Only. 121:235-245 (2000).
Saruta et al., TLR8-mediated activation of human monocytes inhibits TL 1A expression. Eur J Immunol 39:2195-2202 (2009).
Sategna-Guidetti et al., Tumor necrosis factor cachectin in Crohn's disease—relation of C385 serum concentration to disease activity. Recenti Progressi 84:93-99 (1993).
Satsangi et al., The genetics of inflammatory bowel disease. Gut 40:572-574 (1997).
Saxon et al., A distinct subset of antineutrophil cytoplasmic antibodies is associated with inflammatory bowel disease. J Allergy Clin. Immunol. 86:202-210 (1990).
Schimanski et al., Effect of chemokine receptors CXCR4 and CCR7 on the metastatic behavior of human colorectal cancer Clinical Cancer Research 11:1743-1750 (2005).
Schluender et al., Does infliximab influence surgical morbidity or long-term outcome of Ileal pouch-anal anastomosis in patients with ulcerative colitis. Abstract only. (2006). Journal Unknown.
Schluender et al., Does preoperative wireless endoscopic capsule predict long-term outcome after Ileal pouch-anal anastomosis (IPAA)? Abstract only. (2006). Journal unknown.
Schoelmerich. Inflammatory Bowel Diseases: early symptoms and differential (Reprints available from University of Freiburg, Department of Internal Medicine, Hugstetter Strasse 55, 0-7800 Freiburg, W. Germany pp. 2-20 (2017).
See et al., Increased tumor necrosis factor alpha (TNF-alpha) and natural killer cell (NK) function using an integrative approach in late stage cancers. Immunological Investigations 31:137-153 (2002).
Shanahan et al., Inflammatory Bowel Disease. Textbook of Internal Medicine. W.N. Kelle et al. (editor) 2nd edition J. B. Lippincott Company, Philadelphia 81:489-502 (1992).
Shetty et al., Pharmacogenomics of response to anti-tumor necrosis factor therapy in patients with Crohn's disease. American Journal of Pharmacogenomics 2:215-221 (2002).
Shovam et al., Evaluation of the BioPiex 2200 ANA screen: Analysis of 510 healthy subjects: incidence of natural/predictive autoantibodies. Annals of the New York Academy of Science, 1050:380-388 (2005).
Silman et al., Epidemiology and genetics of rheumatoid arthritis. Arthritis Research 4 Supp 3:S265-S272 (2002).
Silverberg et al., Evidence for linkage between Crohn's disease (CD) and a locus near the major histocompatibility complex (MHC) on chromosome 6 in a Canadian inflammatory bowel disease (IBO) population. Gastroenterology 116:G3560 AGA Abstracts (1999).
Silverberg et al., The HLA DRBL 0103 allele is associated with Crohn's disease (CD) in a Toronto inflammatory bowel disease (IBO) population. Gastroenterology 116:G3559 AGA Abstracts (1999).
Singal et al., D6S273 microsatellite polymorphism and susceptibility to Rhematoid Arthritis. Tissue Antigens 52:353-358 (1998).
Singal et al., Genetics of rheumatoid arthritis (RA): two separate regions in the major histocompatibility complex contribute to susceptibility to RA. Immunol Lett 69:301-306, (1999).
Sitaraman et al., Elevated flagellin-specific immunoglobulins in Crohn's disease. Am J Physiol Gastrointest Liver Physiol 288:G403-G406 (2005).
SMITH. Adherence of neutrophils to canine cardiac myocyyes in vitro is dependent on intercellular adhesion molecule-1. J Clin Invest 88:1216-1223 (1991).
SMITH et al., Cooperative interactions of LFA-1 and Mac-1 with intercellular adhesion molecule-1 in facilitating adherence and transendothelial migration of human neurophils in vitro. J Clin Invest 83:2008-2017 (1989).
Smith et al., Estrogen protects against vaginal transmission of simian immunodeficiency virus. J Infectious Diseases 182:708-715 (2000).
SMITH et al., Recognition of an endothelial determinant for CD18-dependent human neutrophil adherence and transendothelial migration. J Clin Invest 82:1746-1756 (1988).
Smith et al. Topical estrogen protects against SIV vaginal transmission without evidence of systemic effect. AIDS 18:1637-1643 (2004).
Smith. Transendothelial Migration, in Breakthroughs in Molecular Biology, vol. 4: Adhesion: Its Role in Inflammatory Disease. Harlan, J. and Liu D., eds., W. H. Freeman & Co. New York. pp. 83-115 (1992).
Springer et al., Adhesion receptors of the immune system. Nature 346:425-433 (1990).
Staunton et al., Primary Structure of ICAM-1 demonstrates interaction between member of the immunoglobulin and integrin supergene families. Cell 52:925-933 (1988).
Staunton et al. The arrangement of the immunoglobulin-like domains of ICAM-1and binding sites for LFA-1 and rhinovirus. Cell 61:243-254 (1990).
Steer et al., Development of rheumatoid arthritis is not associated with two polymorphisms in the Crohn's disease gene CARD15 Rheumatology 42:304-307 (2003).

(56) References Cited

OTHER PUBLICATIONS

Stites et al., Chapter 22 of the 4th edition of Basic and Clinical Immunology, Lange Medical Publications, Los Altos, California, p. 325-365 (1982).
Strater et al., Expression of TRAIL and TRAIL receptors in colon carcinoma: TRAIL-R1 is an independent prognostic parameter. Clinical Cancer Research 8:3734-3740 (2002).
Stulik et al., The different expression of proteins recognized by monoclonal anti-heat shock protein 70 (hsp70) antibody in human colonic diseases. Electrophoresis 18:625-628 (1997).
Su. Different haplotypes of IL 12B (p40) genes are associated with clinical Crohn's disease (CD) and with CD patients expressing Cbir1 antibodies, respectively. Abstract only (2007). Journal unknown.
Sugaya et al., Gene organization of human NOTCH4 and (CTG)n polymorphism in this human counterpart gene of mouse proto-oncogene Int3. Gene 189:235-244 (1997).
Sugaya et al., Three genes in the human MHC class III region near the junction with the class II: gene for receptor of advanced glycosylation end products, PBX2 homeoboxgene and a notch homolog, human counterpart of mouse mammary tumor gene int-3. Genomics 23:408-419 (1994).
Sullivan et al., Prevalence of a mutation causing C2 deficiency in systemic lupus erythematosus. J of Rheumatology 21:1128-1133 (1994).
Takedatsu et al., Linkage of CD-related serological phenotypes: NFKB1 haplotypes are associated with anti-CBir1 & ASCA, and show reduced NF-KB activation. Gut. 58:60-67 (2009).
Takedatsu. Reduced nuclear factor (NF)-kB expression in cell lines from anti-CBir1-associated NFKB1 haplotypes. Abstract only. (2007). Journal unknown.
Targan et al., Antibodies to a novel flagellin (CBir1) define a unique serologic response in Crohn's disease (CD). Gastroenterology Abstract only 126(4), Suppl 2:A113 (2004).
Targan et al., Antibodies to CBir1 flagellin define a unique response that is associated independently with complicated Crohn's disease. Gastroenterology 128:2020-20289 (2005).
Targan et al., Definition of a lamina propia T cells responsive state enhanced cytokine responsiveness of T cells stimulated through the CD2 pathway. J Immunol 154:664-675 (1995).
Tarlow et al., Polymorphism in human IL-1 receptor antagonist gene intron 2 is caused by variable numbers of an 86-bp tandem repeat. Hum Genet 91:403-404 (1993).
Taylor et al., Analysis of IBD5-related polymorphisms: IRF1 but not SLC22A4 or SLC22A5 is associated with 18D in Puerto Rican populations. Digestive Disease Week Abstract only (2006). Journal unknown.
Taylor et al., Genes regulating the expression of antibody to C8ir1 flagellin in humans are located within a syntenic region to the major mouse colitogenic locus Cdcs1. AGA Institute Abstract #444 p. A-64 (2006).
Taylor et al., IL23R haplotypes provide a large population attributable risk for Crohn's disease. Inflammatory Bowel 14:1185-1191 (2008).
Taylor et al., Linkage disequilibrium mapping identifies a Class III major histocompatibility complex (MHC) susceptibility haplotypes to Crohn's disease in Ashkenazi Jews. American Journal of Human Genetics. 65(4): A102, abstract 534 (1999).
Thisteda. What is a P-value. Departments of Statistics and Health Studies. The University of Chicago. (May 25, 1988).
Thomas et al., Estrogen and raloxifen activities on amyloid-beta-induced inflammatory reaction. Microvascular Research 61:28-39 (2001).
Tomassini. et al., cDNA cloning reveals that the major group rhinovirus receptor on Hela cells in intercellular adhesion molecule-1. PNAS USA 86:4907-4911 (1989).
Torok et al., Crohn's disease is associated with a Toll-like receptor-9 polymorphism. Gastroenterology 127:365-368 (2004).
Torres et al., Newborn screening for Hermansky-pudlak syndrome Type 3 in Puerto Rico. Blood 108:3290 (2006).
Tountas et al., Genetic association between allele 2 of IL-1 receptor antagonist (IL-1 ra) and ulcerative colitis in Los Angeles based hispanic population. Abstract XP000673112 only. Gastroenterology 108:806-813 (1995).
Tountas et al. Heterogenous association between allele 2 of IL-2 receptor antagonist (ILC4371 RA) and ulcerative colitis in Jewish and non-Jewish populations. Abstract XP000673114 only. J. Investigative Medicine 44(1) (1996).
Tountas et al., Increased carriage of allele 2 of IL-1 receptor antagonist (IL-1ra) in Jewish population: the strongest known genetic association in ulcerative colitis. American Gastroenterology Association Abstract Only (1996).
Trachtenberg et al., Rare HLA DR-DQ haplotypes associated with inflammatory bowel disease. Human Immunol 55 (supp. 1):59 Abstract #42 (1997).
Trowsdale et al., Map of the human MHC. Immunol. Today 12:443-446 (1991).
Turchan et al., Estrogen protects against the synergistic toxicity by HIV proteins, methamphetamine and cocaine. BMC Neuroscience 2:3 (2001).
Udalova et al., Highly informative typing of the human TNF locus using six adjacent polymorphic markers Genomics 16:180-186 (1993).
U.S. Appl. No. 08/196,003 Office Action dated Dec. 12, 1995.
U.S. Appl. No. 08/196,003 Office Action dated Oct. 2, 1996.
U.S. Appl. No. 08/245,297 Office Action dated Dec. 9, 1996.
U.S. Appl. No. 08/245,297 Office Action dated Jan. 22, 1996.
U.S. Appl. No. 08/245,297 Office Action dated Jul. 11, 1996.
U.S. Appl. No. 08/245,297 Office Action dated Mar. 15, 1995.
U.S. Appl. No. 08/587,911 Office Action dated Apr. 15, 1997.
U.S. Appl. No. 08/587,911 Office Action dated Jan. 5, 1998.
U.S. Appl. No. 08/587,911 Office Action dated Jul. 6, 1998.
U.S. Appl. No. 08/798,668 Notice of Allowance dated Apr. 29, 1999.
U.S. Appl. No. 08/798,668 Office Action dated Aug. 10, 1997.
U.S. Appl. No. 08/798,668 Office Action dated Jan. 29, 1998.
U.S. Appl. No. 08/798,668 Office Action dated Jun. 6, 1997.
U.S. Appl. No. 08/933,824 Office Action dated Apr. 14, 1998.
U.S. Appl. No. 08/933,824 Office Action dated Jan. 5, 1999.
U.S. Appl. No. 09/395,345 Office Action dated May 3, 2000.
U.S. Appl. No. 09/395,345 Office Action dated Nov. 21, 2000.
U.S. Appl. No. 09/419,406 Notice of Allowance dated Mar. 19, 2002.
U.S. Appl. No. 09/419,406 Office Action dated Apr. 24, 2000.
U.S. Appl. No. 09/419,406 Office Action dated Dec. 28, 2000.
U.S. Appl. No. 09/419,406 Office Action dated Jul. 17, 2001.
U.S. Appl. No. 09/419,408 Office Action dated Feb. 1, 2000.
U.S. Appl. No. 10/075,425 Office Action dated Jun. 17, 2005.
U.S. Appl. No. 10/075,425 Office Action dated Oct. 1, 2004.
U.S. Appl. No. 10/356,736 Office Action dated Apr. 10, 2006.
U.S. Appl. No. 10/356,736 Office Action dated Apr. 26, 2007.
U.S. Appl. No. 10/356,736 Office Action dated Aug. 14, 2008.
U.S. Appl. No. 10/356,736 Office Action dated Jul. 7, 2005.
U.S. Appl. No. 10/356,736 Office Action dated Nov. 30, 2007.
U.S. Appl. No. 10/526,256 Office Action dated Aug. 25, 2009.
U.S. Appl. No. 10/526,256 Office Action dated Dec. 29, 2008.
U.S. Appl. No. 10/526,256 Office Action dated May 9, 2008.
U.S. Appl. No. 11/720,785 Office Action dated Dec. 23, 2010.
U.S. Appl. No. 11/720,785 Office Action dated Jul. 19, 2010.
U.S. Appl. No. 12/530,390 Office Action dated Mar. 25, 2011.
U.S. Appl. No. 12/599,549 Office Action dated Apr. 26, 2011.
Vaidya et al., The cytotoxic T lymphocyte antigen-4 is a major Graves' disease locus. Human Molecular Genetics 8:1195-1199 (1999).
Vasiliauskas et al., Marker antibody expression stratifies Crohn's disease into immunilogically homogenous subgroups with distinct clinical characteristics. Gut 47:487-496 (2000).
Vasiliauskas et al., Perinuclear antineutrophil cytoplasmic antibodies in patients with Crohn's disease define a clinical subgroups. Gastroenterology 110:1810-1819 (1996).

(56) References Cited

OTHER PUBLICATIONS

Vavassori et al., CARD15 mutation analysis in an Italian population: Leu1007fsinsC but neither Arg702Trp norGly908Arg mutations are associated with Crohn's disease. Inflamm Bowel Dis 10:116-121 (2004).
Verdu et al., Modulatory effects of estrogen in two murine models of experimental colitis. American J Physiology 283:G27-G36 (2002).
Vermiere et al., CARD15 genetic variation in a Quebec population: prevalence, genotype-phenotype relationship and haplotype structure. Am J Hum Genet 71:74-83 (2002).
Vermiere et al., Current status of genetics research in inflammatory bowel disease. Genes and Immunity 6:637-645 (2005).
Verthelyi et al. Sex hormone levels correlate with the activity of cytokine-secreting cells in vivo. Immunology 100:384-390 (2000).
Voraberger et al., Cloning on the human gene for intercellular adhesion molecule-1 and analysis of its 5'-regulatory region. J Immunol 147:2777-2786 (1991).
Warzocha et al., Tumor necrosis factor ligand receptor system can predict treatment outcome of lymphoma patients. Journal of Clinical Oncology 15:499-508 (1997).
Webb et al., Genetic variability at the human tumor necrosis factor loci. J. Immunol 145:1278-1285 (1993).
Weber et al. Abundant class of human DNA polymorphisms which can be typed using the polymerase chain reaction. Am J Hum Genet 44:388-396 (1989).
Wen et al., TL1A-induced NF-kB activation and c-IAP2 production prevent DR3-mediated C456 apoptosis in TF-1 cells. J Biol Chem 278:39251-39258 (2003).
Williams et al., Optimization strategies for the polymerase chain reaction. Biotechniques 7:762-768 (1989).
Wouters et al., Inter- and intra-individual variation of endotoxin- and beta (1-3)-glucan-induced cytokine responses in a whole blood assay. Toxicology and Industrial Health 18:15-27 (2002).
Wu et al. Tamoxifen alleviates disease severity and decreases double negative T cells in autoimmune MRL-Ipr/Ipr mice. Immunology 100:110-118 (2000).
Wu et al., Tamoxifen decreases renal inflammation and alleviates disease severity in autoimmune NZBIW F1 mice. Scandinavian Journal of Immunology 52:393-400 (2000).
Xiao et al., Interaction of Cocksackievirus A21 with its cellular receptor ICAM-1. J Viral 75:2444-2451 (2001).
Yamamoto-Furusho et al., Complotype SC30 is associated with susceptibility to develop severe C462 ulcerative colitis in Mexicans. J Clin Gasterol 27:178-180 (1998).
Yamazaki et al., Absence of mutation in the NOD2/CARD15 gene among 483 Japanese patients with Crohn's disease. Hum Mol Genet 47:469-472 (2002).
Yamazaki et al., Association analysis of genetic variants in IL23R, ATG16L 1 and 5p13.1 loci with Crohn's disease in Japanese patients. J Hum Genet 52:575-582 (2007).
Yang et al., Association of intercellular adhesion molecule-1 (ICAM-1) gene with subsets of Inflammatory Bowel Disease (IBO) stratified by anti-neutrophil cytoplasmic antibodies I (AN CAs). Clinical Research Abstract only 42(1):76A (1994).
Yang et al., Familial empirical risks for inflammatory bowel disease: differences between Jews and non-Jews. Gut 34:517-524 (1993).
Yang et al., Genetic Heterogeneity within UC and Crohn's defined by anti-neutrophil cytoplasmic antibodies (AN CAs) and intercellular adhesion molecule-1 (ICAM-1) polymorph isms. Gastroenterology 106(4):A794 AGA Abstract (1994).
Yang et al., Intercellular adhesion molecule 1 gene association with immunologic subsets of inflammatory bowel disease. Gastroenterology 109:440-448 (1995).
Yang et al., Linkage of Crohn's disease to the major histocompatibility complex region is detected by multiple non-parametric analyses. Gut. 44 p. 519-526 (1999).
Yang et al. The R241 allele if ICAM-1 is associated with a distinct clinical subgroup of Crohn's disease (CD) characterized by perinuclear ANCA (pANCA) production. Abstract only. American Gastroenterological Association and American Association for the study of Liver disease. May 19-22, 1996.
Yang et al., Ulcerative colitis: a genetically heterogenous disorder defined by genetic (HLA class II) and subclinical (antineutrophil cytoplasmic antibodies) markers J. Clin. Invest., 92:1080-1084 (1993).
Yoon et al., Decreased potency of the Vibrio cholerae sheathed flagellum to trigger host innate immunity. Infection and Immunity 76:1282-1288 (2008).
Younes et al., Clinical implication of the tumor necrosis factor family in benign and malignant hematologic disorders. Cancer 98:458-467 (2003).
Younes et al., Emerging applications of the tumor necrosis factor family if ligands and receptors in cancer therapy. J Clin Oncol 21:3526-3534, (2003).
Zaahl et al., Analysis of the three common mutations in the CARD15 gene (R702W, G908R and 1007fs) in South African colored patients with inflammatory bowel disease. Molecular and Cellular Probes 19:278-281 (2005).
Zhang et al., Critical role of IL-17 receptor signaling in acute TNBS-induced colitis. Inflamm Bowel Dis 12:382-388 (2006).
Zhang et al. Estrogen affects the differentiation and function of splenic monocyte-derived dendritic cells from normal rats. Abstract Only. 20:129-134 (2004).
Ziegler et al., Detectable serum flagellin and liposaccharide and upregulated anti-flagellin and liposaccharide immunoglobulins in human short bowel syndrome. Am J Physiol Regul IntegrComp Physiol. 294:R402-R410 (2008).
Spinelli et al., Intestinal Fibrosis in Crohn's Disease: Medical Treatment or Surgery?, Current Drug Targets, 11(2):242-248, 2010.
Springer, T. A. et al., Leukocyte adhesion molecules structure function and regulation. New York, Springer-Verlag 1990 Book-Table of Contents Book not included.
Stratagene Catalog. 1988; p. 39. Gene Characterization Kits. Table of Contents.
Strober et at, Proinflammatoly Cytokines in Pathogenesis of Inflammatory Bowel Diseases, Gastroenterology, 140(6):1756-1767, 2011.
Strong, S. Surgical management of Crohn's disease, in: Surgical Treatment: Evidence Based and Problem Oriented. Holzheimerand Mannick, editors. Munich: Zuckschwerdt, 7 pages, 2001.
Takedatsu et al., TL 1A (TNFSF15) regulates the development of chronic colitis by modulating both T helper (TH)1 and TH17 activation. Gastroenterology vol. 135:552-567 (2008).
Targan et al., TL1A (TNFSFI5): A Master Regulator of Mucosal Inflammation, Advances in Experimental Medicine and Biology, 691:681-683, 2011.
Taylor et al., ANCA pattern and LTA haplotype relationship to clinical responses to anti-TNF antibody treatment in Crohn's disease. Gastroenterology, 120:1347-1355, 2001.
Taylor et al., Specific clinical and immunological features in Crohn's disease patients are associated with the MHC class III marker Notch4. Gastroenterology. 118(Supp 2):A869, Abstract 4830 (2000).
The Wellcome Trust Case Control Consortium, Genome-Wide Association Study of 14,000 Cases of Seven Common Diseases and 3,000 Shared Controls, Nature, 2007, vol. 447, pp. 661-678.
Thomas et al., The TNF Family Member TL1A induces IL-22 Secretion in Committed Human TH17 Cells Via IL-9 nduction, Journal of Leukocyte Biology, 101:1-20, 2016.
Tomlinson I. and Holliger P. Methods for generating multivalent and bispecific antibody fragments. Methods Enzymol 326:461-479, 2000.
Torres et al., The Hermansky-pudlak 1 (HPS1) gene is associated with IBD in Puerto Rico independent of the known HPS1 insertion mutation. Abstract only, 2006 Journal unknown, 1 page.
Tremelling et al., Contribution of TNFSF15 Gene Variants to Crohn's Disease Susceptibility Confirmed in UK Population, Inflammatory Bowel Diseases, 14(6):733-737, 2008.
U.S. Appl. No. 09/395,345 Office Action dated May 9, 2001.
U.S. Appl. No. 09/419,408 Office Action dated May 30, 2002.
U.S. Appl. No. 09/419,408 Office Action dated Nov. 14, 2002.
U.S. Appl. No. 12/032,442 Restriction Requirement dated May 11, 2010.

(56) References Cited

OTHER PUBLICATIONS

U.S. Appl. No. 12/196,505 Final Office Action dated Dec. 7, 2012.
U.S. Appl. No. 12/196,505 Final Office Action dated Nov. 4, 2011.
U.S. Appl. No. 12/196,505 Final Office Action dated Nov. 9, 2010.
U.S. Appl. No. 12/196,505 Non-Final Office Action dated Apr. 12, 2010.
U.S. Appl. No. 12/196,505 Non-Final Office Action dated Jun. 14, 2013.
U.S. Appl. No. 12/196,505 Non-Final Office Action dated Mar. 25, 2011.
U.S. Appl. No. 12/196,505 Non-Final Office Action dated May 15, 2012.
U.S. Appl. No. 12/196,505 Restriction Requirement dated Apr. 23, 2009.
U.S. Appl. No. 12/527,376 Final Office Action dated May 25, 2012.
U.S. Appl. No. 12/527,376 Office Action dated Oct. 19, 2011.
U.S. Appl. No. 12/527,376 Restriction Requirement dated Sep. 1, 2011.
U.S. Appl. No. 12/528,055 Office Action dated Jul. 21, 2014.
U.S. Appl. No. 12/528,055 Office Action dated Apr. 30, 2015.
U.S. Appl. No. 12/528,055 Office Action dated Jun. 27, 2011.
U.S. Appl. No. 12/528,055 Office Action dated Mar. 1, 2016.
U.S. Appl. No. 12/528,668 Final Office Action dated Mar. 21, 2012.
U.S. Appl. No. 12/528,668 Non-Final Office Action dated Sep. 25, 2013.
U.S. Appl. No. 12/528,668 Office Action dated Sep. 2, 2011.
U.S. Appl. No. 12/528,668 Restriction Requirement dated May 18, 2011.
U.S. Appl. No. 12/529,106 Office Action dated Oct. 14, 2011.
U.S. Appl. No. 12/675,718 Office Action dated Feb. 6, 2013.
U.S. Appl. No. 12/675,718 Restriction Requirement dated Aug. 7, 2012.
U.S. Appl. No. 13/130,998 Office Action dated Apr. 29, 2015.
U.S. Appl. No. 13/130,998 Office Action dated Aug. 14, 2015.
U.S. Appl. No. 13/130,998 Office Action dated Feb. 21, 2017.
U.S. Appl. No. 13/130,998 Office Action dated Feb. 4, 2014.
U.S. Appl. No. 13/130,998 Office Action dated Jun. 13, 2016.
U.S. Appl. No. 13/130,998 Office Action dated Oct. 4, 2017.
U.S. Appl. No. 13/130,998 Office Action dated Sep. 16, 2013.
U.S. Appl. No. 13/140,874 Restriction Requirement dated Feb. 22, 2013.
U.S. Appl. No. 13/263,707 Office Action dated Apr. 6, 2015.
U.S. Appl. No. 13/263,707 Office Action dated Aug. 1, 2014.
U.S. Appl. No. 13/263,707 Office Action dated Dec. 22, 2015.
U.S. Appl. No. 13/263,707 Office Action dated Feb. 26, 2014.
U.S. Appl. No. 13/263,707 Office Action dated Jul. 6, 2017.
U.S. Appl. No. 13/263,707 Office Action dated Jun. 19, 2013.
U.S. Appl. No. 13/263,707 Office Action dated Jun. 27, 2016.
U.S. Appl. No. 13/263,707 Office Action dated Nov. 28, 2016.
U.S. Appl. No. 13/263,707 Office Action dated Sep. 17, 2018.
U.S. Appl. No. 13/372,359 Office Action dated Jan. 12, 2016.
U.S. Appl. No. 13/372,359 Office Action dated Jan. 23, 2015.
U.S. Appl. No. 13/372,359 Office Action dated Jul. 21, 2016.
U.S. Appl. No. 13/372,359 Office Action dated Jul. 27, 2015.
U.S. Appl. No. 13/372,359 Office Action dated Jun. 23, 2014.
U.S. Appl. No. 13/372,359 Office Action dated Jun. 8, 2017.
U.S. Appl. No. 13/372,359 Office Action dated Nov. 17, 2016.
U.S. Appl. No. 14/722,018 Office Action dated May 12, 2017.
U.S. Appl. No. 14/722,018 Office Action dated Nov. 14, 2017.
U.S. Appl. No. 14/779,893 Office Action dated Jul. 5, 2017.
U.S. Appl. No. 14/779,893 Office Action dated Mar. 21, 2018.
U.S. Appl. No. 14/779,893 Office Action dated Sep. 7, 2018.
U.S. Appl. No. 14/847,705 Office Action dated Sep. 8, 2017.
U.S. Appl. No. 14/890,699 Office Action dated Mar. 7, 2018.
U.S. Appl. No. 14/890,699 Office Action dated May 19, 2017.
U.S. Appl. No. 14/890,712 Office Action dated Dec. 6, 2017.
U.S. Appl. No. 14/900,024 Office Action dated Apr. 16, 2018.
U.S. Appl. No. 14/915,544 Office Action dated Mar. 22, 2018.
U.S. Appl. No. 15/245,875 Office Action dated Jan. 18, 2018.
U.S. Appl. No. 15/245,875 Office Action dated Jun. 12, 2018.
U.S. Appl. No. 15/792,266 Office Action dated Aug. 6, 2018.
U.S. Appl. No. 15/868,763 Office Action dated Feb. 21, 2019.
U.S. Appl. No. 15/868,763 Restriction Requirement dated Dec. 6, 2108.
U.S. Appl. No. 13/130,998 Office Action dated Apr. 2, 2018.
US13130998_52388-707-831_Notice of Abandonment_ dated Dec. 17, 2018.
Verhoeyen et al. Reshaping human antibodies: Grafting an antilysozyme activity. Science 239:1534-1536, 1988.
Walder et al. Oligodeoxynucleotide-directed mutagenesis using the yeast transformation system. Gene 42:133-139, 1986.
Wall et al., Transgenic Dairy Cattle: Genetic Engineering on a Large Scale, J. Dairy Sci, 80: 2213-2224, 1997.
Wang et al., Diverse Genome-Wide Association Studies Associate the IL12/1L23 pathway with Crohn Disease, Am J. Hum. Genet., 2009, vol. 84(3), pp. 399-405.
Ward et al. Binding activities of a repertoire of single immuno-globulin variable domains secreted from *Escherichia coli*. Nature 334:544-54, 1989 .
Whisnant et al., Rheumatoid Arthritis: Treatment with Azathioprine (IMURAN (R)), Clinical Side-Effects and Laboratory Abnormali-ties, Ann Rheum Dis., 1982, vol. 41, pp. 44-47.
Yagi et al., Interleukin-31 stimulates production of inflammatory mediators from human colonic subepithelial myofibroblasts. Inter-national Journal of Molecular Medicine, 19:941-946, 2007.
Yang et al. Genetic aspects of idiopathic inflammatory bowel disease. Kirschner and Shorter (Eds.), Inflammatory Bowel Disease Baltimore: Williams and Wilkins pp. 301-331 (1995).
Yang, Suk-Kyun et al., Association of TNFSF15 with Crohn's Disease in Koreans, American Journal of Gastroenterology 2008;103:1437-1442.
Yeager et al., Genome-wide association study of prostate cancer identifies a second risk locus at 8q24. Nature Genetics, 39(5):645-649, 2007.
Yoon et al. Colonic Phenotypes Are Associated with Poorer Response to Anti-TNF Therapies in Patients with IBD. Inflammatory Bowel Diseases. 23(8):1382-1393 (2017).
Zill et al., SNP and Haplotype Analysis of a Novel Tryptophan Hydroxylase Isoform (TPH2) Gene Provide Evidence for Associa-tion with Major Depression, Molecular Psychiatry, 2004, vol. 9, pp. 1030-1036.
Adams et al., Two-stage genome-wide methylation profiling in childhood-onset Crohn's Disease implicates epigenetic alterations at the VMP1/MIR21 and HLA loci. Inflamm Bowel Dis. 20(10):1784-1793 (2014).
Andoh et al.: Mucosal cytokine network in inflammatory bowel disease. World J Gastroenterol. 14(33):5154-5161 (2008).
Bamias et al.: Expression, localization, and functional activity of TL1A, a novel Th1-polarizing cytokine in inflammatory bowel disease. Journal of Immunology 171(9):4868-4874 (2003).
Benedict et al., Immunoglobulin Kappa light chain variable region, Partial (Mus musculus). GenBank: AAD39789.1, Jul. 26, 2016, 1 page.
Biener-Ramanujan et al., Functional signaling of membrane-bound TL 1A induces IFNgamma expression. FEBS Lett 11:2376-2380 (2010).
Burke et al.: Transcriptomic analysis of intestinal fibrosis-associated gene expression in response to medical therapy in Crohn's disease. Inflammatory Bowel Diseases. 14(9):1197-1204 (2008).
Camoglio et al.: Altered expression of interfero-gamma and interleukin-4 in inflammatory bowel disease; Inflamm Bowel Dis., 4(4): 285-290; Abstract only (1998).
Chu et al.: A genome-wide association study identifies two new risk loci for Graves' disease. Nature Genetics; 43/9:897-901 (2011).
Dambacher et al.: Interleukin 31 mediates MAP kinase and STAT1/3 activation in intestinal epithelial cells and its expression is upregulated in inflammatory bowel disease. GUT. 56:1257-1265 (2007).
dbSNP Short Genetic Variations. Submitted SNP (ss) Details: SS566368983. NCBI. Uploaded Nov. 22, 2012. Retrieved Aug. 6, 2020. URL: https://www.ncbi.nlm.nih.gov/projects/SNP/snp_ss.cgi?subsnp_id=566368983.
Dermot et al.: Genetic epistasis of IL23/IL17 pathway genes in Crohn's disease. Inflamm Bowel Dis. 15(6):883-889 (2009).

(56) References Cited

OTHER PUBLICATIONS

European Patent Application No. 17767679.8 Supplementary European Search Report dated Jul. 22, 2019.
European Patent Application No. 18201967.9 European Search Report dated Mar. 6, 2019.
European Patent Application No. EP14773989.0Strawman Limited Opposition Against EP2978440 dated Jul. 1, 2020.
Fransen et al., Inflammatory bowel disease: the genetic background and beyond. University of Groningen PhD Dissertation http://www.rug.nl/research/portal/files/12805965/Complete_dissertation.pdf (2014).
GeneCard DR3 retrieved from: http://www.genecards.org/cgi-bin/carddisp.pl?gene=TNFRSF25&search=DR3 on Apr. 3, 2018; 16 pages.
GeneCards for JAK2 retrieved from: http://www.genecards.org/cgi-bin/carddisp.pl?gene=JAK2&search=jak2 on Oct. 25, 2019.
Heusch et al., IL-9 exacerbates colitis induced by CD4+ CD45RBhigh T cells transfer, via directed activation of in vivo antigen-experienced T cells. Cytokine 56:PS1-056, p. 31 (2011).
Hundorean et al., Functional relevance of T helper 17 (Th17) cells and the IL-17 cytokine family in inflammatory bowel disease. Inflammatory Bowel Disease 18:180-186 (2012).
International Search Report for PCT/US2011/028694 dated Jul. 27, 2011.
Jikihara et al., Interferon-y Inhibits the Synthesis and Release of Renin from Human Decidual Cells, Biology of Reproduction, 54:1311-1316, 1996.
Jostins et al.: Host-microbe interactions have shaped the genetic architecture of inflammatory bowel disease. Nature; 491/7422:119-124 (2012).
Leong et al., NOD2/CARD15 gene polymorphisms and Crohn's disease in the Chinese population. Aliment Pharmacol Thera 17:1465-1470 (2003).
McGovern et al., Genetics of inflammatory bowel diseases. Gastroenterology 149(5): 1163-1173 (2015).
Nalleweg et al., Inflammatory bowel disease patients failing anti-TNF therapy show activation of the Th9/TH17 pathway. Gastroenterol 142(5)(Suppl1):S867-868; Abstract No. Tu1878 (2012).
Nowak et al., IL-9 as a mediator of Th17-driven inflammatory disease. Journal of Experimental Medicine 206(8):1653-1660 (2009).
Oh et al., A randomized, controlled trial to evaluate the effect of an anti-interleukin-9 monoclonal antibody in adults with uncontrolled asthma. Respiratory Research 14:93 (2013).
Papadakis et al.: Dominant Role for TL1A/DR3 Pathway in IL-12 plus IL-18-Induced IFN-y Production by Peripheral Blood and Mucosal CCR9+ T Lymphocytes, the Journal of Immunology. 174:4985-4900 (2005).
Pappu et al., TL1A-DR3 interaction regulates Th17 cell function and Th17-Mediated autoimmune disease. Journal of Experimental Medicine, 205(5):1049-1062, 2008.
PCT/US2008/057820 International Preliminary Report on Patentability dated Sep. 22, 2009.
PCT/US2008/080526 International Preliminary Report on Patentability dated Apr. 20, 2010.
PCT/US2009/059190 International Preliminary Report on Patentability dated Apr. 5, 2011.
PCT/US2009/061698 International Preliminary Report on Patentability dated Apr. 26, 2011.
PCT/US2009/069531 International Preliminary Report on Patentability dated Jun. 29, 2011.
PCT/US2014/038333 International Search Report and Written Opinion dated Nov. 20, 2014.
PCT/US2014/054425 International Preliminary Report on Patentability dated Mar. 8, 2016.
PCT/US2017/023082 International Search Report and Written Opinion dated Aug. 15, 2017.
Prehn et al., The T Cell Costimulator TL 1A Is Induced by Fe R Signaling in Human Monocytes and Dendritic Cells. J Immunol 178:4033-4038 (2007).
Prometheus Biosciences, Inc. Form S-1 Registration Statement as filed with the Securities and Exchange Commission on Feb. 19, 2021 (246 pages).
Reference SNP (refSNP) Cluster Report: rs598672, pp. 1-4 printed from http://www.ncbi.nlm.nih.gov (2020).
Reference SNP (refSNP) Cluster Report: rs666595, pp. 1-4 printed from http://www.ncbi.nlm.nih.gov (2020).
Syvanen, Ann-Christine, Accessing Genetic Variation: Genotyping Single Nucleotide Polymorphisms, Nature Reviews, 2: 930, 2001.
UniprotKB Database, Q8NI17 (IL31R_Human), Retrieved online Sep. 5, 2019. Retrieved from< url https://www.uniprot.org/uniprot/Q8NI17>. Jul. 31, 2019</url>.
U.S. Appl. No. 12/528,055 Office Action dated Mar. 27, 2012.
U.S. Appl. No. 12/528,055 Restriction Requirement dated Apr. 6, 2011.
U.S. Appl. No. 14/779,893 Final Office Action dated Apr. 26, 2019.
U.S. Appl. No. 14/779,893 Office Action dated Sep. 12, 2019.
U.S. Appl. No. 15/557,213 Restriction Requirement dated May 21, 2019.
U.S. Appl. No. 15/868,763 Final Office Action dated Oct. 1, 2019.
U.S. Appl. No. 15/921,160 Office Action dated Feb. 27, 2020.
U.S. Appl. No. 15/946,632 Office Action dated May 1, 2020.
U.S. Appl. No. 15/946,632 Restriction Requirement dated Nov. 22, 2019.
U.S. Appl. No. 16/025,769 Office Action dated Jul. 6, 2020.
U.S. Appl. No. 16/025,769 Restriction Requirement dated Feb. 11, 2020.
U.S. Appl. No. 16/355,376 Restriction Requirement dated Jun. 5, 2020.
U.S. Appl. No. 16/388,101 Restriction Requirement dated Jul. 10, 2020.
Written Opinion for PCT/US2011/028694 dated Jul. 27, 2011.
Yamazaki et al., Single nucleotide polymorphisms in TNFSF15 confers susceptibility to Crohn's disease. Hum Mol Genet 14:3499-3506 (2005).
Zhang et al.: Structures and biological functions of IL-31 and IL-31 receptors. Cytokine Growth Factor. 19(5-6):347-356 (2008).
Zheng et al.: 2013 AGA Abstracts 2013 144 5 Supplement 1: p. S-132; Abstract 735 (2013).
Zheng et al.: Dynamic expression and significance of IL-31 in the process of pulmonary fibrosis in experimental mice. Shadong Medical Journal. 49(13):26-27 (2009).
Zheng et al.: Sustained TL1A (TNFSF15) Expression on both Lymphoid and Myeloid Cells Leads to Mild Spontaneous Intestinal Inflammation and Fibrosis. European Journal of Microbiology and Immunology 3(1):11-20 (2013).
Gonsky et al.: Association of RNASET2 Gene Polymorphisms with Decreased Expression and Clinical Characteristics of Severity in Crohn's Disease; HHS Public Access; Gastroenterology; 153(1); 219-232 (2017).
Kang et al.: Polymorphisms of the centrosomal gene (FGFR1OP) and lung cancer risk: a meta-analysis of 14 463 cases and 44 188 controls. Carcinogenesis. 37(3):280-289 (2016).
PCT/US2019/063429 International Preliminary Report on Patentability dated Jun. 10, 2021.
PCT/US2019/063429 International Search Report and Written Opinion dated Mar. 3, 2020.
Roiz et al.: Human recombinant RNASET2: A potential anti-cancer drug; Oncoscience; vol. 3, No. 2; 71-84 (2016).
Smirnoff et al.: A Recombinant Human RNASET2 Glycoprotein With Antitumorigenic and Antiangiogenic Characteristics; American Cancer Society, 107(12), 2760-2769 (2006).

* cited by examiner

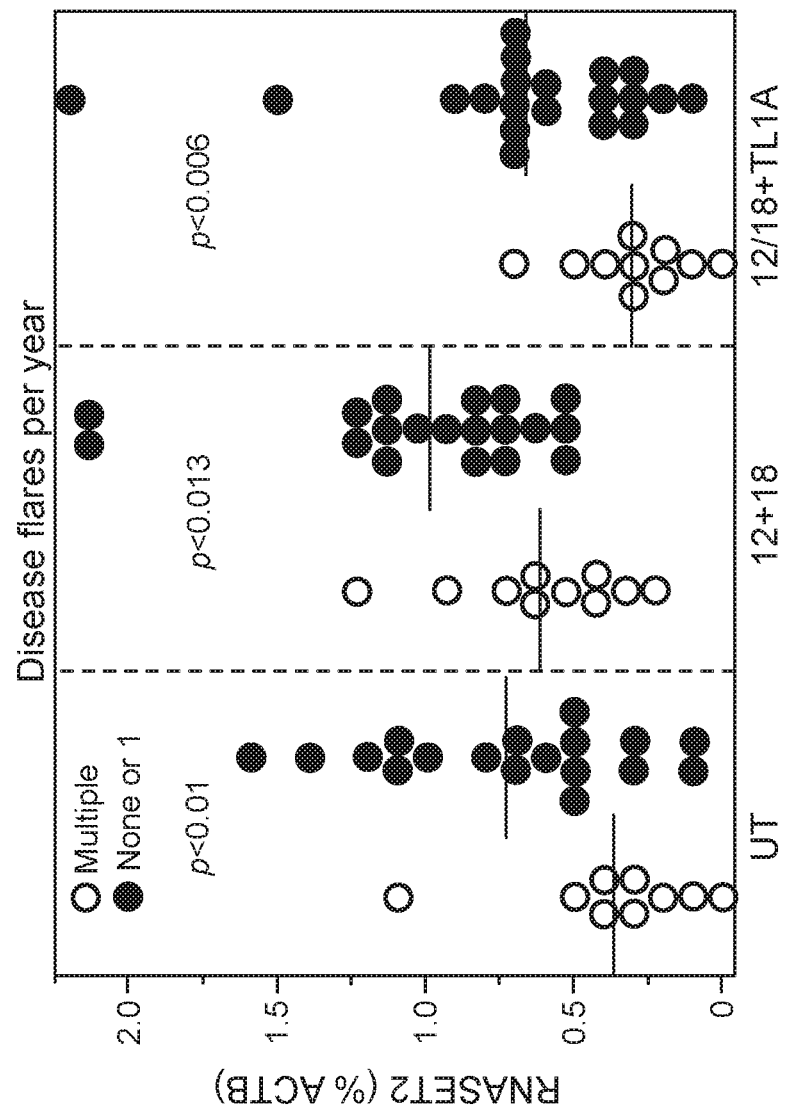

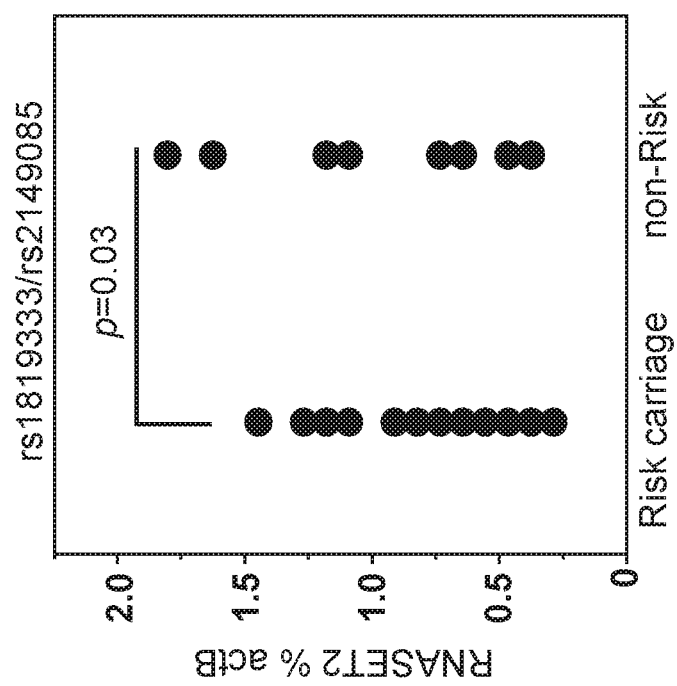

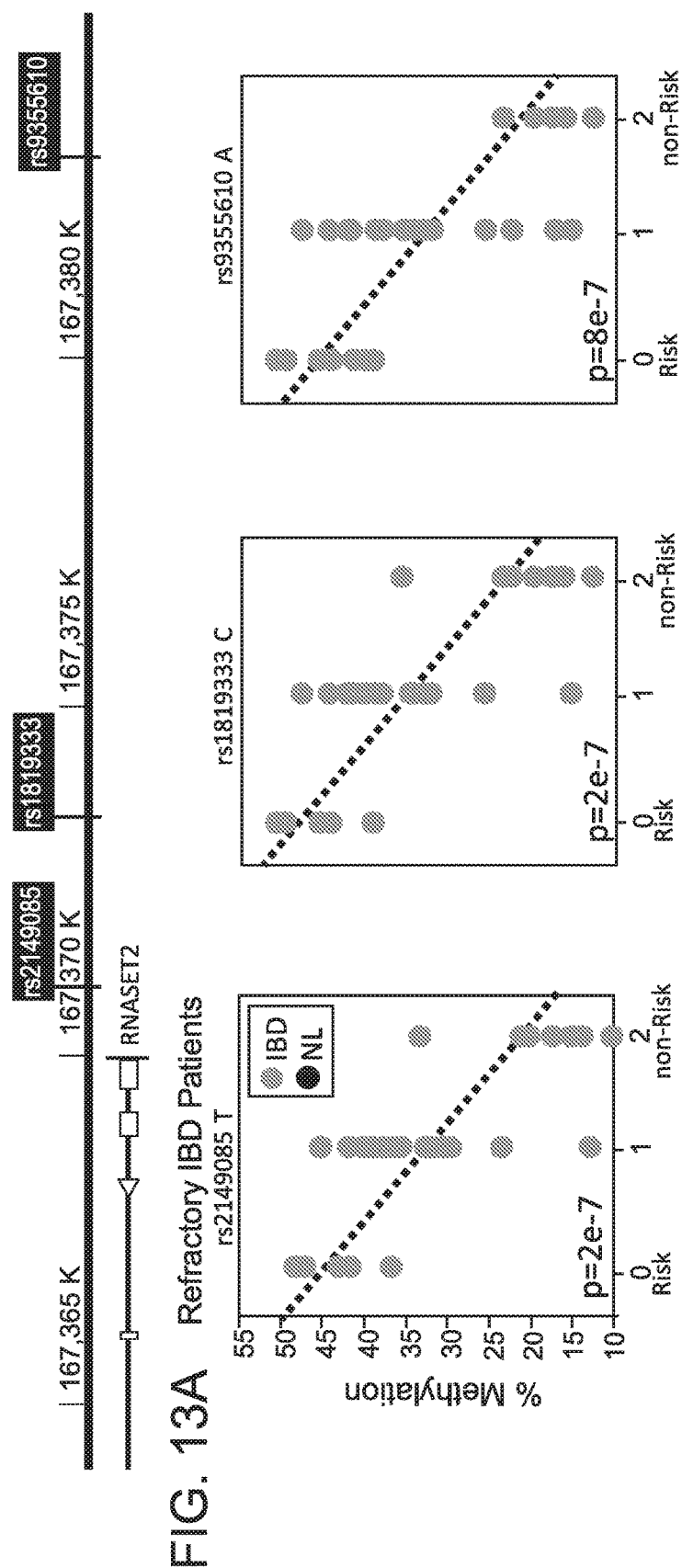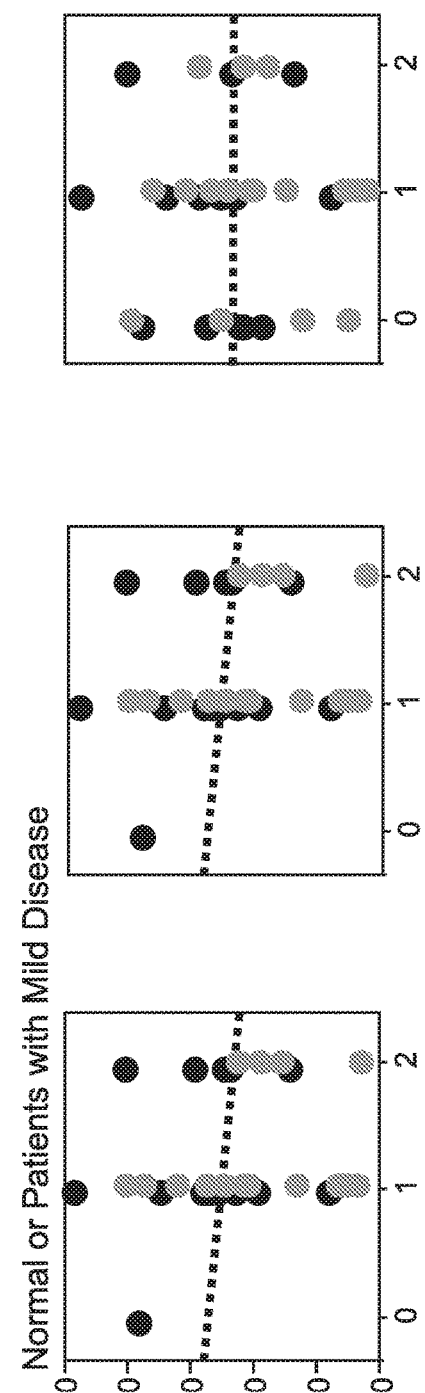
FIG. 13A
FIG. 13B

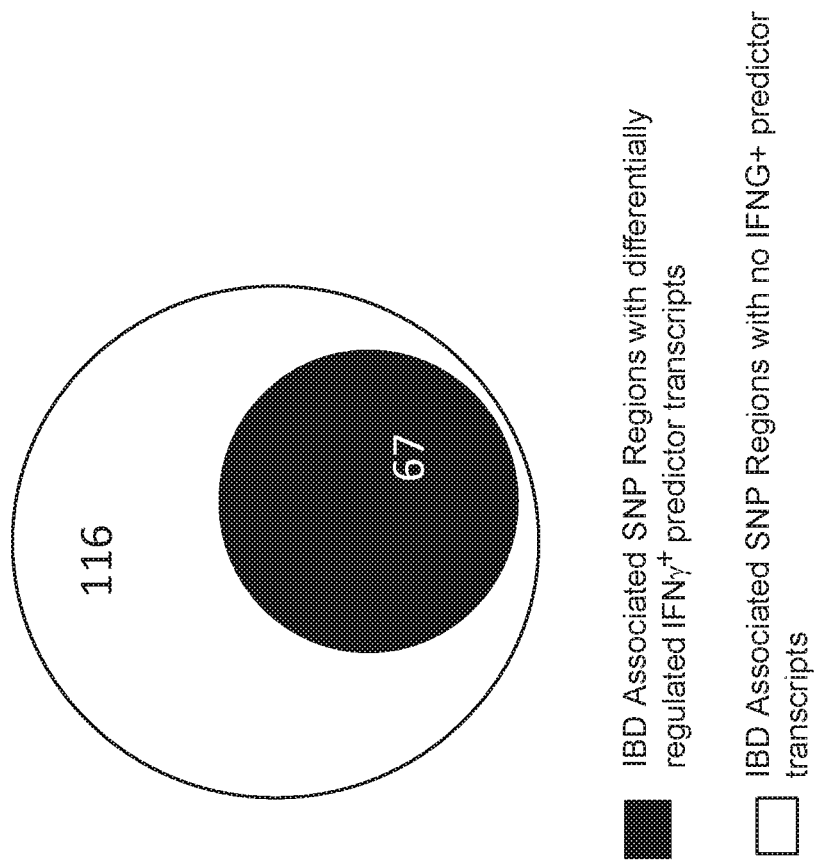

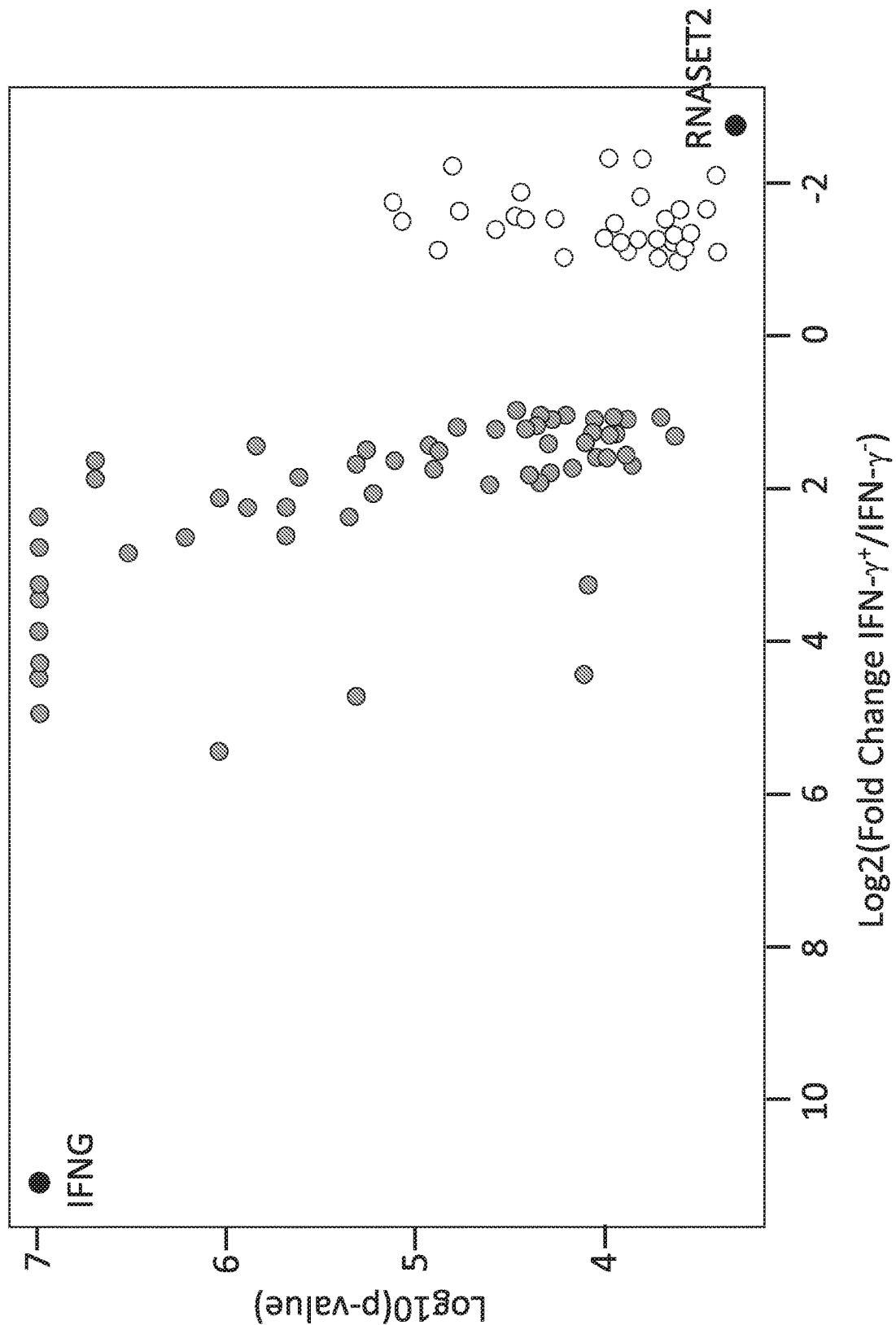

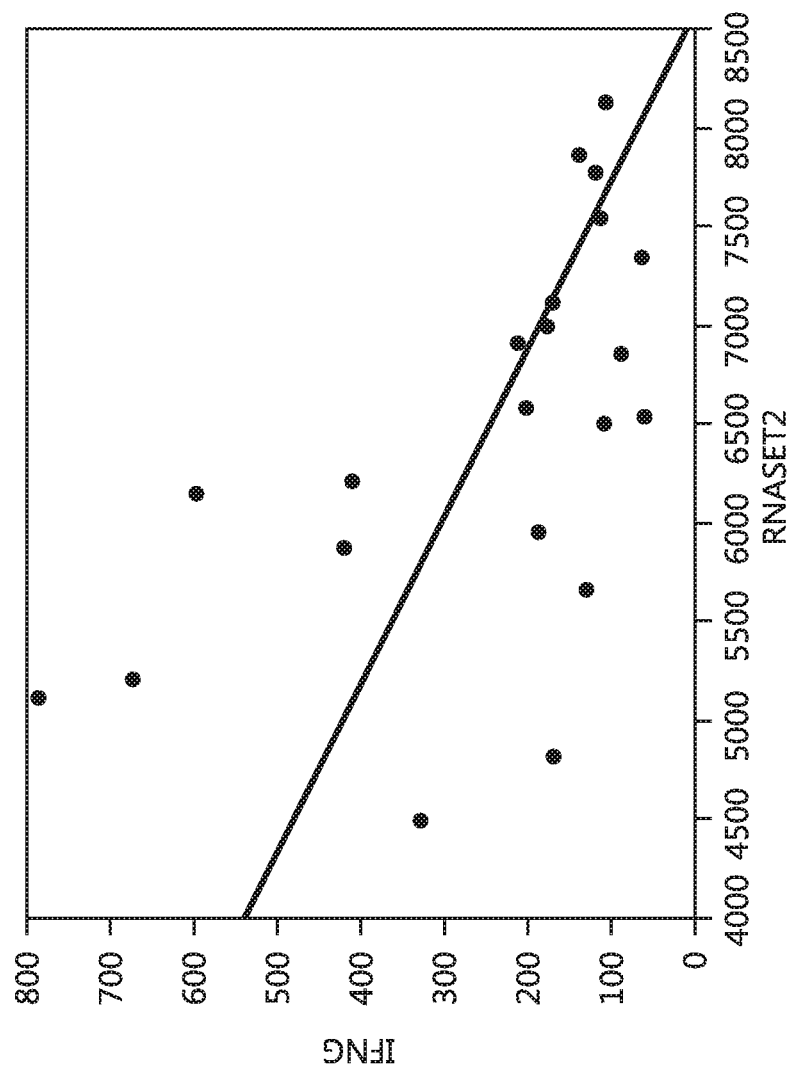

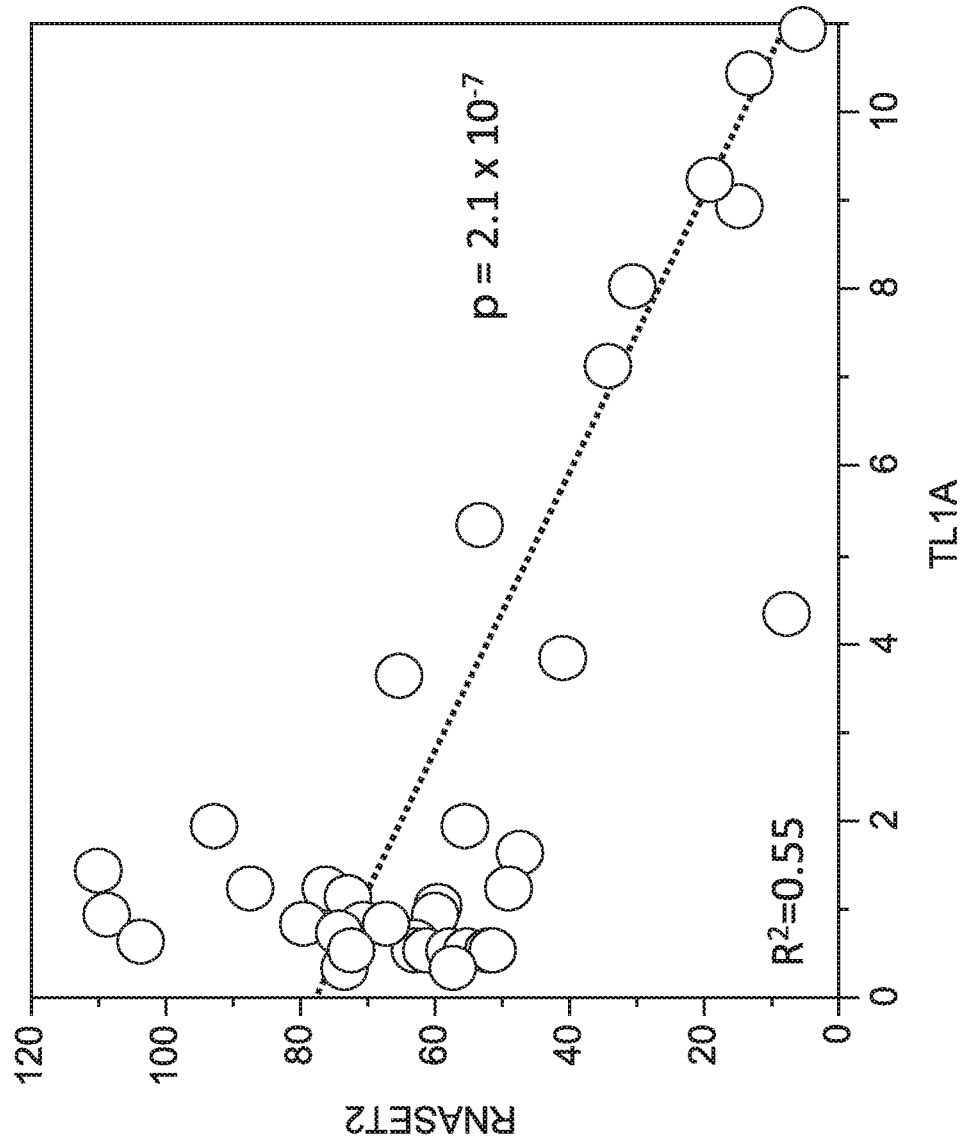

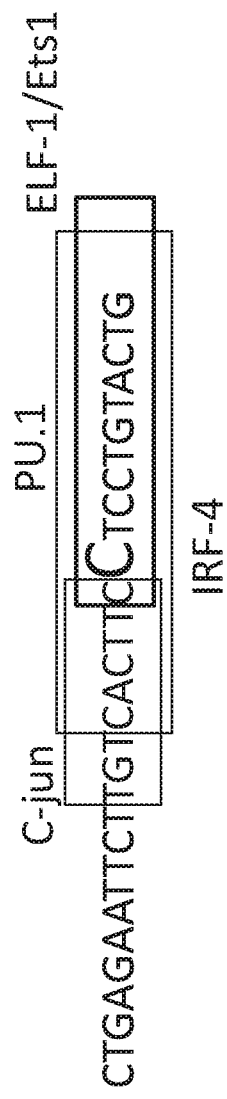
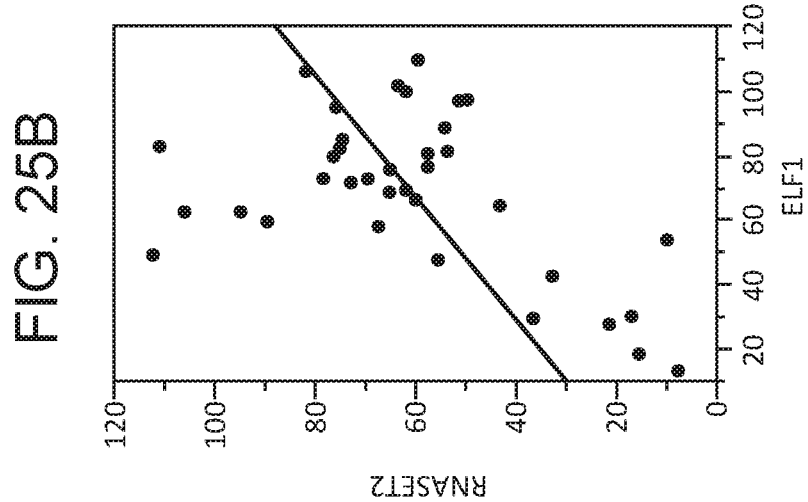
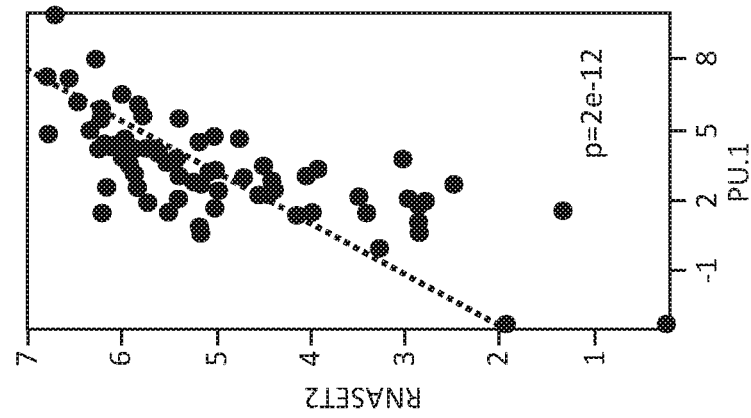
FIG. 25A
FIG. 25B

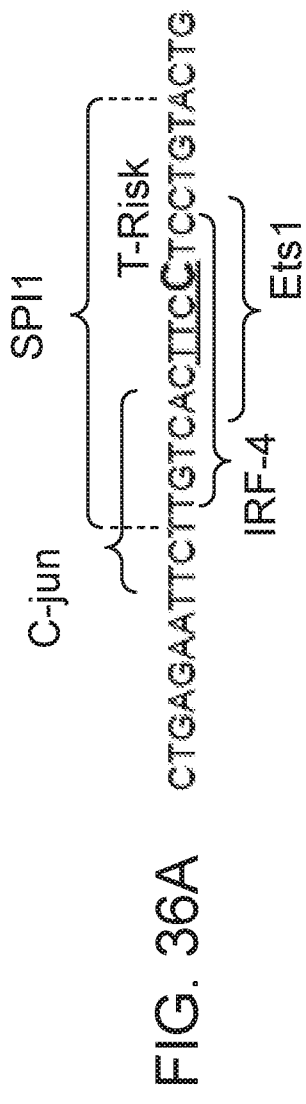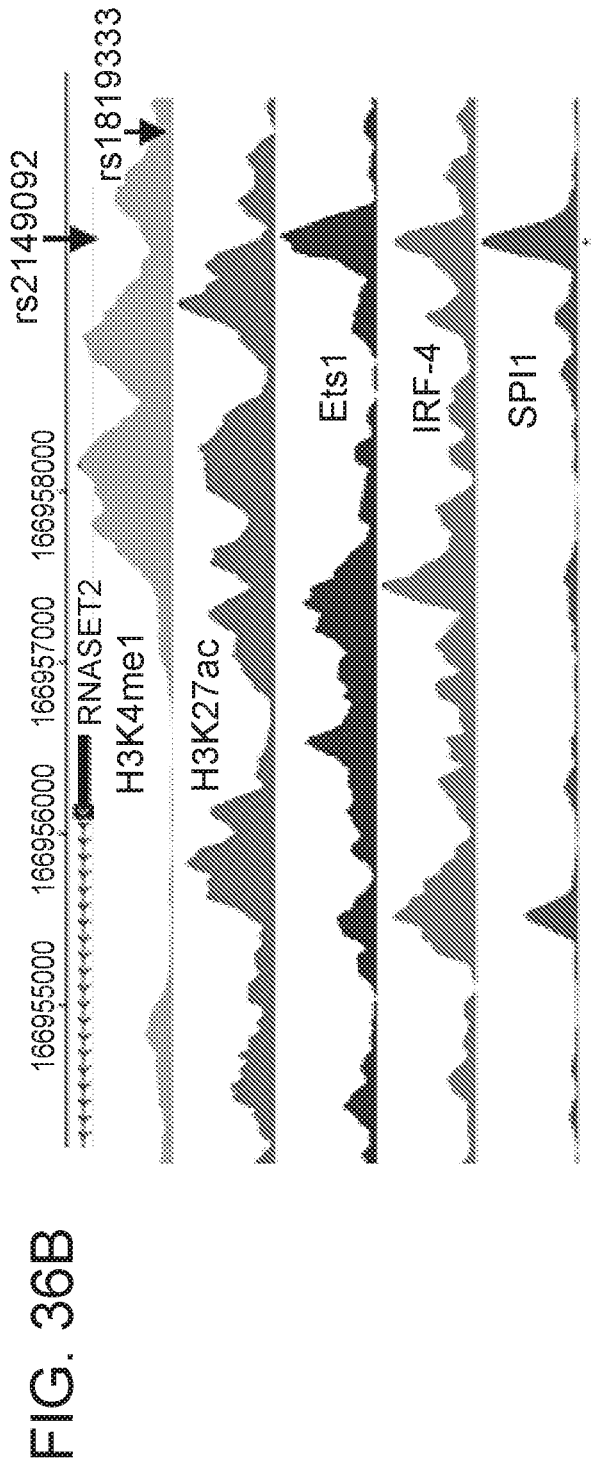
FIG. 36A
FIG. 36B

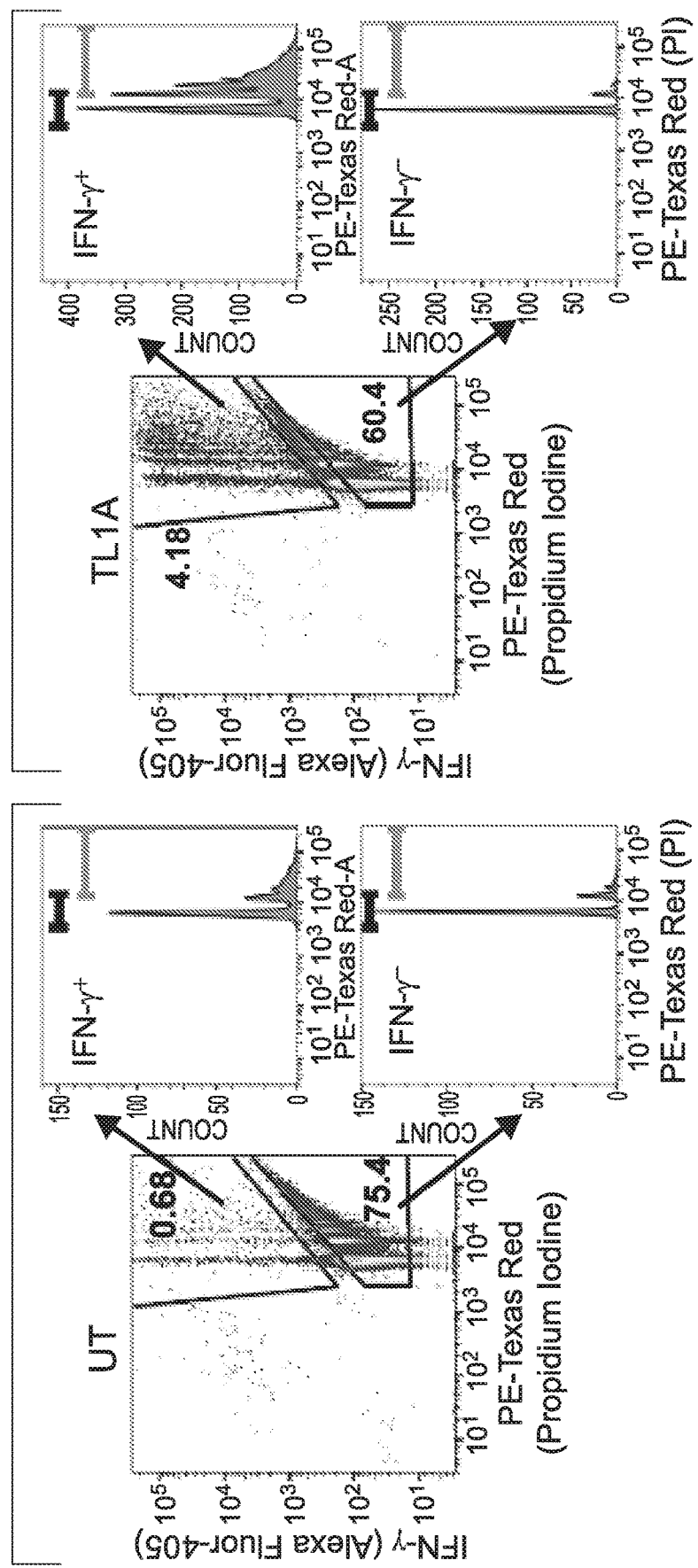

SEQUENCE LISTING

```
<160> NUMBER OF SEQ ID NOS: 16

<210> SEQ ID NO 1
<211> LENGTH: 1001
<212> TYPE: DNA
<213> ORGANISM: Homo sapiens

<400> SEQUENCE: 1
ctggcatggg ccccaccaag accccatatc tcattccgta ttcacaattt taccttcttg      60
ttcttaaaga aggacatcca aatggaaaag ctctcaaccc cccaaaactt ggatgtgaac     120
ctggagcatc tgtcatctgt cttgttcact acttgtccac ctaccaggat cctaaacgga     180
accctacgta gggaagaggc agtggctgta aaggctggat ttgggtctgg aagccgccca     240
gctttacgaa aacaaagagg gctccagcat caagcaggtg ggcaggggcc agagtgggaa     300
ttacattgac tcacacaaca tagtgtaaaa gggtacaaac tatgaggttt aaaagatgct     360
gctggcttgt atagaaacat gtccttagga gaggggaggg ggacaggatg gcaacagcca     420
tgtctatgaa cagacatcct taaatccttg ttaattctga agagaccaag atactttcac     480
```

| | |
|---|---|
| cacacaacct cttcttggca ktagctccag gtttcctgtt tccatgccag cttttgctgg | 540 |
| gttatgctac aataatacac cgccccaaa tctcagtgtc tcacttaaac ggaagttgat | 600 |
| catttatcat tcatttgccc atattccatg ctggctatgc gtcagatgcc actgtggtcc | 660 |
| acggtatttt tcactctgga acccaggcgg taggaacagc ccatatctgg tgctggccat | 720 |
| tccaatggca gagcagtggc acaactacac agtttaggat tctcatgctc taaagagctt | 780 |
| tgtcacactt gaaagaatct caccttaaaa actcctttcc atcctgaatt acttatttgc | 840 |
| tgagaaagtg aggccagctg ctgggtgttt ccctgcccct tctcttcttt ttcttttct | 900 |
| ttttttttt ttgagacaga gtctcactct gtcagccagg ctggagtgca gtcagtggca | 960 |
| caatctcggc tcacagcaac ctccgtctcc caggctcaaa c | 1001 |

<210> SEQ ID NO 2
<211> LENGTH: 1001
<212> TYPE: DNA
<213> ORGANISM: Homo sapiens

<400> SEQUENCE: 2

| | |
|---|---|
| attagatcag agaaggttga ccccgtggcc agcctgttct cagggggac tgactcaggc | 60 |
| taagatgagg ccaaaagtcc tcagcctcgg gggaagagag gagcctcacc aagtttgctt | 120 |
| aacaagtgtg ttatttctat tgactggctc atcattgatg aggtgaagaa tgggaattgg | 180 |
| aggatctgtg tctggctttg tcctaggtaa tgggtagggg gtggagtgag gggagcatcc | 240 |
| gtcactttc cttttttttt ttttttttt ggagacagcg cccagctgca tcacttctat | 300 |
| cactcttacc tatgttatgt ggggaagaag ggggtctctc gcagcaagcc actttccaca | 360 |
| actcacagag aggagatttt tatcagataa attcagcagc gtcctaccca gcctgaagaa | 420 |
| gccacccagt catttcctgt tgcacttcct tgtttatttt cgacacagtt ctccccaccc | 480 |
| ctgagaattc ttgtcacttc ytcctgtact gcccacttct actcccccac ccccacatcg | 540 |
| gaagctaatg aggagcttca ggcccccttgc tggcatgggc cccaccaaga ccccatatct | 600 |
| cattccgtat tcacaatttt accttcttgt tcttaaagaa ggacatccaa atggaaaagc | 660 |
| tctcaacccc ccaaaacttg gatgtgaacc tggagcatct gtcatctgtc ttgttcacta | 720 |
| cttgtccacc taccaggatc ctaaacggaa ccctacgtag ggaagaggca gtggctgtaa | 780 |
| aggctggatt tgggtctgga agccgccag ctttacgaaa acaaagaggg ctccagcatc | 840 |
| aagcaggtgg gcaggggcca gagtgggaat tacattgact cacacaacat agtgtaaaag | 900 |
| ggtacaaact atgaggttta aaagatgctg ctggcttgta tagaaacatg tccttaggag | 960 |
| aggggagggg gacaggatgg caacagccat gtctatgaac a | 1001 |

<210> SEQ ID NO 3
<211> LENGTH: 1001
<212> TYPE: DNA
<213> ORGANISM: Homo sapiens

<400> SEQUENCE: 3

| | |
|---|---|
| acatatcttt gcattttcct ttaatctctt tcaagcattt ggccacaaat taaaaagtag | 60 |
| agtctattta gtctaaaggc tatcttgttc cttcctcaaa atatagttag tcattaaagt | 120 |
| aatttacttt tactcttgga gctgatttg gcttgggaag ctagttaaac cacaaaattg | 180 |
| ttacctgga ctagattaag atgatgactt atgacttgtc ttcactagct tgaagtaaac | 240 |
| cagatgtcct catcatttgg cttttattat tgtcctaata agtctgtgtg tgggatggct | 300 |
| aattggctca tcatagtgtt aaccttctgt acatgtctgt taatatcaac atcaaacaga | 360 |

```
agcatcgggg gaaagaacat taaaggcagg tacaggggaa gagactgaag gttgctctgc    420
accagacaag caacaggaat agaaaatgca ccagaacgca aagccagcca tggcgcatgg    480
ctcagaatac tagaaattag rcttttcccc agtctaactg tctctactgg tgtgctaacc    540
tttcatctta gcatctctgc tggtagtttc tgctccttct gcccttcaca tcctcttcat    600
ttgtcaaaat gcaactcata tttcatcttt ttcttgaaac ttggcacaat ctaagctgat    660
ccggatcagc tacttcaaaa tggagcaggg gtggggctc cagcagcagg aagagcagtt    720
tcagaactaa gggcgtcaaa taaggaacag atgtgggttg ttacagattg ggaacggatg    780
tgggttacag attgggaacg gctggaaggt tgtttactgt aattacgggc aaggaggcaa    840
ggtagttagg ctttgaaaat aaaggacaag aggaaccttt gaggaggaac tcactgtttc    900
caacaacttt tagaatcttg ctaggataca aatgcaaatt attttttgtct catagaaaag    960 ataatttctg aagttaagtt ttagttctct gaaggtgcat t                      1001
```

<210> SEQ ID NO 4
<211> LENGTH: 1001
<212> TYPE: DNA
<213> ORGANISM: Homo sapiens

<400> SEQUENCE: 4

```
ctactcgggt cactctcctg gaaacctctc cagtctcccg gtgctaggtg ctgggagcac     60
caacattcct agaagggcct ggccctcacc cagccctggg cctcacctgc ccctccccgc    120 gggcccagg agcccggaag tcatctctgt gggggcagca aagagccgcc tcggggcgcg    180
acctgggaag tcatcttgtg agggatcccc tcccagaggg acgggccacc ccccacggat    240 gaagggact tcatgtcagc cccaccttgg cgtagccagg gccagtccca taggcccggt    300
ctcctccccc aacaccctgg ccttcccagc ccttcagagg cacgggttcc cctgcacccg    360
cggccccgcc cacgggctgt gcacccggca ttgtctctgc agatgtttct cctctttccc    420
ttccctgtcc gcacacccac agctagttaa ggctattcct atttacacgt cgagtaaact    480
gcgccttcct cggggtcctc ygccactggt aactgtctaa atagcaggtg ggcctgtagc    540
ctgctctccc acaggcctgg accttgcctg catgcattac cattctttga acaaaatat    600 ttaaatgatt aatctgtttt tcccactaga ctgcaaggca aggcccatgt ctattttgcc    660
caccttgagt ccctgccact gagcacagtg gatggggac agtcggtgct caataaaatg    720
ccacctgtgg aacagatggg gggggaaaat ggctgacacc tccttagctc ctccaggacc    780
tcctacaggt catggtgtta ttctcgttct ccttttccct aacgacttat ttgtttcttt    840
ccggctcctt tcattccttc ctctcaagaa tataggcaca cgccacagtt cttttctct    900 tttctttttaa gctaaaaaaa taattttctt aaaacaaaag tgcttcccag aatcctcatt    960
ttcctttaaa tcacagtccg gtgtgtttaa acagccctt g                      1001
```

<210> SEQ ID NO 5
<211> LENGTH: 1001
<212> TYPE: DNA
<213> ORGANISM: Homo sapiens

<400> SEQUENCE: 5

```
agtatctctc tctcccgacc ccctccccac ggtggacaca ttctccttca cagaagaaag     60
gccctgggac ccctcagcta ccggtcccga aactgcaaac ctagaccccc ctgtgctcca    120
acctcctctt ggatgagggg cctcctcctc gctctactga gggagtcctc ccccactgct    180
```

| | |
|---|---|
| tctgcctcgt gccttctgac tcaaacctcc taggaggaca cctgcatcct ctcagcctcg | 240 |
| tactctggct ttgggggggca ccaagctggg gtcaccagct ccagcagatg cctttttgccc | 300 |
| cttgcctcag acactgtcca ctccttccac gaagctctcc tgtgggcctc ctgagcacct | 360 |
| gctccactga ccgcctggct gccggctgcc attcctgccc catctccttg gcctccttct | 420 |
| tctccttcac ttatggcgag ttttcactgc cttccattgg aagctatctt ttccacccca | 480 |
| tggcttccct cccatccaga gctctcttcc tggactctgc agagagctcc aattcgaact | 540 |
| gtccatgcag ggtctgatca tcctcccctc ttgccaagct tctgacacca gcaaatgtca | 600 |
| ctcctatgga ggcctgaggc aggacctctg cctctcccat cccctgtcc caaacggcca | 660 |
| agtccaagct ccccacacta tcccttcctc tccagctgca tagccatagg cccagattcc | 720 |
| cccagcatgt gacctactcg gagggtctct gtgcctagcc tctccccagt accacgggga | 780 |
| cagcaacaag caaacacccc ggcctactca gagctcagcg ctgctggagg atgaggtcct | 840 |
| catgtctatg gctcccaccc ggccccttcc caaccctcct gctctgcccc tgagcccct | 900 |
| caagaagcaa ctggtcccat atctcccagc ccccagcccc cagctctgct ccactgaacc | 960 |
| actcccctca gggcctgggc aggctgcagg cctccatctc a | 1001 |

<210> SEQ ID NO 6
<211> LENGTH: 2332
<212> TYPE: DNA
<213> ORGANISM: Homo sapiens

<400> SEQUENCE: 6

| | |
|---|---|
| ctcagtgctc agcggcagat ccttgctgtg actgtttatg gcactaagtg tctgttccaa | 60 |
| cacatttgcg cggaagagta cgcaggtact tttaaattaa ctttattgag gctaatttat | 120 |
| atgcaataaa tgtcaccgat tgaagggtac aattcaacag gtcttgacaa gggcaccag | 180 |
| ccatgtgcca cccccacaat caggatagag gacatttctg ccaccacaaa agccccttgt | 240 |
| gtcgcccaac cccagccaat cccttcttcc cgtcctgatg acaatccctg atttcattcc | 300 |
| tgccactgtt attttgcctt ttctagaaat gttagggggtg gaatggtgca gtgcatggtc | 360 |
| tcttctgcct ggatttctta ccgagcgaag gttttgagtc accccgttg gagcatgcat | 420 |
| tagtcgcccg ttccttttca tggttgagta gtatatgctg ttgcatggat acacttcaac | 480 |
| tcgggtatct gctcaccagt tcacagacat ttgggtcttt ttcagtttgg gacggttaag | 540 |
| aataaacctg ctgggaatgt tccagtgtta atcctcccat gtctcttggg tagacatgta | 600 |
| ggagtcggtt gcaggttccc atggtggatg catgttcagc tgtgcaagaa aggacccccac | 660 |
| tgtctccttg gagtggctgt gtgatcttgc agtcccacca acaaagtgtg agagcccag | 720 |
| atgcaccatg tcctctccca gcttccagcc ccctgtttaa tcttagtcct tccagtggga | 780 |
| tctctgtgtg tgtgtctgtg tgtgtgtgtg tatgtgtgtg tgtgttttgg acggagtctc | 840 |
| tctctgtcac ccaggctgga ctgcagtggc gtaatctcag ctcattgcaa cctccgcctc | 900 |
| ccgggttcaa ctgattctcc tgcctcagcc ccccaagtag ctgggattac aggagcacgc | 960 |
| catcacgcct ggctaatttt tgtattttta gtaaagatgg ggtttcacca tgttggccag | 1020 |
| gatggtctcg aactcctgga cttaagtggt ccgtctgcct cggcctccca aattgctggg | 1080 |
| attacaggcc tgagccactg ttcccagcct tcattgtggt tttaatttgc attttcctca | 1140 |
| tgattaatgg cattgagcgt cttttttgtg tgtgtatttg ccatccatgt attttccttg | 1200 |
| gtgaattgcc tgttcacatt tccccctgtt tcttattgtt tatgtttttg ataggggagtt | 1260 |
| gtaaaaatta tttgtatatt ctggrtataa cctattatca gatataagct ttaacatact | 1320 |

-continued

```
ttttctatt caatatatat atgtttcact ttcttgagtg tctttcaaag agcagaagtt    1380
ttacattttg tacaatcaag tacaatttat catttttttt acagttcatt cttttgcaa     1440 tttatataag aagcttcttt ttccagggtc acaaagattt tctcccattt ttccttctag   1500
atgttttatg ctttagctct cacatttaga tttataactc atttgagtta ccttttgcaa   1560
atggtgtgag gtaagcagta aggatcgact ttttgttcat gtcattccag gaccatttac   1620
tgaagactgt tcttttccca ttgagttacc ttggcaccta agttaaaaat cagtccgcca   1680
tctatatgtg gatctatgtc tggcctctgt tctgttccag tgatttatgt aactgtcctt   1740
tcagaaatcc aacaccgtca tggttagtgt agttccttgt cagctctgag actgggtagt   1800
gtgagtcctc cattttttt ttatcttttt caaaattgtt ttggctatt taatttcctt     1860 gaatttctat aaaaattttg gaattgactt gtcaatttct caaaaaaaaa acctaccat    1920 aattttgatt tagtttatgt tgtatctaca gatcgatttg gggagaaatt atatcttgaa   1980
attgaatctt tgataaattt gaacatgaaa tgtcattgaa aattgaacat gataaatttc   2040
tccattaatt taggtcttat ttaattttg ccaacaatgt tttgtagttt ttagcatata   2100
aatctcacat aaattttgtt agagctatcc ataagtattt tacattttat gatacaattg   2160
tatatataat tattgatact attatatatg atatatgtgt gtatatatat atatatatat   2220
atatatatat atatatatag ttttaacatc caaatggtaa ttccaattgg tgtattttat   2280
tttacatatt gtatatttca cctcccatgc cctccacccc tgccatgctc tg            2332
```

```
<210> SEQ ID NO 7
<211> LENGTH: 25
<212> TYPE: RNA
<213> ORGANISM: Artificial Sequence
<220> FEATURE:
<223> OTHER INFORMATION: synthetic construct

<400> SEQUENCE: 7
gcaagagaaa uucacaaacu gcagc                                              25

<210> SEQ ID NO 8
<211> LENGTH: 27
<212> TYPE: RNA
<213> ORGANISM: Artificial Sequence
<220> FEATURE:
<223> OTHER INFORMATION: synthetic construct

<400> SEQUENCE: 8
gcugcaguuu gugaauuucu cuugcuu                                            27

<210> SEQ ID NO 9
<211> LENGTH: 25
<212> TYPE: RNA
<213> ORGANISM: Artificial Sequence
<220> FEATURE:
<223> OTHER INFORMATION: synthetic construct

<400> SEQUENCE: 9
cuuccucucu uucucucccu uguga                                              25

<210> SEQ ID NO 10
<211> LENGTH: 27
<212> TYPE: RNA
<213> ORGANISM: Artificial Sequence
<220> FEATURE:
<223> OTHER INFORMATION: synthetic construct
```

```
<400> SEQUENCE: 10
ucacaaggga gagaaagaga ggaagga                                    27

<210> SEQ ID NO 11
<211> LENGTH: 22
<212> TYPE: DNA
<213> ORGANISM: Artificial Sequence
<220> FEATURE:
<223> OTHER INFORMATION: synthetic construct

<400> SEQUENCE: 11
ttgggttctc ttggctgtta ct                                         22

<210> SEQ ID NO 12
<211> LENGTH: 23
<212> TYPE: DNA
<213> ORGANISM: Artificial Sequence
<220> FEATURE:
<223> OTHER INFORMATION: synthetic construct

<400> SEQUENCE: 12
atccgctaca tctgaatgac ctg                                        23

<210> SEQ ID NO 13
<211> LENGTH: 21
<212> TYPE: DNA
<213> ORGANISM: Artificial Sequence
<220> FEATURE:
<223> OTHER INFORMATION: synthetic construct

<400> SEQUENCE: 13
cttccttgca ggactcacca c                                          21

<210> SEQ ID NO 14
<211> LENGTH: 22
<212> TYPE: DNA
<213> ORGANISM: Artificial Sequence
<220> FEATURE:
<223> OTHER INFORMATION: synthetic construct

<400> SEQUENCE: 14
gctgatgtga aggtgcaaac tc                                         22

<210> SEQ ID NO 15
<211> LENGTH: 17
<212> TYPE: DNA
<213> ORGANISM: Artificial Sequence
<220> FEATURE:
<223> OTHER INFORMATION: synthetic construct

<400> SEQUENCE: 15
cgtgctgctg accgagg                                               17

<210> SEQ ID NO 16
<211> LENGTH: 23
<212> TYPE: DNA
<213> ORGANISM: Artificial Sequence
<220> FEATURE:
<223> OTHER INFORMATION: synthetic construct

<400> SEQUENCE: 16
aaggtctcaa acatgatctg ggt                                        23
```

METHODS OF DIAGNOSING INFLAMMATORY BOWEL DISEASE THROUGH RNASET2

CROSS-REFERENCE TO RELATED APPLICATIONS

This application is a U.S. National Phase of International Application No. PCT/US2017/023082 filed Mar. 17, 2017, which claims the benefit of U.S. Provisional Ser. Nos. 62/457,048 filed Feb. 9, 2017 and 62/309,817 filed Mar. 17, 2016, all of which are incorporated herein in their entirety.

STATEMENT REGARDING FEDERALLY SPONSORED RESEARCH OR DEVELOPMENT

This invention was made with government support under Grant Nos. DK043211, DK046763, DK062413, HS021747, AI067068, DE023798, DK084554, RR033176 and TR000124 awarded by the National Institutes of Health. The government has certain rights in the invention.

FIELD OF INVENTION

The invention relates to inflammatory bowel disease and RNASET2 as a biomarker for disease severity and targeting anti-TL1A therapy.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Inflammatory bowel disease (IBD) has two common forms, Crohn's disease (CD) and ulcerative colitis (UC), which are chronic, relapsing inflammatory disorders of the gastrointestinal tract. Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). Moreover, genetic analyses have linked IBD to specific genetic variants. CD and UC are thought to be related disorders that share some genetic susceptibility loci but differ at others.

IBD is generally believed to be triggered in genetically susceptible individuals by an inappropriate immune response to the commensal flora. The high clinical heterogeneity and genetic complexity of CD and UC suggest that the underlying biological pathways driving disease almost certainly differ in subgroups of patients. Thus, the development of early and targeted therapeutics requires subgroup stratification and prognostic biomarker identification, particularly in predicting an overall mild, compared to severe, disease course. Although 201 IBD susceptibility loci have been identified, little is known regarding their functional significance. Genetic variation in TNFSF15 is associated with CD in multiple populations, and the protein it encodes, TL1A, is a key mediator of mucosal inflammation. TL1A expression is up-regulated in inflamed regions of the intestine in both CD and UC. In IBD patients, elevated TL1A levels correlate with TNFSF15 genotype and disease severity. CD patients with elevated serum/tissue levels of TL1A have increased risk of developing fibrosis/stricturing disease behavior. In vitro, TL1A synergizes with interleukin 12 (IL-12) and interleukin 18 (IL-18) (12/18), leading to rapid enhancement of IFN-γ production, another key mediator of mucosal inflammation.

Therefore, there remains a need in the art for methods of diagnosing and identifying patients for treatment with IBD, CD, UC and/or MR-UC.

BRIEF DESCRIPTION OF THE FIGURES

Exemplary embodiments are illustrated in referenced figures. It is intended that the embodiments and figures disclosed herein are to be considered illustrative rather than restrictive.

FIGS. 8A-8C depict RNASET2 expression in CD patients, in accordance with various embodiments of the invention. A) RNASET2 expression in patients with none or 1 multiple disease flares per year. B) RNASET2 expression following TL1A treatment in patients who were medically refractive requiring surgical intervention for disease management or no surgery. C) RNASET2 expression based upon disease flares per year in 32 CD patients, encompassing additional data samples.

FIG. 9 shows a decreased expression of RNASET2 in IBD patients with RNASET2 risk alleles, in accordance with various embodiments of the invention.

FIGS. 13A-13D depict the mQTL of RNASET2 in refractory IBD, in accordance with various embodiments of the invention. A) mQTL of RNASET2 in refractory IBD and B) normal or mild disease patients. C) mQTL (cg25258033) of CD3+ peripheral T cells from 20 CD patients with refractory disease requiring surgical intervention for disease management and D) 16 patients who were responsive to IBD therapeutics and 9 normal controls, encompassing additional data samples.

FIG. 19 depicts 183 transcribed IBD associated SNP regions in the T cells, in accordance with various embodiments of the invention.

FIG. 20 depicts a volcano plot of the class predictor GWAS transcripts of IBD risk predictor genes, in accordance with various embodiments of the invention.

FIG. 22 demonstrates the inverse correlation of IFN-γ and RNASET2 expression in accordance with various embodiments of the invention.

FIGS. 24A-24D depict correlation of RNASET2 and TNFSF15 expression in CD3+ T cells from patients with refractory disease requiring surgical intervention for disease management, using RNA-seq, in accordance with various embodiments of the invention. A) Correlation of RNASET2 versus TL1A in refractory CD. B) Correlation of RNASET2 and TNFSF15 expression in CD3+ peripheral T cells from 38 CD patients, C) depicts data from 100 CD patients and D) depicts combined data from 138 patients.

FIG. 25 depicts the correlation expression of RNASET2 versus A) PU.1 and B) ELF1, in accordance with various embodiments of the invention. The risk SNP rs2149092 C/T (SEQ ID NO: 2) abolishes the IRF4, PU.1, and ELF-1 binding site. C— non-risk and T=risk allele.

FIGS. 36A-36C depict identification of potential regulatory function of RNASET2 disease associated variant rs2149092 (SEQ ID NO: 2) the prospective regulatory role of RNASET2 variant rs2149092 (C-non-risk allele/T-risk allele), in accordance with various embodiments of the invention. A) Predicted disruption of rs2149092 C to T variation in the binding motifs for ETS and IRF4 transcription factors. Central ETS in the variant motif is underlined. B) CHIP-seq and histone modification profiles for ETS1, IRF4 and SPI1 transcription factor binding and histone H3K4me1 and H3K4ac aligned with the genomic sequence surrounding rs2149092 variant. C) Correlation of expression of RNASET2 and multiple ETS and JUN transcription factors in CD3+ peripheral T cells from 108 CD patients requiring surgical intervention for disease management, using RNA-seq.

FIGS. 37A-37G depict the effect of RNASET2 silencing on IFN-γ secretion and cellular aggregation, in accordance with various embodiments of the invention. A) Silencing of RNASET2 expression by RNASET2 or control (NC) siRNA. B) Effect of RNASET2 silencing on IFN-γ secretion. Panels A and B are representative of 6 out of 7 experiments (FIG. 29) with similar results. C) CD4+ T cells were either not treated (UT) or D) stimulated with TL1A for 24 hours. Intracellular IFN-γ staining and cellular aggregations were measured by flow cytometry. Cells were gated on IFN-γ secreting and non-secreting populations (left panels) and then using propidium iodide (PI) analyzed for single and aggregate cell fractions (histograms, right panels). The first peak in each histogram corresponds to single cells (black bracket) and the remaining peaks to cellular aggregates (gray bracket). Representative of 4 experiments. E) Proportion of single cells and cellular aggregates in IFN-γ secreting (IFN-γ+) and non-secreting (IFN-γ−) populations following TL1A stimulation. F) Fold increase in number of IFN-γ secreting cells (Average of 4 experiments). G) CD4+ T cells were pretreated with control IgG or LFA1 blocking Ab (aLFA1) prior to TL1A stimulation. Overall p value for LFA1 mediated blocking of IFN-γ secretion, measured by ELISA, was 0.047.

DESCRIPTION OF THE INVENTION

Figure 1:
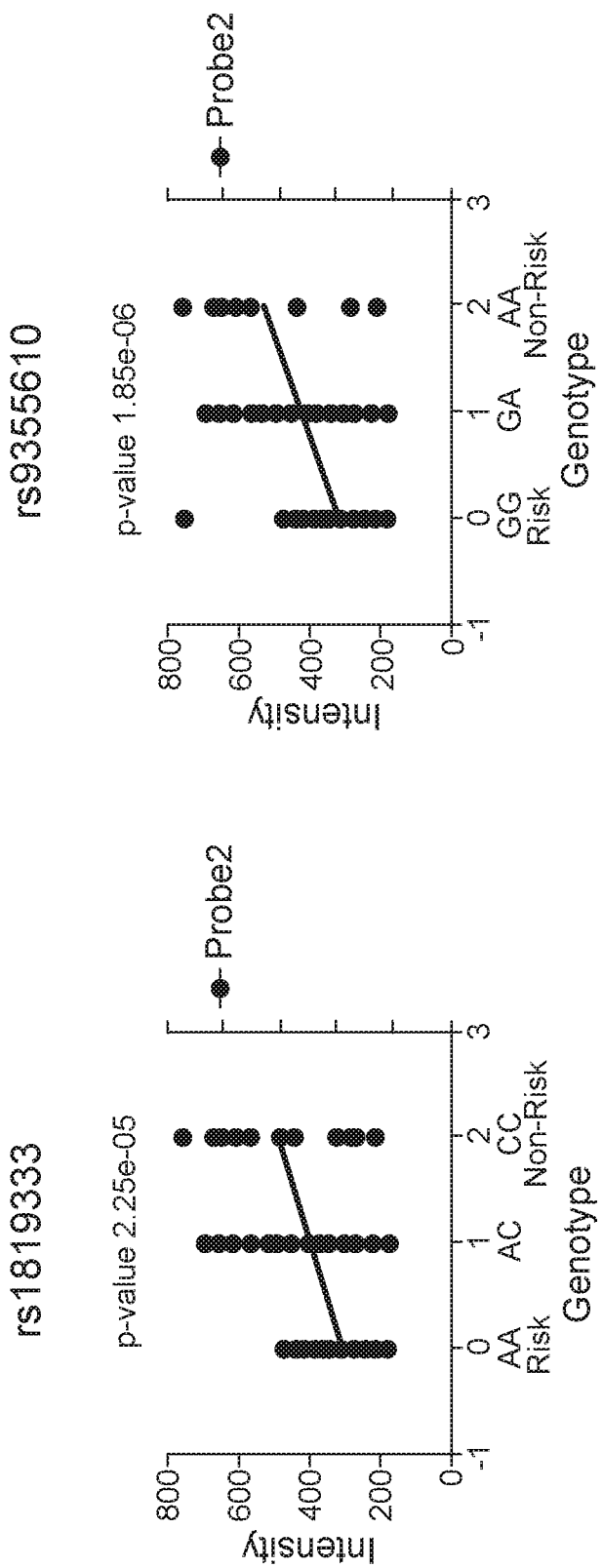
FIG. 1 depicts RNASET2 eQTL microarray in uninvolved small intestine, in accordance with various embodiments of the invention.
Figure 2:
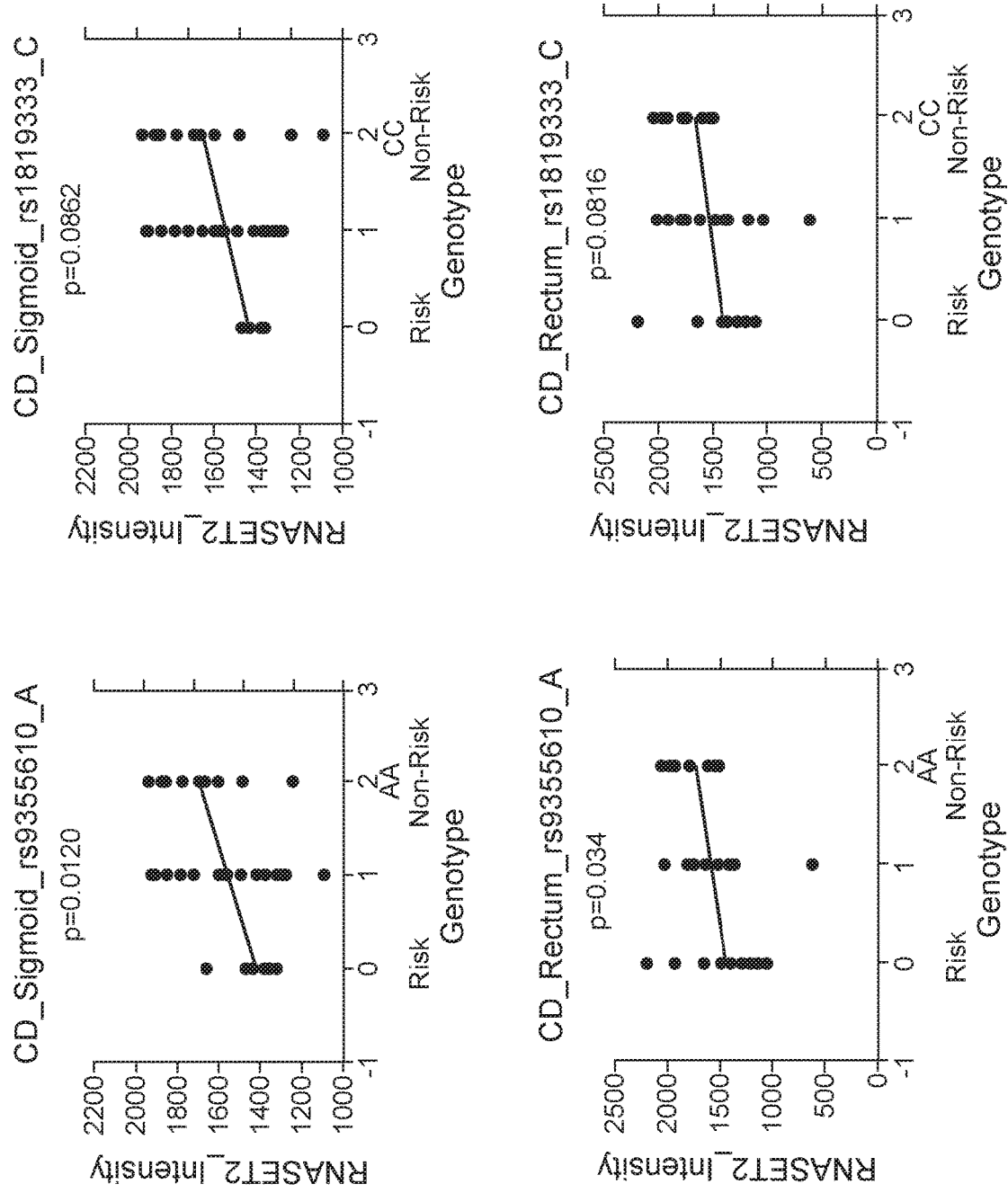
FIG. 2 shows that the RNASET2 major allele is associated with decreased expression of RNASET2 in sigmoid colon and rectum of CD patients, in accordance with various embodiments of the invention.
Figure 3:
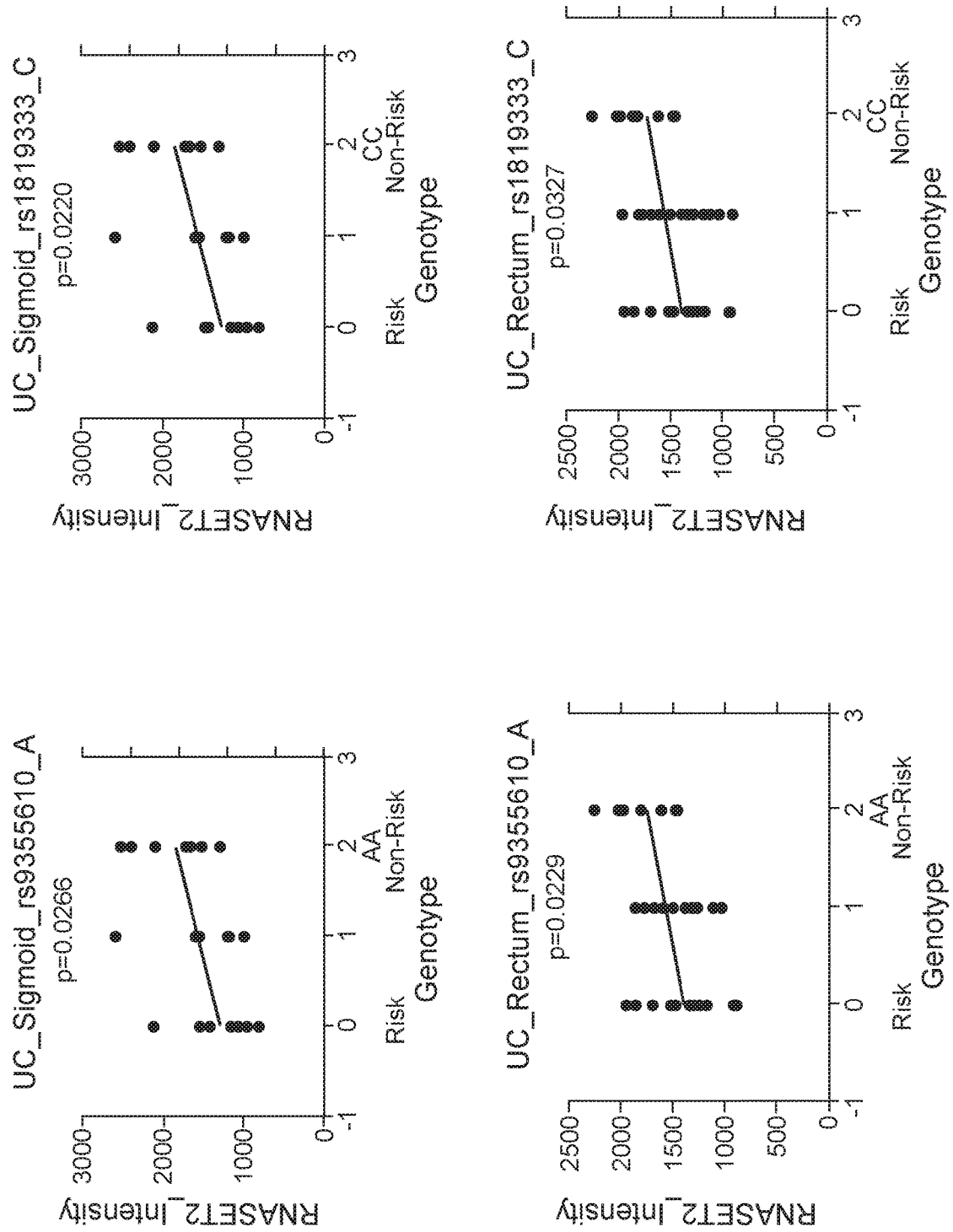
FIG. 3 shows that the RNASET2 major allele is associated with decreased expression of RNASET2 in sigmoid colon and rectum of UC patients, in accordance with various embodiments of the invention.
Figure 4:
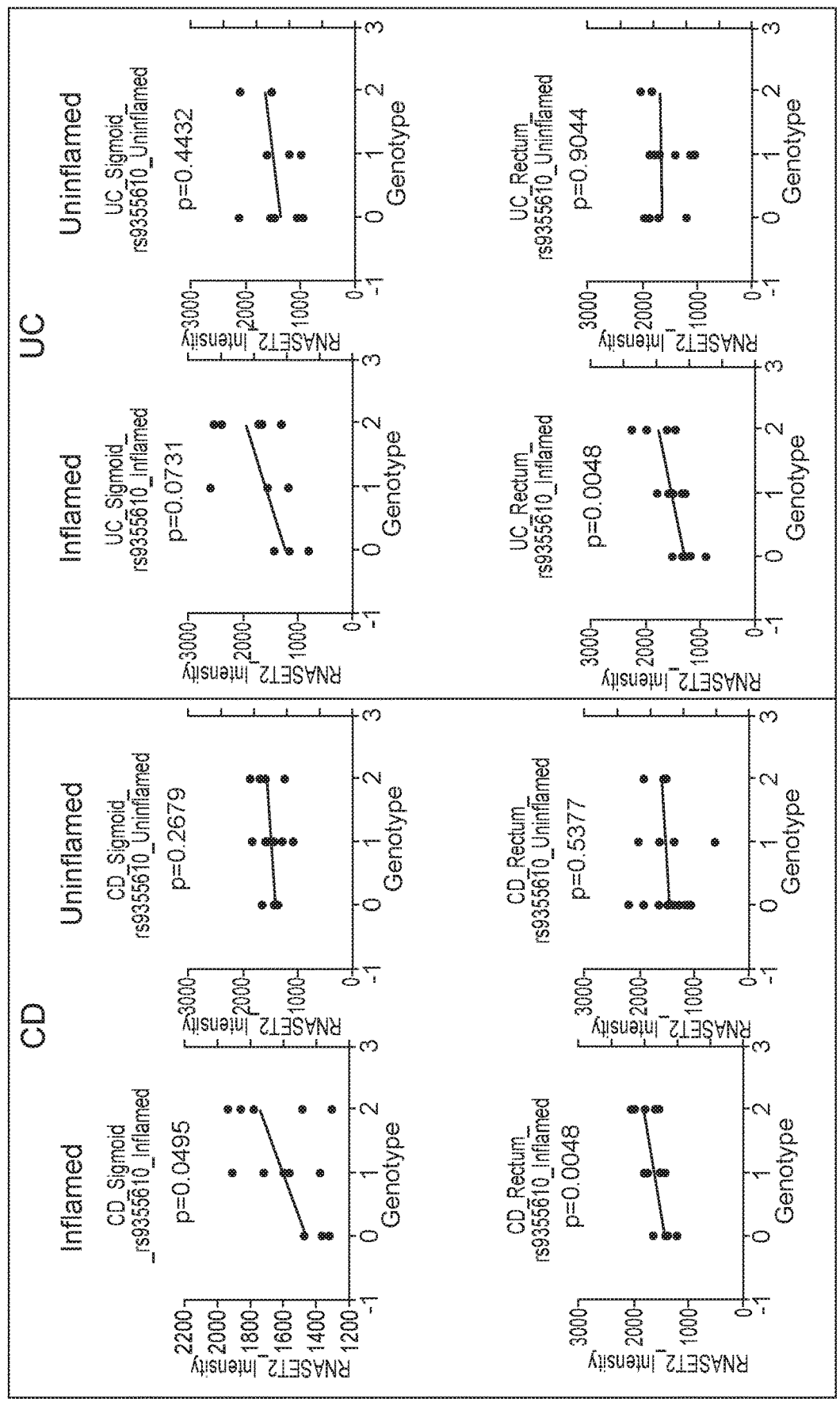
FIG. 4 shows that the RNASET2 risk allele is associated with decreased expression of RNASET2 in inflamed large bowel in CD and UC patients, in accordance with various embodiments of the invention. Similar results were observed for rs1819333.
Figure 5:
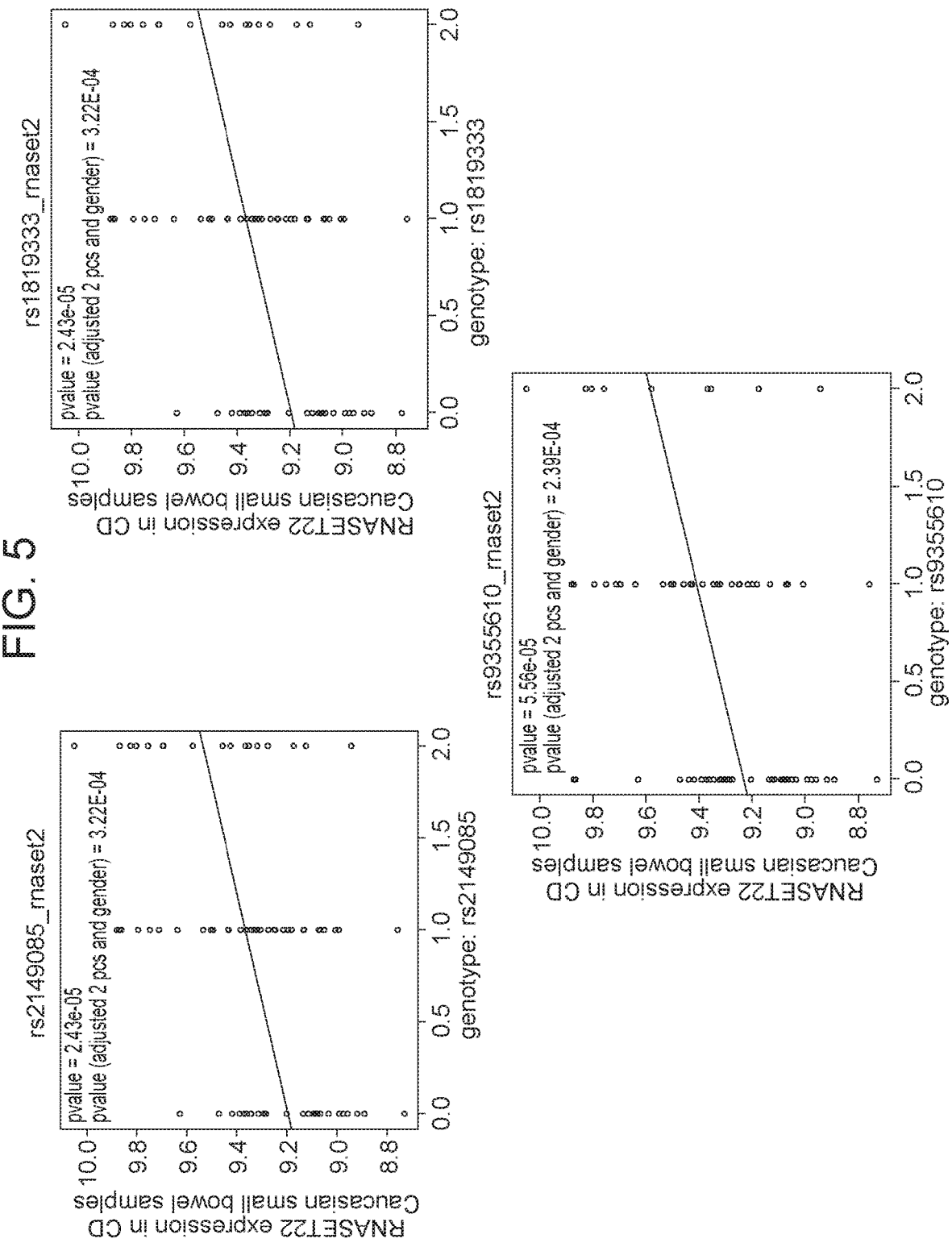
FIG. 5 shows that the RNASET2 major allele is associated with decreased RNASET2 expression in small bowel from CD surgeries, in accordance with various embodiments of the invention.
Figure 6:
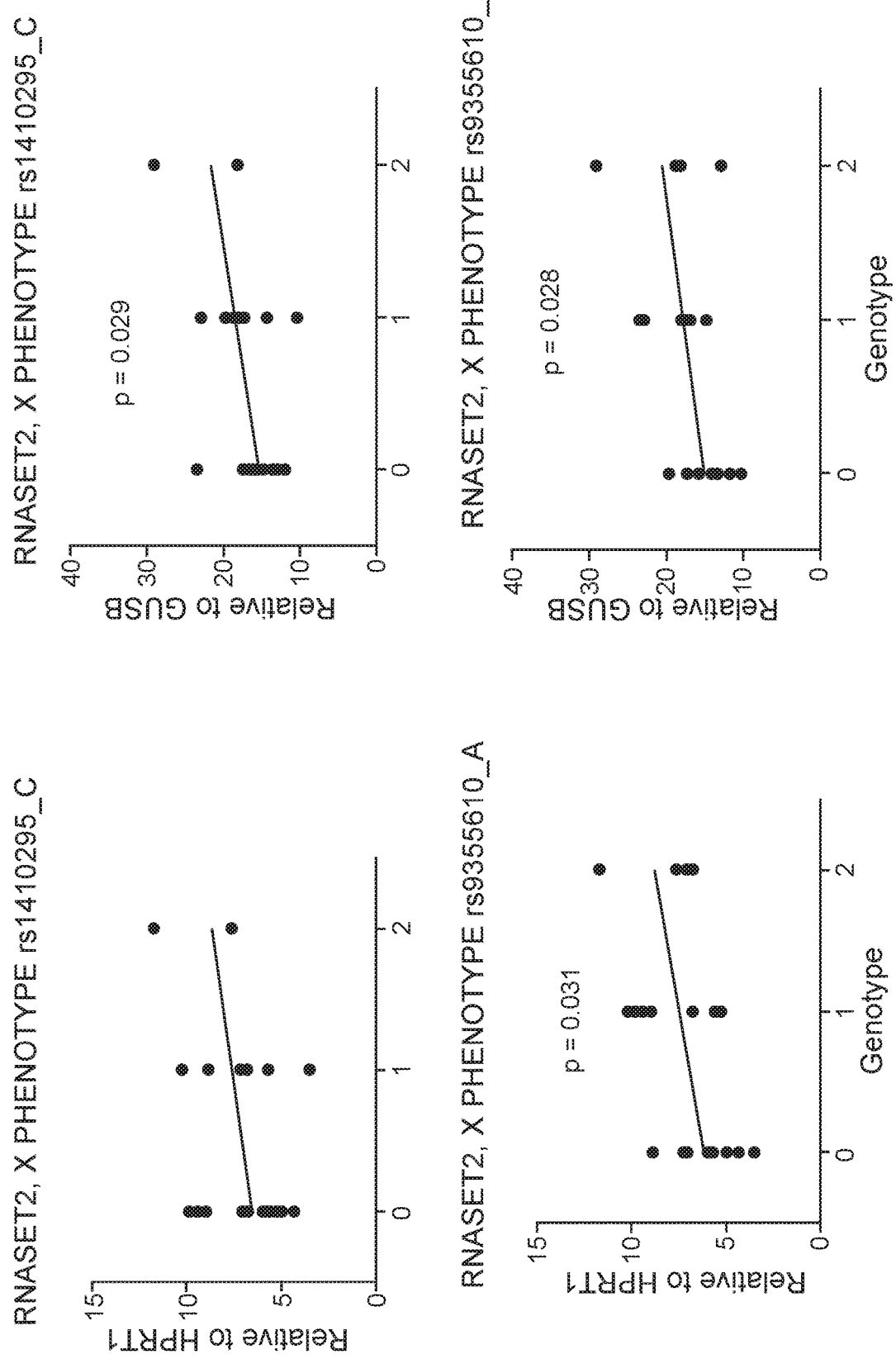
FIG. 6 depicts RNASET2 eQTL in EBV Transformed B Cell Lines, in accordance with various embodiments of the invention. The major allele is associated with lower levels of RNASET2 mRNA expression in EBV transformed B cell lines.

All references cited herein are incorporated by reference in their entirety as though fully set forth. The sequences related to RNASET2 are also incorporated by reference in their entirety as though fully set forth via the rs number disclosed. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., Revised, J. Wiley & Sons (New York, N.Y. 2006); and Sambrook et al., *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; Riechmann et al., Nature 332: 323 (1988); Bird, Science 242:423-42 (1988); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Non-limiting examples of "Biological sample" as used herein means any biological material from which nucleic acids and/or proteins can be obtained. As non-limiting examples, the term encompasses whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. Alternatively, a sample can be obtained through primary patient derived cell lines, or archived patient samples in the form of preserved samples, or fresh frozen samples.

"Treatment" and "treating" as used herein refer to both therapeutic treatment and prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Those in need of treatment include those already with the condition as well as those prone to have the condition or those in whom the condition is to be prevented.

"SNP" as used herein means single nucleotide polymorphism.

"Risk variant" as used herein refers to an allele, whose presence is associated with an increase in susceptibility to an inflammatory bowel disease, including but not limited to Crohn's Disease, Ulcerative Colitis and Medically Refractory-Ulcerative Colitis, relative to an individual who does not have the risk variant.

"IBD", "CD", "UC" and "MR-UC" as used herein refer to Inflammatory Bowel Disease, Crohn's Disease, Ulcerative Colitis and Medically Refractive Ulcerative Colitis, respectively.

As used herein, "IBD" includes "CD", "UC" and/or "MR-UC".

As used herein, "ANCA" means anti-neutrophil cytoplasmic antibodies.

As used herein, "OmpC" means outer membrane protein C.

As used herein, "eQTL" means expression quantitative trait loci.

As used herein, "mQTL" means methylation quantitative trait loci.

Non-limiting examples of RNASET2 SNPs are rs1819333, rs2149092, rs9355610, rs2149085, rs1410295 and rs9366093.

Described herein are methods of diagnosing inflammatory bowel disease using RNASET2, TL1A and/or IFN-γ as a biomarker of disease severity in a patient population and selecting the patient population for anti-TL1A therapy. Further described are methods of treating these patient populations.

RNASET2 (ribonuclease T2) encodes an extracellular RNase and is the only member of the human Rh/T2/S family of acid ribonucleases (acid hydrolyses), which are only active in acidic pH. The optimal activity of RNASET2 is at pH 5 and it has a preferential cleavage of poly-A and poly-U. It contains two regions with catalytic function and demonstrates a cleavage preference near adenylic acid followed by guanylic acid. Three isoforms have been detected for RNASET2, the 27KD, 31KD and 36KD isoforms. The 27KD and 31KD isoforms are thought to result from proteolytic cleavage of the 36KD isoform. All three isoforms are glycosylated. Subcellular fractionation reveals that full length RNASET2 is located in the endoplasmic reticulum and the two smaller RNASET2 proteolytic products are located in the lysosome fraction. RNASET2 is highly conserved among the phyla, from viruses to humans, suggesting an important evolutionary function.

TL1A (TNFSF15) is a tumor necrosis factor family member expressed primarily on activated cells of the immune system, such as monocytes, macrophages, and dendritic cells, following stimulation by immune complexes or through interaction with enteric microorganisms. TL1A expression is enhanced in inflammatory bowel disease and higher TL1A levels are associated with disease severity. Genome-Wide Association Studies (GWAS) have identified TNFSF15 SNPs to be associated with IBD. Studies have shown that neutralizing TL1A antibodies attenuate colitis in murine colitis models, while constitutive TL1A expression depicts a worsened murine ileo-cecal inflammation and intestinal fibrostenosis.

IFN-γ plays a key role in the generation and perpetuation of mucosal inflammation in IBD. TL1A augments IL-12/IL-18-mediated IFN-γ secretion in PB T cells.

The inventors identify RNASET2, an IBD susceptibility gene, as a component of TL1A-mediated enhancement of IFN-γ production. Moreover, functional variants of RNASET2 are associated with a more 'severe' CD phenotype characterized by one or more disease flares and stricturing/penetrating disease behavior. Without being bound to any particular theory, the inventor believes that RNASET2 serves as a therapeutic biomarker associated with severe disease pathobiology and allows for the identification of a patient population most likely to benefit from therapy targeted to the TL1A-driven inflammatory pathway. The TNFSF15 disease-associated variants are correlated with increased and sustained expression of TL1A. TNFSF15 has been identified and confirmed in GWAS as an IBD-associated gene and is believed to play a role in modulating the location and severity of intestinal inflammation, as well as development of stricturing disease. Transgenic mice with constitutive expression of TL1A developed intestinal inflammation along with ileal and colonic fibrosis, which was reversed by anti-TL1A treatment. In UC, there is a strong association between development of a medically refractory disease and the TL1A locus. Although TL1A is an important pro-inflammatory cytokine associated with IBD pathogenesis, the molecular pathways underlying enhanced cytokine secretion and inflammation were poorly understood. Described herein, the inventors investigated the TL1A-dependent molecular triggers that induce cytokine expression, particularly IFN-γ, in T cells. This approach identified down-modulation of RNASET2 as a component of TL1A-mediated enhancement of IFN-γ production.

The inventors demonstrate a functional association of RNASET2 disease risk SNPs with decreased expression and hyper-methylation in T cells isolated from CD patients, as well as, an association with clinical parameters suggestive of complicated/resistant disease behavior and rapid recurrence of disease. The inventors show the regulatory potential for ETS TF in modulating RNASET2 expression and the involvement of homotypic T cell aggregation via ICAM1 as a component of RNASET2 mediated up-regulation of IFN-γ production. The data distinguish RNASET2 as a potential therapeutic biomarker and identify unique pathways for additional therapeutic modulation within a defined IBD population.

The inventors found that, in IBD patients, there was a significant inverse correlation between the expression of RNASET2 and TNFSF15. In addition, the inventors demonstrate a functional association between DNA hyper-methylation and decreased expression of RNASET2.

The inventors found that there was significant eQTL overlap with RNASET2 IBD risk alleles identified through GWAS in samples isolated from the peripheral T cells and small bowel surgical resections. Significant RNASET2 eQTL (rs429083) has been described in a recent report that measured autoimmune associated risk variants in whole thymic tissue samples. This SNP demonstrated the most significant eQTL in the data, as well. Moreover, the study provides clinically relevant evidence that decreased expression levels of RNASET2 were correlated in CD patients with clinical parameters suggestive of complicated and resistant disease. Notably, CD patients carrying the RNASET2 disease risk SNPs displayed an increase in development of stricturing/penetrating disease behavior. RNASET2 expression was significantly lower in T cells isolated from CD patients exhibiting one or more disease flares per year. Similarly, RNASET2 expression is decreased in small bowel mucosal samples, as well as, in peripheral samples from medically refractory CD patients (9 out of 11 which were non-responsive to anti-TNF therapy), requiring surgical intervention for disease management. Consistent with the finding, a recent study reported significant RNASET2 eQTL in whole blood from patients resistant to anti-TNF therapy. Moreover, RNASET2 disease-associated SNPs correlated with therapeutic failure of anti-TNF therapy, and intestinal resection of >40 cm clinical characteristic of overall disease severity. In patients with a history of multiple resections, RNASET2 disease risk SNP was associated with a faster time to reoperation. Likewise, RNASET2 disease associated SNPs were associated in patients with endoscopic recurrence characterized by a more severe (>2) Rutgeerts score, which without being bound to any particular theory, can be predictive for early clinical recurrence and need for reoperation.

The transcriptional regulatory regions and binding factors modulating RNASET2 expression are likewise poorly defined. The majority of disease associated variants identified by GWAS reside within regulatory non-coding regions corresponding to promoters or enhancer sequences. Without being bound to any particular theory, studies suggest that alteration in transcriptional regulation via disruption of transcription factor binding sites may play a role in the disease process. In the present study the inventors utilized TF motif analysis to prioritize and identify from the large number of variants demonstrating eQTL and mQTL a prospective regulatory SNP. The rs2149092 disease associated SNP alters the conserved ETS consensus binding sequence and likely disrupts binding of multiple overlapping TF binding sites including IRF4, SPI1 and ELF1. Moreover, there is a strong positive correlation between the levels of RNASET2 expression and ETS and JUN TF family members. Interestingly, IRF4, SPI1 and ELF1 have been implicated in T cell development and IRF4 and ELF1 have been associated by GWAS with IBD. Without being bound to any particular theory, these data support a functional role for rs2049092 as a modulator of TF-DNA interactions and set the stage for future studies to determine the mechanistic pathways by which TL1A attenuates expression of RNASET2 in disease.

In the present study the inventors describe a functional relationship between RNASET2 and the cell adhesion molecule, ICAM1. Enhanced IFN-γ secretion in response to TL1A was accompanied by a decrease in RNASET2 expression on the one hand and an increase in ICAM1 levels on the other. TL1A mediated IFN-γ secretion was inhibited by Ab blockade of the ICAM1-LFA1 interaction. Although ICAM1-LFA1 engagement is classically defined as occurring between endothelial and T cells, these interactions have more recently been shown to play a critical role in mediating homotypic cellular aggregation of activated T cells. Homotypic T-T aggregates have been shown to promote synaptic-based cytokine delivery of IFN-γ and IL2 from one T cell to another, resulting in IL-2 receptor ligation and subsequent STAT5 phosphorylation. The inventors demonstrate that enhanced cellular aggregation is a hallmark of IFN-γ producing cells and TL1A-stimulation increases the number and size of the cellular aggregates. Without being bound to any particular theory, these findings suggest that RNASET2 may act through the integrin signaling pathway to modulate downstream IFN-γ secretion.

In conclusion, the inventors identified a novel functional and biological relationship between two IBD susceptibility genes, TNFSF15 and RNASET2. The inventors provide evidence that decreased RNASET2 expression is functionally implicated in both the TL1A driven pro-inflammatory cytokine production by activated T cells and functionally associated with the RNASET2 IBD susceptibility variants. Likewise, the present study demonstrates an association between decreased RNASET2 expression and a more severe form of IBD inflammation, which without wishing to be bound by any particular theory, we believe underlie disease pathology triggered by TL1A mediated pathways. Decreased expression and altered epigenetic DNA methylation of RNASET2 characterize a subset of IBD patients with a more severe disease phenotype. The inventors demonstrate a functional association of RNASET2 disease risk SNPs with decreased expression and hyper-methylation in T cells isolated from CD patients, as well as, an association with clinical parameters suggestive of complicated/resistant disease behavior and rapid recurrence of disease. The inventors show the regulatory potential for ETS TF in modulating RNASET2 expression and the involvement of homotypic T cell aggregation via ICAM1 as a component of RNASET2 mediated upregulation of IFN-γ production. The data distinguish RNASET2 as a potential therapeutic biomarker and identify unique pathways for additional therapeutic modulation within a defined IBD population. Thus, RNASET2 expression serves as a novel disease biomarker of a more severe form of inflammation identifying a patient population not responsive to current treatment strategies, whom may benefit from alternate RNASET2 mediated therapeutic approaches.

As disclosed herein, the inventors have identified RNASET2 associated SNPs in an IBD patient cohort. The inventors have identified RNASET2 associated SNPs in a CD patient cohort. The inventors have identified RNASET2 associated SNPs in a UC patient cohort. The inventors have identified RNASET2 associated SNPs in a MR-UC patient cohort. The SNPs were associated with disease location, disease behavior and need for surgery. The inventors have further identified RNASET2 as a biomarker for disease severity and associated RNASET2 risk SNPs in an IBD patient cohort. RNASET2 has been identified as a biomarker for disease severity and associated RNASET2 risk SNPs in a CD patient cohort. RNASET2 has been identified as a biomarker for disease severity and associated RNASET2 risk SNPs in a UC patient cohort. RNASET2 has been identified as a biomarker for disease severity and associated RNASET2 risk SNPs in a MR-UC patient cohort. In addition, the inventors demonstrate a correlation between RNASET2, TL1A expression and IFN-γ secretion.

The present invention is based, at least in part, on these findings. The present invention addresses the need in the art for methods of diagnosing patients with IBD and identifying patients in need of treatment, using RNASET2, TL1A and/or IFN-γ. The invention further provides a process for patient identification and/or stratification.

Diagnosis

Various embodiments of the present invention provide for a method of diagnosing inflammatory bowel disease (IBD) in a subject, comprising: obtaining a sample from the subject; subjecting the sample to an assay adapted to determine the presence or absence of one or more risk variants at the RNASET2 gene; and diagnosing IBD in the subject based on the presence of one or more risk variants at the RNASET2 gene. In some embodiments, inflammatory bowel disease is Crohn's disease, ulcerative colitis or medically refractive ulcerative colitis. In various embodiments, the one or more risk variants at the RNASET2 gene is rs1819333, rs2149092, rs9355610, rs2149085, rs1410295 or rs9366093. In various embodiments, the subject is diagnosed with IBD if 2, 3, 4, 5 or 6 RNASET2 risk variants as described herein are present. In various embodiments, the risk allele for rs2149085 is the T allele. In various other embodiments, the RNASET2 risk variants are the RNASET2 risk variant rs429083 and an RNASET2 risk variant selected from the group consisting of rs1819333, rs2149092, rs9355610, rs2149085, rs1410295, rs9366093, and combinations thereof. In various other embodiments, the RNASET2 risk variants is one or more of the RNASET2 risk variants in Tables 2, 3, 4, 5, 6, 7, 8, 9, 10, and 13 and an RNASET2 risk variant selected from the group consisting of rs1819333, rs2149092, rs9355610, rs2149085, rs1410295, rs9366093, and combinations thereof. In various other embodiments, the one or more risk variants at the RNASET2 gene is rs1819333, rs2149092, rs9355610 or rs2149085. In various embodiments, the subject is diagnosed with IBD if 2, 3, or 4, RNASET2 risk variants rs1819333, rs2149092, rs9355610 or rs2149085, as described herein are present. In other embodiments, the presence of a greater number of risk variants in the sample indicates that the subject is in greater need of treatment. In some embodiments, the detection of RNASET2 risk variants is indicative of the need for treatment in the subject. In yet other embodiments, the subject is identified as needing anti-TL1A therapy. In various embodiments, the subject diagnosed with IBD demonstrates therapeutic failure of thiopurine and anti-TNF therapy. In various other embodiments, the subject diagnosed with IBD is determined to need surgical intervention. In some embodiments, the surgical intervention is intestinal resection.

TABLE 1

RNASET2 risk variants

| SNP | SEQ ID NO: |
|---|---|
| rs1819333 | 1 |
| rs2149092 | 2 |

TABLE 1-continued

RNASET2 risk variants

| SNP | SEQ ID NO: |
|---|---|
| rs9355610 | 3 |
| rs2149085 | 4 |
| rs1410295 | 5 |
| rs9366093 | 6 |

In other embodiments, the method of diagnosing inflammatory bowel disease (IBD) in a subject described herein comprises determining the expression level of RNASET2, TL1A and/or IFN-γ. In some embodiments, a subject with decreased RNASET2, and/or increased TL1A and/or IFN-γ levels is diagnosed with IBD. In various embodiments, inflammatory bowel disease is Crohn's disease. In various embodiments, inflammatory bowel disease is ulcerative colitis. In various embodiments, inflammatory bowel disease is medically refractive ulcerative colitis. In various embodiments, inflammatory bowel disease is a CD patient who required surgical intervention for disease management. In yet other embodiments, a subject with decreased RNASET2, and/or increased TL1A and/or IFN-γ levels is identified as a subject in need of a treatment that increases RNASET2, and/or decreases TL1A and/or IFN-γ. In other embodiments, the subject is identified as needing anti-TL1A therapy. In yet other embodiments, the subject is identified as needing a treatment that causes an increase in RNASET2. In certain other embodiments, the subject is identified as needing a treatment that causes a decrease in IFN-γ and/or TL1A.

In various embodiments, the detection of RNASET2 risk variants and/or RNASET2, TL1A and/or IFN-γ expression levels can be accomplished by analyzing nucleic acids of a biological sample from the subject. A variety of apparatuses and/or methods, including, without limitation, polymerase chain reaction based analysis, sequence analysis and electrophoretic analysis can be used to detect RNASET2 risk variants. The expression levels of RNASET2, TL1A and/or IFN-γ can be detected using a variety of apparatuses and/or methods, including, without limitation, quantitative PCR, northern blot and microarrays. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

In various other embodiments, determining the expression level of RNASET2, TL1A and/or IFN-γ can be accomplished by analyzing the proteins of a biological sample from the subject. A variety of apparatuses and/or methods, including, without limitation, ELISA, immunohistochemistry, and western blot can be used to detect RNASET2, TL1A and/or IFN-γ expression levels.

Various embodiments of the present invention also provide for a method of diagnosing medically refractive ulcerative colitis (MR-UC), comprising: obtaining a sample from the subject; subjecting the sample to an assay adapted to determine the presence or absence of one or more risk variants at the RNASET2; and diagnosing MR-UC in the subject based on the presence of one or more risk variants at the RNASET2 gene. In various embodiments, the one or more risk variants at the RNASET2 gene are rs1819333, rs2149092, rs9355610, rs2149085, rs1410295 or rs9366093. In various embodiments, the risk allele for rs2149085 is the T allele. In various other embodiments, the RNASET2 risk variants are the RNASET2 risk variant rs429083 and an RNASET2 risk variant selected from the group consisting of rs1819333, rs2149092, rs9355610, rs2149085, rs1410295, rs9366093, and combinations thereof. In various other embodiments, the RNASET2 risk variants is one or more of the RNASET2 risk variants in Tables 2, 3, 4, 5, 6, 7, 8, 9, 10, and 13 and an RNASET2 risk variant selected from the group consisting of rs1819333, rs2149092, rs9355610, rs2149085, rs1410295, rs9366093, and combinations thereof. In various other embodiments, the one or more risk variants at the RNASET2 gene is rs1819333, rs2149092, rs9355610 or rs2149085. In various embodiments, the subject is diagnosed with IBD if 2, 3, or 4, RNASET2 risk variants rs1819333, rs2149092, rs9355610 or rs2149085 as described herein are present.

In various embodiments, the subject diagnosed with MR-UC demonstrates therapeutic failure of thiopurine and anti-TNF therapy. In various other embodiments, the subject diagnosed with MR-UC is determined to need surgical intervention. In some embodiments, the surgical intervention is intestinal resection. In various embodiments, the subject diagnosed with MR-UC is determined to need RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

In various other embodiments, the methods further comprise determining the level of methylation of RNASET2, and diagnosing IBD in a subject who has an increase in RNASET2 methylation. In other embodiments, the level of RNASET2 methylation is determined to diagnose a subject with MR-UC. In some embodiments, the subject is identified as needing a treatment that causes a decrease in RNASET2 methylation. In other embodiments, the subject is identified as needing an anti-TL1A therapy.

Various embodiments of the present invention provide for the treatment of subjects diagnosed with MR-UC. MR-UC subjects are refractory to current conventional medical therapy used, such as anti-TNF therapy, thiopurine therapy, corticosteroids and cyclosporine. In various embodiments, the subjects diagnosed with MR-UC are treated with non-conventional treatments, such as, but not limited to treatments that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various embodiments, the subject diagnosed with MR-UC is determined to need RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

In various embodiments, the subject is identified as needing a treatment that mimics, RNASET2, TL1A and/or IFN-γ. In other embodiments, the subject is identified as needing a treatment that modulates RNASET2, TL1A and/or IFN-γ. In some other embodiments, the subject is identified as needing a treatment that targets RNASET2, TL1A and/or IFN-γ. In yet other embodiments, the subject is identified as needing a treatment that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various embodiments, the disease is IBD. In various embodiments, the disease is CD. In various embodiments, the disease is UC. In various embodiments, the disease is MR-UC. In various embodiments, the subject diagnosed is a CD patients who required surgical intervention for disease management.

In various embodiments, the presence of one or more risk variants at the RNASET2 gene is associated with decreased expression of RNASET2. In other embodiments, the presence of one or more risk variants at the RNASET2 gene is associated with decreased expression of RNASET2 in peripheral and mucosal tissues. In some other embodiments, the presence of one or more risk variants at the RNASET2 gene is associated with DNA hypermethylation in patients requiring surgical intervention for disease management. In yet other embodiments, the presence of one or more risk variants at the RNASET2 gene is associated with therapeutic failure of thiopurine and/or anti-TNF therapy. In some other embodiments, the presence of one or more risk variants at the RNASET2 gene is associated with ANCA sero-positivity. In various other embodiments, the presence of one or more risk variants at the RNASET2 gene is associated with increased overall length of intestinal resection.

Subject Identification and/or Stratification

Various embodiments of the present invention provide for a process of identifying a subject with inflammatory bowel disease for treatment, comprising: determining the expression level of RNASET2, TL1A and/or IFN-γ; and identifying the subject in need of treatment as a subject with decreased RNASET2, and/or increased TL1A and/or IFN-γ levels. In various embodiments, the inflammatory bowel disease is Crohn's disease. In various embodiments, the inflammatory bowel disease is ulcerative colitis. In various embodiments, the inflammatory bowel disease is medically refractive ulcerative colitis. In various other embodiments, the subject is identified as needing a treatment that causes an increase in RNASET2. In yet other embodiments, the subject is identified as needing a treatment that causes a decrease in TL1A and/or IFN-γ. In certain embodiments, the subject is identified as needing anti-TL1A therapy. In some embodiments, the subject is identified as needing a treatment that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides.

"Patient Risk Stratification" as used herein means the process of separating subjects into risk groups in need of treatment.

Various embodiments of the present invention provide for a process of patient risk stratification to identify a subject in need of treatment, relative to a healthy individual. In various embodiments, the subject is stratified based on the detection of RNASET2, TL1A and/or IFN-γ in a biological sample from the subject. In some embodiments, a decrease in RNASET2 is indicative of a patient having IBD, in need of treatment. In some embodiments, a decrease in RNASET2 is indicative of a patient having CD, in need of treatment. In some embodiments, the patient is a CD patient who requires surgical intervention for disease management. In some embodiments, a decrease in RNASET2 is indicative of a patient having UC, in need of treatment. In some embodiments, a decrease in RNASET2 is indicative of a patient having MR-UC in need of treatment. In various other embodiments, an increase in TL1A and/or IFN-γ is indicative of a patient having IBD, in need of treatment. In various other embodiments, an increase in TL1A and/or IFN-γ is indicative of a patient having CD, in need of treatment. In various other embodiments, an increase in TL1A and/or IFN-γ is indicative of a patient having UC, in need of treatment. In various other embodiments, an increase in TL1A and/or IFN-γ is indicative of a patient having MR-UC, in need of treatment. In certain other embodiments, a decrease in RNASET2, an increase in TL1A, and an increase in IFN-γ is indicative of a subject having IBD, in need of treatment. In certain other embodiments, a decrease in RNASET2, an increase in TL1A, and an increase in IFN-γ is indicative of a subject having CD, in need of treatment. In certain other embodiments, a decrease in RNASET2, an increase in TL1A, and an increase in IFN-γ is indicative of a subject having UC, in need of treatment. In certain other embodiments, a decrease in RNASET2, an increase in TL1A, and an increase in IFN-γ is indicative of a subject having MR-UC, in need of treatment. In various embodiments, detection of the genes provides a guide for the treatment of the subject. In certain embodiments, the subject is identified as needing a treatment that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various other embodiments, the process of patient risk stratification to identify a subject in need of treatment is relative to a healthy individual who has been previously treated. In various other embodiments, the process of patient risk stratification to identify a subject in need of treatment is relative to a medically responsive individual.

Various embodiments of the present invention provide for the treatment of subjects diagnosed with MR-UC. MR-UC subjects are refractory to current conventional medical therapy used, such as anti-TNF therapy, thiopurine therapy, corticosteroids and cyclosporine. In various embodiments, the subjects diagnosed with MR-UC are treated with non-conventional treatments, such as, but not limited to treatments that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various embodiments, the subject diagnosed with MR-UC is determined to need RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

In other embodiments, the process for subject identification and/or stratification described herein comprises determining the presence of one or more risk variants. In certain embodiments, the one or more risk variants comprise rs1819333, rs2149092, rs9355610, rs2149085, rs1410295 or rs9366093. In various embodiments, the process comprises identifying the subject with IBD in need of treatment if 2, 3, 4, 5 or 6 RNASET2 risk variants as described herein are present. In various embodiments, the risk allele for rs2149085 is the T allele. In various other embodiments, the RNASET2 risk variants are the RNASET2 risk variant rs429083 and an RNASET2 risk variant selected from the group consisting of rs1819333, rs2149092, rs9355610, rs2149085, rs1410295, rs9366093, and combinations thereof. In various other embodiments, the RNASET2 risk variants is one or more of the RNASET2 risk variants in Tables 2, 3, 4, 5, 6, 7, 8, 9, 10, and 13 and an RNASET2 risk variant selected from the group consisting of rs1819333, rs2149092, rs9355610, rs2149085, rs1410295, rs9366093, and combinations thereof. In various other embodiments, the one or more risk variants at the RNASET2 gene is rs1819333, rs2149092, rs9355610 or rs2149085. In various embodiments, the subject is diagnosed with IBD if 2, 3, or 4, RNASET2 risk variants rs1819333, rs2149092, rs9355610 or rs2149085 as described herein are present. In various other embodiments, the detection of the risk variants in the biological sample stratifies the subject into a group needing treatment. In other embodiments, the presence of a greater number of risk variants in the sample indicates that the subject is in greater need of treatment. In some embodiments, the detection of RNASET2 risk variants is indicative of the need for treatment in the subject. In some embodiments, the subject is identified as needing anti-TL1A therapy. In various embodiments, the subject identified as needing RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

In various embodiments, the detection of RNASET2 risk variants can be accomplished by analyzing nucleic acids of a biological sample from the subject, as discussed herein.

In other embodiments, the process for subject identification and/or stratification described herein further comprises assaying the sample to detect the level of RNASET2 methylation, relative to a healthy individual. In some embodiments, a subject with an increased level of RNASET2 methylation is identified as a subject in need of treatment. In some embodiments, the sample is assessed for the level of RNASET2 methylation and one or more RNASET2 risk variants. In certain embodiments, a subject who has an increase in RNASET2 methylation and the presence of one or more RNASET2 risk variants is identified as a subject in need of treatment. In other embodiments, the sample is assessed for the level of RNASET2 methylation and the expression levels of RNASET2, TL1A and/or IFN-γ. In certain embodiments, a subject who has an increase in RNASET2 methylation and a decrease in RNASET2, an increase in TL1A and/or IFN-γ is identified as a subject in need of treatment. In certain embodiments, the subject is identified as needing a treatment that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In some embodiments, the subject is identified as needing anti-TL1A therapy. In some embodiments, the subject is identified as needing a treatment that causes a decrease in RNASET2 methylation. In various other embodiments, the detection of an increase in RNASET2 methylation is indicative of a patient with severe CD requiring surgery. In a further embodiment, the subject is identified as needing a treatment that comprises colectomy and/or anti-TL1A therapy.

In various other embodiments, the process for subject identification and/or stratification described herein can further comprise assaying the sample to detect an increase or decrease of at least one microbial antigen (serological factor), relative to a healthy individual. In some embodiments, the microbial antigens (serological factors) assessed comprise ANCA, ASCA, OmpC, I2 and CBir. In some embodiments, the sample is assessed for one or more microbial antigens (serological factors) and one or more RNASET2 risk variants. In certain embodiments, a subject who has one or more risk serological factors and the presence of one or more RNASET2 risk variants is identified as a subject in need of treatment. In yet other embodiments, the sample is assessed for one or more risk serological factors and the expression levels of RNASET2, TL1A and/or IFN-γ. In certain embodiments, a subject who has one or more risk serological factors and a decrease in RNASET2, an increase in TL1A and/or IFN-γ is identified as a subject in need of treatment. In some embodiments, the subject is identified as needing a treatment that mimics, modulates and/or targets RNASET2, TL and/or IFNγ. In various embodiments, treatments that mimics, modulates and/or targets RNASET2, TL1A and/or IFN-γ can comprise antibodies and or silencing oligonucleotides. In other embodiments, the treatment is anti-TL1A therapy. In various embodiments, the treatment is an RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

In various embodiments the subject identified with IBD demonstrates therapeutic failure of thiopurine and anti-TNF therapy. In various other embodiments, the subject identified with IBD is determined to need surgical intervention. In some other embodiments, the surgical intervention is intestinal resection. Various embodiments of the present invention also provide for a method of selecting surgery for a subject having Inflammatory Bowel Disease, comprising: obtaining a sample from the subject; subjecting the sample to an assay adapted to determine the presence or absence of one or more risk variants at the RNASET2 gene; diagnosing MR-UC in the subject based on the presence of one or more risk variants at the RNASET2 gene; and selecting surgery for the subject diagnosed with MR-UC. In some embodiments, the one or more risk variants at the RNASET2 gene is rs1819333, rs2149092, rs9355610, rs2149085, rs1410295 or rs9366093. In various other embodiments, the RNASET2 risk variants are the RNASET2 risk variant rs429083 and an RNASET2 risk variant selected from the group consisting of rs1819333, rs2149092, rs9355610, rs2149085, rs1410295, rs9366093, and combinations thereof. In various other embodiments, the RNASET2 risk variants is one or more of the RNASET2 risk variants in Tables 2, 3, 4, 5, 6, 7, 8, 9, 10, and 13 and an RNASET2 risk variant selected from the group consisting of rs1819333, rs2149092, rs9355610, rs2149085, rs1410295, rs9366093, and combinations thereof. In various other embodiments, the one or more risk variants at the RNASET2 gene is rs1819333, rs2149092, rs9355610 or rs2149085. In various embodiments, the subject is diagnosed with IBD if 2, 3, or 4, RNASET2 risk variants rs1819333, rs2149092, rs9355610 or rs2149085 as described herein are present. In some embodiments, the method further comprises determining the level of methylation of RNASET2. In various embodiments, a subject with an increased level of RNASET2 methylation is identified as a subject in need of surgery. In other embodiments, the subject with an increase in RNASET2 methylation and the presence of one or more risk variants at the RNASET2 gene is identified as a subject in need of surgery.

In various embodiments, the presence of one or more risk variants at the RNASET2 gene is associated with decreased expression of RNASET2. In other embodiments, the presence of one or more risk variants at the RNASET2 gene is associated with decreased expression of RNASET2 in peripheral and mucosal tissues. In some other embodiments, the presence of one or more risk variants at the RNASET2 gene is associated with DNA hypermethylation in patients requiring surgical intervention for disease management. In yet other embodiments, the presence of one or more risk variants at the RNASET2 gene is associated with therapeutic failure of thiopurine and/or anti-TNF therapy. In some other embodiments, the presence of one or more risk variants at the RNASET2 gene is associated with ANCA sero-positivity. In various other embodiments, the presence of one or more risk variants at the RNASET2 gene is associated with increased overall length of intestinal resection.

Various embodiments of the present invention provide for a method of selecting a therapy for a subject having Inflammatory Bowel Disease, comprising: obtaining a sample from the subject; subjecting the sample to an assay adapted to determine the presence or absence of one or more risk variants at the RNASET2 gene; diagnosing medically refractive ulcerative colitis (MR-UC) in the subject based on the presence of one or more risk variants at the RNASET2 gene; and selecting surgery as the therapy and not selecting thiopurine or anti-TNF as the therapy for the subject diagnosed with MR-UC. In various embodiments, the one or more risk variants at the RNASET2 gene is rs1819333, rs2149092, rs9355610, rs2149085, rs1410295 or rs9366093. In various other embodiments, the RNASET2 risk variants are the RNASET2 risk variant rs429083 and an RNASET2 risk variant selected from the group consisting of rs1819333, rs2149092, rs9355610, rs2149085, rs1410295, rs9366093, and combinations thereof. In various other embodiments, the RNASET2 risk variants is one or more of the RNASET2 risk variants in Tables 2, 3, 4, 5, 6, 7, 8, 9, 10, and 13 and an RNASET2 risk variant selected from the group consisting of rs1819333, rs2149092, rs9355610, rs2149085, rs1410295, rs9366093, and combinations thereof. In various other embodiments, the one or more risk variants at the RNASET2 gene is rs1819333, rs2149092, rs9355610 or rs2149085. In various embodiments, the subject is diagnosed with IBD if 2, 3, or 4, RNASET2 risk variants rs1819333, rs2149092, rs9355610 or rs2149085 as described herein are present. In yet other embodiments, the method further comprises determining the level of methylation of RNASET2, wherein increased methylation is indicative of a subject requiring surgical intervention.

Various embodiments of the present invention provide for the treatment of subjects diagnosed with MR-UC. MR-UC subjects are refractory to current conventional medical therapy used, such as anti-TNF therapy, thiopurine therapy, corticosteroids and cyclosporine. In various embodiments, the subjects diagnosed with MR-UC are treated with non-conventional treatments, such as, but not limited to treatments that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various embodiments, the subject diagnosed with MR-UC is determined to need RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

Detection of Methylation

Various embodiments provide for a method of diagnosing a subject with inflammatory bowel disease (IBD). In some embodiments, the method comprises determining the level of methylation of RNASET2; and identifying the subject with IBD as a subject with increased RNASET2 methylation. In other embodiments, the method comprises identifying the subject with IBD as a subject who has increased RNASET2 methylation and who has the presence of one or more risk variants at the RNASET2 gene. In various other embodiments, the method comprises determining the expression level of RNASET2, TL1A and/or IFN-γ; and diagnosing the subject with IBD if the subject has a decrease in RNASET2, an increase in TL1A, an increase in IFN-γ and/or an increase in RNASET2 methylation.

Various embodiments provide for a process of identifying a subject with inflammatory bowel disease (IBD) in need of treatment. In some embodiments, the method comprises determining the level of methylation of RNASET2; and identifying the subject in need of treatment as a subject with increased RNASET2 methylation. In other embodiments, the expression level of RNASET2, TL1A and/or IFN-γ and the level of methylation of RNASET2 are determined, to identify a subject with inflammatory bowel disease in need of treatment. In various embodiments, the method comprises determining a subject in need of treatment as a subject who has a decrease in RNASET2, an increase in TL1A, an increase in IFN-γ, and/or an increase in RNASET2 methylation. In various other embodiments, the method comprises determining the presence or absence of one or more risk variants at the RNASET2 gene and identifying a subject with IBD in need of treatment as a subject who has an increase in RNASET2 methylation and the presence of one or more RNASET2 risk variants.

In various embodiments, an increase in methylation is indicative of a subject requiring surgical intervention. In yet other embodiments, an increase in RNASET2 methylation is indicative of requiring surgical intervention.

Various methods to detect levels of methylation include, but are not limited to the following assays, mass spectrometry, methylation-specific PCR (MSP), whole genome bisulfite sequencing, (BS-Seq), the HELP assay, ChIP-on-chip assays, restriction landmark genomic scanning, methylated DNA immunoprecipitation (MeDIP, MeDIP-chip, MeDIPseq), pyrosequencing of bisulfite treated DNA, molecular break light assay for DNA adenine methyltransferase activity, methyl sensitive southern blotting, separate native DNA into methylated and unmethylated fractions using MethylCpG Binding Proteins (MBPs) and/or Methyl Binding Domain (MBD), MethylationEPIC BeadChip, Illumina Infinium Methylation 450 BeadChip, High Resolution Melt Analysis (FIRM or HRMA), and/or ancient DNA methylation reconstruction.

Various embodiments of the invention provide for the treatment of a subject diagnosed with inflammatory bowel disease (IBD) by the method comprising obtaining a sample from the subject; subjecting the sample to an assay adapted to determine the presence or absence of one or more risk variants at the RNASET2 gene; and diagnosing IBD in the subject based on the presence of one or more risk variants at the RNASET2 gene. In various embodiments, inflammatory bowel disease is Crohn's disease, ulcerative colitis or medically refractive ulcerative colitis.

Various embodiments of the invention provide for the treatment of a subject diagnosed with medically refractive ulcerative colitis (MR-UC) by the method comprising, obtaining a sample from the subject; subjecting the sample to an assay adapted to determine the presence or absence of one or more risk variants at the RNASET2; and diagnosing MR-UC in the subject based on the presence of one or more risk variants at the RNASET2 gene.

Various embodiments of the present invention provide for the treatment of subjects diagnosed with MR-UC. MR-UC subjects are refractory to current conventional medical therapy used, such as anti-TNF therapy and thiopurine therapy. In various embodiments, the subjects diagnosed with MR-UC are treated with non-conventional treatments, such as, but not limited to treatments that mimics, modulates and/or targets RNASET2, TL1A and/or IFN-γ. In various embodiments, treatments that mimics, modulates and/or targets RNASET2, TL1A and/or IFN-γ can comprise antibodies and or silencing oligonucleotides. In various embodiments, the subject diagnosed with MR-UC is determined to need RNASET2 mediated therapy, such as but not limited to recombinant RNASET2 and anti-ICAM1. In various embodiments, the RNASET2 mediated therapy is an antibody or small molecule that targets genes that are upstream and/or downstream of RNASET2.

Biological Samples, Sample Preparation and Gene Expression Detection

In various embodiments, the steps involved in the current invention comprise obtaining a biological sample from a subject. The biological sample may be obtained either through surgical biopsy or surgical resection. Alternatively, a sample can be obtained through primary patient derived cell lines, or archived patient samples in the form of FFPE (Formalin fixed, paraffin embedded) samples, or fresh frozen samples. A sample may also comprise whole blood, peripheral blood, plasma, serum, saliva, cheek swab, or other bodily fluid or tissue. In various embodiments, the sample comprises tissue from the large and/or small intestine. In various other embodiments, the large intestine sample comprises the cecum, colon (the ascending colon, the transverse colon, the descending colon, and the sigmoid colon), rectum and/or the anal canal. In yet other embodiments, the small intestine sample comprises the duodenum, jejunum, and/or the ileum.

Nucleic acid or protein samples derived from the biological sample (i.e., tissue and/or cells) of a subject that can be used in the methods of the invention can be prepared by means well known in the art. For example, surgical procedures or needle biopsy aspiration can be used to collect the biological samples from a subject. In some embodiments, it is important to enrich and/or purify the abnormal tissue and/or cell samples from the normal tissue and/or cell samples. In other embodiments, the abnormal tissue and/or cell samples can then be microdissected to reduce the amount of normal tissue contamination prior to extraction of genomic nucleic acid or pre-RNA for use in the methods of the invention. Such enrichment and/or purification can be accomplished according to methods well-known in the art, such as needle microdissection, laser microdissection, fluorescence activated cell sorting, and immunological cell sorting.

Analysis of the nucleic acid and/or protein from an individual may be performed using any of various techniques. In various embodiments, assaying gene expression levels for RNASET2 comprises northern blot, reverse transcription PCR, real-time PCR, serial analysis of gene expression (SAGE), DNA microarray, tiling array, RNA-Seq, or a combination thereof. In various other embodiments, the gene expression levels for RNASET2, TL1A and/or IFN-γ are assayed. In other embodiments, the level of RNASET2 methylation is determined.

In various embodiments, methods and systems to detect protein expression include but are not limited to ELISA, immunohistochemistry, western blot, flow cytometry, fluorescence in situ hybridization (FISH), radioimmuno assays, and affinity purification.

The analysis of gene expression levels may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

A DNA sample suitable for hybridization can be obtained, e.g., by polymerase chain reaction (PCR) amplification of genomic DNA, fragments of genomic DNA, fragments of genomic DNA ligated to adaptor sequences or cloned sequences. Computer programs that are well known in the art can be used in the design of primers with the desired specificity and optimal amplification properties, such as Oligo version 5.0 (National Biosciences). PCR methods are well known in the art, and are described, for example, in Innis et al., eds., 1990, PCR Protocols: A Guide to Methods And Applications, Academic Press Inc., San Diego, Calif. It will be apparent to one skilled in the art that controlled robotic systems are useful for isolating and amplifying nucleic acids and can be used.

Hybridization

The nucleic acid samples derived from a subject used in the methods of the invention can be hybridized to arrays comprising probes (e.g., oligonucleotide probes) in order to identify RNASET2, TL1A and/or IFN-γ and in instances wherein a housekeeping gene expression is also to be assessed, comprising probes in order to identify selected housekeeping genes. In particular embodiments, the probes used in the methods of the invention comprise an array of probes that can be tiled on a DNA chip (e.g., SNP oligonucleotide probes). Hybridization and wash conditions used in the methods of the invention are chosen so that the nucleic acid samples to be analyzed by the invention specifically bind or specifically hybridize to the complementary oligonucleotide sequences of the array, preferably to a specific array site, wherein its complementary DNA is located. In some embodiments, the complementary DNA can be completely matched or mismatched to some degree as used, for example, in Affymetrix oligonucleotide arrays. The single-stranded synthetic oligodeoxyribonucleic acid DNA probes of an array may need to be denatured prior to contact with the nucleic acid samples from a subject, e.g., to remove hairpins or dimers which form due to self-complementary sequences.

Optimal hybridization conditions will depend on the length of the probes and type of nucleic acid samples from a subject. General parameters for specific (i.e., stringent) hybridization conditions for nucleic acids are described in Sambrook and Russel, *Molecular Cloning: A Laboratory Manual* 4$^{th}$ ed., Cold Spring Harbor Laboratory Press (Cold Spring Harbor, N.Y. 2012); Ausubel et al., eds., 1989, Current Protocols in Molecules Biology, Vol. 1, Green Publishing Associates, Inc., John Wiley & Sons, Inc., New York, at pp. 2.10.1-2.10.16. Exemplary useful hybridization conditions are provided in, e.g., Tijessen, 1993, Hybridization with Nucleic Acid Probes, Elsevier Science Publishers B. V. and Kricka, 1992, Nonisotopic DNA Probe Techniques, Academic Press, San Diego, Calif.

Oligonucleotide Nucleic Acid Arrays

In some embodiments of the methods of the present invention, DNA arrays can be used to determine the expression levels of genes, by measuring the level of hybridization of the nucleic acid sequence to oligonucleotide probes that comprise complementary sequences. Various formats of DNA arrays that employ oligonucleotide "probes," (i.e., nucleic acid molecules having defined sequences) are well known to those of skill in the art. Typically, a set of nucleic acid probes, each of which has a defined sequence, is immobilized on a solid support in such a manner that each different probe is immobilized to a predetermined region. In certain embodiments, the set of probes forms an array of positionally-addressable binding (e.g., hybridization) sites on a support. Each of such binding sites comprises a plurality of oligonucleotide molecules of a probe bound to the predetermined region on the support. More specifically, each probe of the array is preferably located at a known, predetermined position on the solid support such that the identity (i.e., the sequence) of each probe can be determined from its position on the array (i.e., on the support or surface). Microarrays can be made in a number of ways, of which several are described herein. However produced, microarrays share certain characteristics, they are reproducible, allowing multiple copies of a given array to be produced and easily compared with each other.

In some embodiments, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes. Oligonucleotide probes can be synthesized directly on a support to form the array. The probes can be attached to a solid support or surface, which may be made, e.g., from glass, plastic (e.g., polypropylene, nylon), polyacrylamide, nitrocellulose, gel, or other porous or nonporous material. The set of immobilized probes or the array of immobilized probes is contacted with a sample containing labeled nucleic acid species so that nucleic acids having sequences complementary to an immobilized probe hybridize or bind to the probe. After separation of, e.g., by washing off, any unbound material, the bound, labeled sequences are detected and measured. The measurement is typically conducted with computer assistance. DNA array technologies have made it possible to determine the expression level of RNASET2, TL1A and/or IFN-γ, housekeeping genes and the methylation state of RNASET2.

In certain embodiments, high-density oligonucleotide arrays are used in the methods of the invention. These arrays containing thousands of oligonucleotides complementary to defined sequences, at defined locations on a surface can be synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; 5,510,270; 5,445,934; 5,744,305; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors And Bioelectronics 11:687-690; Blanchard, 1998, in Synthetic DNA Arrays in Genetic Engineering, Vol. 20, J. K. Setlow, Ed., Plenum Press, New York at pages 111-123). Another method for attaching the nucleic acids to a surface is by printing on glass plates, as is described generally by Schena et al. (1995, Science 270:467-470). Other methods for making microarrays, e.g., by masking (Maskos and Southern, 1992, Nucl. Acids. Res. 20:1679-1684), may also be used. When these methods are used, oligonucleotides (e.g., 15 to 60-mers) of known sequence are synthesized directly on a surface such as a derivatized glass slide. The array produced can be redundant, with several oligonucleotide molecules corresponding to each informative locus of interest (e.g., SNPs, RFLPs, STRs, etc.).

One exemplary means for generating the oligonucleotide probes of the DNA array is by synthesis of synthetic polynucleotides or oligonucleotides, e.g., using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, Nature 363:566-568; U.S. Pat. No. 5,539,083). In alternative embodiments, the hybridization sites (i.e., the probes) are made from plasmid or phage clones of regions of genomic DNA corresponding to SNPs or the complement thereof. The size of the oligonucleotide probes used in the methods of the invention can be at least 10, 20, 25, 30, 35, 40, 45, or 50 nucleotides in length. It is well known in the art that although hybridization is selective for complementary sequences, other sequences which are not perfectly complementary may also hybridize to a given probe at some level. Thus, multiple oligonucleotide probes with slight variations can be used, to optimize hybridization of samples. To further optimize hybridization, hybridization stringency condition, e.g., the hybridization temperature and the salt concentrations, may be altered by methods that are well known in the art.

In various embodiments, the high-density oligonucleotide arrays used in the methods of the invention comprise oligonucleotides corresponding to RNASET2, TL1A and/or IFN-γ and housekeeping genes. In other embodiments, the oligonucleotides correspond to methylated RNASET2. The oligonucleotide probes may comprise DNA or DNA "mimics" (e.g., derivatives and analogues) corresponding to a portion of each informative locus of interest (e.g., SNPs, RFLPs, STRs, etc.) in a subject's genome. The oligonucleotide probes can be modified at the base moiety, at the sugar moiety, or at the phosphate backbone. Exemplary DNA mimics include, e.g., phosphorothioates. For each SNP locus, a plurality of different oligonucleotides may be used that are complementary to the sequences of sample nucleic acids. For example, for a single informative locus of interest (e.g., SNPs, RFLPs, STRs, etc.) about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more different oligonucleotides can be used. Each of the oligonucleotides for a particular informative locus of interest may have a slight variation in perfect matches, mismatches, and flanking sequence around the SNP. In certain embodiments, the probes are generated such that the probes for a particular informative locus of interest comprise overlapping and/or successive overlapping sequences which span or are tiled across a genomic region containing the target site, where all the probes contain the target site. By way of example, overlapping probe sequences can be tiled at steps of a predetermined base interval, e. g. at steps of 1, 2, 3, 4, 5, 6, 7, 8, 9, or 10 bases intervals. In certain embodiments, the assays can be performed using arrays suitable for use with molecular inversion probe protocols such as described by Wang et al. (2007) *Genome Biol.* 8, R246. For oligonucleotide probes targeted at nucleic acid species of closely resembled (i.e., homologous) sequences, "cross-hybridization" among similar probes can significantly contaminate and confuse the results of hybridization measurements. Cross-hybridization is a particularly significant concern in the detection of SNPs since the sequence to be detected (i.e., the particular SNP) must be distinguished from other sequences that differ by only a single nucleotide. Cross-hybridization can be minimized by regulating either the hybridization stringency condition and/or during post-hybridization washings. Highly stringent conditions allow detection of allelic variants of a nucleotide sequence, e.g., about 1 mismatch per 10-30 nucleotides. There is no single hybridization or washing condition which is optimal for all different nucleic acid sequences, these conditions can be identical to those suggested by the manufacturer or can be adjusted by one of skill in the art. In some embodiments, the probes used in the methods of the invention are immobilized (i.e., tiled) on a glass slide called a chip. For example, a DNA microarray can comprises a chip on which oligonucleotides (purified single-stranded DNA sequences in solution) have been robotically printed in an (approximately) rectangular array with each spot on the array corresponds to a single DNA sample which encodes an oligonucleotide. In summary the process comprises, flooding the DNA microarray chip with a labeled sample under conditions suitable for hybridization to occur between the slide sequences and the labeled sample, then the array is washed and dried, and the array is scanned with a laser microscope to detect hybridization. In certain embodiments there are at least 250, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 50,000, 60,000, 70,000, 80,000, 90,000, 100,000 or more or any range in between, of RNASET2, TL1A and/or IFN-γ or housekeeping genes for which probes appear on the array (with match/mismatch probes for a single locus of interest or probes tiled across a single locus of interest counting as one locus of interest). The maximum number of RNASET2, TL1A and/or IFN-γ or housekeeping genes being probed per array is determined by the size of the genome and genetic diversity of the subjects species. DNA chips are well known in the art and can be purchased in pre-fabricated form with sequences specific to particular species. In other embodiments, SNPs and/or DNA copy number can be detected and quantitated using sequencing methods, such as "next-generation sequencing methods" as described further above.

Labeling

In some embodiments, the protein, polypeptide, nucleic acid, fragments thereof, or fragments thereof ligated to adaptor regions used in the methods of the invention are detectably labeled. For example, the detectable label can be a fluorescent label, e.g., by incorporation of nucleotide analogues. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes.

Radioactive isotopes include that can be used in conjunction with the methods of the invention, but are not limited to, 32P and 14C. Fluorescent molecules suitable for the present invention include, but are not limited to, fluorescein and its derivatives, rhodamine and its derivatives, texas red, 5'carboxy-fluorescein ("FAM"), 2', 7'-dimethoxy-4', 5'-dichloro-6-carboxy-fluorescein ("JOE"), N, N, N', N'-tetramethyl-6-carboxy-rhodamine ("TAMRA"), 6-carboxy-X-rhodamine ("ROX"), HEX, TET, IRD40, and IRD41.

Fluorescent molecules which are suitable for use according to the invention further include: cyamine dyes, including but not limited to Cy2, Cy3, Cy3.5, CY5, Cy5.5, Cy7 and FLUORX; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin and colloidal gold.

Two-color fluorescence labeling and detection schemes may also be used (Shena et al., 1995, *Science* 270:467-470). Use of two or more labels can be useful in detecting variations due to minor differences in experimental conditions (e.g., hybridization conditions). In some embodiments of the invention, at least 5, 10, 20, or 100 dyes of different colors can be used for labeling. Such labeling would also permit analysis of multiple samples simultaneously which is encompassed by the invention.

The labeled nucleic acid samples, fragments thereof, or fragments thereof ligated to adaptor regions that can be used in the methods of the invention are contacted to a plurality of oligonucleotide probes under conditions that allow sample nucleic acids having sequences complementary to the probes to hybridize thereto. Depending on the type of label used, the hybridization signals can be detected using methods well known to those of skill in the art including, but not limited to, X-Ray film, phosphor imager, or CCD camera. When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al. (1996) *Genome Res.* 6, 639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al. (1996) *Genome Res.* 6, 639-645. Alternatively, a fiber-optic bundle can be used such as that described by Ferguson et al. (1996) *Nat. Biotech.* 14, 1681-1684. The resulting signals can then be analyzed to determine the expression of RNASET2, TL1A and/or IFN-γ and housekeeping genes, using computer software.

In other embodiments, where genomic DNA of a subject is fragmented using restriction endonucleases and amplified prior to analysis, the amplification can comprise cloning regions of genomic DNA of the subject. In such methods, amplification of the DNA regions is achieved through the cloning process. For example, expression vectors can be engineered to express large quantities of particular fragments of genomic DNA of the subject (Sambrook and Russel, *Molecular Cloning: A Laboratory Manual* $4^{th}$ ed., Cold Spring Harbor Laboratory Press (Cold Spring Harbor, N.Y. 2012)).

In yet other embodiments, where the DNA of a subject is fragmented using restriction endonucleases and amplified prior to analysis, the amplification comprises expressing a nucleic acid encoding a gene, or a gene and flanking genomic regions of nucleic acids, from the subject. RNA (pre-messenger RNA) that comprises the entire transcript including introns is then isolated and used in the methods of the invention to analyze and provide a genetic signature of a cancer. In certain embodiments, no amplification is required. In such embodiments, the genomic DNA, or pre-RNA, of a subject may be fragmented using restriction endonucleases or other methods. The resulting fragments may be hybridized to SNP probes. Typically, greater quantities of DNA are needed to be isolated in comparison to the quantity of DNA or pre-mRNA needed where fragments are amplified. For example, where the nucleic acid of a subject is not amplified, a DNA sample of a subject for use in hybridization may be about 400 ng, 500 ng, 600 ng, 700 ng, 800 ng, 900 ng, or 1000 ng of DNA or greater. Alternatively, in other embodiments, methods are used that require very small amounts of nucleic acids for analysis, such as less than 400 ng, 300 ng, 200 ng, 100 ng, 90 ng, 85 ng, 80 ng, 75 ng, 70 ng, 65 ng, 60 ng, 55 ng, 50 ng, or less, such as is used for molecular inversion probe (MIP) assays. These techniques are particularly useful for analyzing clinical samples, such as paraffin embedded formalin-fixed material or small core needle biopsies, characterized as being readily available but generally having reduced DNA quality (e.g., small, fragmented DNA) and/or not providing large amounts of nucleic acids.

Once the expression levels have been determined, the resulting data can be analyzed using various algorithms, based on well-known methods used by those skilled in the art.

Kits

The present invention is also directed to a kit to diagnose a subject with IBD and/or identifying a subject in need of treatment. The kit is useful for practicing the inventive method of diagnosing a subject and/or identifying a subject in need of treatment. The kit is an assemblage of materials or components, including at least one of the inventive compositions. Thus, in some embodiments the kit contains a composition including primers and probes for RNASET2, TL1A and/or IFN-γ, as described above.

The exact nature of the components configured in the inventive kit depends on its intended purpose. For example, some embodiments are configured for the purpose of assessing risk variants and/or gene expression levels. In some embodiments, the kit is configured to detect the gene expression levels of RNASET2 in a sample. In yet other embodiments, the kit is configured to detect the gene expression levels of RNASET2 and/or TL1A in a sample. In some other embodiments, the kit is configured to detect the gene expression levels of RNASET2, TL1A and/or IFN-γ in a sample. In various other embodiments, the kit is configured to detect RNASET2 risk variants in a sample. In yet other embodiments, the kit is configured to detect the level of RNASET2 methylation in a sample. In one embodiment, the kit is configured particularly for the purpose of assessing mammalian subjects. In another embodiment, the kit is configured particularly for the purpose of assessing human subjects. In further embodiments, the kit is configured for veterinary applications, assessing subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose a subject with IBD and/or identify a subject with IBD in need of treatment. Optionally, the kit also contains other useful components, such as, primers, diluents, buffers, pipetting or measuring tools or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in gene expression assays. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing primers and probes for RNASET2, TL1A, IFN-γ and/or RNASET2 methylation. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Loss of RNASET2 in zebrafish results in accumulation of undigested rRNA within lysosomes. The major allele of RNASET2 (i) is a risk for IBD, CD (rs9355610), B1 and both ANCA levels and pos/neg (rs1410925) and (ii) protective for B3 and both ASCA IgA and IgG levels and pos/neg (rs1410925) (Table 2). The major allele rs9355610 is associated with lower levels of RNASET2 mRNA expression in CD small intestine and rectum, EBV transformed B cells and CD3+ PBL from IBD patients. The major allele is also associated with RNASET2 mRNA in CD sigmoid colon. Low levels of RNASET2 and increased levels of pANCA are associated with the major allele. Methylation at the RNASET2 locus is inversely correlated with RNASET2 mRNA expression.

TABLE 2

Non-Jewish Qualitative and Quantitative Trait Association Data

| | iChip | CH | BP | A1-minor | Test | NMISS | OR | STAT | *P | |
|---|---|---|---|---|---|---|---|---|---|---|
| rs9355610 | CD | 6 | 167383075 | A | ADD | 3859 | 0.754 | −4.041 | 5.33E−05 | minor allele protective |
| | IBD | 6 | 167383075 | A | ADD | 4172 | 0.8591 | −2.607 | 9.12E−03 | |

| | Trait | CH | BP | A1-minor | Test | NMISS | | STAT | P | |
|---|---|---|---|---|---|---|---|---|---|---|
| rs1410295 | | | | | | | OR | | | |
| | B1 | 6 | 167345503 | C | ADD | 538 | 0.7168 | −2.588 | 9.64E−03 | minor allele protective |
| | ANCA | 6 | 167345503 | C | ADD | 875 | 0.7365 | −2.626 | 8.65E−03 | |
| | B3 | 6 | 167345503 | C | ADD | 537 | 1.408 | 2.337 | 1.95E−02 | minor allele risk |
| | ASCA IgG | 6 | 167345503 | C | ADD | 820 | 1.379 | 2.926 | 3.44E−03 | |
| | ASCA Panel | 6 | 167345503 | C | ADD | 820 | 1.216 | 1.843 | 6.53E−02 | |
| | | | | | | | BETA levels | | | |
| | ANCA | 6 | 167345503 | C | ADD | 872 | −4.608 | −3.137 | 1.77E−03 | minor allele protective |
| | ASCA IgA | 6 | 167345503 | C | ADD | 820 | 4.024 | 2.363 | 1.84E−02 | minor allele risk |
| | ASCA IgG | 6 | 167345503 | C | ADD | 820 | 5.745 | 2.821 | 4.90E−03 | |

| All Non-Jewish | | A1 | A2 | | Non-Jewish CD | | A1 | A2 | |
|---|---|---|---|---|---|---|---|---|---|
| CHR | SNP | Minor | Major | MAF | CHR | SNP | Minor | Major | MAF |
| 6 | rs1410295 | C | G | 0.3541 | 6 | rs1410295 | C | G | 0.3484 |
| 6 | rs9355610 | A | G | 0.3305 | 6 | rs9355610 | A | G | 0.2915 |

*Bonferroni p-value 1.7E−04

TABLE 3

RNASET2 Major allele is a risk for IBD and CD in a non-Jewish cohort

| SNP | CH | A1 | A2 | NMISS | OR | P | Pheno Type | OR | P | Pheno type | OR | P | Pheno type |
|---|---|---|---|---|---|---|---|---|---|---|---|---|---|
| rs9355610 | 6 | A | G | 5913 | 0.8218 | 4.50E−05 | IBD | 0.756 | 1.22E−06 | CD | 0.94 | 0.3695 | UC |
| rs1819333* | 6 | C | A | 5813 | 0.8523 | 3.91E−04 | IBD | 0.782 | 4.04E−06 | CD | 0.988 | 0.8575 | UC |

| SNP | CH | A1 | A2 | MAF | NCHROBS |
|---|---|---|---|---|---|
| rs1819333 | 6 | C | A | 0.4894 | 21278 |
| rs9355610 | 6 | A | G | 0.3608 | 21278 |

A1 = minor allele;
A2 = major allele

TABLE 4

Qualitative Trait Associations in non-Jewish CD. Major allele is risk for colonic disease in non-Jewish CD.

| CD-Phenotype | CHR | SNP | BP | A1 | A2 | NMISS | OR | STAT | p | A1 Freq |
|---|---|---|---|---|---|---|---|---|---|---|
| B1 | 6 | rs62436418 | 167265792 | G | A | 592 | 0.6992 | −2.853 | 4.33E−03 | 0.3787 |
| B2 | 6 | rs62436418 | 167265792 | G | A | 592 | 1.395 | −2.648 | 8.09E−03 | |
| Colon | 6 | rs62436418 | 167265792 | G | A | 593 | 0.6275 | −3.161 | 1.57E−03 | |
| B2 | 6 | rs9355610 | 167303065 | A | G | 592 | 1.433 | 2.709 | 6.75E−03 | 0.3608 |
| Colon | 6 | rs9355610 | 167303065 | A | G | 593 | 0.7299 | −2.04 | 4.14E−02 | |

A1 = minor allele;
A2 = major allele

TABLE 5

RNASET2 SNPs Associated with CD and IBD. Major allele is risk for CD and IBD.

| Phenotype | CHR | SNP_rsid | BP | A1 | A2 | TEST | NMISS | OR | STAT | P | LOCATION | MAF |
|---|---|---|---|---|---|---|---|---|---|---|---|---|
| CD | 6 | rs2149085 | 167291100 | G | A | ADD | 4360 | 0.8414 | −4.016 | 5.93E−05 | INTERGENIC | 0.4751 |
| CD | 6 | rs1819333 | 167293537 | C | A | ADD | 4361 | 0.8446 | −3.93 | 8.51E−05 | INTERGENIC | 0.4753 |
| CD | 6 | rs3823208 | 167267836 | G | A | ADD | 4361 | 0.8507 | −3.64 | 2.73E−04 | INTRON | 0.3446 |
| CD | 6 | rs62436418 | 167265762 | G | A | ADD | 4361 | 0.8569 | −3.539 | 4.01E−04 | INTERGENIC | 0.3861 |
| CD | 6 | rs2769345 | 167286384 | G | A | ADD | 4361 | 0.8593 | −3.53 | 4.15E−04 | INTRON | 0.4811 |
| CD | 6 | rs9459813 | 167287827 | A | T | ADD | 4361 | 0.8028 | −3.104 | 1.91E−03 | INTRON | 0.1102 |
| CD | 6 | rs2236313 | 167280379 | G | A | ADD | 4361 | 0.8784 | −3.016 | 2.56E−03 | INTRON | 0.4476 |
| CD | 6 | rs9355610 | 167303065 | A | G | ADD | 4361 | 0.9084 | −2.163 | 3.05E−02 | INTERGENIC | 0.3502 |
| IBD | 6 | rs41269599 | 167267869 | A | G | ADD | 5110 | 0.844 | −1.982 | 4.75E−02 | INTRON | 0.0635 |

A1 = minor allele;
A2 = major allele

TABLE 6

RNASET2 SNPs Associated with Subclinical Phenotypes of CD

| PHENOTYPE | CHR | RSID | BP | A1 | A2 | TEST | NMISS | OR | STAT | P | LOCATION | MAF |
|---|---|---|---|---|---|---|---|---|---|---|---|---|
| PDM | 6 | rs3798303 | 167274358 | G | A | ADD | 2093 | 1.38 | 3.019 | 2.54E−03 | INTRON | 0.09853 |
| Iritis | 6 | rs41269599 | 167267869 | A | G | ADD | 1436 | 2.806 | 2.973 | 2.95E−03 | INTRON | 0.06876 |
| Iritis | 6 | rs181130555 | 167277010 | D | — | ADD | 1434 | 2.744 | 2.932 | 3.37E−03 | INTRON | 0.07108 |
| Iritis | 6 | rs3777721 | 167272065 | C | G | ADD | 1436 | 2.761 | 2.92 | 3.50E−03 | INTRON | 0.07084 |
| Iritis | 6 | rs41269597 | 167267663 | C | G | ADD | 1436 | 2.711 | 2.868 | 4.13E−03 | INTRON | 0.07234 |
| Iritis | 6 | imm_6_167277028 | 167277028 | A | — | ADD | 1435 | 2.609 | 2.776 | 5.51E−03 | INTRON | 0.07369 |
| Iritis | 6 | rs1079145 | 167280714 | A | G | ADD | 1436 | 2.424 | 2.717 | 6.59E−03 | INTRON | 0.0893 |
| Iritis | 6 | rs10946197 | 167268406 | A | C | ADD | 1436 | 0.3753 | −2.717 | 6.60E−03 | INTRON | 0.256 |
| PDM | 6 | rs3777723 | 167273691 | A | G | ADD | 2093 | 1.334 | 2.648 | 8.09E−03 | INTRON | 0.09552 |

A1 = minor allele;
A2 = major allele;
D = deletion

TABLE 7

RNASET2 Associations with Subclinical Phenotypes in non-Jewish CD Patients

| PHENOTYPE | CHR | RSID | BP | A1 | A2 | TEST | NMISS | OR | STAT | P | MAF |
|---|---|---|---|---|---|---|---|---|---|---|---|
| Iritis | 6 | rs1079145 | 167280714 | A | G | ADD | 680 | 3.646 | 2.99 | 2.79E−03 | 0.07357 |
| Iritis | 6 | rs3777721 | 167272065 | C | G | ADD | 680 | 3.844 | 2.97 | 2.98E−03 | 0.05932 |
| Iritis | 6 | rs181130555 | 167277010 | D | — | ADD | 679 | 3.622 | 2.909 | 3.63E−03 | 0.0613 |
| Iritis | 6 | imm_6_167277028 | 167277028 | A | — | ADD | 679 | 3.511 | 2.848 | 4.40E−03 | 0.06168 |
| Iritis | 6 | rs3778439 | 167278341 | A | G | ADD | 680 | 3.535 | 2.671 | 7.55E−03 | 0.05277 |

TABLE 7-continued

RNASET2 Associations with Subclinical Phenotypes in non-Jewish CD Patients

| PHENO TYPE | CHR | RSID | BP | A1 | A2 | TEST | NMISS | OR | STAT | P | MAF |
|---|---|---|---|---|---|---|---|---|---|---|---|
| Iritis | 6 | rs3734246 | 167278058 | A | G | ADD | 680 | 3.535 | 2.671 | 7.55E−03 | 0.05277 |
| PDM | 6 | rs2769339 | 167275844 | G | A | ADD | 977 | 1.553 | 2.929 | 3.41E−03 | 0.09707 |
| PDM | 6 | rs2757045 | 167270953 | G | A | ADD | 977 | 1.499 | 2.73 | 6.34E−03 | 0.09977 |
| PDM | 6 | rs3798303 | 167274358 | G | A | ADD | 977 | 1.491 | 2.669 | 7.62E−03 | 0.09669 |
| PDM | 6 | rs2757048 | 167271110 | A | G | ADD | 977 | 1.479 | 2.637 | 8.37E−03 | 0.099 |
| Uveitis | 6 | rs3777723 | 167273691 | A | G | ADD | 674 | 3.78 | 2.657 | 7.89E−03 | 0.09091 |

A1 = minor alele;
A2 = major allele;
D = deletion

TABLE 8

RNASET2 Association with Serologies in CD Patients

| Phenotype | CHR | SNP_rsid | BP | A1 | A2 | TEST | NMISS | BETA/OR | STAT | P | LOCATION | MAF |
|---|---|---|---|---|---|---|---|---|---|---|---|---|
| CBIR | 6 | rs425145 | 167321292 | G | A | ADD | 2432 | 4.175 | 2.167 | 3.03E−02 | INTERGENIC | 0.1121 |
| CBIR | 6 | rs415356 | 167326817 | G | A | ADD | 2432 | 4.16 | 2.164 | 3.06E−02 | INTERGENIC | 0.1121 |
| CBIR | 6 | rs435359 | 167317604 | G | A | ADD | 2432 | 4.16 | 2.164 | 3.06E−02 | INTERGENIC | 0.1123 |
| CBIR | 6 | rs375883 | 167304704 | T | A | ADD | 2430 | 4.119 | 2.14 | 3.24E−02 | INTERGENIC | 0.112 |
| CBIR | 6 | rs62438869 | 167320907 | A | G | ADD | 2432 | −3.722 | −2.101 | 3.57E−02 | INTERGENIC | 0.1281 |
| CBIR | 6 | rs9459813 | 167287827 | A | T | ADD | 2432 | 4.073 | 2.015 | 4.40E−02 | INTRON | 0.09872 |
| CBIR | 6 | rs443297 | 167304286 | A | G | ADD | 2432 | 3.978 | 1.972 | 4.88E−02 | INTERGENIC | 0.09947 |
| IgG.ASCA | 6 | rs1410295 | 167265493 | C | G | ADD | 2326 | 2.342 | 1.936 | 5.29E−02 | INTERGENIC | 0.3474 |

A1 = minor allele;
A2 = major allele

TABLE 9

RNASET2 Associations with Serologies of non-Jewish CD Patients

| SEROLOGY | CHR | RSID | BP | A1 | A2 | TEST | NMISS | BETA | STAT | P | MAF |
|---|---|---|---|---|---|---|---|---|---|---|---|
| ANCA | 6 | rs41269599 | 167267869 | A | G | ADD | 1143 | −7.159 | −2.709 | 6.85E−03 | 0.05586 |
| CBIR | 6 | rs9459813 | 167287827 | A | T | ADD | 1208 | 8.021 | 2.854 | 4.40E−03 | 0.1159 |
| CBIR | 6 | rs9459812 | 167287711 | A | C | ADD | 1208 | 7.699 | 2.735 | 6.33E−03 | 0.1156 |
| IgA.ASCA | 6 | rs3823208 | 167267836 | G | A | ADD | 1130 | 4.153 | 3.102 | 1.97E−03 | 0.3139 |
| IgG.ASCA | 6 | rs3823208 | 167267836 | G | A | ADD | 1130 | 4.99 | 3.115 | 1.89E−03 | 0.3139 |
| IgG.ASCA | 6 | imm_6_167277028 | 167277028 | A | — | ADD | 1129 | 8.352 | 2.725 | 6.53E−03 | 0.06168 |

A1 = minor allele.
A2 = major allele

TABLE 10

RNASET2 Associations with Expression in Small Bowel

| SNP_rsid | gene | beta | p-value | FDR |
|---|---|---|---|---|
| rs72079749 | RNASET2 | 0.151129328 | 1.66E−04 | 0.371075825 |
| rs66591848 | RNASET2 | 0.154066135 | 2.27E−04 | 0.42289639 |
| rs1951459 | RNASET2 | 0.161888591 | 2.39E−04 | 0.429556929 |
| rs4710149 | RNASET2 | 0.161888591 | 2.39E−04 | 0.429556929 |
| rs933243 | RNASET2 | 0.161888591 | 2.39E−04 | 0.429556929 |
| rs9355610 | RNASET2 | 0.161888591 | 2.39E−04 | 0.429556929 |
| rs9356551 | RNASET2 | 0.161888591 | 2.39E−04 | 0.429556929 |
| rs9366078 | RNASET2 | 0.161888591 | 2.39E−04 | 0.429556929 |
| rs1819333 | RNASET2 | 0.15479148 | 3.22E−04 | 0.461149469 |
| rs2013815 | RNASET2 | 0.15479148 | 3.22E−04 | 0.461149469 |
| rs2149085 | RNASET2 | 0.15479148 | 3.22E−04 | 0.461149469 |
| rs2769345 | RNASET2 | 0.128393311 | 3.08E−03 | 0.777560209 |
| rs2236313 | RNASET2 | 0.096154247 | 3.09E−02 | 0.908151161 |

Major allele is risk for small bowel expression.

TABLE 11

RNASET2 Associations for Expression in Large bowel

| | snp_rsid | gene | beta | t-stat | p-value | FDR |
|---|---|---|---|---|---|---|
| CD | | | | | | |
| Rectum | rs683571 | RNASET2 | −0.57902 | −3.65206 | 0.00115 | 0.460077 |
| Rectum | rs2031846 | RNASET2 | −0.48099 | −3.27469 | 0.002992 | 0.679028 |
| Rectum | rs62436763 | RNASET2 | −0.50894 | −3.24339 | 0.003235 | 0.692932 |
| Rectum | rs41463945 | RNASET2 | −0.58473 | −3.11594 | 0.004434 | 0.693762 |
| Sigmoid | rs162289 | RNASET2 | 0.147287 | 2.955434 | 0.007311 | 0.619358 |
| Sigmoid | rs162291 | RNASET2 | 0.147287 | 2.955434 | 0.007311 | 0.619358 |
| Sigmoid | rs162293 | RNASET2 | 0.147287 | 2.955434 | 0.007311 | 0.619358 |
| Sigmoid | rs162294 | RNASET2 | 0.147287 | 2.955434 | 0.007311 | 0.619358 |
| Sigmoid | rs162295 | RNASET2 | 0.147287 | 2.955434 | 0.007311 | 0.619358 |
| Sigmoid | rs162297 | RNASET2 | 0.147287 | 2.955434 | 0.007311 | 0.619358 |
| Sigmoid | rs2236312 | RNASET2 | 0.162431 | 3.419281 | 0.002456 | 0.451404 |
| Sigmoid | rs3756838 | RNASET2 | 0.14602 | 3.147931 | 0.00467 | 0.576607 |
| Sigmoid | rs3798307 | RNASET2 | 0.162431 | 3.419281 | 0.002456 | 0.451404 |
| Sigmoid | rs62436424 | RNASET2 | 0.14602 | 3.147931 | 0.00467 | 0.576607 |
| Sigmoid | rs7772112 | RNASET2 | 0.14602 | 3.147931 | 0.00467 | 0.576607 |
| Sigmoid | rs9366076 | RNASET2 | 0.14602 | 3.147931 | 0.00467 | 0.576607 |
| UC | | | | | | |
| Rectum | rs57237533 | RNASET2 | 0.572002 | 3.665898 | 0.001643 | 0.436982 |
| Rectum | rs56213919 | RNASET2 | 0.572002 | 3.665898 | 0.001643 | 0.436982 |
| Sigmoid | rs10946198 | RNASET2 | −0.36397 | −3.11588 | 0.008192 | 0.704927 |
| Sigmoid | rs1819333 | RNASET2 | −0.36397 | −3.11588 | 0.008192 | 0.704927 |
| Sigmoid | rs2149085 | RNASET2 | −0.36397 | −3.11588 | 0.008192 | 0.704927 |
| Sigmoid | rs2769345 | RNASET2 | −0.36397 | −3.11588 | 0.008192 | 0.704927 |

TABLE 12

Hits with Small Bowel Tissue Expression

| Genes in Locus | IBD iCHIP (pValue)* | Sub-Phenotype Association (CD)* | Sm Bowel eQTL pValue | "Near Gene" Pathway eQTL pValue | Cellular Location | EBV Cell Line | Published Pre-Clinical IBD Model |
|---|---|---|---|---|---|---|---|
| RNASET2_FGFR1OP | IBD: (9.7E−03) CD: (5.3E−05) | B2, Serology | <1E−04 RNASET2 | N/A | Intracellular (RNSET 2) | Yes | No |

TABLE 13

RNASET2 Exome CHIP

| dis | SNP/rsID | n.case | n.ctrl | CHR | BP | A1 | A2 | MAF | NMISS | OR | P | geneList | Function GVS | Assoc Locus |
|---|---|---|---|---|---|---|---|---|---|---|---|---|---|---|
| CD | exm-rs2236313 | 5742 | 5725 | 6 | 1.7E+08 | G | A | 0.4134 | 11467 | 0.8932 | 3.28E−05 | RNASET2 | intron | IBD |
| IBD | exm-rs2236313 | 10523 | 5725 | 6 | 1.7E+08 | G | A | 0.4145 | 16248 | 0.9219 | 0.00061 | RNASET2 | intron | IBD |

A1 = minor allele;
A2 = major allele

Allele risk is defined by the Odds ratio (OR). When the A1 allele and an OR of <1 is depicted, then the major allele is the risk allele (A2 is risk). If the OR is >1, then the minor allele (A1) is risk allele. Knowing A1 and the Odds Ratio allows you to determine which allele is risk and which is protective.

Example 2

The molecular mechanisms of TL1A augmentation of inflammation via enhanced IFN-γ expression were defined using RNAseq. CD4+ T cells were analyzed in untreated conditions or treated with IL12 and IL18 or IL12 and IL18 and TLA1 at the 1 ug scale. On a 10 ng scale, CD4+ T cells were analyzed when treated with IL12 and IL18 and TLA1, either with or without IFN-γ. The RNAseq data prescreen removed all failed probe data, all genes with fewer than 3 samples with FPKM>5. Using this criteria, 8695 genes passed the prescreen and BRB Array Tools were used for class comparison using paired samples.

The inventors demonstrate that at the molecular level, TL1A treatment mediates enhanced expression of IFN-γ, in addition to mediating a decreased expression of RNASET2. The decreased expression of RNASET2 is detected in CD patients: 1) with chronically active disease, 2) with refractive disease requiring surgical intervention, 3) with patients naïve to anti-TNF therapy, 4) is associated with OmpC+, ANCA-- serological factors, and 5) is associated with RNASET2 risk SNPs rs9355610, rs1819333, rs2149085.

Example 3

TNFSF15 and the protein it encodes TL1A, is associated with IBD and are key mediators of mucosal inflammation. In IBD patients, elevated TL1A levels correlate with disease severity and genotype. TL1A mediates marked enhancement of IFN-γ production. TL1A response biomarkers were identified by RNAseq and verified by qPCR in T cells isolated from IBD patients (20 Crohn's [CD], 20 ulcerative colitis [UC]) compared to normal (NL). An additional cohort of samples from NL and IBD patients was used to validate and measure expression/methylation quantitative trait loci (eQTL/mQTL) in the context of GWAS. RNAseq expression clustering differentiated TL1A treated versus non-treated cells. RNASET2, a gene encoding an extracellular T2 RNase, was down-regulated following TL1A treatment. Previous studies associated RNASET2 with susceptibility for CD. RNASET2 expression in CD patients was lower in "severe" vs. mild disease, i.e., multiple disease flare-ups ($p<0.009$), medically refractory ($p<0.024$). Disease risk allele for RNASET2 rs1819333 ($p=0.015$) and TNFSF15 allele associated with enhanced TL1A expression, rs6478108, rs6478109 and rs7848647 ($p=0.01$) were correlated with decreased RNASET2 expression. Moreover, siRNA silencing of RNASET2 enhanced TL1A mediated IFN-γ secretion. Without being bound to any particular theory, the inventors believe that down-regulation of RNASET2 is a hallmark of TL1A driven severe CD.

RNASET2 expression and DNA methylation were examined in a separate cohort of freshly isolated un-stimulated T cells from NL, CD or UC patients. Methylation at RNASET2 locus inversely correlated with mRNA expression. eQTL of RNASET2 alleles was associated with decreased expression. Significantly enhanced RNASET2 methylation was observed in CD patients with severe disease requiring surgical intervention (Table 14). No correlation was observed in NL or patients with mild disease. Likewise, increased RNASET2 methylation was associated with TNFSF15 risk alleles associated with enhanced TL1A expression (Table 14). Epigenetically, the RNASET2 eQTL/mQTL region overlaps with histone H3K4me3 and H3K27ac and DNase HS activation sites. This region co-localizes with transcription factor binding for NFκB, jun, ATF3 and CEBPD—all of which are up-regulated in response to TL1A treatment. The results identify RNASET2 as a TL1A response gene involved in regulation of IFN-γ production. In CD patients with severe disease there is hyper-methylation and decreased expression of RNASET2, which may be reflective of prior exposure in-vivo to TL1A. Thus, without being bound to any particular theory, the inventors believe that RNASET2 serves as a novel potential disease severity biomarker to identify a subset of CD patients most likely to benefit from anti-TL1A therapy.

TABLE 14

Increased RNASET2 methylation associated with TNFSF15 risk allele.

| | RNASET2 | | | | | TNFSF15 | | |
|---|---|---|---|---|---|---|---|---|
| p value | rs62436418 | rs2236313 | rs2769345 | rs1819333 | rs9355610 | rs6478108 | rs6478109 | rs7848647 |
| eQTL | 0.013 | 0.024 | 0.038 | 0.038 | 0.011 | na | na | na |
| mQTL (RNASET2) | 0.001 | $2.7 \times 10^{-13}$ | $2.7 \times 10^{-13}$ | $2.7 \times 10^{-13}$ | $1.4 \times 10^{-9}$ | 0.005 | 0.013 | 0.003 |

The inventors further analyzed 3 cohorts of patients including 11 UC CD3+ PBT (medically refractive), 43 CD CD3+ PBT (23 were medically refractive and 20 were mild) and 17 normal CD3+ PBT. The samples were run on the Infinium 450 Methylation Array and 11 CD, 12 UC and 4 NL samples were run on the Infinium Expression Array. The inventors demonstrate that RNASET2 expression is decreased following TL1A treatment of CD4+ T cells and that silencing of RNASET2 enhances TL1A mediated IFN-γ secretion.

TABLE 15

Clinical Features

| RNASET2 | Expression | Methylation |
|---|---|---|
| Multiple disease flares | ↓ | |
| Refractive disease requiring surgical intervention | ↓ | ↑ |
| Patients naïve to anti-TNF therapy | ↓ | ↑ |
| RNASET2 risk allele SNPs rs9355610, rs1819333, rs62436418, rs22236313, rs2769345 | ↓ | ↑ |
| RNASET2 risk allele SNPs | | |
| Refractive disease | ↓ | ↑ |
| Normal or Mild disease | | ↔ |

Epigenetic studies demonstrated that RNASET2 eQTL/mQTL region overlaps with epigenetic activation sites for 1) histone H3K4me3 and H3K27ac, 2) DNase HS, 3) co-localizes with transcription factor binding for NFkB, jun, ATF3 and CEBPD, all of which are up-regulated in response to TL1A treatment. Furthermore, the enhancer element in primary T memory cells from peripheral blood, the DNAse HS site in CD4+ naïve T cells and the eQTL RPS6KA2 monocytes were linked to the rs1819333 allele.

Example 4

Figure 15:
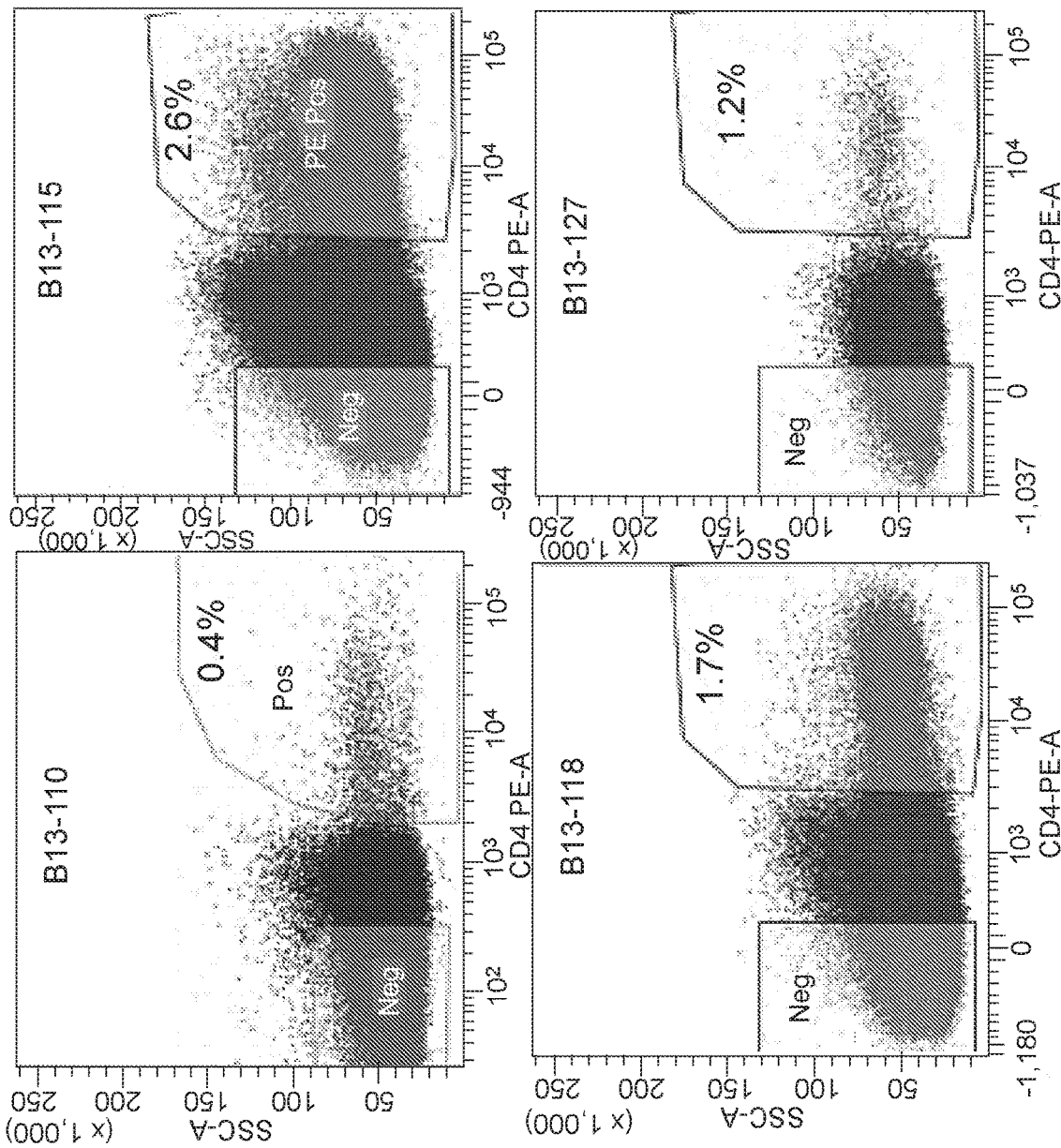
FIG. 15 depicts sorting and IFNγ expression of CD4+ T cells stimulated with IL-12, IL-18 and/or TL1A, in accordance with various embodiments of the invention. Histograms of side scatter vs. IFN-γ for CD4+ T cells stimulated with recombinant human IL-12 (500 pg/ml) and IL-18 (50 ng/ml) and TL1A (100 ng/ml) for 8 h from 4 donor (D1-4).
Figure 16:
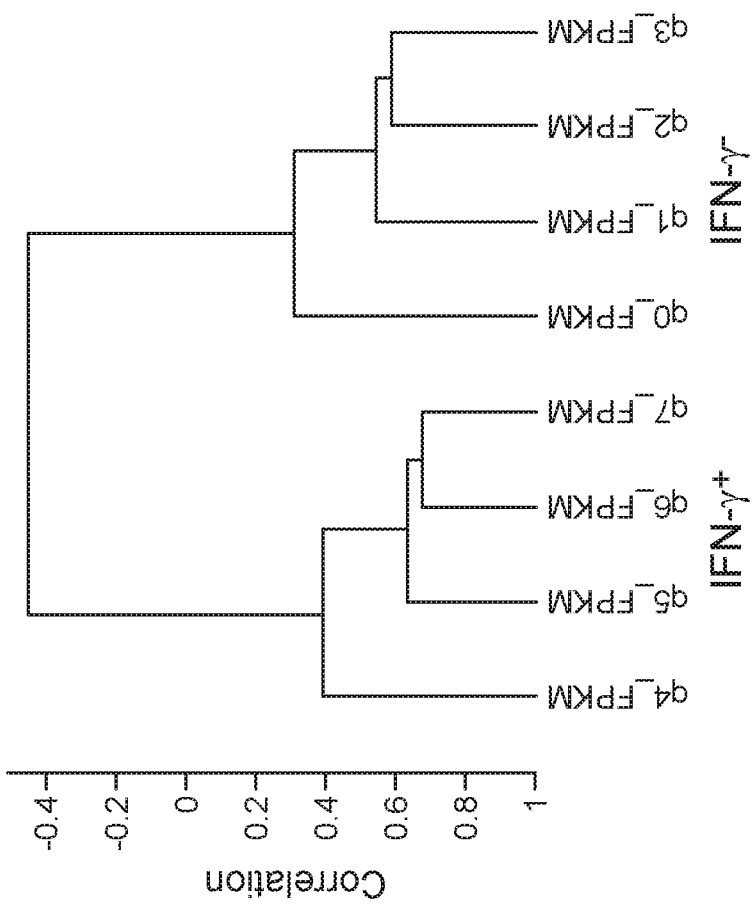
FIG. 16 depicts a dendrogram of hierarchical clustering using centered correlation and average linkage, in accordance with various embodiments of the invention.

TL1A synergizes with IL-12/IL-18 resulting in a rapid (within 6-8 hours) and marked enhancement of IFN-γ expression. RNAseq analysis was used to identify the TL1A response genes regulating IFN-γ expression. Twenty genes were differentially expressed (at least 2-fold) in TL activated total CD4+ T cell population. This can be largely due to the fact that IFN-γ secreting T cells constitute only a very small subset (1-3%) of the total CD4+ T cell population (FIG. 15). CD4 T cells from healthy donors were treated with IL12/IL18 and TL1A for 8 hours and then sorted into IFN-γ-secreting and non-secreting subsets (FIG. 15) and whole-genome transcriptional analyses (GWAS) of mRNA was performed. Unsupervised hierarchical clustering of the entire 8075 expressed gene set clearly distinguished between the TL1A mediated IFN-γ-secreting and non-secreting subgroups (FIG. 16).

Figure 17:
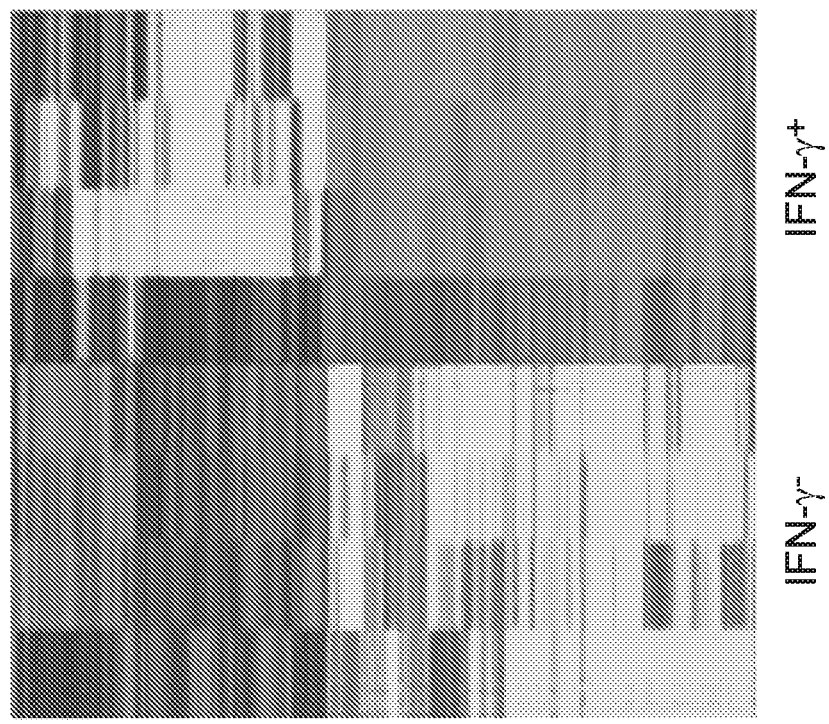
FIG. 17 depicts a class prediction analysis classifying the IFNγ-secreting and non-secreting subgroups based on expression level, in accordance with various embodiments of the invention. Heatmap of 764 predictor genes.
Figure 18:
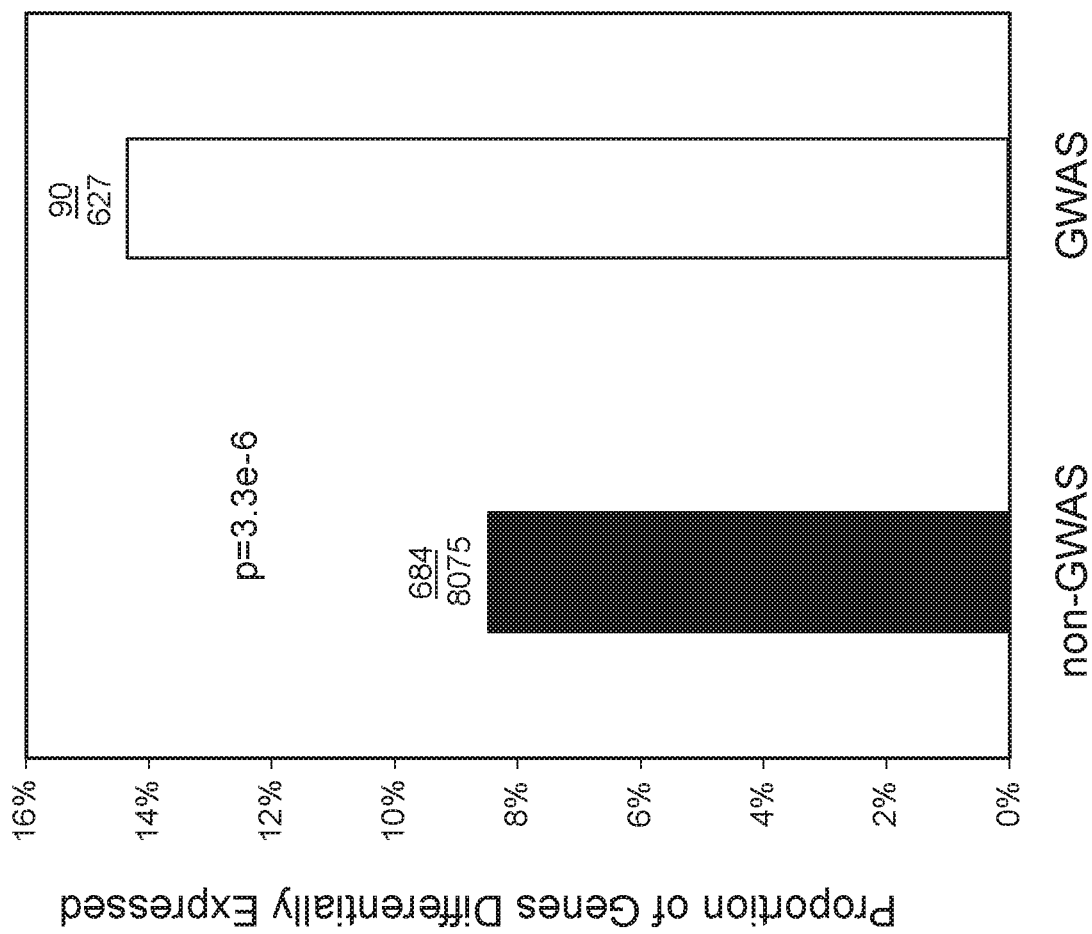
FIG. 18 depicts a proportion of genes differentially expressed that was increased in GWAS versus other regions, in accordance with various embodiments of the invention.

A class prediction analysis classifying the IFN-γ-secreting and non-secreting subgroups based on expression levels was performed. The best predictor transcript list consisted of 764 genes with at least two fold differential expression between the IFN-γ secreting subset (p-value<0.00005) (FIG. 17). Gene ontology analysis showed that the differentially expressed genes were enriched for those in pathways associated with proteasome, apoptosis, RNA expression and T cell receptor signaling, and were downstream targets of Infliximab (activation z score=−4, p value=2e-15). GWAS has identified multiple IBD risk variant SNPs. There was a significant increase in the proportion of transcripts located within 0.5 MB from an IBD risk SNPs (14% vs. 9%, p value=3.3e-6) compared to proportion of predictor genes in other regions. In fact, differentially expressed transcripts mapped to 34% of all IBD risk associated regions (FIG. 18). Without being bound to any particular theory, the data demonstrate a strong contribution for these genes not only in TL1A mediated modulation of IFN-γ expression but as contributing factors modulating IBD susceptibility and pathogenesis.

Figure 7:
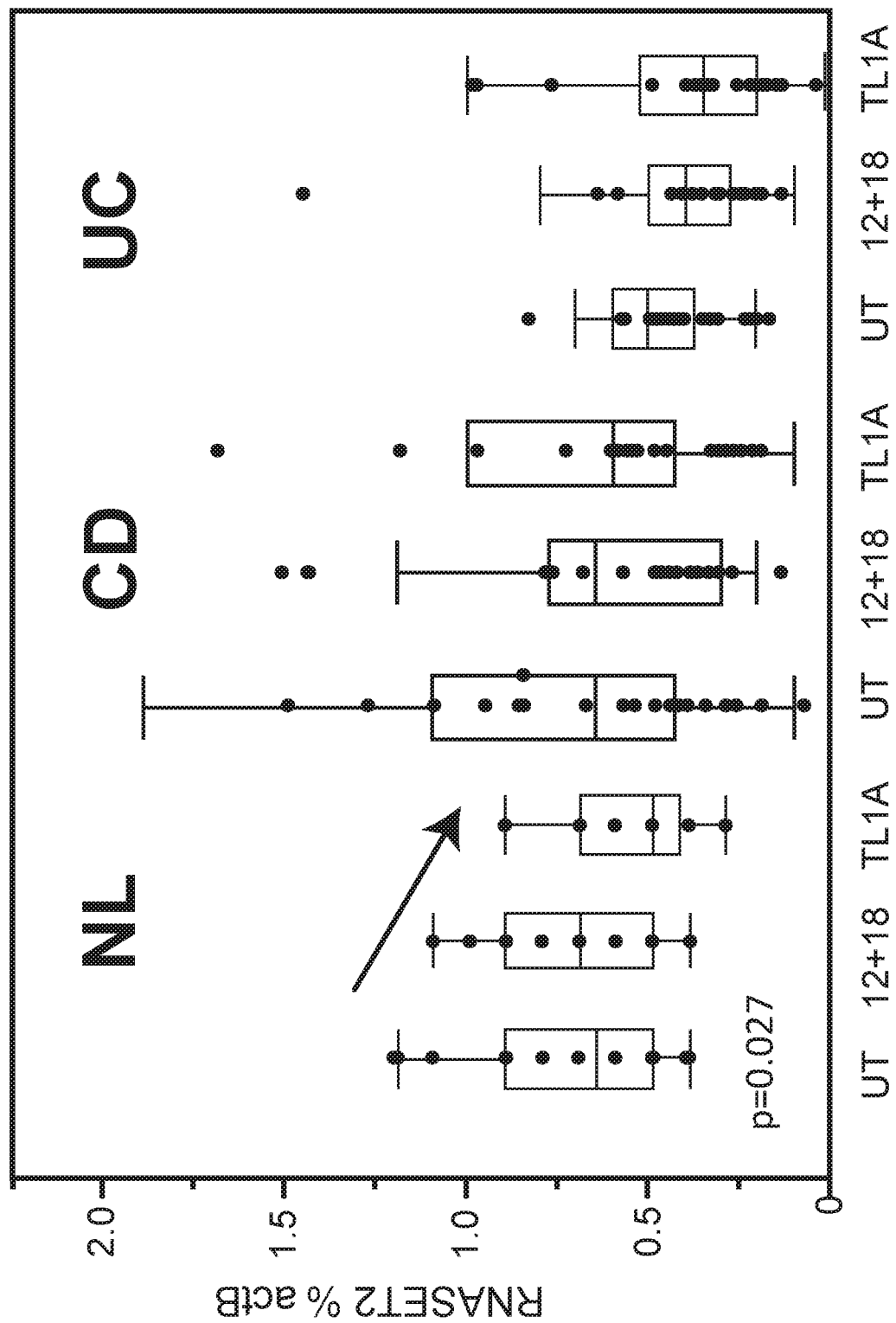
FIG. 7 depicts RNASET2 expression following IL-12, IL-18, and/or TL1A and treatment, in accordance with various embodiments of the invention.
Figure 8A:
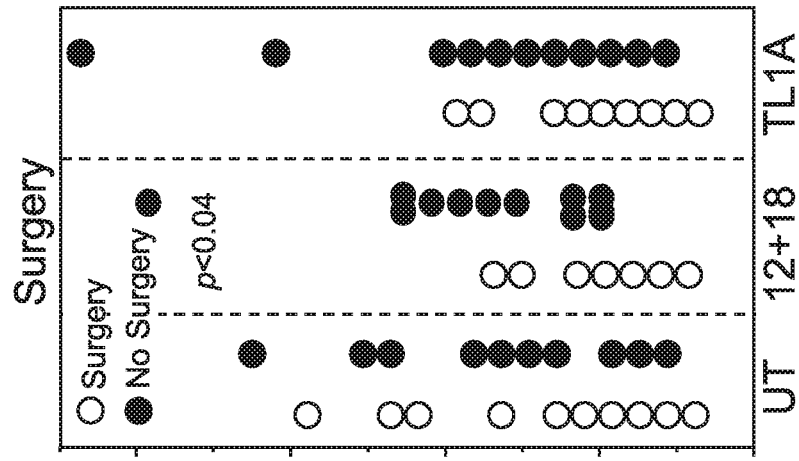
Figure 8B:
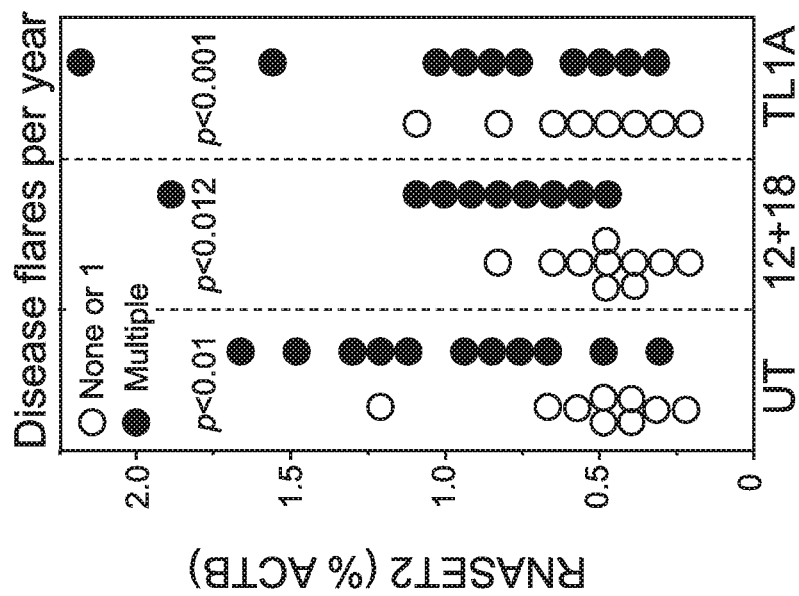

A volcano plot visualizing the significance and magnitude of differentially expressed predictor transcripts associated with IBD risk loci, allowed us to prioritize candidate genes (FIG. 20). Of these genes, TL mediated expression of IFN-γ was confirmed to be most significantly up-regulated and RNASET2 as most significantly down-regulated (FIG. 20). RNASET2, a member of the Rh/T2/S family of ribonuclease, was the only IBD risk associated gene displaying a greater than 5 fold TL1A mediated down-regulation in expression. RNASET2 has been identified by GWAS as a potential IBD risk gene. As the functional role of RNASET2 in IBD pathogenesis was unknown, the regulation of RNASET2 expression in IBD was examined. Without being bound to any particular theory, the inventors believe that since RNASET2 is a 'class predictor' gene, differential expression can be detected in total CD4+ T cells. Resting or IL12/IL18 treated CD4+ T cells from CD, UC patients or NL controls were isolated and RNASET2 levels were compared in the presence or absence of TL1A for 8 hours. As seen in FIG. 7, in contrast to what we had been observed in cells from NL donors, IBD patients did not display a TL1A mediated decrease in RNASET2 expression levels. Rather decreased expression levels of RNASET2 were associated in CD patients with "severe" compared to mild disease course. RNASET2 expression was significantly lower in cells isolated from CD patients exhibiting multiple disease flares per year (p<0.001) (FIGS. 8A and 8C) and likewise decreased RNASET2 expression was detected in CD patients who were medically refractive requiring surgical intervention for disease management (p<0.024) (FIG. 8B). A similar trend was seen in UC patients.

Figure 21B:
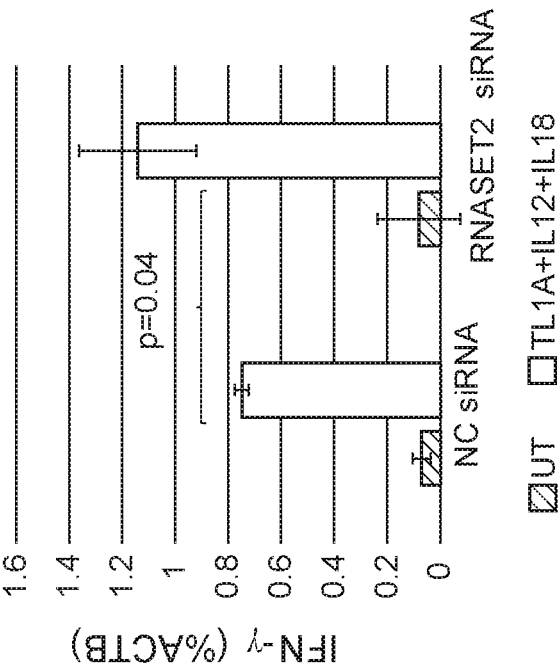
FIGS. 21A-21B show that silencing RNASET2 enhances IFN-γ secretion, in accordance with various embodiments of the invention. A) Inhibition of RNASET2 by RNASET2 siRNA. B) Effect of RNASET2 silencing on IFN-γ secretion. Enhanced IFN-γ expression in cellos transfected with RNASET2 siRNA compared to control scrambled siRNA.
Figure 21A:
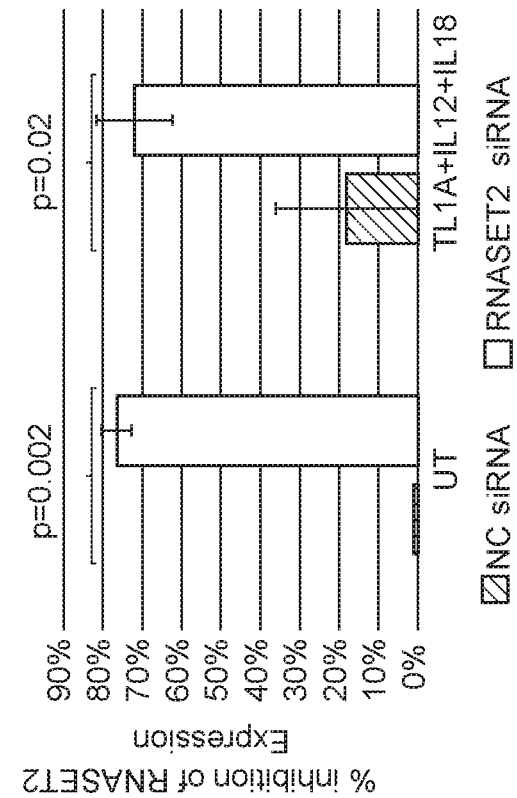

Gene expression quantitative trait (eQTL) was performed to characterize the functional correlation between RNASET2 gene variation and the gene transcript expression level. The IBD risk SNP tagging in Caucasians, rs1819333, and rs2149085 identified in the CD Korean population, are both located within −3.5 kb from the transcriptional start site, within the RNASET2 promoter region. An additional promoter SNP, rs9355610, has been shown to be associated with susceptibility with Grave's autoimmune thyroid disease. In peripheral cells isolated from CD patients the RNASET2 disease risk alleles rs1819333 (p=0.015) and rs2149085 (p=0.015), as well as, rs9355610 (p=0.04) display eQTL and were correlated with decreased RNASET2 expression (FIG. 9). Without being bound to any particular theory, the data indicates a pathway whereby down-regulation of RNASET2 alters IFN-γ expression. The functional role of RNASET2 in regulation of IFN-γ expression was confirmed using siRNA mediated silencing. CD4+ T cells were transfected with siRNA targeting RNASET2 mRNA or control siRNA and then treated with IL12/IL18 and TL1A. The expression of RNASET2 mRNA itself displayed a 60-70% inhibition by RNASET2 siRNA (FIG. 21A). In parallel, a significant enhancement (>1.5 fold) in IFN-γ expression was seen in cells transfected with RNASET2 siRNA compared to control scrambled siRNA (FIG. 21B).

Figure 10:
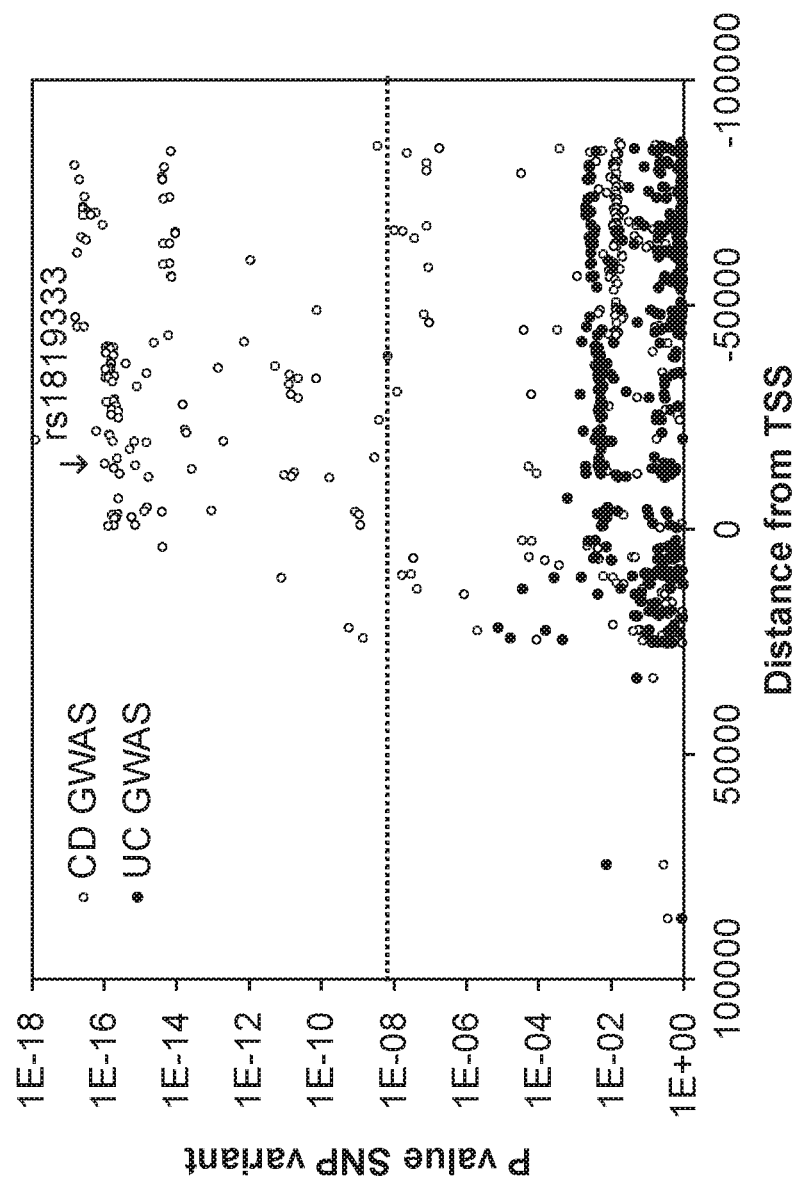
FIG. 10 depicts RNASET2 methylation versus GWAS p values in CD and UC patients, in accordance with various embodiments of the invention.
Figure 23:
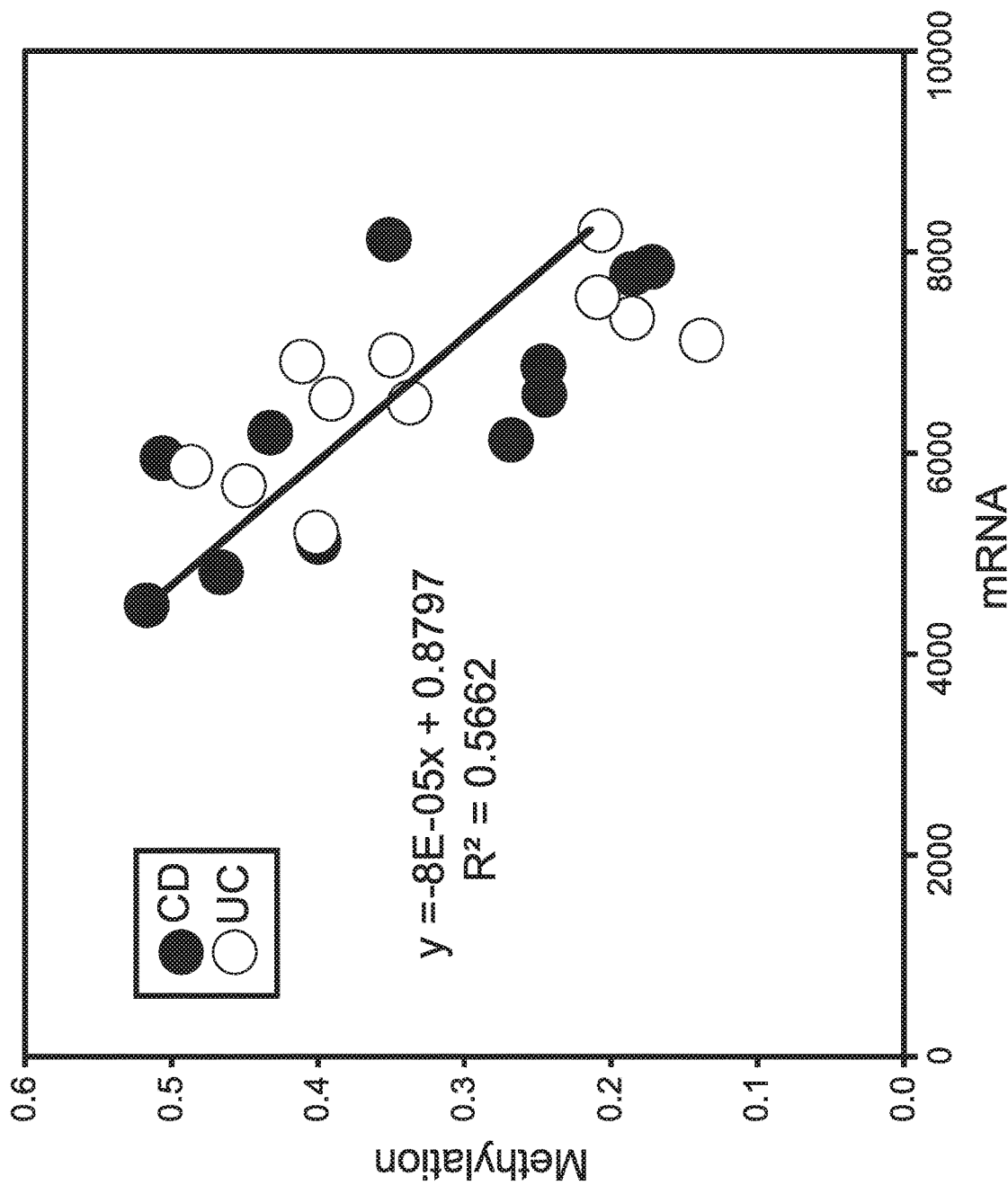
FIG. 23 demonstrates a negative correlation of RNASET2 methylation and expression in CD3+ T cells (cg25258033, located 1.4 kb within the first intron) in 21 IBD patients, in accordance with various embodiments of the invention.

Without being bound to any particular theory, the inventors believe that considering the pivotal role of IFNγ in pathogenesis of Crohn's disease these data collectively indicate that down-regulation of RNASET2 may serve as a biomarker of TL1A driven severe CD. RNASET2 expression was examined in a separate cohort of freshly isolated unstimulated T cells from NL, CD and UC patients. Since DNA methylation impacts upon gene expression and since most disease-risk genetic polymorphisms map outside of the transcribed exome in regions subject to epigenetic modification, the DNA methylation status of RNASET2 was examined as well. In unstimulated T cells from CD and UC patients an inverse correlation was observed between IFNγ expression levels and RNASET2 (FIG. 22). Moreover, as seen in FIG. 10, there was a significant negative correlation between expression and methylation which was inversely related to distance, mainly within 50 kb upstream and downstream from the transcriptional start site (TSS). Additionally, there was a significant overlap between IBD disease risk genetic variants and regions correlative for methylation and expression levels (FIG. 10). The strongest correlation ($p=8.5\times10^{-5}$) was observed at a CpG site (1.4 kb) within the first intron (FIG. 23).

Figure 11:
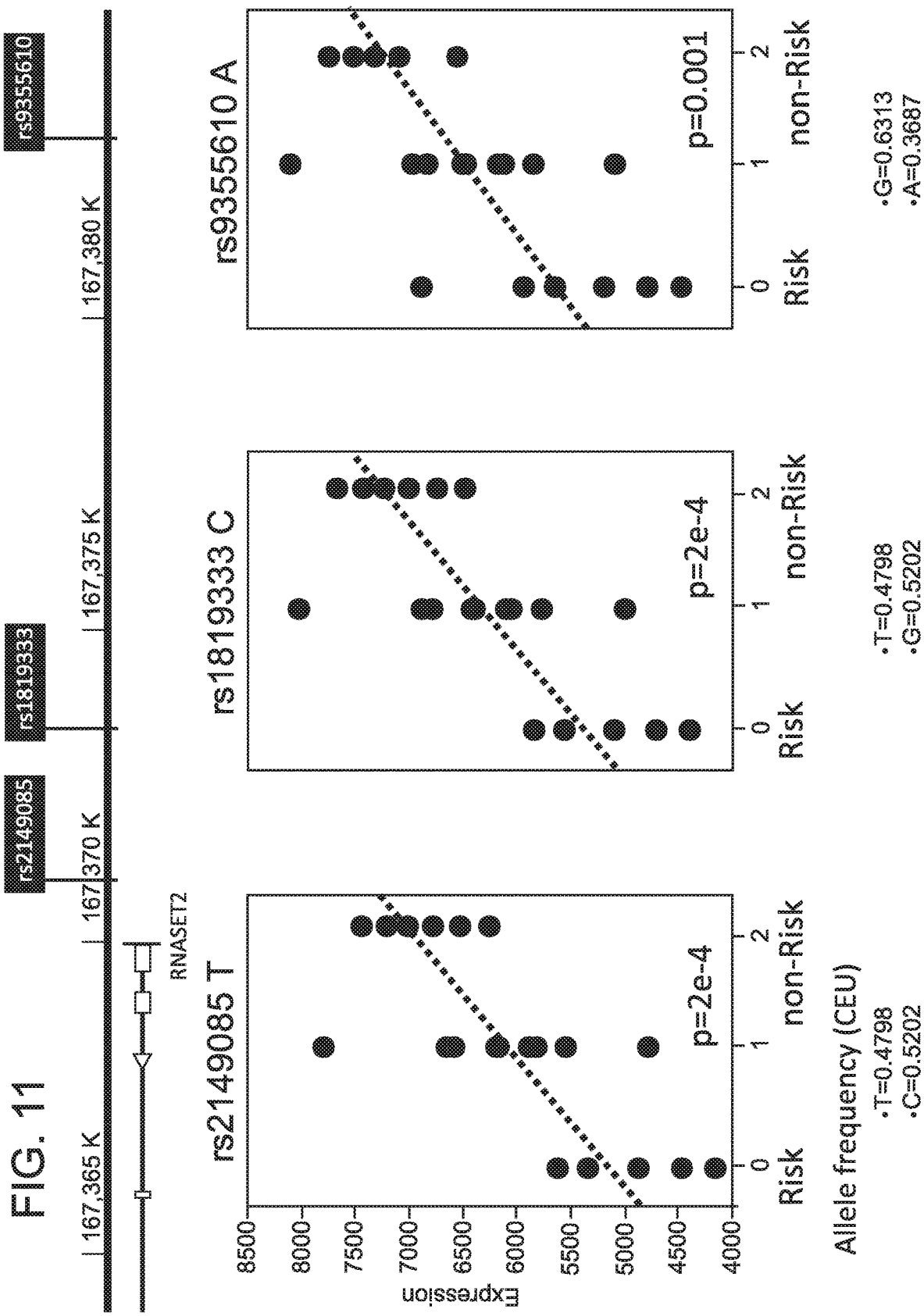
FIG. 11 depicts the eQTL of RNASET2 in refractory IBD, in accordance with various embodiments of the invention. RNASET2 SNPs (rs2149085, rs1819333 and rs9355610) from CD3+ peripheral T cells from 11 CD and 10 UC patients requiring surgical intervention for disease management, using an Illumina expression array.
Figure 12:
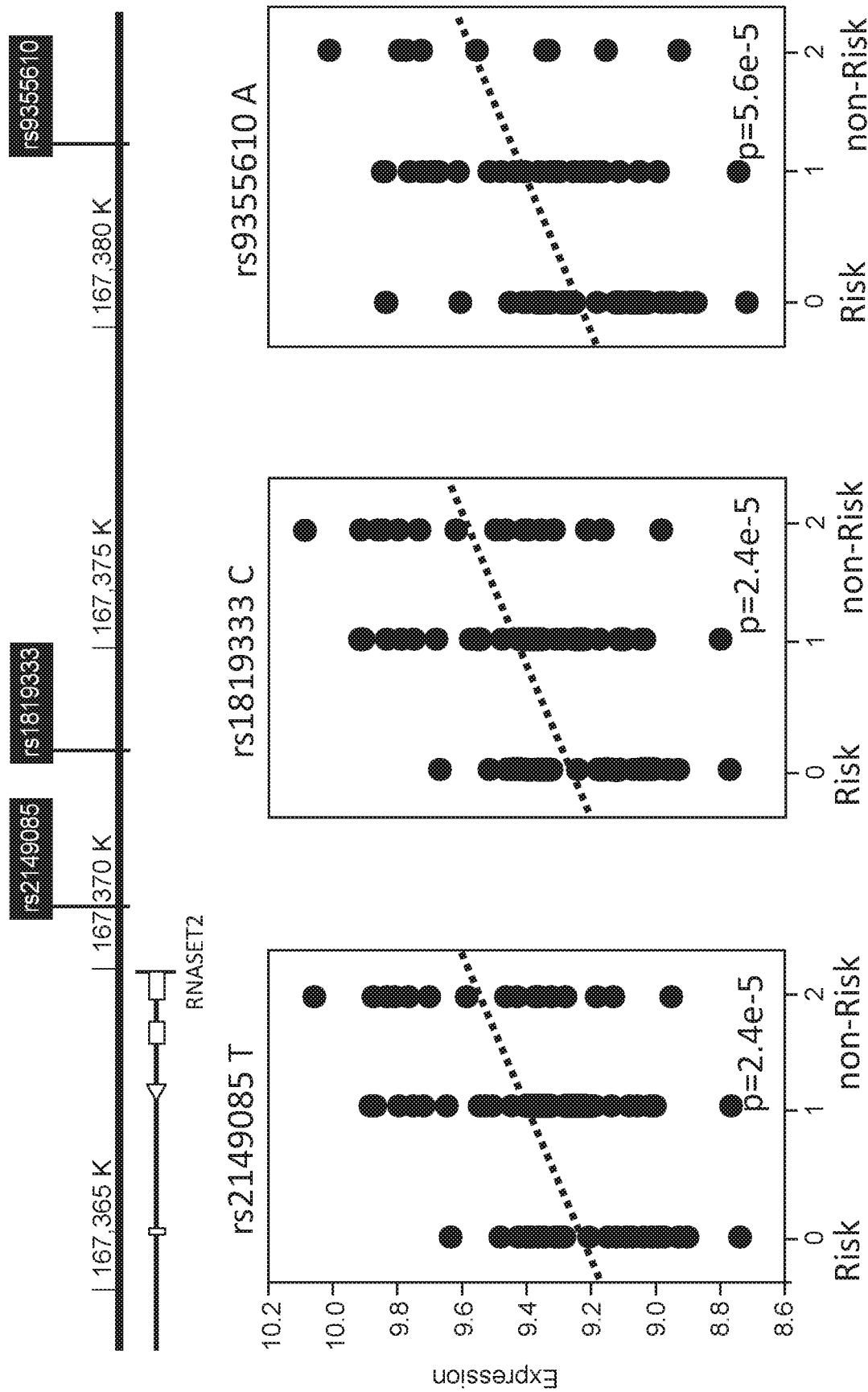
FIG. 12 depicts the eQTL of RNASET2 in CD small bowel (ileal) surgical resection of 85 CD patients using an Agilent expression array, in accordance with various embodiments of the invention.

The functional correlation between RNASET2 gene variation and the gene transcript expression level was confirmed in unstimulated peripheral T cells from IBD patients with refractory disease (FIG. 11), with decreased expression correlating with the RNASET2 risk allele variant SNP. Moreover, a similar eQTL was observed for mRNA extracted from tissue obtained from surgical resection of the small bowel using gene expression microarray (FIG. 12). The correlation between RNASET2 gene variation and methylation, mQTL was also examined and a significant mQTL was observed with an increase in methylation in IBD patients with refractory disease (FIGS. 13A-13D). In contrast, no mQTL was detected in cells isolated from patients with mild disease or NL subjects.

Figure 14A:
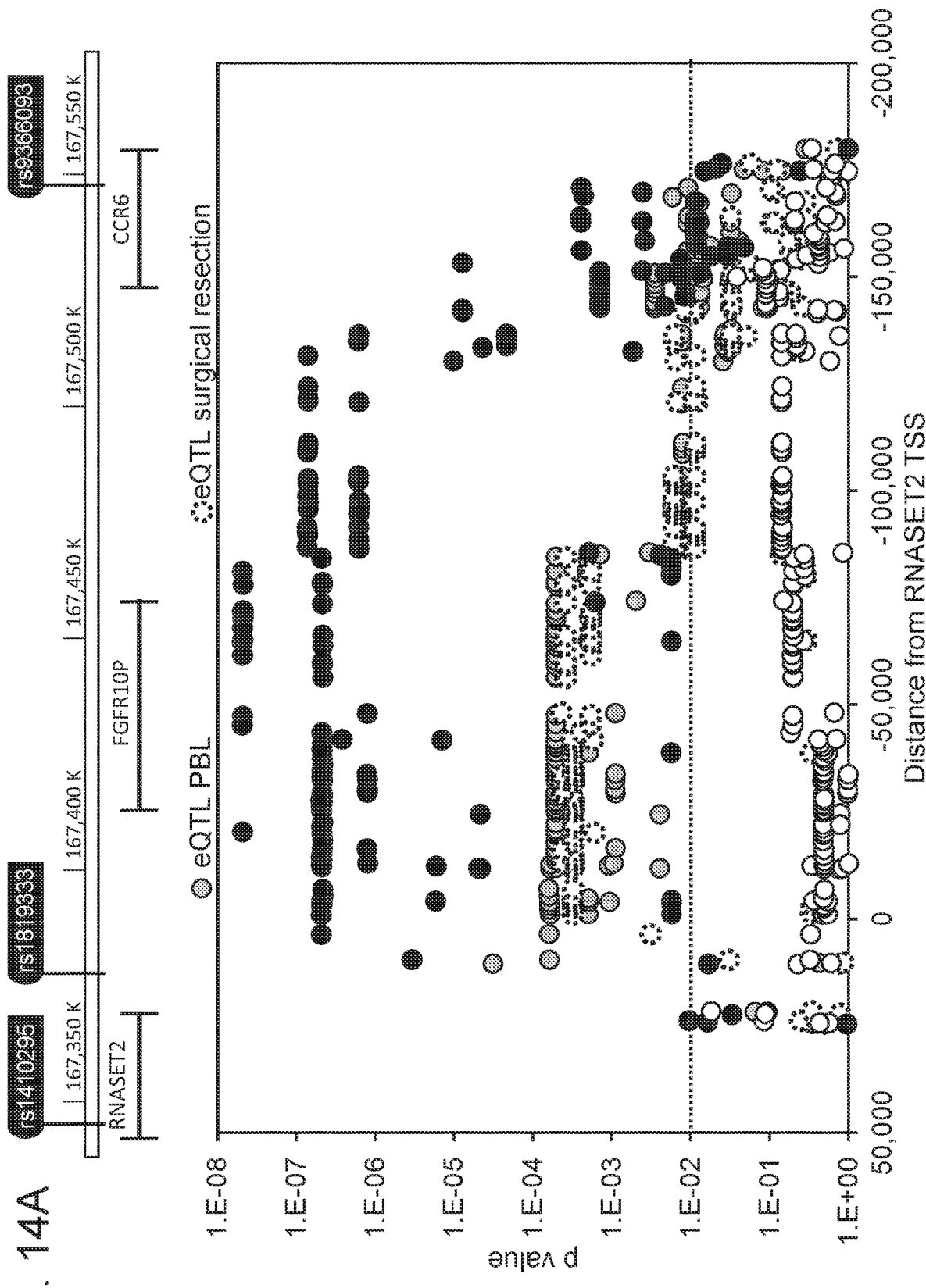
FIGS. 14A-14B depict the mapping of eQTL and mQTL across RNASET2 in patients with refractory or mild disease, in accordance with various embodiments of the invention. A) eQTL and mQTL across RNASET2 in patients with refractory or mild disease. B) eQTL and mQTL calculated using CD3+ T cells from both the periphery and mucosal compartments from patients with refractory or mild disease (including normal patients), encompassing additional data samples.
Figure 14B:
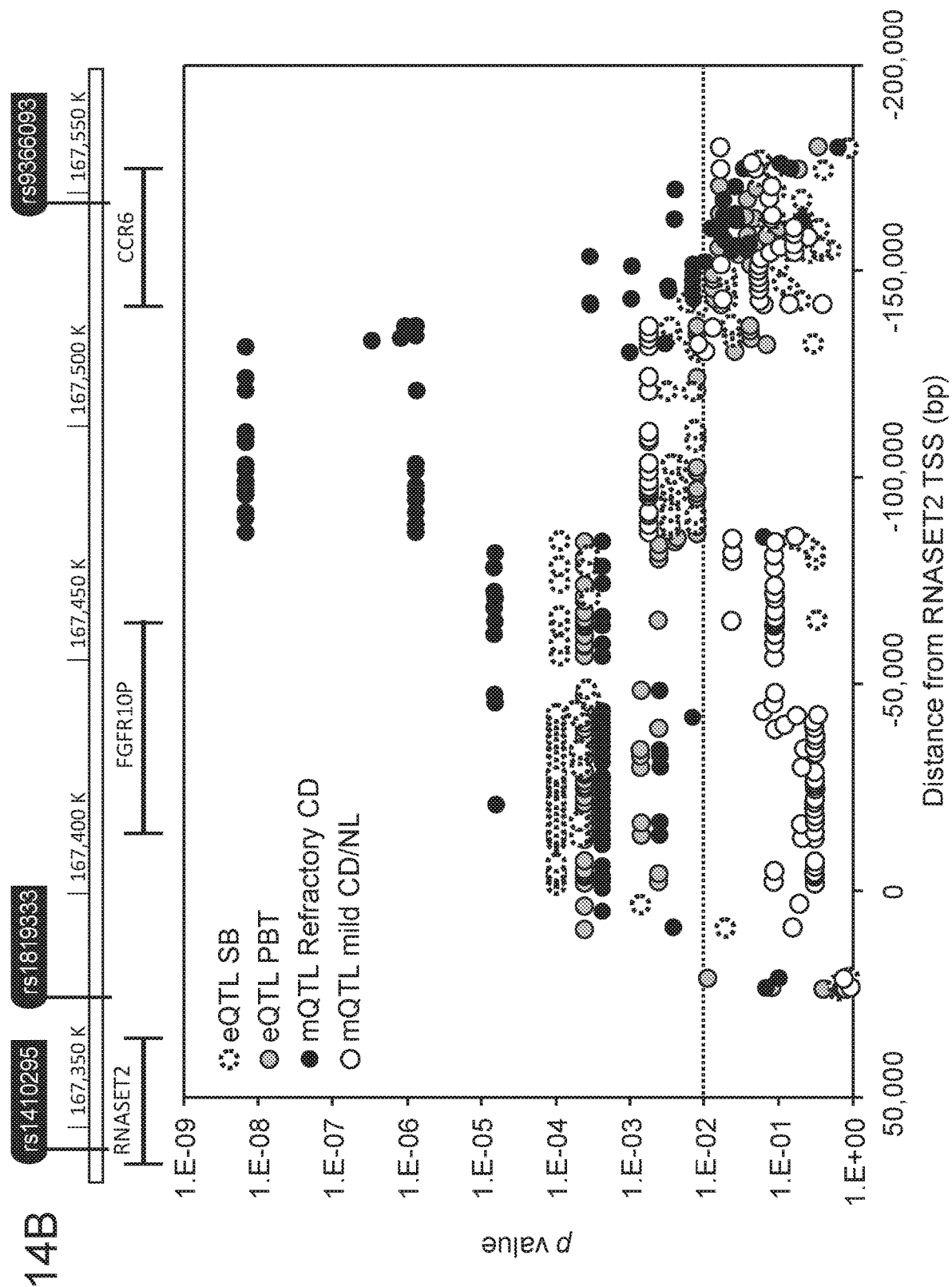

The role of these genetic variations affecting gene expression (eQTL) and DNA methylation (mQTL) was mapped across all informative SNPs spanning the RNASET2 locus (FIG. 14). In T cells isolated from IBD patients with medically refractory disease, there is strong overlapping eQTL and mQTL from 10 kb downstream of RNASET2 TSS to −170 Kb upstream, within the CCR6 locus. Likewise, there was a remarkable overlap in eQTL when comparing RNSASET2 expression from unstimulated peripheral T cells to small bowel surgical resection in patients with refractory disease. In contrast, in patients with mild disease or NL subjects no mQTL was detected (FIGS. 14A and 14B). This without being bound to any particular theory, the data suggests that down-modulation of RNASET2 is a component of TL1A mediated enhancement of IFN-γ expression. Additionally, epigenetic modulation of RNASET2 and reduced gene expression in IBD patients with a known IBD risk variant SNP is associated with a more severe course of disease.

Example 5

Methods

Peripheral T cells isolated from NL (normal) donors were cultured with or without TL1A for 8 hours. Gene expression profiling was performed by RNA sequencing (RNA-seq) and quantitative polymerase chain reaction (qPCR) using the subset of interferon gamma (IFN-γ)-producing cells purified by flow cytometry. Enzyme-linked immunosorbent assay (ELISA) and small interfering RNA (siRNA) inhibition and qPCR were used to measure the role of ribonuclease T2 (RNASET2) in TL1A mediated expression of IFN-γ. The role of RNASET2 in IBD was investigated using peripheral T cells isolated from IBD patients (20 CD and 20 UC) stimulated in a similar fashion. Findings were validated using additional samples of unstimulated T cells from NL and IBD patients or small bowel (SB) surgical resection and analyzed for expression quantitative trait loci (eQTL) and methylation quantitative trait loci (mQTL) based on genotyping and clinical data.

Screening for predicted motif disruption of transcription factor (TF) binding sites identified candidate regulatory SNPs. Proteomic analysis and measurement of cytokine secretion were used to determine effect of RNASET2-directed small interfering RNA (siRNA) on protein expression. Cell aggregation was measured by flow cytometry.

Study Subjects

Human subjects were recruited through the MIRIAD IBD Biobank at the F. Widjaja Foundation Inflammatory Bowel and Immunobiology Research Institute at Cedars-Sinai Medical Center. All control subjects were healthy individuals, free of medication, and with no known personal or family history of autoimmune disease or IBD. Informed consent (approved by the Institutional Review Board at Cedars-Sinai Medical Center) was obtained from all participating subjects. IBD patients were defined as "refractory" if surgical intervention was required for disease management following failure of medical therapy. IBD patients were defined as "mild" if they had no prior surgeries and no active disease at time of sample collection. CD patients exhibiting one or more disease flares per year were defined to have "severe disease" compared to patients with no disease flares per year. Clinical characteristics were prospectively collected from 564 CD patients who had undergone surgical resection.

Isolation of Lymphocyte Populations

Peripheral blood mononuclear cells (PBMC) were isolated from healthy volunteers by separation on Ficoll-Hypaque gradients. CD3$^+$ T cells (PBT) were isolated using CD3-immunomagnetic beads (Miltenyi Biotech, Auburn, Calif.) and were at least 95% pure. CD4$^+$ T cells were isolated using negative selection by depletion with magnetic beads (Stemcell Technologies, Vancouver, BC, Canada) and were at least 95% pure.

Infinium 450K Bead Chip Assay

DNA samples from CD3$^+$ T cells were bisulfite converted using the Zymo EZ DNA Methylation kit (Zymo Research) with an input of 1 μg. The assay was carried out as per the Illumina Infinium Methylation instructions, using the Infinium HumanMethylation450 BeadChip Kit (Illumina Inc., San Diego, Calif.). Data were visualized and normalized using the GenomeStudio software. The methylation β values were recalculated as the ratio of (methylated probe signal)/(total signal).

IFN-γ Assay

IFN-γ was measured by an amplified ELISA. Greiner Bio-One (Longwood, Fla.) ELISA plates were coated overnight with 100 μl of 5 μg/ml monoclonal anti-IFN-γ (BD Biosciences, Woburn, Mass.). Samples and standards were added for 24 h followed by addition of 100 μl of 2.5 μg/ml polyclonal biotinylated rabbit anti-IFN-γ (BD Biosciences) for 2 h. This was followed by addition of 100 μl of 1/1000 diluted alkaline phosphatase-conjugated streptavidin (Jackson ImmunoResearch Laboratories, West Grove, Pa.) for 2 h. Substrate, 0.2 mM NADP (Sigma-Aldrich, St. Louis, Mo.) was added for 30 min followed by addition of amplifier (3% 2-propanol, 1 mM iodonitrotetrazolium violet, 75 μg/ml alcohol dehydrogenase, and 50 μg/ml diaphorase; Sigma-Aldrich) for 30 min. Plates were read at 490 nm using an E max plate reader (Molecular Devices, Sunnyvale, Calif.).

Gene Expression Assay for CD3+ T Cells

Expression analysis of CD3+ T cells was performed using the Illumina genome-wide expression BeadChip (HumanHT-12_V4_0_R2) (Illumina) or Nugen human FFPE RNA-seq library system. Illumina Gene expression data were processed using the BRB array tools and the lumi package in R. The data were $\log_2$-transformed and normalized using robust spline normalization. Libraries for RNA-Seq were prepared with Nugen human FFPE RNA-seq library system. The workflow consists of cDNA generation, fragmentation, end repair, adaptor ligation and PCR amplification. Different adaptors were used for multiplexing samples in one lane. Sequencing was performed on Illumina NextSeq 500 for a single read 75 run. Data quality check was done on Illumina SAV. Demultiplexing was performed with Illumina Bcl2fastq2 v 2.17 program. The reads were first mapped to the latest UCSC transcript set using Bowtie2 version 2.1.0 and the gene expression level was estimated using RSEM v1.2.15. FPKM was used to normalize the gene expression.

siRNA Inhibition and Quantitative Proteomic Analysis

Freshly isolated CD4+ T cells ($15\times10^6$) were cultured overnight in RPMI 1640 medium containing 10% fetal calf serum, washed, resuspended in 250 fresh medium, and electroporated in the presence of 150 pmole of RNASET2 siRNA or control siRNA (600 V, for 9 pulses of 500 µsec, with 100 µsec between pulses) using 4 mm (gap width) cuvettes in a BTX Electro Square Porator ECM 830 (Genetronics, Inc., San Diego, Calif.). Sequences used in siRNA inhibition are depicted in Table 16.

TABLE 16 siRNA sequences

| Sequence Name | Sequence | SEQ ID NO |
|---|---|---|
| RNASET2 siRNA-sequence forward | 5'-GCAAGAGAAAUUCACAAACUGCAGC-3' | 7 |
| RNASET2 siRNA-sequence reverse | 5'-GCUGCAGUUUGUGAAUUUCUCUUGCUU-3' | 8 |
| Control siRNA-sequence forward | 5'-CUUCCUCUCUUUCUCUCCCUUGUGA-3' | 9 |
| Control siRNA-sequence reverse | 5'-UCACAAGGGAGAGAAAGAGAGGAAGGA-3' | 10 |

Tandem mass tagging (TMT)-based quantitative proteomics analysis was conducted as described (Qu et al., Sci Rep 2016; 6:32007). For each sample, 50 µg proteins were digested in parallel into tryptic peptides using filter-aided sample preparation (FASP) (Wisniewski et al., Nat. Methods 2009; 6:359-62). Peptides derived from eight samples and a pooled internal standard were labeled with a set of TMT10plex reagents (Thermo Scientific), mixed, desalted, separated into 24 fractions by high-pH liquid chromatography, and concatenated into 8 fractions. Fractionated peptides were resolved on a 50 cm EASY-Spray analytical column, and analyzed by an LTQ Orbitrap Elite mass spectrometer (Thermo Scientific) in the data-dependent acquisition mode, using the higher-energy collisional dissociation (HCD) method for tandem mass spectrometry. Acquired raw data were searched against the human Uniprot database (released on Oct. 17, 2015, containing 20,982 sequences) with Proteome Discoverer (v2.1), using the SEQUEST algorithm. A stringent 1% false discovery rate was set to filter peptide and protein identifications. Peptides with >30% precursor ion interference were excluded from protein quantification.

Flow Cytometry and Analysis of Cellular Aggregation

IFN-γ-secreting CD4+ T cells was isolated by flow cytometry following activation of cells with recombinant human IL-12 (500 pg/ml, R&D Systems, Minneapolis, Minn.) and IL-18 (50 ng/ml, R&D Systems) and TL1A (100 ng/ml, Fitzgerald Industries International, Acton, Mass.) for 8 h. IFN-γ-secreting CD4+ T cells were detected using an IFN-γ secretion assay cell enrichment and detection kit (Miltenyi Biotec, San Diego, Calif.). Cells were sorted on a FACS Aria II (BD Biosciences, San Jose, Calif.).

Intracellular IFN-γ production and analysis of cellular aggregation was conducted essentially as described (Dezorella et al., Cytometry B Clin Cytom 2016;90:257-66) Briefly, cells were either rested or stimulated for 24 h with IL12/IL18 and TL1A and Berfeldin A (10 ug/ml) was added for the last 4 h. Cells were fixed with 4% paraformaldehyde, permeabilized with 0.1% Triton X-100 and 0.2% saponin and stained for intracellular IFN-γ (brilliant violet 421-IFN-γ, eBioscience) or isotype control. Samples were washed and stained for cellular aggregation (propidium iodide). Cells were acquired on a CyAn™ ADP Flowcytometer (Dako, Carpinteria, Calif., USA) and analyzed with FlowJosoftware (TreeStar Inc., Ashland, Oreg., USA). For LFA1 blocking analysis cells were pre-incubated overnight in conical microplates with monoclonal control mouse IgG1k (15 ug/ml) or anti-LFA1 (TS1/18) followed by stimulation with IL12, IL18 and TL1A for 24 h.

qPCR

Total RNA was isolated using the RNeasy kit (Qiagen, Inc., Valencia, Calif.) and gene expression was measured by real-time quantitative RT-PCR. Five hundred nanograms of total RNA were used in each RT-PCR reaction, with oligo (dT) (Integrated DNA Technologies) as primer, using the Omniscript kit and protocol (Qiagen). Real-time PCR was performed using a Mastercycler® ep realplex PCR detection system (Eppendorf, Hauppauge, N.Y.). PCR assays were run in duplicate. Primer sequences (Integrated DNA Technologies) spanned introns and are depicted in Table 17.

TABLE 17

Primer sequences

| Sequence Name | Sequence | SEQ ID NO |
|---|---|---|
| IFN-γ forward | 5'-TTGGGTTCTCTTGGCTGTTACT-3' | 11 |
| IFN-γ reverse | 5'-ATCCGCTACATCTGAATGACCTG-3' | 12 |
| RNASET2 forward | 5'-CTTCCTTGCAGGACTCACCAC-3' | 13 |

TABLE 17-continued

Primer sequences

| Sequence Name | Sequence | SEQ ID NO |
|---|---|---|
| RNASET2 reverse | 5'-GCTGATGTGAAGGTGCAAACTC-3' | 14 |
| ACTB forward | 5'-CGTGCTGCTGACCGAGG-3' | 15 |
| ACTB reverse | 5'-AAGGTCTCAAACATGATCTGGGT-3' | 16 |

Genotyping

Genotype data was obtained for Caucasian subjects using Illumina HumanImmuno BeadChip array. Markers were excluded based on: test of Hardy-Weinberg Equilibrium with significance threshold of $p \leq 10^{-3}$; if genotyping rate was <100% (for eQTL and mQTL associations) or <98% (for GWAS) and if minor allele frequency was <5%. Identity-by-descent was used to exclude related individuals (Pi-hat scores >0.25) using PLINK. ADMIXTURE was used to perform ethnicity analysis to get ethnicity proportion estimation for individuals. An individual with Caucasian proportion ≥0.75 was classified as Caucasian. Independent Caucasian samples were identified based on relatedness check (using cut-off pi-hat scores) and ethnicity analysis from admixture and all subsequent associations were performed using these samples. Principal components in genotype data for independent Caucasian samples were generated using TRACE. LDHeatmap R package was used to generate LD plot for the SNPs in RNASET2 locus using genotype data for 139 subjects. Details of the QC and genotyping in IIBDGC cohort can be found in previous reports (Jostins et al., Nature 2012; 491:119-24 and Liu et al., Nat Genet 2015; 47:979-86). In brief, 18,602 CD cases and 33,938 non-IBD controls genotyped using ImmunoChip were included in the analysis after samples with >5% missing data, samples of non-European ancestry from population stratification or with abnormal mean intensity values, and SNPs with >2% missing data or HWE p-value $<10^{-10}$ in controls were removed. Of the CD cases from IIBDGC, 13,511 have disease behavior information collected based on Montreal classification as reported previously (Cleynen et al., Lancet 2016; 387:P156-67) (described as B1, non-stricturing, non-penetrating, B2, stricturing and B3, penetrating diseases).

Expression Data for Small Bowel Surgical Samples

Single channel microarray expression data extracted using Agilent feature extraction software were received from Genome Technology Access Center at Washington University, St. Louis. Raw expression data available in technical duplicates were normalized using LIMMA package implemented in R version 3.2.2. The expression data preprocessing included background correction of the expression data, followed by log 2-transformation and quantile-normalization.

EQTL and mQTL Mapping eQTL and mQTL mapping was implemented in Matrix eQTL R package. For small bowel surgery samples, eQTL mapping was done using independent Caucasian samples (n=85). Associations between genotype and probe expression level (for eQTL) or methylation β values (for mQTL) were performed using a linear regression model with additive genotype effects. All associations were conducted with gender and first two principal components in genotype data as covariates along with genotype. Around 200 genetic variants within 200 KB of RNASET2 TSS were used to perform associations with RNASET2 gene expression or methylation levels.

Motif Analysis and Identification of Candidate Regulatory SNPs

All variants exhibiting eQTL and mQTL were analyzed for predicted disruption of TF binding motifs using the bioconductor motifbreakR package (Coetzee et al., Bioinformatics 2015; 31:3847-9). Only T cell specific TFs identified as being expressed using RNAseq data from CD patients, were carried forward. Candidate regulatory SNPs were then analyzed for potential functionality based on Roadmap Epigenomics Mapping Consortium (REMC) data (Roadmap Epigenomics C. et al, Nature 2015; 518:317-30). Potential active enhancer regions were determined based on overlap of the histone modification H3K4me1 with H3K27ac signals (Coetzee et al., Hum Mol Genet 2015; 24:3595-607). Potential functionality of TF regulation was determined based on REMC CHIP-seq binding signal and Regulome data.

Pathway Analysis

Pathway analysis was accomplished through the use of Qiagen's Ingenuity® Pathway Analysis (IPA®, Qiagen, Redwood City, www.qiagen.com/ingenuity) and The Database for Annotation, Visualization and Integrated Discovery (DAVID, http://david.abcc.ncifcrf.gov).

Statistical Analysis

Modeling, data analysis, and data mining were performed using the BRB array tools (brb.nci.nih.gov/BRB-Array-Tools) and R-program (version 2.2.2; www.r-project.org). Class prediction analysis used compound covariate predictor, diagonal linear discriminant analysis, k-nearest neighbor (using k=1 and 3), nearest centroid, and support vector machines, based upon a minimum p value of 0.001. Cluster analysis was performed using Cluster 3.0 and Java Treeview 1.1.6r4. Tests for statistical significance were determined using JMP Statistical Software (Cary, N.C.). Test for clinical association between of rs1819333 and rs9355610 SNPs and therapeutic failure, ANCA sero-positivity, resected bowel length and time to reoperation were calculated by parametric Student's T test and Pearson correlation; test of association and trend using Fisher's exact test and Kaplan-Meier Survival Curves. Association with endoscopic recurrence was calculated by Cochran-Armitage trend test.

Results

In this study, the inventors identified down-modulation of RNASET2, an IBD susceptibility gene, as a component of TL1A-mediated enhancement of cytokine production and as a novel potential biomarker of disease severity. Down-regulation of RNASET2 following siRNA silencing resulted in increased IFN-γ secretion, without being bound to any particular theory, supporting a role in regulating inflammatory response. A decrease in RNASET2 expression was also observed in peripheral T cells from CD patients with one or more yearly disease flares compared to patients with no yearly disease flares. Functionally, quantitative trait loci were associated with RNASET2 disease-risk variants for decreased expression (eQTL) in peripheral and mucosal tissues and DNA hypermethylation (mQTL) from CD patients with medically refractory, but not mild disease. Additionally, RNASET2 disease-risk variants were associated with an increase in development of stricturing/penetrating disease behavior. Furthermore, RNASET2 disease-risk variants were associated with a complicated/resistant CD phenotype defined in part by therapeutic drug failure, ANCA sero-positivity, increased length of intestinal resection, shorter time to reoperation and post-operative endoscopy with a high (>2) Rutgeerts score. Motif screening of RNA-SET2 disease-risk variants identified rs2149092 with predicted disruption of a consensus ETS-TF binding site located within a potential enhancer region, providing insight into RNASET2 cis-regulatory elements. RNASET2 correlated with expression of multiple ETS-transcription factors. Finally siRNA silencing of RNASET2 resulted in enhanced IFN-γ, increased ICAM1 and concomitant T cell aggregation while anti-LFA1 blocking of aggregation suppressed IFN-γ secretion.

Figure 27:
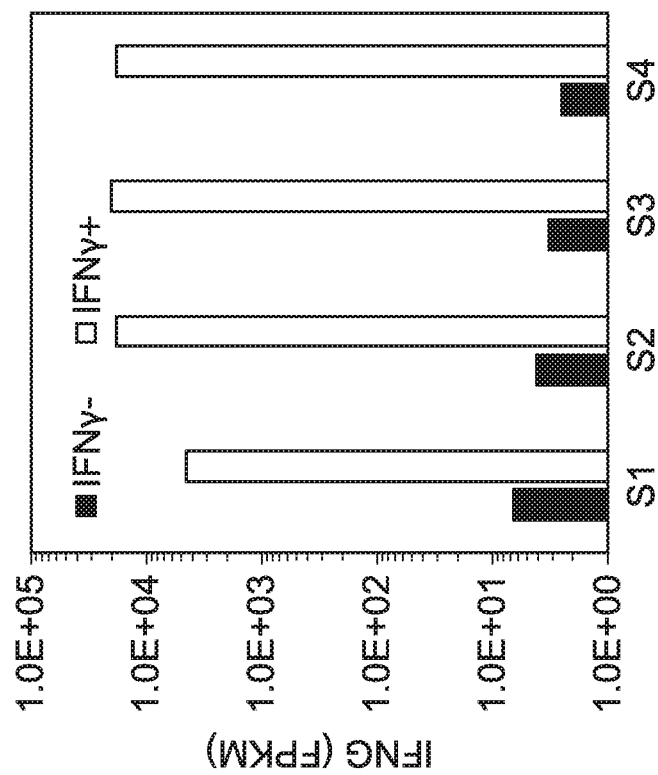
FIG. 27 depicts IFN-γ expression of IFN-γ producing and non-producing levels in CD4+ T cells, in accordance with various embodiments of the invention.

Identification of Differential Gene Expression Associated with TL1A-Mediated Enhancement of IFN-γ Production To identify the underlying molecular pathways involved in TL1A-mediated enhancement of IFN-γ production, a key IBD proinflammatory cytokine, CD4$^+$ T cells were treated with TL1A, sorted into IFN-γ-secreting and non-secreting subsets and analyzed by RNA-seq (FIG. 15 and FIG. 27). Unsupervised hierarchical clustering of the set of expressed genes clearly distinguished TL1A-mediated IFN-γ-secreting and non-secreting groups (FIG. 16). Seven hundred and sixty-four "predictor" genes with at least two-fold differential expression between the IFN-γ secreting/non-secreting subsets (p value <1×10$^{-5}$) (FIG. 17) were identified. Gene ontology analysis indicated that differentially expressed genes were enriched in pathways associated with T cell receptor signaling, apoptosis, and RNA expression, and were downstream targets of infliximab, an anti-TNF biologic drug. Predictor genes were significantly enriched in regions flanking GWAS identified IBD susceptibility variants (0.25 MB upstream or downstream of the single nucleotide polymorphism (SNP) compared to other regions (14% vs. 9%, p value is 3.3×10$^{-6}$, hypergeometric test). Without being bound to any particular theory, these data suggest that these genes contribute not only to TL1A-mediated modulation of IFN-γ expression, but also overlap with IBD risk-associated loci. Of the IBD-risk associated predictor genes, expression of IFN-γ was confirmed as the most significantly upregulated and RNASET2 as the most significantly down regulated gene (FIG. 20). RNASET2 was the only IBD risk associated gene with greater than 5-fold down regulation in the IFN-γ secreting CD4$^+$ subset.

Figure 24D:
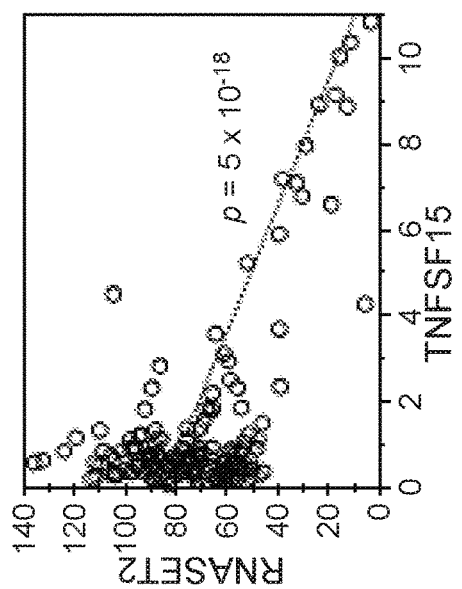
Figure 24C:
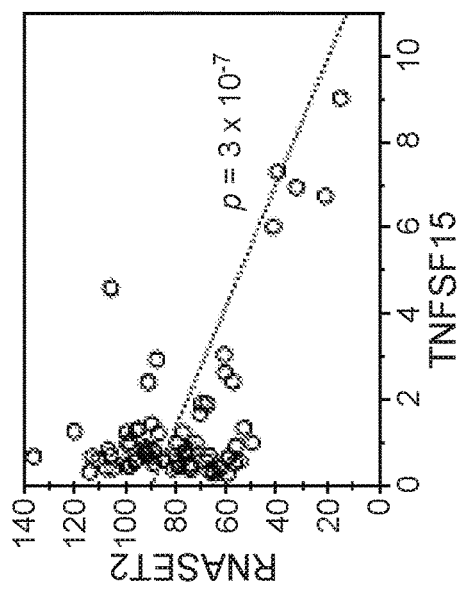
Figure 24B:
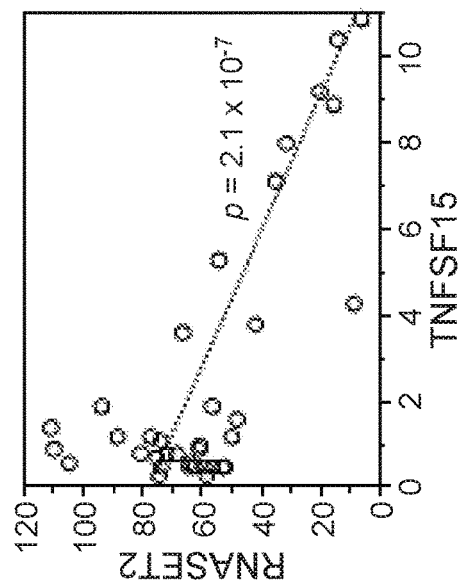
Figure 26:
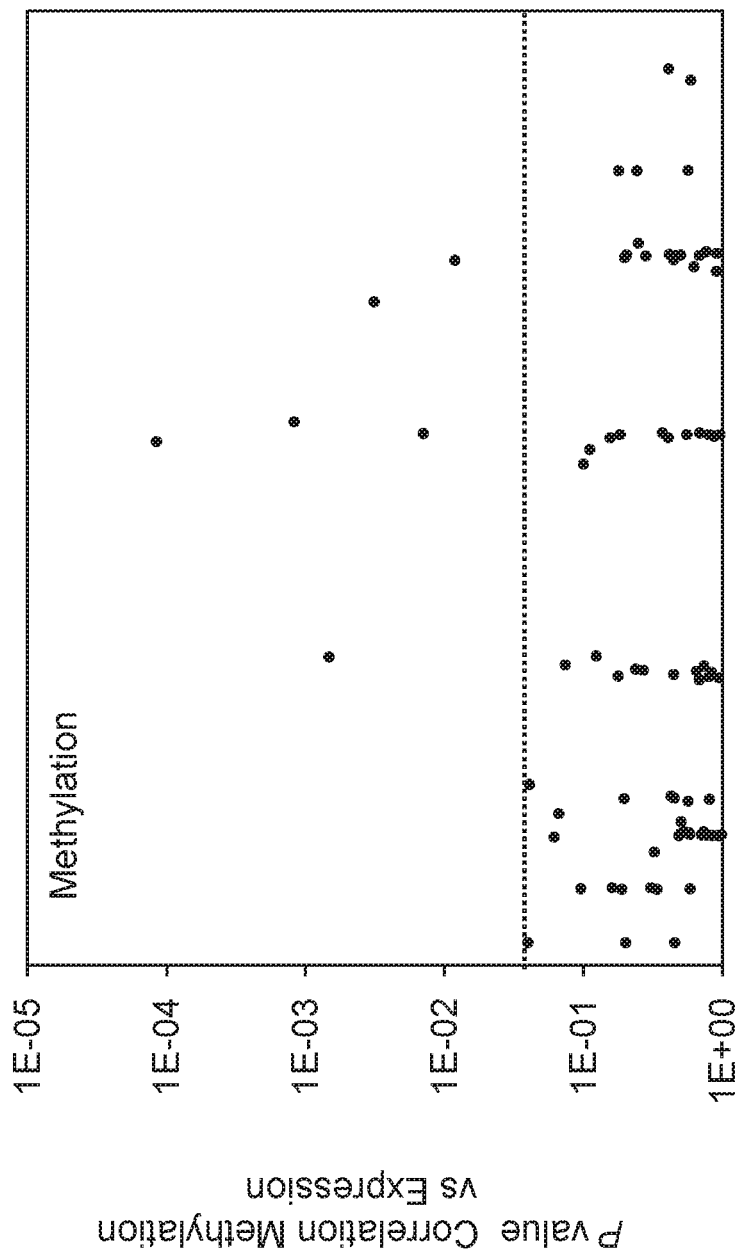
FIG. 26 depicts correlation of expression and methylation located within 100 kb of the RNASET2 transcriptional start site in 21 IBD patients, in accordance with various embodiments of the invention.

RNASET2 Regions Displaying Inverse Correlation of Expression and DNA Methylation Levels Overlap with Regions Flanking Disease-Risk Associated Variants RNASET2 is the only human member of the Rh/T2/S family of ribonucleases and its expression is decreased in ovarian cancer, melanoma and non-Hodgkin lymphoma. Considering the key role for IFN-γ in pathogenesis of Crohn's disease/IBD, without being bound to any particular theory, these data collectively suggest that down regulation of RNASET2 identifies TL1A mediated 'severe' CD. RNASET2 expression was examined in freshly-isolated, unstimulated peripheral CD3$^+$ T cells from a separate cohort of NL, CD and UC patients. Since DNA methylation is understood to be one of the mechanisms that impacts gene expression, particularly in disease-associated genetic variants that map outside transcribed exomes, we examined the DNA methylation status across the RNASET2 locus. RNA-seq analysis demonstrated there was an inverse correlation between TNFSF15 expression levels and RNASET2 in peripheral T cells from two independent cohorts comprised of a combined 138 CD patients (FIGS. 24A and 24D). These results were consistent even when each cohort was analyzed separately (FIGS. 24B and 24C). Moreover, there was a significant negative correlation between expression and methylation (FIG. 23), mainly within 50 kb upstream and downstream from the transcriptional start site (TSS) (FIG. 26). The strongest correlation of methylation and expression (p=8.5×10$^{-5}$) was observed at a CpG site (1.4 kb) within the first intron of RNASET2 (FIG. 26). Additionally, CD disease genetic risk variants, including the IBD risk SNP tagging the RNASET2 locus in European ancestry populations, rs1819333, overlapped with regions correlative for methylation and expression levels (FIG. 10).

Figure 13C:
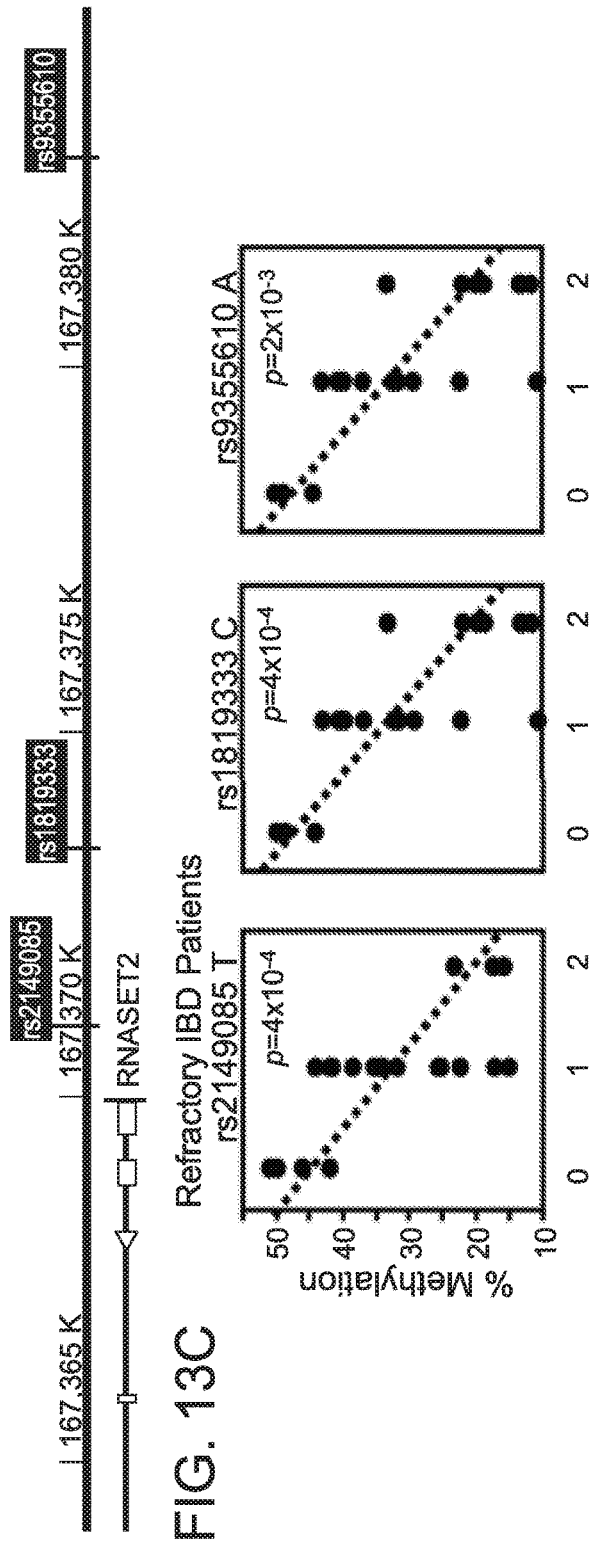
Figure 13D:
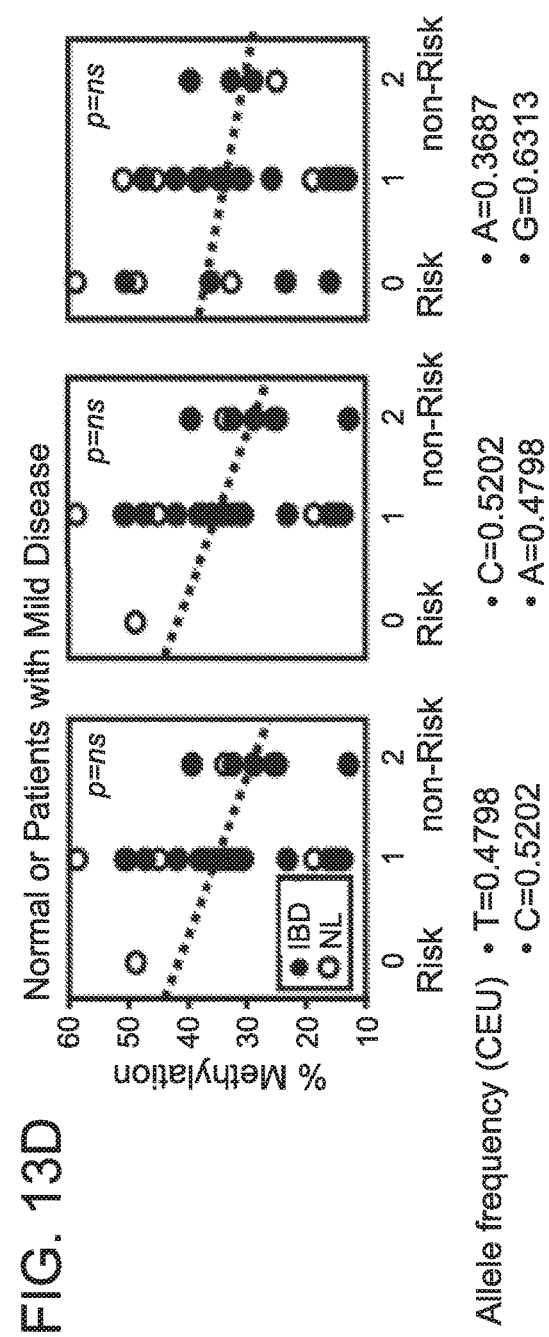

RNASET2 Disease-Risk Alleles are Associated with Decreased RNASET2 Expression and Increased DNA Methylation in CD Patients with Refractory Disease Gene expression quantitative trait (eQTL) was performed to characterize the functional correlation between RNASET2 gene variation and the gene transcript expression level. The disease associated SNPs for IBD risk in Europeans, rs1819333, and Koreans, rs2149085, as well as the risk SNP associated with Graves' disease, rs9355610, are located −13 kb from the transcriptional start site of RNASET2. The functional correlation between RNASET2 IBD-risk genotypes and the gene transcript expression levels were established in unstimulated peripheral CD3$^+$ T cells isolated from IBD patients with refractory disease. The data demonstrated significantly decreased RNASET2 expression in T cells from subjects carrying the RNASET2 risk alleles rs2149085, rs1819333, and rs9355610 (FIG. 11). These findings were confirmed with significant eQTL observed for mRNA extracted from uninflamed small bowel tissue obtained from CD subjects at surgical resection (FIG. 12). The correlation between RNASET2 gene variation and methylation, mQTL was also examined. A significant mQTL was observed with an increase in methylation in CD patients with refractory disease (FIGS. 13A and 13C). In contrast, no mQTL was detected in cells isolated from CD patients with mild disease or NL subjects (FIGS. 13B and 13D). Moreover, there was a significant increase of complicated disease behavior, stricturing/penetrating phenotype (Montreal classification B1 vs. B2 and B3), associated with CD patients carrying the RNASET2 disease risk SNPs (rs1819333/rs2149085 p=0.05, rs9355610 p=0.01).

Figure 28:
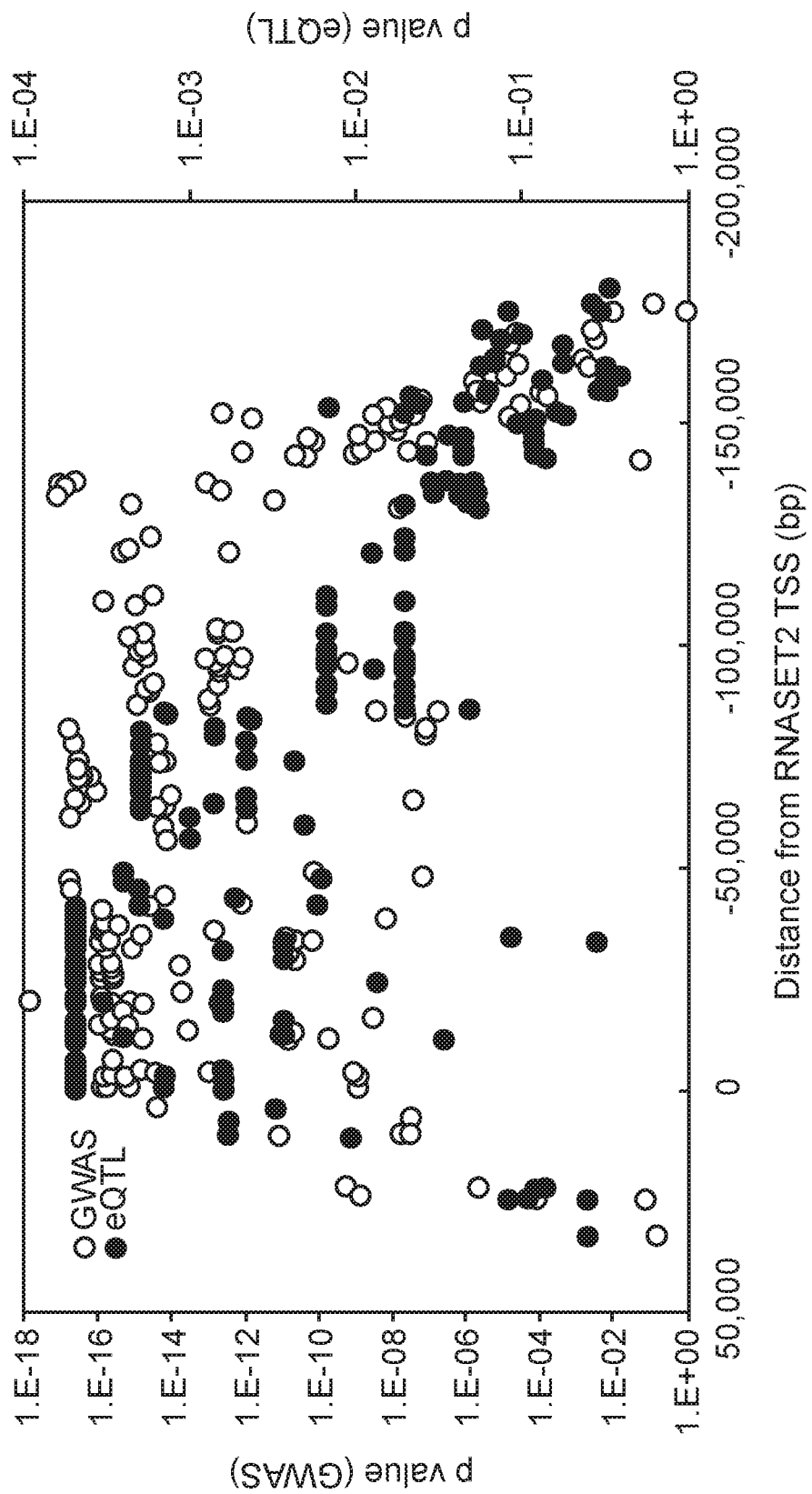
FIG. 28 depicts the correlation of GWAS p values with eQTL p values over the RNASET2 locus, in accordance with various embodiments of the invention. GWAS p values are based upon data from 18729 CD and 34897 controls. eQTL p values are based upon genotyping and RNA-seq based expression of RNASET2 for 71 CD patients with refractory disease, requiring surgical intervention for disease management.
Figure 29:
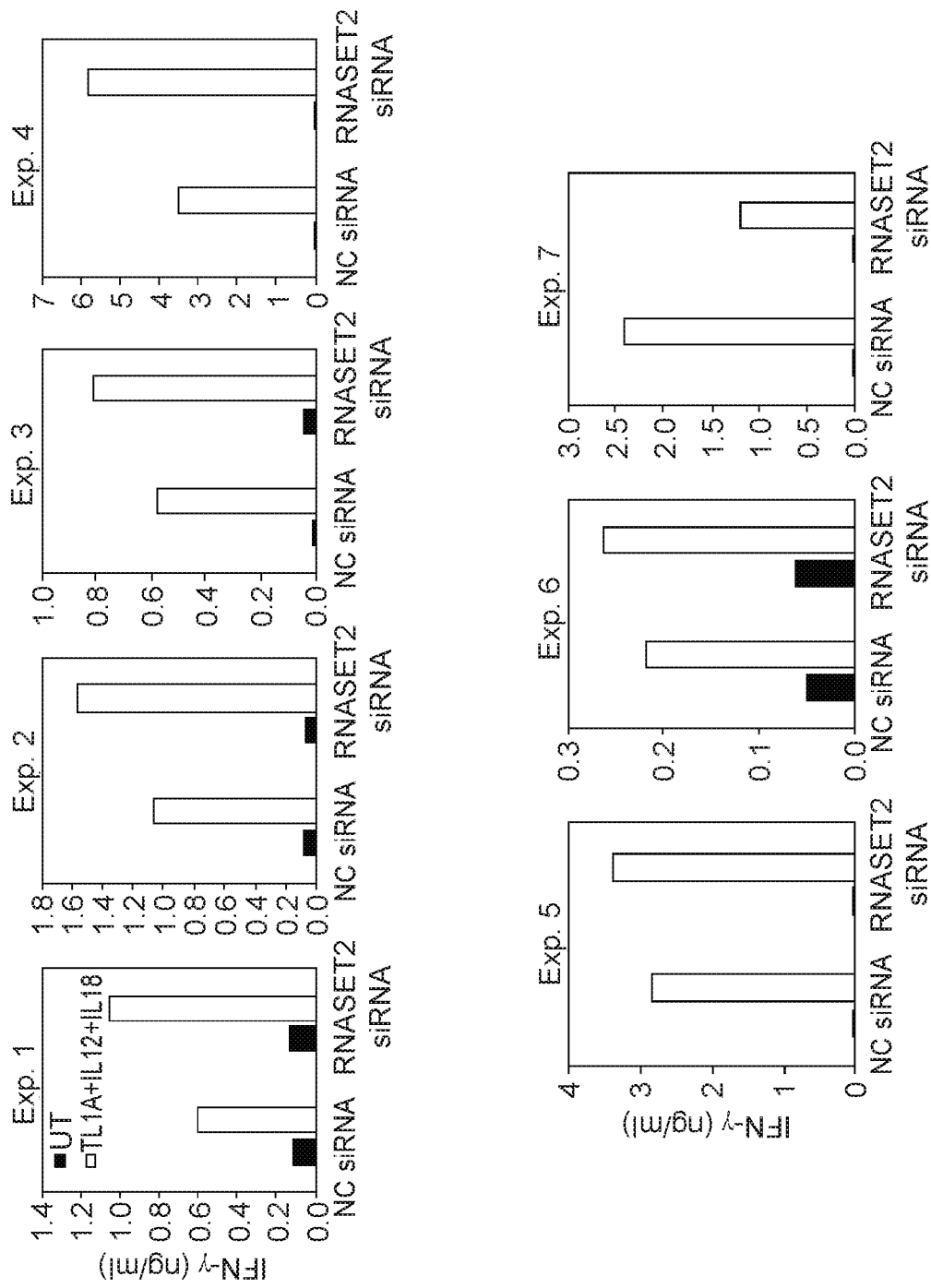
FIG. 29 depicts the effect of RNASET2 silencing on IFN-γ secretion, in accordance with various embodiments of the invention. Inhibition of RNASET2 expression by RNASET2-specific siRNA was greater than 50% in all experiments.

Gene expression (eQTL) and DNA methylation (mQTL) was mapped across all informative SNPs spanning the RNASET2 locus (LD plot). In T cells isolated from patients with medically refractory disease, there is strong overlapping eQTL and mQTL from 10 kb downstream of RNASET2 TSS to −170 kb upstream, spanning fibroblast growth factor receptor 1 oncogene partner (FGFR1OP) to the first intron of chemokine (C—C motif) receptor 6 (CCR6). Likewise, there was overlap in eQTL when comparing RNASET2 expression from unstimulated peripheral T cells to small bowel surgical resection in CD patients with refractory disease. In contrast, few mQTL associations were detected in CD patients with mild disease or NL subjects (FIGS. 14A and 14B). No eQTL association was detected for FGFR1OP or CCR6. These data were further validated in a separate cohort of peripheral T cells isolated from CD patients with medically refractory disease. There was significant overlap between RNASET2 risk variants associated with CD and corresponding eQTL (FIG. 28) which, without being bound to any particular theory, suggest a functional role for RNASET2 in mediating disease.

Attenuated Expression of RNASET2 in CD

To establish a role for RNASET2 in IBD pathogenesis, regulation of RNASET2 expression in CD4$^+$ T cells isolated from IBD patients was examined and compared to normal (NL) donors in the presence or absence of TL1A. As seen in FIG. 7, NL donors, but not IBD patients, exhibited a TL1A-mediated decrease in RNASET2 expression levels. Instead, decreased expression levels of RNASET2 were found in CD patients with more severe disease (exhibiting one or more disease flares per year) compared to patients with no yearly disease flares (FIGS. 8A and 8C).

Figure 32:
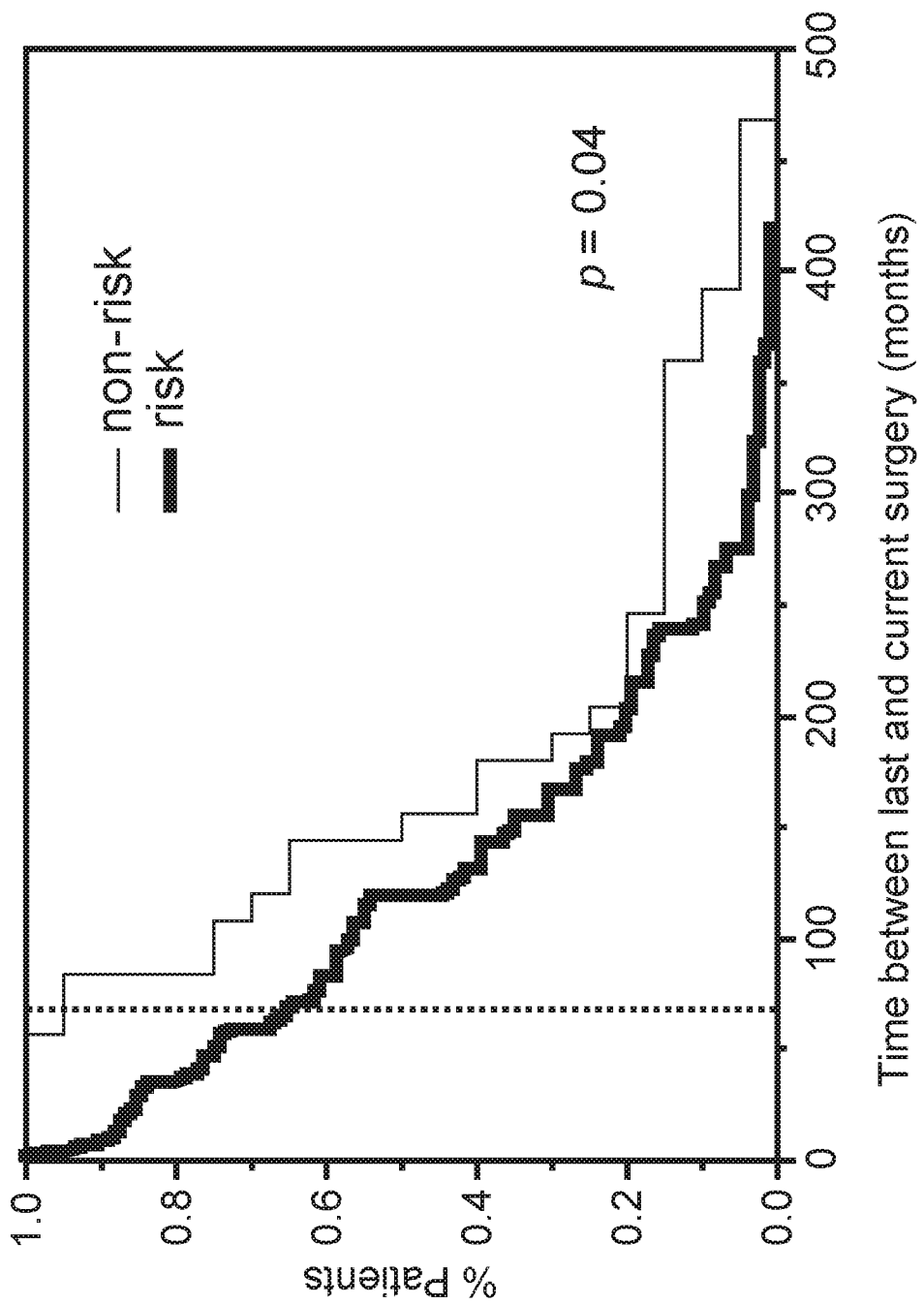
FIG. 32 depicts that patients with RNASET2 disease associated SNPs exhibited a shorter time to reoperation, in accordance with various embodiments of the invention. Time between surgeries based upon carriage for IBD risk SNP rs9355610 (SEQ ID NO: 3) for 154 CD patients who underwent multiple surgeries.
Figure 33:
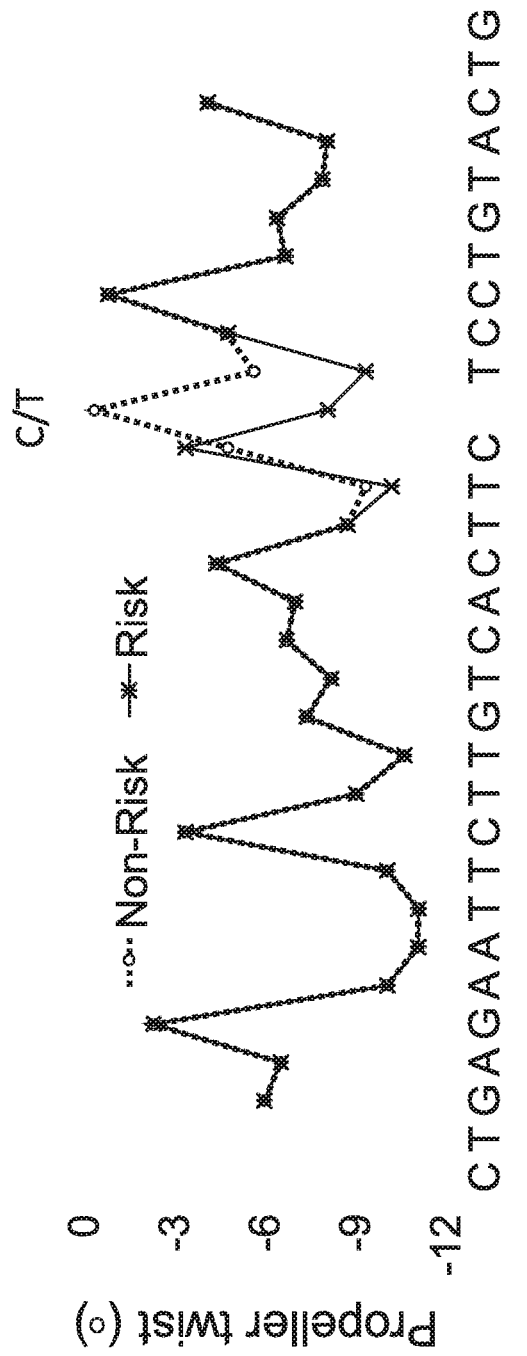
FIG. 33 depicts that the rs2149092 SNP (SEQ ID NO: 2) Alters DNA Shape.
Figure 34:
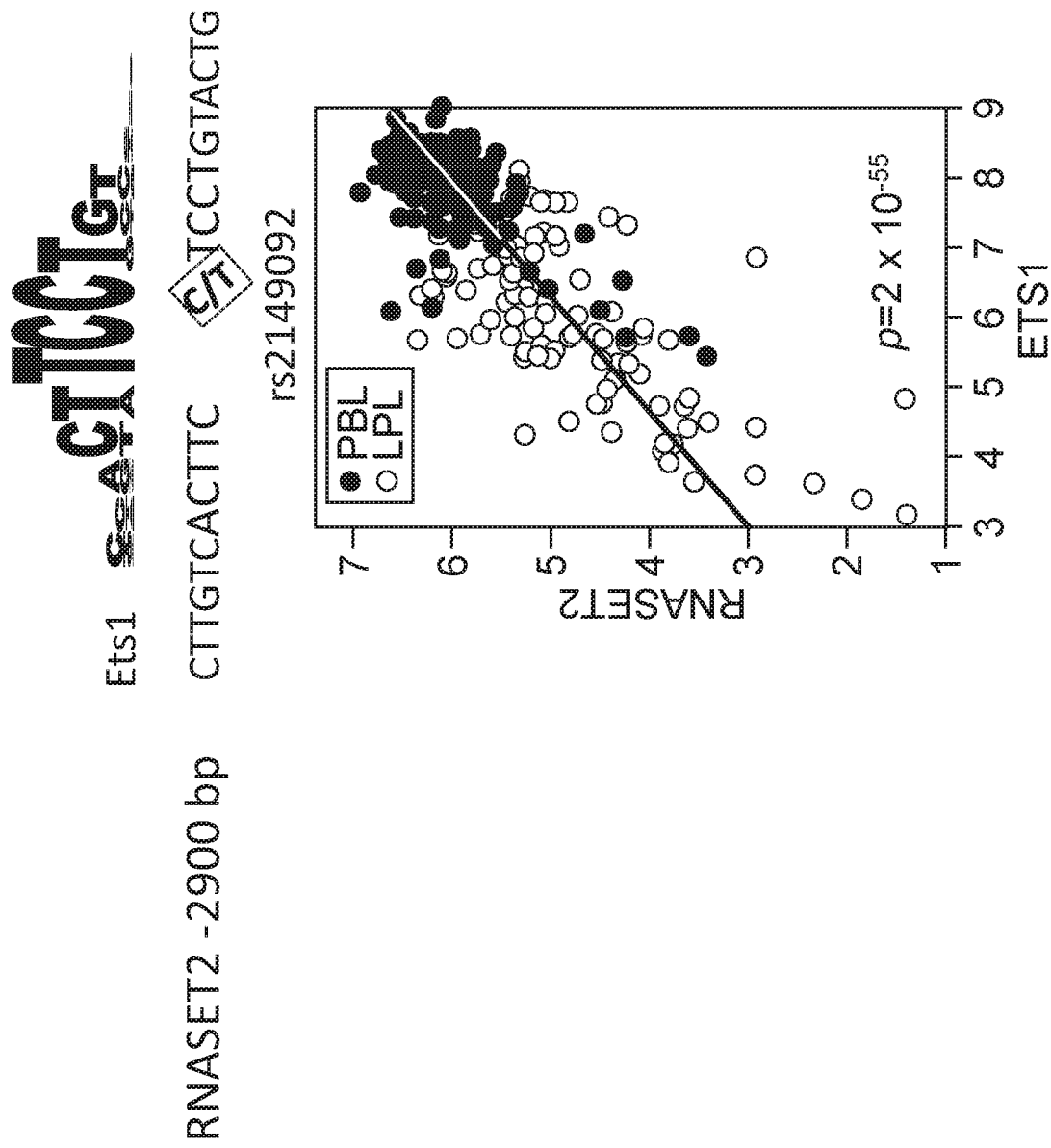
FIG. 34 depicts the correlation of RNASET2 versus Ets1 expression, in accordance with various embodiments of the invention.
Figure 35:
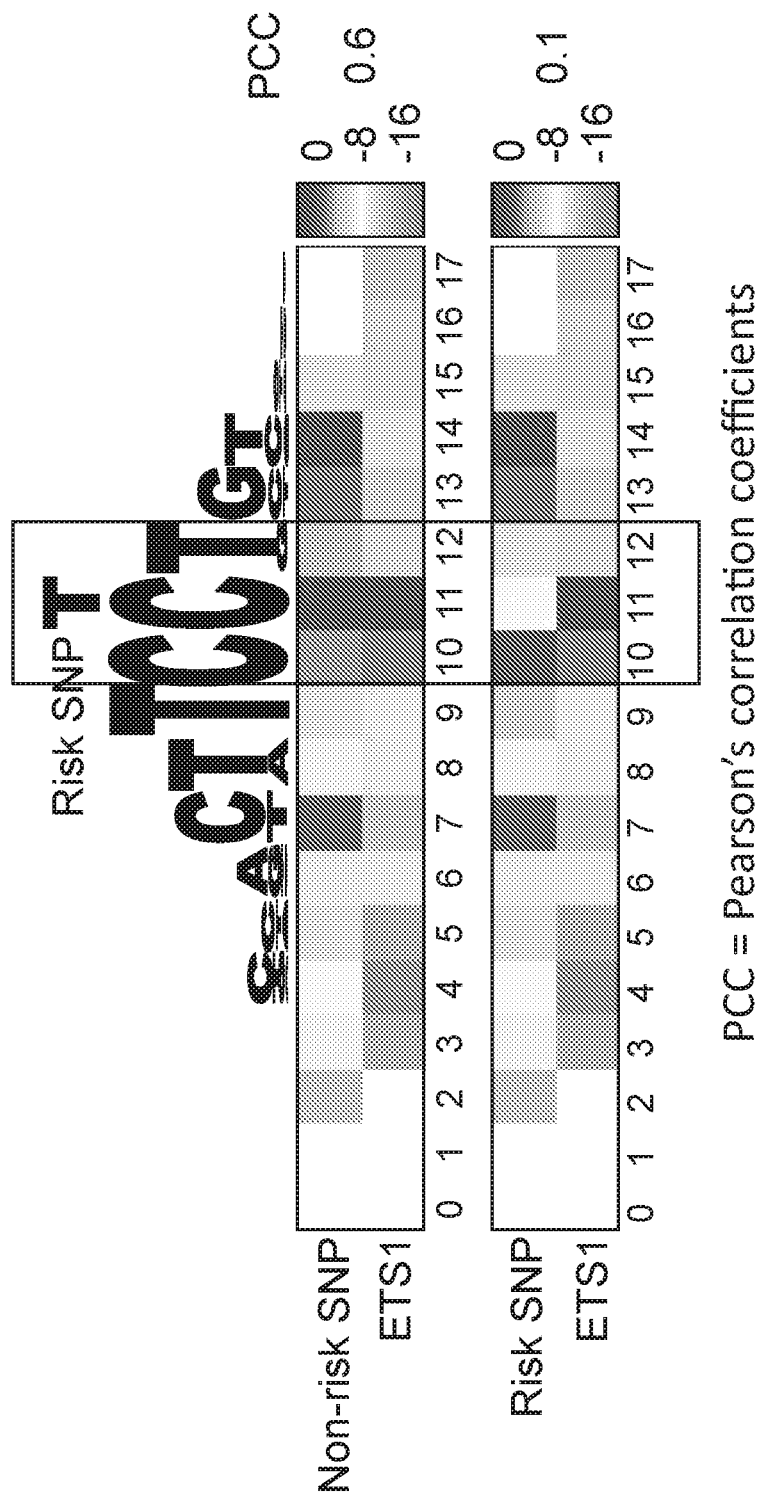
FIG. 35 depicts that the rs2149092 SNP (SEQ ID NO: 2) distorts DNA shape at the Ets1 binding site.
Figure 38:
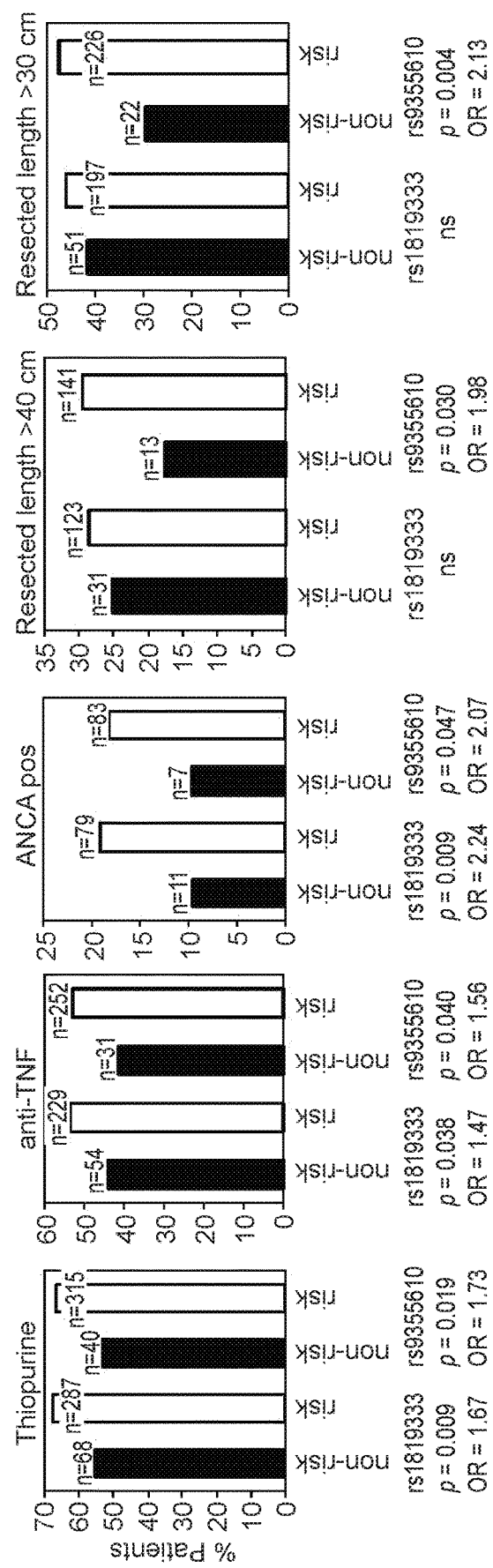
FIG. 38 depicts in accordance with various embodiments of the invention, the association of RNASET2 disease risk variant SNPs at the time of surgery with therapeutic failure of thiopurine or anti-TNF therapy, ANCA sero-positivity and an increased length of intestinal resection (data summarized in Table 18).
Figure 39:
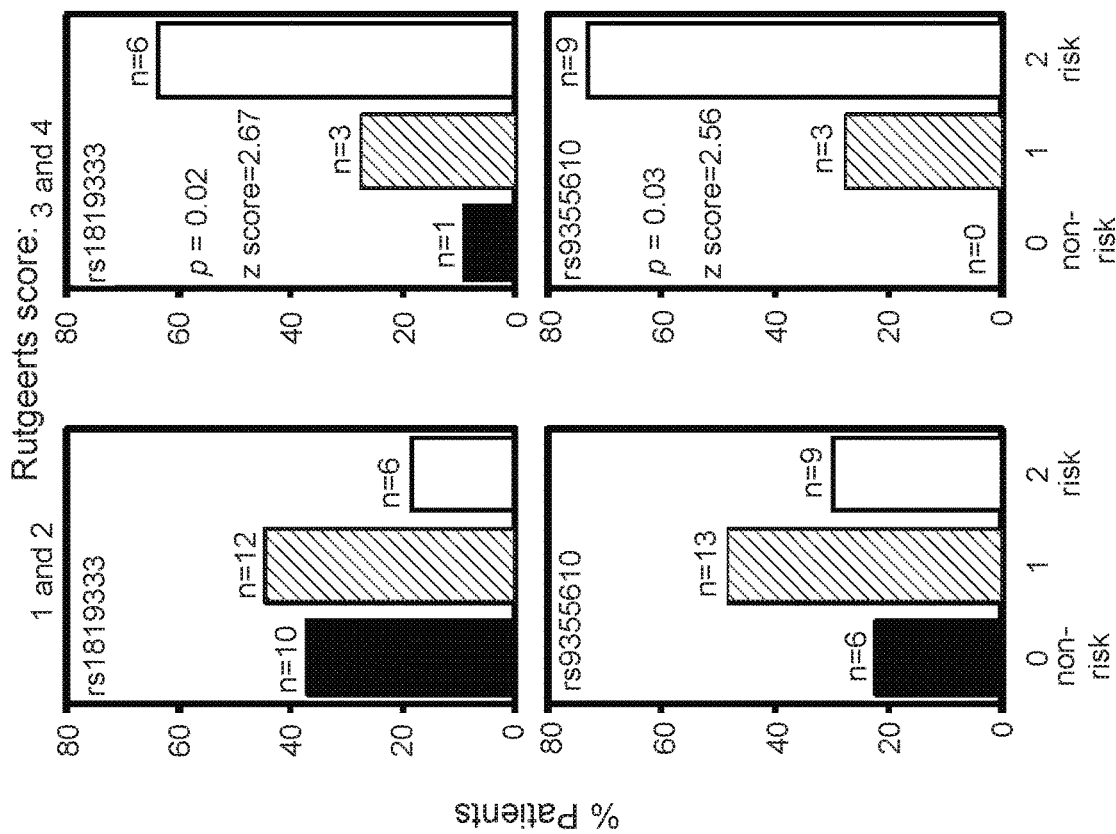
FIG. 39 depicts in accordance with various embodiments of the invention, the association of RNASET2 disease risk variant SNPs with disease recurrence in 38 patients who were not receiving postoperative prophylaxis. Post-operative endoscopies were performed and classified by Rutgeerts score. (data summarized in Table 18).

RNASET2 Disease-Risk Alleles are Associated with Complicated and Resistant Disease Behavior To evaluate the association between RNASET2 and disease activity and severity the inventors utilized a cohort of 564 CD patients who had undergone surgical resection and were then followed prospectively. Clinical characteristics including indication for surgery were assessed for association with RNASET2 risk variants (rs1819333 and rs9355610). RNASET2 disease risk variant SNPs were associated with a complicated stricturing/penetrating phenotype (Montreal classification B1 vs. B2 and B3), (Table 18). At the time of surgery, patients with RNASET2 disease risk variant SNPs were associated with therapeutic failure of thiopurine or anti-TNF therapy, ANCA sero-positivity (a marker associated with lack of response to anti-TNF therapy), and an increased length of intestinal resection characteristic attributed to overall disease severity (Table 18 and FIGS. 38-39). No association was observed for therapeutic failure on steroids or sulfasalazine. Moreover, patients with RNASET2 disease risk variant SNPs who required multiple resections for disease management exhibited a shorter time to reoperation (FIG. 32).

TABLE 18

Clinical disease parameters associated with RNASET2 risk variants.

| | rs1819333 | | rs9355610 | |
|---|---|---|---|---|
| Clinical parameter | p | OR | p | OR |
| Disease Behavior | | | | |
| B2 vs. B1[a] | ns | ns | 0.041 | 1.07 |
| B3 vs. B1[a] | ns | ns | 0.056 | 1.06 |
| B2, B3 vs. B1[a] | 0.051 | 1.05 | 0.016 | 1.07 |
| Therapeutic failure of thiopurine[b] | 0.009 | 1.68 | 0.019 | 1.75 |
| Therapeutic failure of anti-TNF[b] | 0.039 | 1.46 | 0.042 | 1.56 |
| ANCA sero-positivity[b] | 0.009 | 2.24 | 0.047 | 2.07 |
| Resected segment >30 cm[b] | ns | ns | 0.004 | 2.13 |
| >40 cm[b] | ns | ns | 0.031 | 1.96 |
| Endoscopic recurrence Rutgeert's score 3-4 vs 1-2 | p | z score | p | z score |
| No prophylactic meds[b] | 0.025 | 2.24 | 0.024 | 2.25 |

[a]IIBDGC cohort CD (n = 3345)/case control (n = 6277)
[b]CD patients (n = 584) who had undergone surgical resection and followed prospectively.

Figure 30:
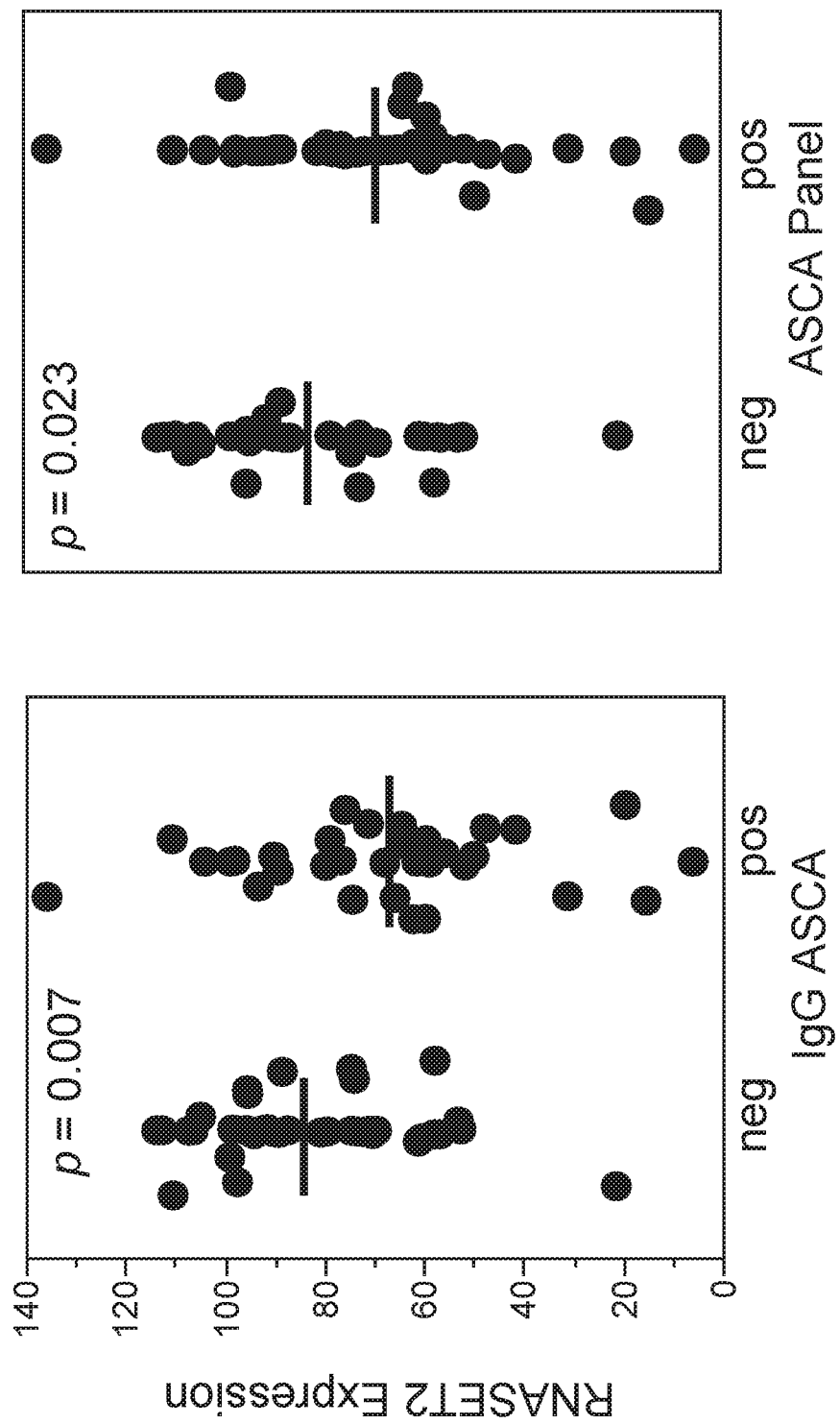
FIG. 30 depicts an association of decreased expression of RNASET2 with ASCA Sero-positivity, in accordance with various embodiments of the invention.
Figure 31:
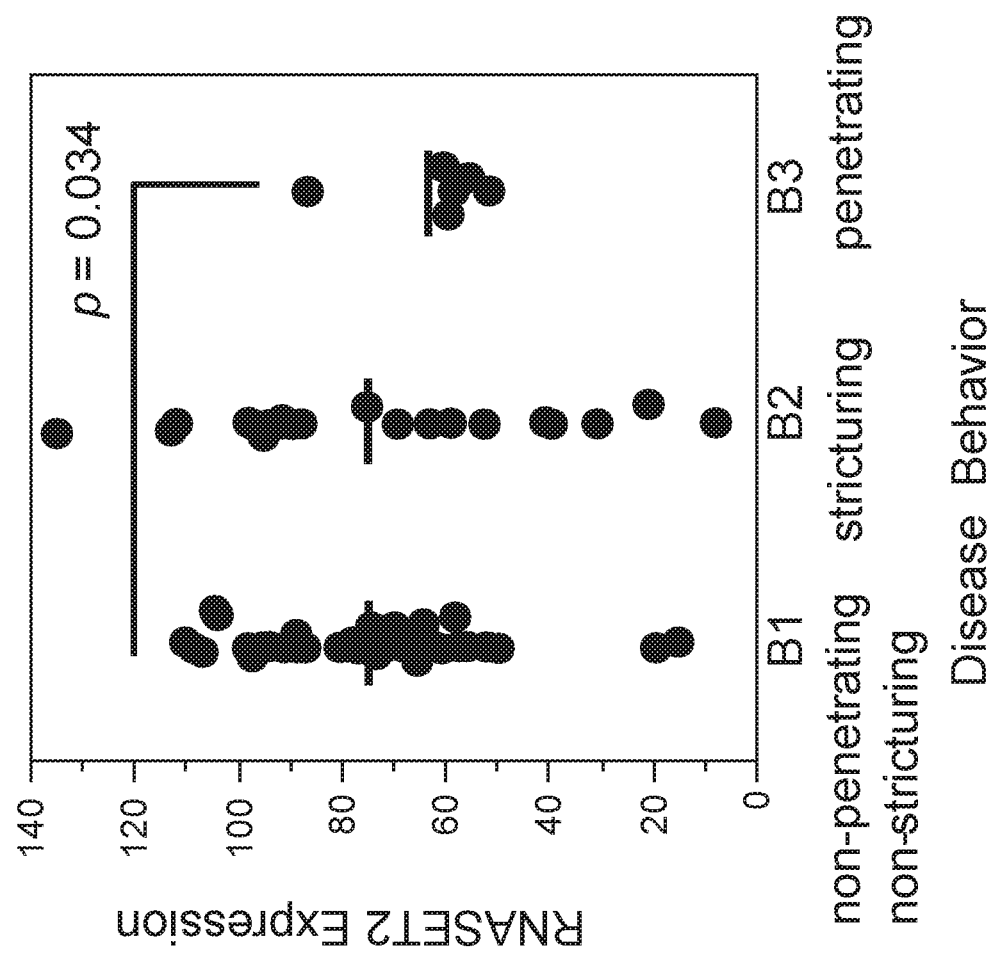
FIG. 31 depicts an association of a decreased expression of RNASET2 with penetrating disease, in accordance with various embodiments of the invention. Expression of RNASET2 by RNA-seq for 71 CD patients based upon Montreal disease classification (B1, B2, and B3).

Likewise, RNASET2 risk SNPs were associated with a more severe disease recurrence. Post-operative endoscopies revealed an association of RNASET2 risk SNPs in patients classified with a high Rutgeerts score (>2) who were not receiving postoperative prophylaxis (Table 18). No association was observed for clinical recurrence. Decreased expression of RNASET2 was also associated with a penetrating disease phenotype (FIG. 31) and ASCA sero-positivity (FIG. 30). Without being bound by any particular theory, this data supports an association of RNASET2 disease risk SNPs with clinical parameters suggestive of complicated and resistant disease behavior.

Figure 36C:
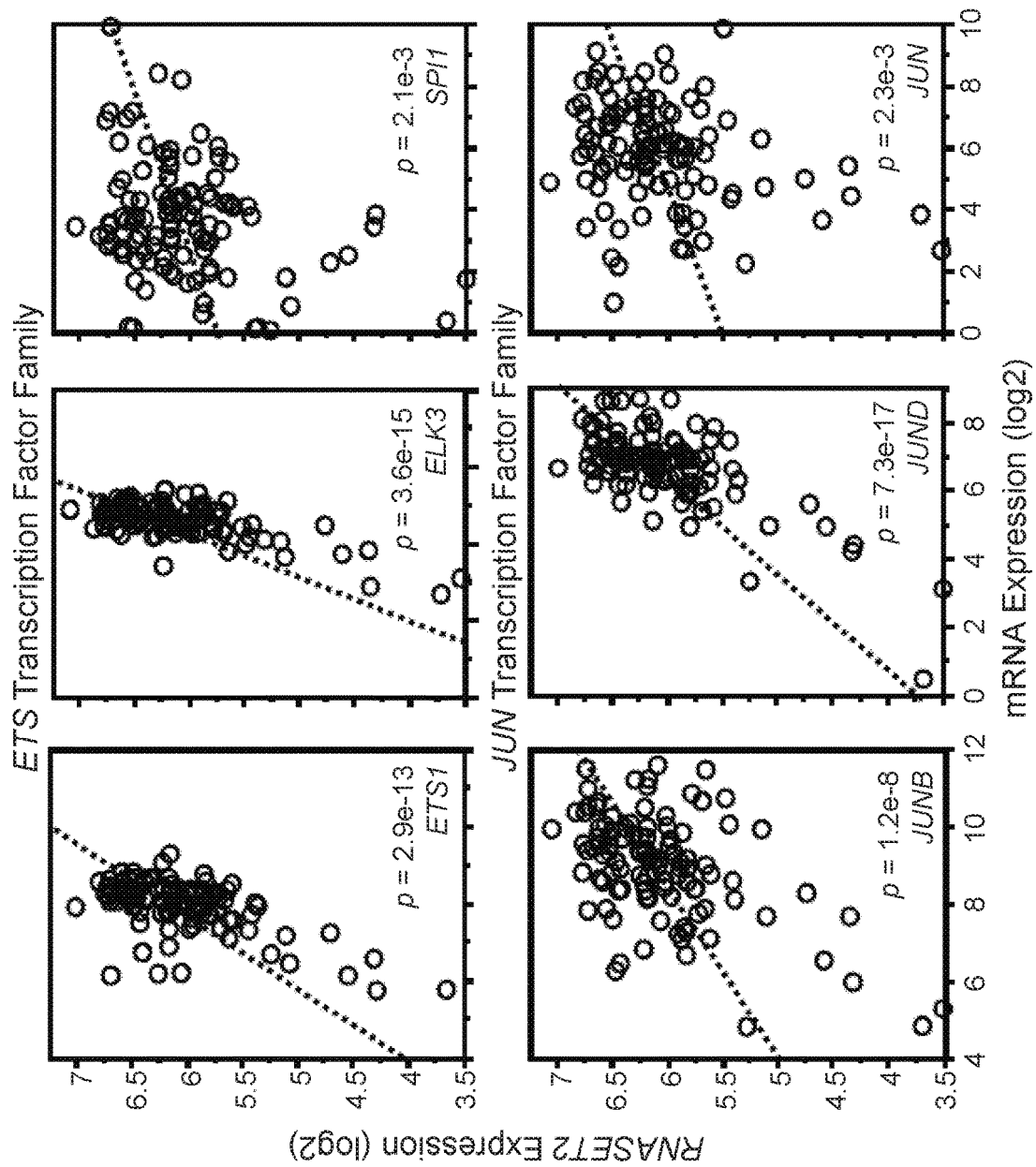
Figure 40:
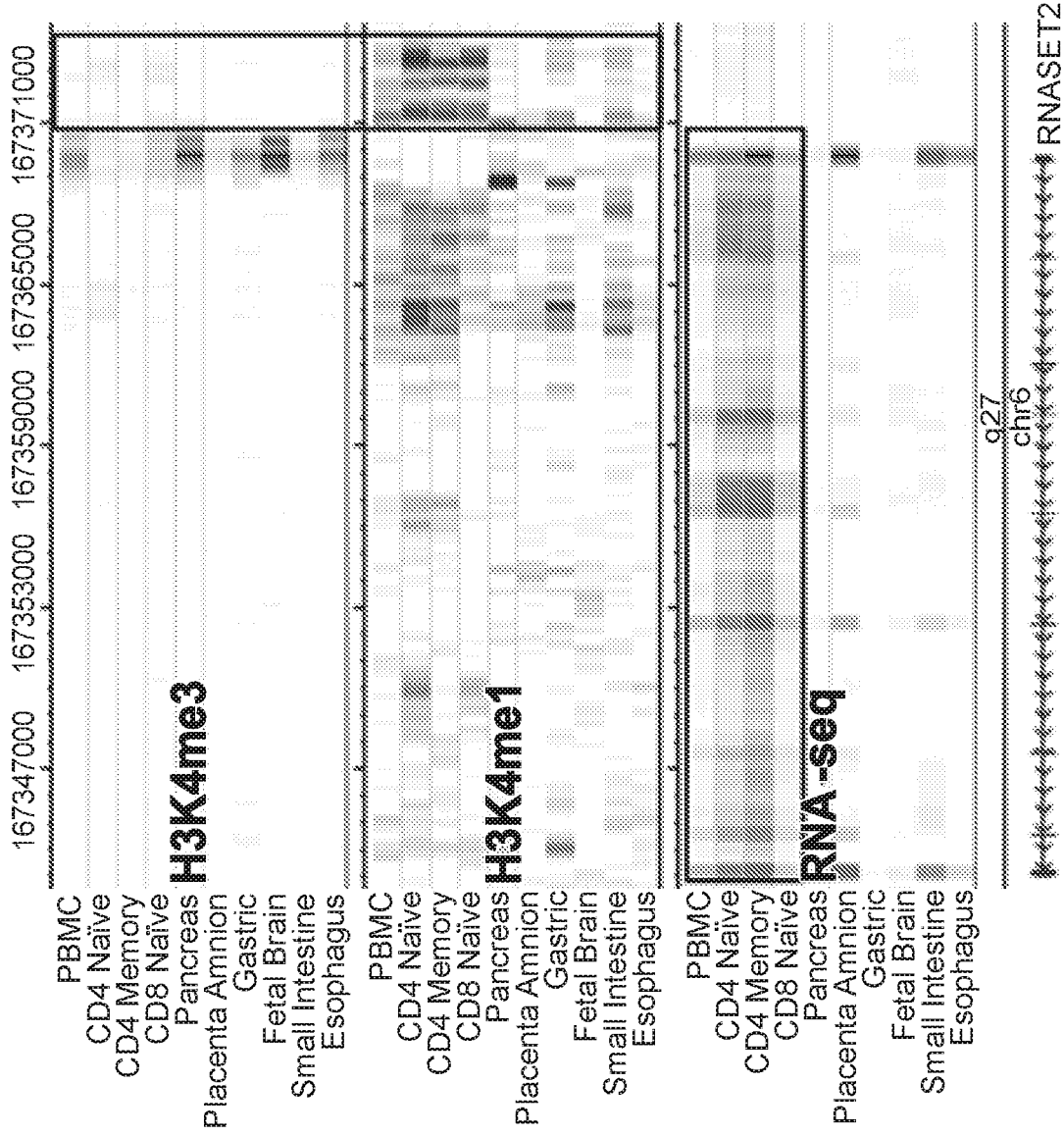
FIG. 40 depicts tissue-specific functional annotation of RNASET2 locus. Heatmap of H3K4me3, H3K4me1 and RNAseq data from REMC.
Figure 41:
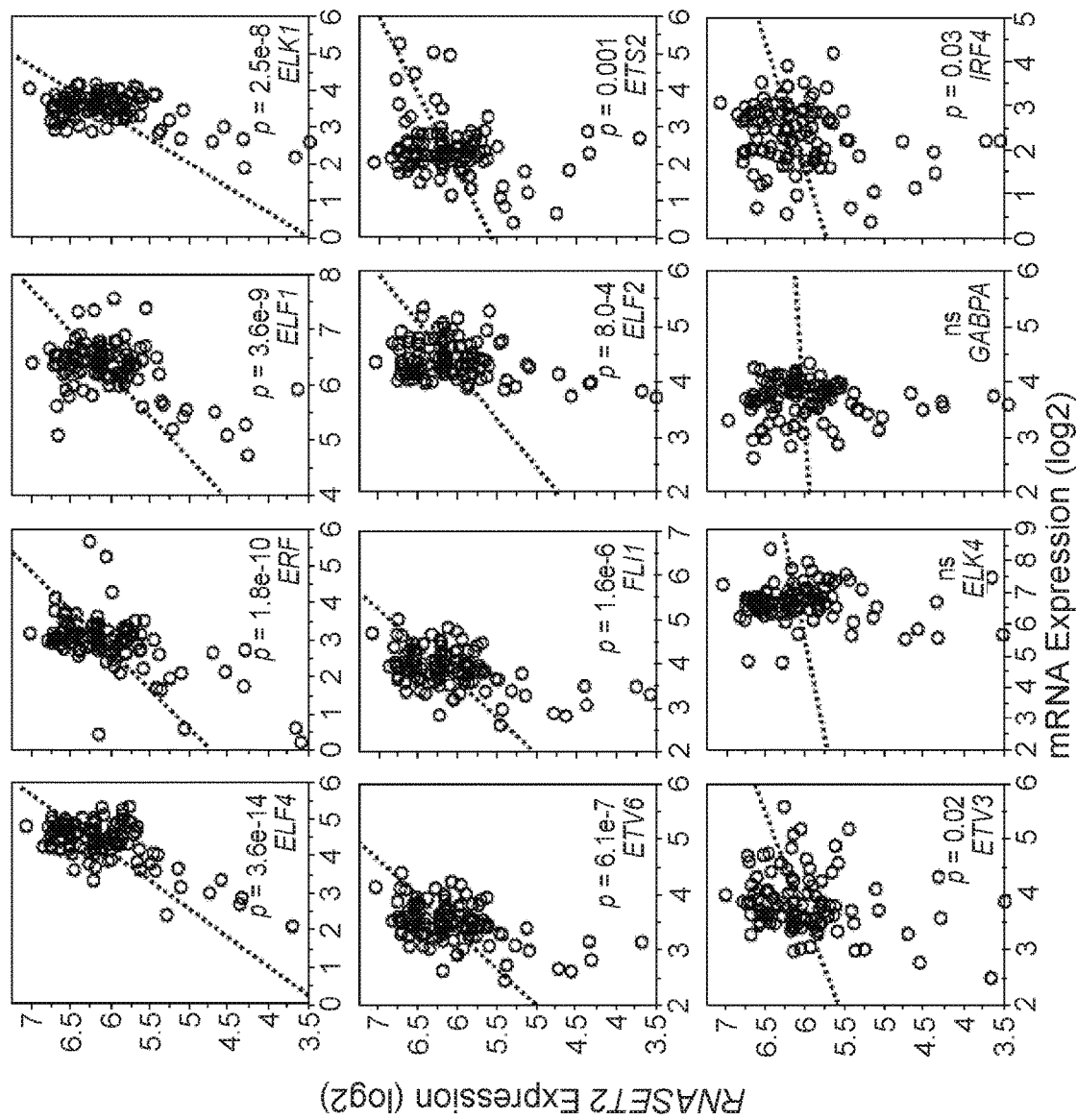
FIG. 41 depicts the correlation of RNASET2 expression and multiple ETS and IRF4 transcription factors in CD3+ peripheral T cells from 108 CD patients with refractory disease, using RNA-seq.

RNASET2 Variant in LD with Disease-Tagging SNP Disrupts ETS Transcription Factor Binding Motif The data presented above demonstrate significant overlap between more than a hundred CD RNASET2 risk variants, many in linkage disequilibrium, associated with eQTL and mQTL creating difficulty in determining functionality/causality. Since the majority of RNASET2 risk variants associated with CD are located in non-coding regions, it is likely that these SNPs alter expression through modulation of regulatory functions. Furthermore, without being bound to any particular theory, studies suggest that SNPs associated with disease often exist within active enhancer regions of cell types relevant to disease and can disrupt TF binding motifs. REMC data demonstrate that the RNASET2 locus is marked in primary T cells, compared to other tissues, by putative active enhancer histone modifications and active gene expression (FIG. 40). To gain insight into the molecular pathways regulating RNASET2 expression and prioritize the number of candidate functional SNPs, the inventors performed motif analysis to predict TF motif disruptions across all SNPs which were associated with eQTL/mQTL. Variants disrupting motifs of TFs expressed in T cells were selected and candidate variants in LD with the RNASET2 disease index SNP rs1819333 were focused on. The rs2049092 SNP disease risk variant, located −569 bp from the index SNP (LD R2=1), lies within the highly conserved TTCC motif, utilized by most ETS transcription factors, and is predicted to disrupt TF binding. Sequence analysis demonstrates an overlap of IRF4 and Spi1 binding sites adjacent to a JUN binding site (FIG. 36A). Regulome and REMC data confirm TF occupancy of ETS1, IRF4 and Spi1 binding in lymphoblastoid cell lines (FIG. 36B) which overlaps with histone modifications indicative of an active enhancer element. Moreover, there is a strong correlation between expression of RNASET2 with multiple members of ETS and JUN TF (FIGS. 36C and 41). No correlation was observed for IRF4 (FIG. 41). Without being bound to any particular theory, these data strengthen the relevance of RNASET2 expression in the immune compartment and support a functional role for ETS and JUN transcription factors in regulating transcription of RNASET2.

Figure 37B:
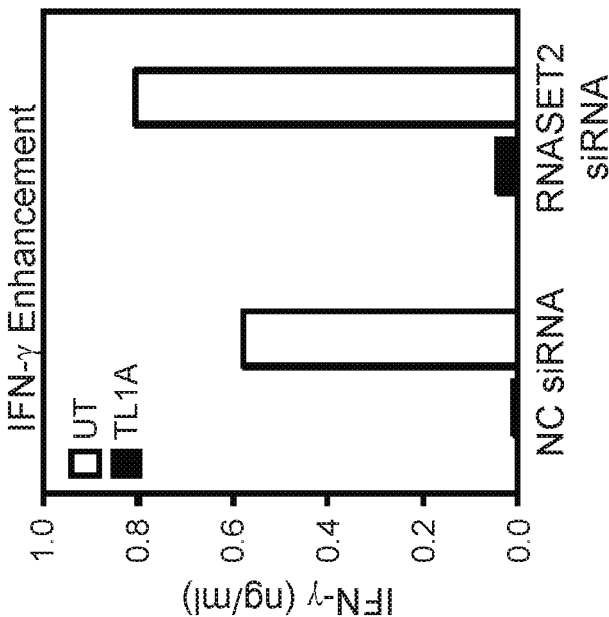
Figure 37A:
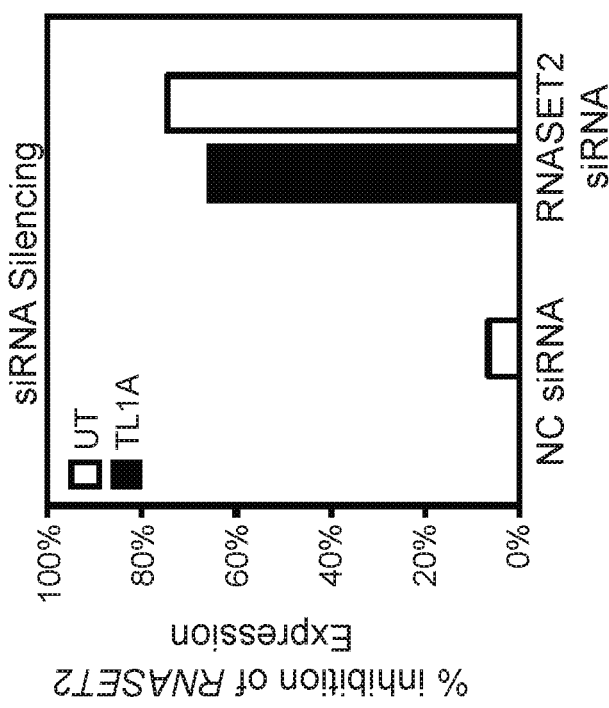

Silencing of RNASET2 Enhances IFN-γ Secretion Via Upregulation of ICAM1 Expression and Homotypic T Cell Aggregation The functional role of RNASET2 in regulation of IFN-γ secretion was tested using siRNA silencing. CD4+ T cells transfected with siRNA targeting RNASET2 mRNA followed by stimulation with TL1A. Cells transfected with siRNA targeting RNASET2 displayed a 60-70% inhibition of RNASET2 expression (FIGS. 21A and 37A), and a parallel significant enhancement (>1.5 fold) in TL1A mediated IFN-γ secretion was seen compared to control siRNA (FIG. 21B and FIG. 37B). Without being bound to any particular theory, these data suggest that down regulation of RNASET2 modulates IFN-γ expression.

Figure 37E:
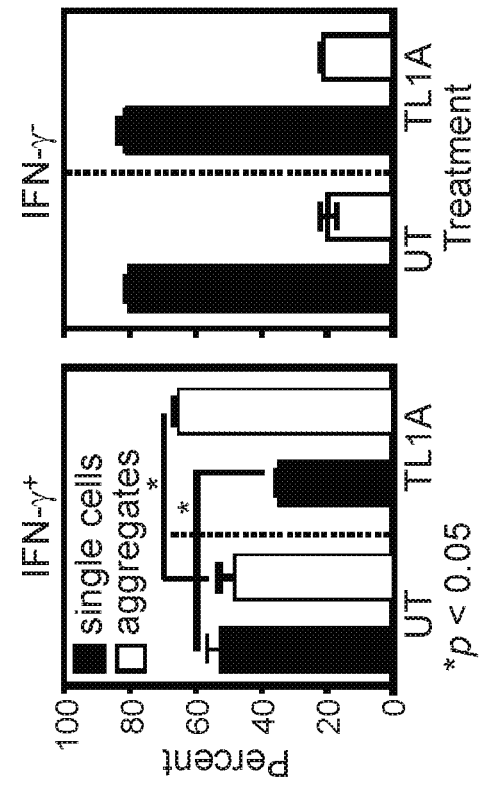
Figure 37F:
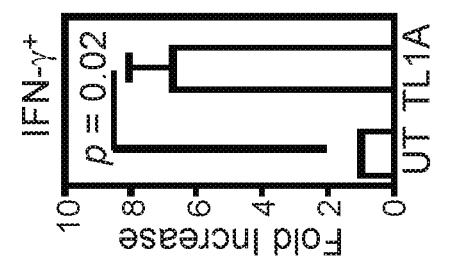
Figure 37G:
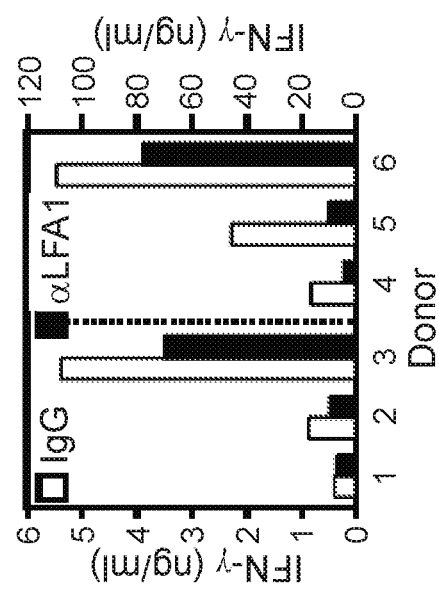
Figure 42:
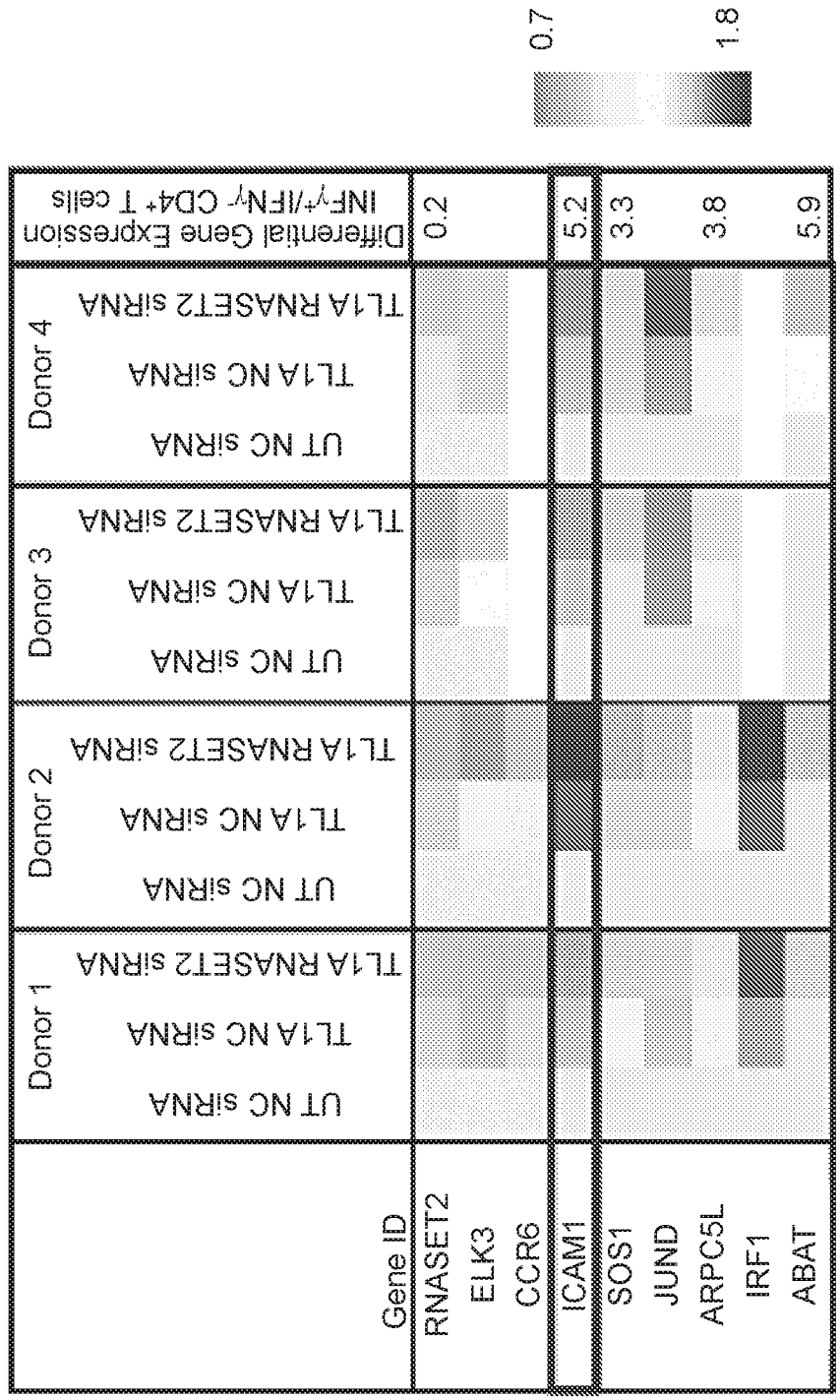
FIG. 42 depicts in accordance with various embodiments of the invention, a heat-map illustrating protein expression of indicated genes in CD4+ T cells relative to untreated cells following silencing with control (NC) or RNASET2 siRNA. Results are from 4 healthy donors. The right column depicts differential gene expression in IFN-γ secreting compared to non-secreting CD4+ T cells.
Figure 43:
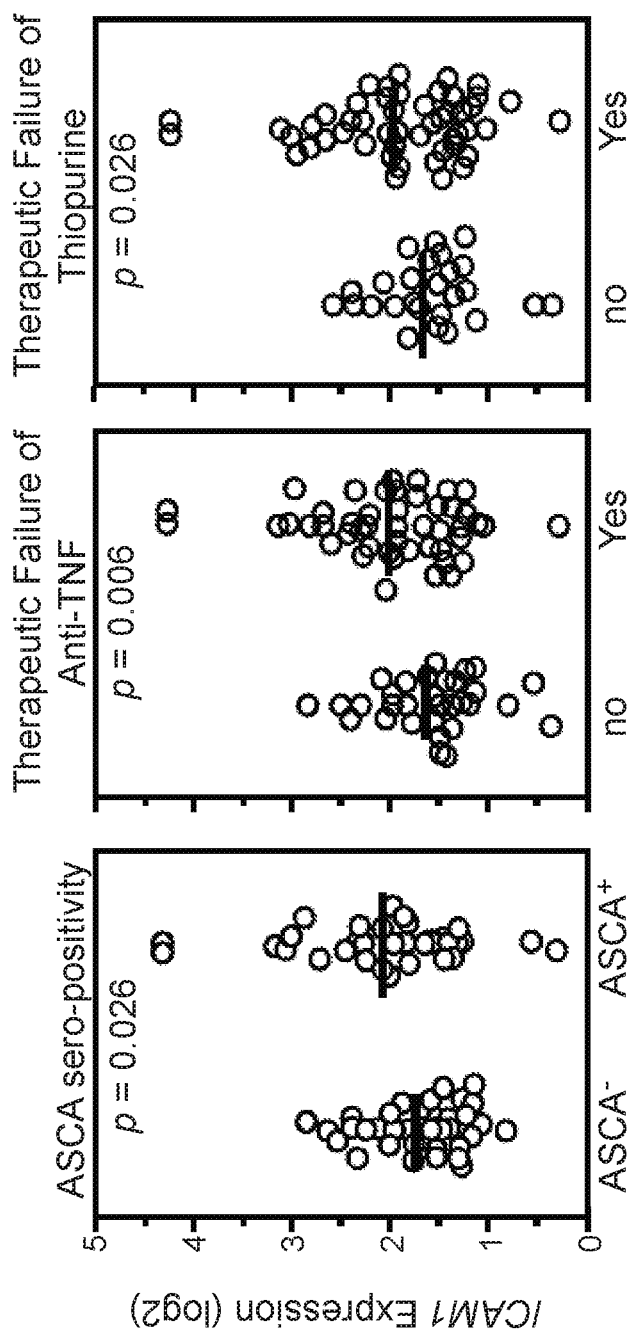
FIG. 43 depicts in accordance with various embodiments of the invention, clinical disease parameters associated with level of ICAM1 expression (measured by RNA-seq) for 71 CD patients based upon IgG ASCA sero-positivity (left panel) or pre-op therapeutic failure of anti-TNF (middle panel) or thiopurine (right panel).

In order to define the signaling pathways involved in this process, proteomic analysis was carried out. Candidate targets were selected on the basis of exhibiting both modulation of expression following siRNA silencing of RNASET2 as well as TL1A-mediated differential expression when comparing IFNγ secreting and non-secreting T cells (data from RNAseq analysis). One of the proteins that was up-regulated in response to RNASET2 silencing and in the IFNγ secreting compared to non-secreting T cells, was ICAM1 (FIG. 42). ICAM1 was recently identified as an IBD susceptibility locus, with up-regulated gene expression associated with the disease-risk variant. ICAM1 is a transmembrane adhesion protein commonly expressed by vascular endothelium and leukocytes. Binding of ICAM to the LFA1 receptor on T cells facilitates and stabilizes cell-cell interactions. Studies have demonstrated increased ICAM1 expression on activated T cells and proposed a role for ICAM1-LFA1 binding in inducing homotypic T cell aggregation and subsequent T cells differentiation. To examine the effect of cell-cell contact on TL1A mediated IFN-γ secretion, cells were incubated in flat bottom and conical bottom microwells. A greater than 3 fold increase in IFN-γ production was consistently observed when cells were incubated in close cell-cell conical geometry (data not shown). Flow cytometry was then used to test the hypothesis that TL1A mediated enhancement of IFN-γ production is facilitated by homotypic T cell aggregation. Briefly, T cells were stimulated in the presence or absence of TL1A and then stained with an antibody for intracellular IFN-γ (FIGS. 37C and 37D, left panels) and for cellular aggregation using propidium iodide (PI) (FIGS. 37C and 37D, upper and lower right panels). The PI-labeled peaks correspond to number of cells per event allowing for identifying single cells versus cellular aggregates. The first peak in each histogram corresponds to single cell events (black brackets) and the successive peaks, to multicellular aggregates (gray brackets). Only a small percentage of the unstimulated T cells secreted IFN-γ, and these cells were almost equally distributed as single cell events and cellular aggregates (FIG. 37E, left panel). Following TL1A stimulation, there was a significant increase in both the percentage and size of cellular aggregates (upper right panels of FIG. 37C compared to FIG. 37D, as well as, the overall number of IFN-γ producing cells (6-fold) (FIGS. 37E and 37F) and a 30-fold increase in IFN-γ secretion (data not shown). In contrast, the majority of T cells that do not produce IFN-γ, are comprised of single cell events regardless of whether they were cultured with or without TL1A stimulation (FIG. 37E, right panel). Without being bound to any particular theory, these results suggest that cellular aggregation may contribute to both an increase in the number of cells producing IFN-γ and to overall amount of IFN-γ production, and TL1A stimulation may enhance this process. The functional role of TL1A in mediating cellular aggregation via ICAM1-LFA1 engagement was tested using an LFA-1 blocking antibody. As seen in FIG. 37G, there was an overall 43% reduction in IFN-γ secretion in response to blocking LFA-1 engagement, compared to IgG control antibody (p value=0.047). Without being bound to any particular theory, taken together these data indicate that TL1A-mediated downregulation of RNASET2 and concomitant enhancement of ICAM1 expression, promotes homotypic T cell aggregation and augmentation of IFN-γ production. It is noted that an increase in expression of ICAM1 was associated in CD with ASCA sero-positivity and pre-op therapeutic failure of anti-TNF and thiopurine (FIG. 43), clinical parameters associated with decreased RNASET2 and disease activity.

Example 6

Both RNASET2 and TNFSF15 have been identified among the 201 GWAS IBD susceptibility loci. TL1A, the protein encoded by TNFSF15, is a key mediator of mucosal inflammation. Elevated TL1A levels correlate with TNFSF15 genotype and disease severity. The inventors have identified that TL1A down regulates expression of RNASET2 in T cells. TNFSF15 and RNASET2 expression is inversely correlated in T cells from CD patients (p=5× $10^{-16}$). The potential of RNASET2 as an IBD prognostic biomarker was examined.

The role for RNASET2 disease associated SNPs in IBD was analyzed by examining expression and methylation quantitative trait loci (eQTL/mQTL) in peripheral T cells from patients undergoing surgery (n=21) and small bowel surgical samples (n=85). CD patients (n=584) who had undergone surgical resection were followed prospectively. Clinical characteristics including indication for surgery were assessed for association with RNASET2 risk variants (rs1819333 and rs9355610).

RNASET2 disease associated SNPs were correlated with decreased RNASET2 expression (eQTL) in peripheral and mucosal tissues (p<0.001) and DNA hypermethylation (mQTL) (p<0.001) in patients requiring surgical intervention for disease management compared to those who were responsive to IBD therapeutics (n=16). RNASET2 disease associated SNPs were associated with therapeutic failure of thiopurine (p=0.02, OR=1.7) or anti-TNF therapy (p=0.04, OR=1.59), ANCA sero-positivity (a marker associated with lack of response to anti-TNF therapy) (p=0.02, OR=2.27), and an increase in overall length of intestinal resection (>30 cm p=0.004, OR=2.13/>40 cm p=0.03, OR=1.96). Patients with RNASET2 disease associated SNPs exhibited a shorter time to reoperation (p=0.04, z score=2.16). Post-operative endoscopies (n=369) with a high Rutgeerts score (>2) were associated with RNASET2 risk SNPs in patients not receiving post-op prophylaxis (p=0.02, z score=2.56) or those on anti-TNF therapy alone (p=0.03, z score=2.46), whereas no association was detected for patients on other IBD therapeutics.

This study identifies functional consequences of RNASET2 disease associated SNPs that are associated with clinically relevant disease behavior. RNASET2 risk SNPs were associated with clinical parameters suggestive of a complicated and resistant disease behavior. Moreover, response to therapeutics following surgery and recurrence of disease were associated with RNASET2 risk SNPs. Without being bound to any particular theory, these results taken together with our previous findings indicate that regulation of RNASET2 may underlie disease pathology triggered by TL1A and serve as a disease biomarker identifying subjects not responsive to current treatment strategies who may benefit from alternate therapeutic approaches.

TABLE 19

Clinical features associated with RNASET2 disease risk SNPs

| | rs1819333 | | rs9355610 | |
|---|---|---|---|---|
| CD phenotype at Time of Surgery | p | OR | p | OR |
| therapeutic failure of thiopurine | 0.009 | 1.68 | 0.019 | 1.75 |
| therapeutic failure of anti-TNF | 0.039 | 1.46 | 0.042 | 1.59 |
| ANCA sero-positivity | 0.009 | 2.24 | 0.047 | 2.07 |
| Length of resected segment >30 cm | | | 0.004 | 2.13 |
| >40 cm | | | 0.031 | 1.96 |
| Family history of disease | 0.030 | 1.58 | 0.030 | 1.78 |
| B2 vs B1 | | | 0.041 | 1.07 |
| B3 vs B1 | | | 0.056 | 1.06 |
| B2, B3 vs B1 | 0.051 | 1.05 | 0.016 | 1.07 |

CD patients (n = 584) who had undergone surgical resection and followed prospectively
IIBDGC cohort CD (n = 7173)/case control (n = 6278)

TABLE 20

Endoscopic Recurrence

| Endoscopic score | Definition | 3-year clinical recurrence rate (%) |
|---|---|---|
| 0 | No lesions | 5 |
| 1 | ≤aphtous lesions | 5 |

TABLE 20-continued

Endoscopic Recurrence

| | | |
|---|---|---|
| 2 | apthous lesions with normal mucosa between the lesions, or skip areas of larger lesions or lesions confined to ileocolonic anastomosis | 15-20 |
| 3 | Diffuse apthous ileitis with diffusely inflamed mucosa | 40 |
| 4 | Diffuse inflammation with already larger ulcers, nodules, and/or narrowing | 90 |

Adapted from Remedica Journals

Post-op

| | rs9355610 | |
|---|---|---|
| Endoscopic recurrence Rutgeert's score 3-4 vs 1-2 | p | z score |
| No prophylactic meds | 0.040 | 2.25 |
| Anti-TNF alone | 0.016 | 2.69 |

The rs2149092 (C-non-risk allele/T-risk allele) risk SNP abolishes IRF4/PU.1/ELF-1 binding site. IRF4 is an IBD susceptibility SNP that is lymphocyte specific and is essential for the differentiation of Th1, Th2, Th9, Th17 and T reg subsets. ELF-1 is a CD susceptibility SNP in the Japanese population. It is an ETS family transcription factor that is expressed in lymphoid cells, acts as both an enhancer and a repressor of expression and is involved in IL2 and IL23 signaling. PU.1 is also an ETS family transcription factor and is essential for early stages of T cell development. It down regulates γδ T Cells which are found in the mucosa and plays a role in innate immunity and when expressed in $T_H9$ cells, these cells drive T cell-mediated colitis via IL-9 receptor signaling in intestinal epithelial cells.

RNASET2 expression is decreased following TL1A treatment in IFN-γ secreting CD4$^+$ T cells and that silencing of RNASET2 enhances TL1A mediated IFN-γ secretion. Clinical correlates have also been identified for RNASET2 disease associated SNPs, which include, but are not limited to therapeutic failure of thiopurine therapy, therapeutic failure of anti-TNF therapy, ANCA Sero-positivity, B2/B3 versus B1 (structuring/penetrating vs non-penetrating/non-stricturing) disease, an increase in length of intestinal resection, decreased time to second surgery and endoscopic recurrence of disease with high Rutgeerts score.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating Inflammatory Bowel Disease (IBD) in a subject, the method comprising administering a therapeutically effective amount of a therapeutic agent to the subject, provided a single nucleotide polymorphism (SNP) at rs2149092 comprising a "T" at a nucleoposition 501 within SEQ ID NO: 2 is detected in a sample obtained from the subject.

2. The method of claim 1, provided a SNP at rs1819333 comprising an "A" allele at a nucleoposition 501 within SEQ ID NO: 1 is detected in the sample obtained from the subject.

3. The method of claim 1, wherein the IBD is severe IBD characterized by at least one of a therapeutic failure of an anti-Tumor Necrosis Factor alpha (TNFa) therapy, multiple flare-ups per year, stricturing disease, penetrating disease, and stricturing and penetrating disease.

4. The method of claim 1, provided a SNP at rs9355610 is detected in the sample obtained from the subject.

5. The method of claim 4, wherein the SNP at rs9355610 comprises a "G" allele at nucleoposition 501 within SEQ ID NO: 3.

6. The method of claim 1, provided a SNP at rs6478109 or a SNP at rs7848647, or a combination thereof, is detected in the sample obtained from the subject.

7. The method of claim 1, wherein the therapeutic agent comprises an anti-Tumor Necrosis Factor Ligand 1 (TL1A) antibody.

8. The method of claim 1, wherein the IBD is Crohn's disease (CD), ulcerative colitis (UC), medically refractory UC (mrUC), or a combination thereof.

9. A method of diagnosing and treating inflammatory bowel disease in a subject, the method comprising:
   a) subjecting a sample obtained from the subject to an assay adapted to determine a presence or an absence of a genotype comprising a single nucleotide polymorphism (SNP) rs2149092 comprising a "T" at a nucleoposition 501 within SEQ ID NO: 2;
   b) detecting the presence or the absence of the genotype;
   c) diagnosing inflammatory bowel disease (IBD) in the subject when the presence of the genotype is detected in step (b); and
   d) treating the IBD in the subject diagnosed in (c) by administering an effective amount of a therapeutic agent to the subject.

10. The method of claim 9, wherein the genotype further comprises a SNP at rs1819333 comprising an "A" allele at a nucleoposition 501 within SEQ ID NO: 1.

11. The method of claim 9, wherein the IBD is severe IBD characterized by at least one of a therapeutic failure of an anti-Tumor Necrosis Factor alpha (TNFa) therapy, multiple flare-ups per year, stricturing disease, penetrating disease, and stricturing and penetrating disease.

12. The method of claim 9, provided the genotype further comprises a SNP at rs9355610 comprising a "G" allele at nucleoposition 501 within SEQ ID NO: 3.

13. The method of claim 9, wherein the assay comprises a genotyping assay selected from the group consisting of quantitative polymerase chain reaction (qPCR), a single nucleotide polymorphism (SNP) array, and sequencing.

14. The method of claim 9, provided the genotype further comprises at least one of a SNP at rs6478109 and a SNP at rs7848647.

15. The method of claim 9, wherein the therapeutic agent comprises an anti-Tumor Necrosis Factor Ligand 1 (TL1A) antibody.

16. The method of claim 9, wherein the IBD is Crohn's disease, ulcerative colitis (UC), medically refractory UC, or a combination thereof.

17. The method of claim 15, wherein the anti-TL1A antibody comprises a neutralizing TL1A antibody.

18. The method of claim 7, wherein the anti-TL1A antibody comprises a neutralizing TL1A antibody.

* * * * *